(12) United States Patent
Lin et al.

(10) Patent No.: US 11,246,877 B2
(45) Date of Patent: Feb. 15, 2022

(54) NANOPARTICLES FOR CHEMOTHERAPY, TARGETED THERAPY, PHOTODYNAMIC THERAPY, IMMUNOTHERAPY, AND ANY COMBINATION THEREOF

(71) Applicant: The University of Chicago, Chicago, IL (US)

(72) Inventors: Wenbin Lin, Chicago, IL (US); Xiaopin Duan, Guangzhou (CN); Christina Chan, Chicago, IL (US); Wenbo Han, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/302,185

(22) PCT Filed: May 22, 2017

(86) PCT No.: PCT/US2017/033822
§ 371 (c)(1),
(2) Date: Nov. 16, 2018

(87) PCT Pub. No.: WO2017/201528
PCT Pub. Date: Nov. 23, 2017

(65) Prior Publication Data
US 2019/0269706 A1    Sep. 5, 2019

Related U.S. Application Data

(60) Provisional application No. 62/339,594, filed on May 20, 2016.

(51) Int. Cl.
*A61K 31/66* (2006.01)
*A61K 47/54* (2017.01)
(Continued)

(52) U.S. Cl.
CPC ............ *A61K 31/66* (2013.01); *A61K 9/1277* (2013.01); *A61K 9/51* (2013.01); *A61K 31/136* (2013.01);
(Continued)

(58) Field of Classification Search
CPC .................................................. A61K 9/1277
See application file for complete search history.

(56) References Cited

U.S. PATENT DOCUMENTS

| 4,405,771 A | 9/1983 | Jagur |
| 5,147,806 A | 9/1992 | Kamin et al. |

(Continued)

FOREIGN PATENT DOCUMENTS

| CA | 2896797 A1 | 7/2014 |
| CN | 1673258 | 9/2005 |

(Continued)

OTHER PUBLICATIONS

S Mura, DT Bui, P Couvreur, J Nicolas. "Lipid prodrug nanocarriers in cancer therapy." Journal of Controlled Release, vol. 208, 2015, pp. 25-41, available online Jan. 21, 2015. (Year: 2015).*

(Continued)

*Primary Examiner* — Isaac Shomer
(74) *Attorney, Agent, or Firm* — Jenkins, Wilson, Taylor & Hunt, P.A.

(57) ABSTRACT

Prodrugs containing lipid moieties attached to drug derivatives, such as anti-cancer drug derivatives, via linkers comprising disulfide groups are described. Also described are nanoparticles coated with a lipid layer containing the prodrugs, formulations comprising the nanoparticles, and the use of the nanoparticles in methods of treating diseases, such as cancer, alone or in combination with additional drug compounds, targeting agents, and/or immunotherapy agents, such as immunosuppression inhibitors that target the CTLA- (Continued)

4, PD-1/PD-L1, IDO, LAG-3, CCR-7 or other pathways, or multiple immunosuppression inhibitors targeting a combination of such pathways. Optionally, the nanoparticles can comprise a photosensitizer or a derivative thereof and can be used in methods involving photodynamic therapy. Synergistic therapeutic effects result from combinations of multiple modalities provided by the disclosed nanoparticles and/or nanoparticle formulations.

34 Claims, 50 Drawing Sheets

(51) Int. Cl.
*A61P 35/00* (2006.01)
*A61K 9/127* (2006.01)
*A61K 31/337* (2006.01)
*A61K 31/357* (2006.01)
*A61K 31/7048* (2006.01)
*A61K 31/704* (2006.01)
*A61K 31/136* (2006.01)
*A61K 31/7068* (2006.01)
*A61K 31/4745* (2006.01)
*C12N 15/11* (2006.01)
*A61K 31/475* (2006.01)
*A61K 9/51* (2006.01)
*A61K 45/06* (2006.01)

(52) U.S. Cl.
CPC .......... *A61K 31/337* (2013.01); *A61K 31/357* (2013.01); *A61K 31/475* (2013.01); *A61K 31/4745* (2013.01); *A61K 31/704* (2013.01); *A61K 31/7048* (2013.01); *A61K 31/7068* (2013.01); *A61K 47/543* (2017.08); *A61P 35/00* (2018.01); *C12N 15/111* (2013.01); *A61K 45/06* (2013.01); *C12N 2310/11* (2013.01); *C12N 2310/14* (2013.01); *C12N 2310/141* (2013.01); *C12N 2320/32* (2013.01)

(56) References Cited

U.S. PATENT DOCUMENTS

| | | | |
|---|---|---|---|
| 5,213,788 A | 5/1993 | Ranney | |
| 5,591,730 A | 1/1997 | Stoller et al. | |
| 5,641,623 A | 6/1997 | Martin | |
| 5,648,508 A | 7/1997 | Yaghi | |
| 5,827,925 A | 10/1998 | Tremont et al. | |
| 5,858,784 A | 1/1999 | Debs et al. | |
| 5,871,710 A | 2/1999 | Bogdanov et al. | |
| 6,013,638 A | 1/2000 | Crystal et al. | |
| 6,022,737 A | 2/2000 | Niven et al. | |
| 6,136,295 A | 10/2000 | Edwards et al. | |
| 6,180,082 B1 | 1/2001 | Woltering et al. | |
| 6,384,019 B1 | 5/2002 | Myhren et al. | |
| 6,565,873 B1 | 5/2003 | Shefer et al. | |
| 6,818,227 B1 | 11/2004 | Uster et al. | |
| 6,878,838 B2 | 4/2005 | Lin et al. | |
| 6,984,400 B2 | 1/2006 | Golomb et al. | |
| 7,060,290 B1* | 6/2006 | Morimoto ............ | A61K 47/544 424/450 |
| 7,196,210 B2 | 3/2007 | Yaghi et al. | |
| 7,263,170 B2 | 8/2007 | Pellegrino | |
| 7,354,912 B2 | 4/2008 | Lichtenberger | |
| 7,430,282 B2 | 9/2008 | Mori et al. | |
| 7,704,972 B2 | 4/2010 | Couvreur et al. | |
| 7,803,785 B2 | 9/2010 | Gallop et al. | |
| 7,985,868 B1 | 7/2011 | Bauer | |
| 8,158,153 B2 | 4/2012 | Liversidge et al. | |
| 8,623,837 B2 | 1/2014 | Fewell | |
| 8,653,292 B2 | 2/2014 | Hafizovic et al. | |
| 8,668,764 B2 | 3/2014 | Brown et al. | |
| 8,691,748 B2 | 4/2014 | Yaghi et al. | |
| 8,722,018 B2 | 5/2014 | Port et al. | |
| 9,072,774 B2 | 7/2015 | Zheng et al. | |
| 9,162,079 B2 | 10/2015 | Levy et al. | |
| 9,302,003 B2 | 4/2016 | Sanche et al. | |
| 9,693,957 B2 | 7/2017 | Lin et al. | |
| 10,118,169 B2 | 11/2018 | Lin et al. | |
| 10,206,871 B2 | 2/2019 | Lin et al. | |
| 10,350,275 B2 | 7/2019 | Aguilar-Cordova | |
| 10,517,822 B2* | 12/2019 | Lin ................ | A61P 43/00 |
| 10,596,116 B2 | 3/2020 | Lin et al. | |
| 10,780,045 B2 | 9/2020 | Lin et al. | |
| 10,806,694 B2 | 10/2020 | Lin et al. | |
| 2001/0018187 A1 | 8/2001 | Sun et al. | |
| 2002/0064520 A1* | 5/2002 | Rozenberg ............ | A61P 43/00 424/93.2 |
| 2002/0115747 A1 | 8/2002 | Feldheim et al. | |
| 2002/0127224 A1 | 9/2002 | Chen | |
| 2002/0187184 A1 | 12/2002 | Golomb et al. | |
| 2005/0112131 A1 | 5/2005 | Pogue et al. | |
| 2005/0147963 A1 | 7/2005 | Su et al. | |
| 2005/0227929 A1 | 10/2005 | Masferrer | |
| 2006/0204754 A1 | 9/2006 | Kang | |
| 2006/0210639 A1 | 9/2006 | Liversidge et al. | |
| 2006/0228554 A1 | 10/2006 | Tan et al. | |
| 2006/0233883 A1 | 10/2006 | Ishihara et al. | |
| 2007/0076851 A1 | 4/2007 | Pellegrino | |
| 2007/0088161 A1 | 4/2007 | Stockel et al. | |
| 2007/0218049 A1 | 9/2007 | Chen et al. | |
| 2007/0259966 A1 | 11/2007 | Cagnoni et al. | |
| 2008/0063714 A1 | 3/2008 | Sahouani et al. | |
| 2008/0095699 A1 | 4/2008 | Zheng et al. | |
| 2008/0124281 A1 | 5/2008 | Gao et al. | |
| 2008/0280851 A1 | 11/2008 | Myhren et al. | |
| 2008/0286352 A1 | 11/2008 | Kumar et al. | |
| 2008/0292714 A1 | 11/2008 | Garlich et al. | |
| 2009/0317335 A1 | 12/2009 | Lin et al. | |
| 2010/0189222 A1 | 7/2010 | Eaton et al. | |
| 2010/0286022 A1 | 11/2010 | Yaghi et al. | |
| 2011/0053862 A1 | 3/2011 | Xie et al. | |
| 2011/0135571 A1 | 6/2011 | Lin et al. | |
| 2011/0238001 A1 | 9/2011 | Chen et al. | |
| 2011/0281815 A1 | 11/2011 | Ahrabi et al. | |
| 2012/0093918 A1 | 4/2012 | Sanche et al. | |
| 2012/0130146 A1 | 5/2012 | Picard et al. | |
| 2012/0142641 A1 | 6/2012 | Venkatraman | |
| 2012/0226217 A1 | 9/2012 | Klaveness et al. | |
| 2012/0253191 A1 | 10/2012 | Zheng et al. | |
| 2012/0301537 A1 | 11/2012 | Ishida et al. | |
| 2013/0171228 A1 | 7/2013 | Morris | |
| 2014/0066625 A1 | 3/2014 | Mautino et al. | |
| 2014/0107333 A1 | 4/2014 | Ma et al. | |
| 2014/0127763 A1 | 5/2014 | Zheng et al. | |
| 2014/0220143 A1 | 8/2014 | Dhar et al. | |
| 2014/0234210 A1* | 8/2014 | Lin ................ | A61K 9/5115 424/1.21 |
| 2014/0235568 A1 | 8/2014 | Song et al. | |
| 2014/0335015 A1 | 11/2014 | Pottier et al. | |
| 2015/0086541 A1 | 3/2015 | Aguilar-Cordova | |
| 2016/0346204 A1 | 12/2016 | Lin et al. | |
| 2017/0182486 A1 | 6/2017 | Lin et al. | |
| 2017/0231903 A1 | 8/2017 | Lin et al. | |
| 2017/0333347 A1 | 11/2017 | Lin et al. | |
| 2018/0153796 A1 | 6/2018 | Lin et al. | |
| 2018/0214563 A1* | 8/2018 | Li ................ | A61K 47/6907 |
| 2018/0361370 A1 | 12/2018 | Lin et al. | |
| 2019/0209460 A1 | 7/2019 | Lin et al. | |
| 2020/0085742 A1 | 3/2020 | Lin et al. | |
| 2020/0222321 A1 | 7/2020 | Lin et al. | |

FOREIGN PATENT DOCUMENTS

| | | |
|---|---|---|
| CN | 102448497 | 5/2012 |
| CN | 102573914 A | 7/2012 |
| CN | 102648004 | 8/2012 |
| CN | 105457038 A | 4/2016 |
| CN | 109310702 A | 2/2019 |
| CN | 105873569 B | 7/2020 |
| EP | 3439666 A1 | 2/2019 |

(56) References Cited

FOREIGN PATENT DOCUMENTS

| EP | 3 494 974 A1 | 6/2019 | |
|---|---|---|---|
| JP | 2010-523595 A | 7/2010 | |
| JP | 2013507399 A | 3/2013 | |
| JP | 6731404 B2 | 7/2020 | |
| WO | WO 2004/028508 A1 | 4/2004 | |
| WO | WO2004/101575 A2 | 11/2004 | |
| WO | WO 2006/087722 A1 | 8/2006 | |
| WO | WO2006/102117 | 9/2006 | |
| WO | WO2007/090295 | 8/2007 | |
| WO | WO2007/108618 | 9/2007 | |
| WO | WO2007/124131 | 11/2007 | |
| WO | WO 2008/016172 A1 | 2/2008 | |
| WO | WO 2008/102632 A1 | 8/2008 | |
| WO | WO 2008/124639 A2 | 10/2008 | |
| WO | WO 2009/014532 A1 | 1/2009 | |
| WO | WO2009/139939 | 11/2009 | |
| WO | WO 2010/065751 A2 | 6/2010 | |
| WO | WO 2010/096464 A1 | 8/2010 | |
| WO | WO 2011/044671 A1 | 4/2011 | |
| WO | WO 2011/049743 A1 | 4/2011 | |
| WO | WO 2012/042024 | 4/2012 | |
| WO | WO 2012/161196 A1 | 11/2012 | |
| WO | WO 2013/009701 A2 | 1/2013 | |
| WO | WO 2013/009701 A9 | 1/2013 | |
| WO | WO 2013/068965 | 5/2013 | |
| WO | WO 2013/188763 A1 | 12/2013 | |
| WO | WO 2015/069926 A1 | 5/2015 | |
| WO | WO-2015069926 A1 * | 5/2015 | ............. A61P 35/00 |
| WO | WO 2015/149068 A1 | 10/2015 | |
| WO | WO 2015/149072 A1 | 10/2015 | |
| WO | WO 2016/061256 A1 | 4/2016 | |

OTHER PUBLICATIONS

Y Wang et al. "Disulfide Bond Bridge Insertion Turns Hydrophobic Anticancer Prodrugs into Self-Assembled Nanomedicines." Nano Letters, vol. 14, 2014, pp. 5577-5583, published Sep. 4, 2014. (Year: 2014).*
PJ Stevens, M Sekido, and RJ Lee. "A Folate Receptor-Targeted Lipid Nanoparticle Formulation fora Lipophilic Paclitaxel Prodrug." Pharmaceutical Research, vol. 21, No. 12, Dec. 2004, pp. 2153-2157. (Year: 2004).*
R Sheng, T Luo, Y Zhu, H Li, J Sun, S Chen, W Sun, A Cao. "The intracellular plasmid DNA localization of cationic reducible cholesterol-disulfide lipids." Biomaterials 32 (2011) pp. 3507-3519. (Year: 2011).*
G Salzano, R Riehle, G Navarro, F Perche, G De Rosa, VP Torchilin. "Polymeric micelles containing reversibly phospholipid-modified anti-survivin siRNA: A promising strategy to overcome drug resistance in cancer." Cancer Letters 343 (2014) pp. 224-231. (Year: 2014).*
C He, K Lu, D Liu, and W Lin. "Nanoscale Metal-Organic Frameworks for the Co-Delivery of Cisplatin and Pooled siRNAs to Enhance Therapeutic Efficacy in Drug-Resistant Ovarian Cancer Cells." Journal of the American Chemical Society, vol. 136, 2014, pp. 5181-5184. (Year: 2014).*
D Landesman-Milo, S Ramishetti, D Peer. "Nanomedicine as an emerging platformformetastatic lung cancer therapy." Cancer Metastasis Reviews, vol. 34, 2015, pp. 291-301, published online May 7, 2015. (Year: 2015).*
Liqiong Cai, Gaofei Xu, Changying Shi, Dandan Guo, Xu Wang, Juntao Luo. "Telodendrimer nanocarrier for co-delivery of paclitaxel and cisplatin: A synergistic combination nanotherapy for ovarian cancer treatment." Biomaterials 37 (2015) pp. 456-468, available online Oct. 31, 2014. (Year: 2014).*
Tao Chen, Mian Li, Ruiwen Zhang, Hui Wang. "Dihydroartemisinin induces apoptosis and sensitizes human ovarian cancer cells to carboplatin therapy." Journal of Cellular and Molecular Medicine, vol. 13 No. 7, 2009, pp. 1358-1370. (Year: 2009).*

Mark S. Bretscher. "Asymmetrical Lipid Bilayer Structure for Biological Membranes." Nature New Biology, vol. 236, Mar. 1, 1972, pp. 11-12. (Year: 1972).*
Anirban Polley, Satyavani Vemparala, and Madan Rao. "Atomistic Simulations of a Multicomponent Asymmetric Lipid Bilayer." The Journal of Physical Chemistry B, vol. 116, 2012, pp. 13403-13410. (Year: 2012).*
Jacqueline Ramirez, Snezana Mirkov, Larry K. House, and Mark J. Ratain. "Glucuronidation of OTS167 in Humans Is Catalyzed by UDP Glucuronosyltransferases UGT1A1, UGT1A3, UGT1A8, and UGT1A10." Drug Metabolism and Disposition, vol. 43, Jul. 2015, pp. 928-935. (Year: 2015).*
Yuan Sun, Chen Kang, Mengchi Wang, Jing Zhu, Liliang Jin, and Xinwei Cheng. "Nanosized camptothecin conjugates for single and combined drug delivery." European Journal of BioMedical Research, vol. 2, Issue 1, pp. 8-13. (Year: 2016).*
Hao Su et al. "Supramolecular Crafting of Self-Assembling Camptothecin Prodrugs with Enhanced Efficacy against Primary Cancer Cells." Theranostics, vol. 6 Issue 7, 2016, pp. 1065-1074. (Year: 2016).*
Simona Mura, Duc Trung Bui, Patrick Couvreur, and Julien Nicolas. "Lipid prodrug nanocarriers in cancer therapy." Journal of Controlled Release, vol. 208, 2015, pp. 25-41. (Year: 2015).*
Sun et al., "Nanosized Camptothecin Conjugates for Single and Combined Drug delivery," European Journal of Biomedical Research, vol. 2, No. 1 pp. 8-15 (2016).
European Search Report corresponding to European application No. 17800330 dated Nov. 12, 2019.
Liu et al., "Self-assembled nanoscale coordination polymers with trigger release properties for effective anticancer therapy," Nature Communications, vol. 5 pp. 1-11 (2014).
Su et al., "Supramolecular Crafting of Self-Assembling Camptothecin Prodrugs with Enhanced Efficacy against Primary Cancer Cells," Theranostics, vol. 6, No. 7 pp. 1065-1074 (2016).
Matsuo et al., "TOPK inhibitor induces complete tumor regression in xenograft models of human cancer through inhibition of cytokinesis," Science Translational Medicine, Oct. 22, 2014, vol. 6, 259ra145, pp. 1-9.
Notification of Transmittal of the International Search Report and the Written Opinion of the International Searching Authority, or the Declaration for International Application No. PCT/US1733822, dated Aug. 29, 2017.
Notification Concerning Transmittal of Copy of International Preliminary Report on Patentability for International Application No. PCT/US2017/033822, dated Nov. 29, 2018.
Lee et al., "Disulfide-Based Multifunctional Conjugates for Targeted Theranostic Drug Delivery," Accounts of Chemical Research, vol. 48, pp. 2935-2946 (2015).
Mura et al., "Lipid prodrug nanocarriers in cancer therapy," Journal of Controlled Release, vol. 208, pp. 1-17 (2015).
Advisory Action corresponding to U.S. Appl. No. 15/034,799 dated Jun. 5, 2018.
Advisory Action corresponding to U.S. Appl. No. 15/613,847 dated Aug. 13, 2019.
Allison et al., "Oncologic photodynamic therapy photosensitizers: A clinical review," Photodiagnosis and Photodynamic Therapy, vol. 7, No. 2, pp. 61-75 (Jun. 2010).
Ash et al., "New drugs and future developments in photodynamic therapy," Eur. J. Cancer, vol. 29A, No. 12, pp. 1781-1783 (1993).
Bechet et al., "Nanoparticles as vehicles for delivery of photodynamic therapy agents," Trends in biotechnology, vol. 26, No. 11, pp. 612-621 (2008).
Biel, "Photodynamic Therapy of Head and Neck Cancers," Photodynamic Therapy, Methods in Molecular Biology, Springer+ Business Media, LLC, vol. 635 (25 pages), pp. 281-296 (2010).
Bonvalot et al. First-In-Human Study Testing a New Radioenhancer Using Nanoparticles (NBTXR3) Activated by Radiation Therapy In Patients With Locally Advanced Soft Tissue Sarcomas. Clinical Cancer Research, vol. 23, No. 4, 1297, pp. 908-917(2016).
Bowden et al., "Hydrothermal syntheses and crystal structures of three zinc succinates: $Zn(C_4H_4O_4)$-α, $Zn(C_4H_4O_4)$-β and $K_2Zn(C_4H_4O_4)_2$," Dalton Transactions. pp. 936-939 (2003).

(56) References Cited

OTHER PUBLICATIONS

Cai et al., "Metal-Organic Framework-Based Nanomedicine Platforms for Drug Delivery and Molecular Imaging," Small Journal, vol. 11, No. 37, pp. 4806-4822 (2015).

Carter et al., "Porphyrin-phospholipid liposomes permeabilized by near-infrared light," Nature communications, vol. 5, No. 3546 (25 pages), pp. 1-11 (Apr. 3, 2014).

Catala et al., "Cyanide-Bridged CrIII-NiII Superparamagnetic Nanoparticles," Advanced Materials. vol. 15, No. 10 pp. 826-829 (2003).

Cavka et al., "A New Zirconium Inorganic Building Brick Forming Metal Organic Frameworks with Exceptional Stability," J. Am. Chem. Soc., vol. 130, No. 42, pp. 13850-13851 (2008).

Che et al., "Generation of Binuclear (d8.d8) Platinum and Rhodium Complexes by Pulse Radiolysis", American Chemical Society, vol. 106, No. 18, pp. 5143-5145 (1984).

Chebbi et al., "In vitro assessment of liposomal neridronate on MDA-MB-231 human breast cancer cells," International Journal of Pharmaceutics 383 pp. 116-122 (2010).

Chen et al., "Biomimetic Catalysis of a Porous Iron-Based Metal-Metalloporphyrin Framework," Inorganic Chemistry, vol. 51, No. 23, pp. 12600-12602 (2012).

Chen et al., "Co-delivery of Doxorubicin and Bcl-2 siRNA by Mesoporous Silica nanoparticiles Enhances the Efficacy of Chemotherapy in Multidrug-Resistant Cancer Cells**," vol. 5, No. 23, pp. 2673-2677 (2009).

Chen et al., "Immuno gold nanocages with tailored optical properties for targeted photothermal destruction of cancer cells," Nano Lett., vol. 7, No. 5, pp. 1318-1322 (11 pages) (Apr. 2007).

Chen et al., "Nanoscintillator-mediated X-ray inducible photodynamic therapy for in vivo cancer treatment," Nano letters, vol. 15, pp. 2249-2256 (2015).

Chen et al., "Synthesis, characterization and osteoconductivity properties of bone fillers based on alendronate-loaded poly(e-caprolactone)/hydroxyapatite microspheres," J Mater Sci. vol. 22 pp. 547-555 (2011).

Chen et al., "Using nanoparticles to enable simultaneous radiation and photodynamic therapies for cancer treatment," Journal of nanoscience and nanotechnology, vol. 6, pp. 1159-1166 (2006).

Cheng et al., "Near Infrared Light-Triggered Drug Generation and Release From Gold Nanoparticle Carriers for Photodynamic Therapy," Small, vol. 10, No. 9, pp. 1799-1804 (13 pages) (Feb. 2014).

Cho et al., "Targeted delivery of siRNA-generating DNA nanocassettes using multifunctional nanoparticles," vol. 9, No. 11, p. 1964-1973 (2013).

Cobley et al., "Gold nanostructures: a class of multifunctional materials for biomedical applications," Chem. Soc. Rev., vol. 40, pp. 44-56 (2011).

Coleman, et al., "Latest research and clinical treatment of advanced-stage epithelial ovarian cancer," Nat Rev Clin Oncol, vol. 10, pp. 211-224 (2013).

Communication of Extended European Search Report corresponding to Application No. 15851357.2 dated Feb. 28, 2018.

Communication of the Extended European Search Report corresponding to European Application No. 14860910.0 dated Jun. 27, 2017.

Cunha et al., "Rationalization of the entrapping of the bioactive molecules into a series of functionalized porous zirconium terephthalate MOFs," J. Mater, Chem., vol. 1, pp. 1101-1108 (2013).

Cutler et al., "Spherical Nucleic Acids," Journal of the American Chemical Society, 134, p. 1376-1391 (2012).

Dai et al. Electron Crystallography Reveals Atomic Structures of Metal-Organic Nanoplates with M12 (μ3-O) 8 (μ3-OH) 8 (μ2-OH) 6 (M= Zr, Hf) Secondary Building Units. Inorganic Chemistry 56, 8128-8134 (2017).

Decision to Grant corresponding to European Patent Application No. 15851357.2 dated Jun. 5, 2020.

Decision to Grant corresponding to Japanese Patent Application No. 2016-528894 dated Aug. 19, 2019.

Decision to Grant corresponding to Japanese Patent Application No. 2017520324 dated Jun. 8, 2020.

Dekrafft et al., "Iodinated Nanoscale Coordination Polymers as Potential Contrast Agents for Computed Tomography**," Angewandte Chemie, vol. 48, pp. 9901-9904 (2009).

Della Rocca et al., "Nanoscale Metal-Organic Frameworks for Biomedical Imaging and Drug Delivery," Acc. Chem. Res., vol. 44, No. 10, pp. 957-968 (2011).

Deng et al., "Irradiation and anti-PD-L1 treatment synergistically promote antitumor immunity in mice," The Journal of clinical investigation, 124, 687 (2014).

Dinca et al., "Hydrogen Storage in Microporous Metal-Organic Frameworks with Exposed Metal Sites," Angew Chem Int Edit 47, p. 6766-6779 (2008).

Dolmans et al., "Photodynamic therapy for cancer." Nature Reviews Cancer, vol. 3, pp. 380-387 (May 2003).

Dougherty, "Photodynamic Therapy," Photochem. and Photobiol., vol. 58, No. 6, pp. 895-900 (Dec. 1993).

Dunn et al., "Cancer immunoediting: from immunosurveillance to tumor escape," Nature immunology, vol. 3, pp. 991-998 (2002). [Abstract—pp. 1-14].

European Decision to Grant corresponding to European Patent Application Serial No. 12810577.2 dated Jan. 7, 2019.

European Intention to Grant for European Patent Application Serial No. 12810577.2 dated Sep. 17, 2018.

Extended European Search Report corresponding to Application No. 12810577.2 dated Feb. 4, 2015.

Extended European Search Report corresponding to European Application No. 19151591.5 dated May 13, 2019.

Fang et al., "The EPR effect: Unique features of tumor blood vessels for drug delivery, factors involved, and limitations and augmentation of the effect," Adv. Drug Deliv. Rev., vol. 63, No. 3, pp. 136-151 (Mar. 2011).

Feng et al., "Metal-Organic Frameworks Based on Previously Unknown Zr8/Hf8 Cubic Clusters," Inorganic Chemistry, vol. 52, No. 21, pp. 12661-12667 (2013).

Feng et al., "Zirconium-Metalloporphyrin PCN-222: Mesoporous Metal-Organic Frameworks with Ultrahigh Stability as Biomimetic Catalysts**," Angew. Chem. Int. Ed., vol. 51, No. 41, pp. 10307-10310 (2012).

Feng et al., "Zirconium-Metalloporphyrin PCN-222: Mesoporous Metal-Organic Frameworks with Ultrahigh Stability as Biomimetic Catalysts**," Angew. Chem., vol. 124, pp. 10453-10456 (2012).

Fire et al., "Potent and specific genetic interference by double-stranded RNA in Caenorhabditis elegans," Nature, vol. 391, p. 806-811 (Feb. 1998).

Foged, "siRNA Delivery with Lipid-based Systems:Promises and Pitfalls," Curr Top Med Chem, vol. 12, p. 97-107 (2012).

Freitas et al., "Biological basis for analysis of lasers' action in infectious processes. Biofilm, Interaction of light with matter,pathophysiological aspects," in Microbial pathogens and strategies for combating them: science, technology and education (A. Méndez-Vilas, Ed.), pp. 306-310 (2013).

Gao et al., "Metal-metalloporphyrin frameworks: a resurging class of functional materials," Chemical Society Reviews, vol. 43, pp. 5841-5866 (2014).

Giger et al. "Gene delivery with bisphosphonate-stabilized calciun1 phosphate nanoparticles," Journal of Controlled Release. vol. 150 pp. 87-93 (2011).

Giraudo et al. "An amino-bisphosphonate targets MMP-9-expressing macrophages and angiogenesis to impair cervical carcinogenesis," The Journal of Clinical Investigation. vol. 114, No. 5 pp. 623-633 (2004).

Giustini et al., "Microstructure and Dynamics of the Water-in-Oil CTAB/n-Pentanol/n-Hexane/Water Microemulsion: A Spectroscopic and Conductivity Study," Journal of Physical Chemistry, vol. 100, No. 8, pp. 3190-3198 (1996).

Graf et al., "A General Method for the Controlled Embedding of Nanoparticles in Silica Colloids," Langmuir, vol. 22, No. 13, pp. 5604-5610 (2006).

Graf et al., "A General Method To Coat Colloidal Particles with Silica," Langmuir, vol. 19, No. 17 pp. 6693-6700 (2003).

(56) References Cited

OTHER PUBLICATIONS

Granados-Oliveros, "Visible light production of superoxide anion with MCarboxyphenylporphyrins (M= H, Fe, Co, Ni, Cu, and Zn) free and anchored on TiO2: EPR characterization," Journal of Molecular Catalysis A: Chemical, vol. 339, 1-2, pp. 79-85 (2011).
Hafeman et al. "Evaluation of liposomal clodronate for treatment of malignant histiocytosis in dogs," Cancer Immunol. Immunother. vol. 59 pp. 441-452 (2010).
Hajri et al., "In vitro and in vivo efficacy of photofrin and pheophorbide a, a bacteriochlorin, in photodynamic therapy of colonic cancer cells," Photochem Photobiol, vol. 75, No. 2, pp. 140-148 (2002).
Hauptvogel et al., "Flexible and Hydrophobic Zn-Based Metal-Organic Framework," Inorg. Chem., vol. 50, pp. 8367-8374 (2011).
He et al., Nanoscale Coordination Polymers Codeliver Chemotherapeutics and siRNAs to Eradicate Tumors of Cisplatin-Resistant Ovarian Cancer, JACS, vol. 138, pp. 6010-6019 (2016).
He et al., "Nanoscale Metal-Organic Frameworks for Real-Time Intracellular pH Sensing in Live Cells," J. Am. Chem. Soc., vol. 136, No. 35, pp. 12253-12256 (2014).
Henderson et al., "Interaction of Photodynamic Therapy and Hyperthermia: Tumor Response and Cell Survival Studies after Treatment of Mice in Vivo," Cancer research, vol. 45, pp. 6071-6077 (1985).
Horcajada et al., "Porous metal-organic-framework nanoscale carriers as a potential platform for drug delivery and imaging," Nat Mater., vol. 9, pp. 172-178 (2010).
Huxford-Phillips et al., "Lipid-coated nanoscale coordination polymers for targeted cisplatin delivery," RSC Advances, vol. 3, No. 34, pp. 14438-14443 (Jan. 2013).
Intention to Grant corresponding to European Application No. 15851357.2 dated Jan. 30, 2020.
Interview Summary corresponding to U.S. Appl. No. 15/034,799 dated Jul. 5, 2018.
Jerjes et al., "Photodynamic therapy vs. photochemical internalization: the surgical margin," Head & Neck Oncology, vol. 3(1):53, pp. 1-2 (2011).
Ji et al., "Size Control of Gold Nanocrystals in Citrate Reduction: The Third Role of Citrate," J. Am. Chem. Soc., vol. 129, pp. 13939-13948 (2007).
Jin et al., "Energy Transfer from Quantum Dots to Metal-Organic Frameworks for Enhanced Light Harvesting," Journal of the American Chemical Society, vol. 135, pp. 955-958 (2013).
Jin et al., "Targeting-Triggered Porphysome Nanostructure Disruption for Activatable Photodynamic Therapy," Advanced Healthcare Materials, vol. 3, No. 8, pp. 1240-1249 (2014).
Kalayda et al., "Synthesis, Structure, and Biological Activity of New Azine-Bridged Dnuclear Platinum(II) Complexes," Eur. J. Inorg. Chem., pp. 4347-4355 (2003).
Kanofsky, "Measurement of singlet-oxygen In Vivo: Progress and Pitfalls," Photochem Photobiol., vol. 87, No. 1, pp. 14-17 (2011).
Kaščáková et al.,"X-ray-induced radiophotodynamic therapy (RPDT) using lanthanide micelles: Beyond depth limitations," Nano Research, vol. 8, No. 7, pp. 2373-2379 (2015).
Kelland, "The resurgence of platinum-based cancer chemotherapy,". Nature Reviews Cancer , 7, 573-584 (2007).
Kitabwalla et al., "RNA interference—a new weapon against HIV and beyond," The New England Journal of Medicine, vol. 347, No. 17, pp. 1364-1367 (Oct. 24, 2002).
Kroemer et al., "Immunogenic Cell Death in Cancer Therapy," Annu. Rev. Immunol., vol. 31, pp. 51-72 (Mar. 2013).
Kudinov et al., "On the Possibility of Combining Radiotherapy and Photodynamic Therapy." CLEO: Science and Innovations. Optical Society of America, pp. 1-2 (2014).
Kumar et al., "In vivo biodistribution and clearance studies using multimodal organically modified silica nanoparticles.," ACS nano, vol. 4, No. 2, pp. 699-708 (19 pages) (Feb. 23, 2010).
Lal et al., "Nanoshell-enabled photothermal cancer therapy: impending clinical impact," Acc. Chem. Res., vol. 41, No. 12, pp. 1842-1851. (Dec. 2008).

Lan et al., "Nanoscale metal-organic frameworks for phototherapy of cancer," Coordination Chemistry Reviews, vol. 379, No. 15, pp. 65-81 (2019).
Lee et al., "Light-Harvesting Metal-Organic Frameworks (MOFs): Efficient Strut-to-Strut Energy Transfer in Bodipy and Porphyrin-Based MOFs," Journal of the American Chemical Society, vol. 133, pp. 15858-15861 (2011).
Lee et al., "Metal-organic framework materials as catalysts," Chem Soc Rev, 38, 1450-1459 (2009).
Lee et al., "Porphyrins & Phthalocyanines web themed issue," Chemical Communications, vol. 48, pp. 5512-5514 (2012).
Leigh, "Comprehensive Coordination Chemistry II From Biology to Nanotechnology," Journal of Organometallic Chemistry. vol. 689, No. 16, pp. 2733-2742 (2004).
Letter regarding decision to grant a Japanese Patent corresponding to Japanese Patent Application No. 2014-520238 dated Oct. 31, 2016.
Levine, D., et al. "Olsalazine-Based Metal-Organic Frameworks as Biocompatible Platforms for H2 Adsorption and Drug Delivery." Journal of the American Chemical Society 138, 10143-10150 (2016).
Li et al., "Design and synthesis of an exceptionally stable and highly porous metal-organic framework," Nature 402, p. 276-279 (1999).
Liu et al., "Coercing bisphosphonates to kill cancer cells with nanoscale coordination polymerst," Chem. Commun. vol. 48 pp. 2668-2670 (2012).
Liu et al., "Phosphorescent Nanoscale Coordination Polymers as Contrast Agents for Optical Imaging**," Angewandte Chemie International Edition, vol. 50, pp. 3696-3700 (2011).
Liu et al., "Self-assembled nanoscale coordination polymers with trigger release properties for effective anticancer therapy," Author manuscript, Nature Communications, pp. 1-25 (2014).
Loo et al., "Immunotargeted Nanoshells for Integrated Cancer Imaging and Therapy," Nano letters, vol. 5, No. 4, pp. 709-711 (2005).
Lovell et al., "Porphysome nanovesicles generated by porphyrin bilayers for use as multimodal biophotonic contrast agents," Nat. Mater., vol. 10, pp. 324-332 (2011).
Lowery et al., "Cost-effectiveness of early palliative care intervention in recurrent platinum-resistant ovarian cancer," Gynecol Oncol 2013, 130, p. 426-430 (2013).
Lu et al., "A Chlorin-Based Nanoscale Metal-Organic Framework for Photodynamic Therapy of Colon Cancer," J. Am. Chem. Soc., vol. 137, No. 24 (11 pages), pp. 7600-7603 (2015).
Lu et al., "Low Dose X-ray Radiotherapy-Radiodynamic Therapy via Nanoscale Metal-organic Frameworks Enhances Checkpoint Blockade Immunotherapy" Nature Biomedical Engineering (Mar. 28, 2018) DOI: 10.1038/S41551-018-0203-4.
Lu et al.. "Nanoscale Metal-Organic Framework for Highly Effective Photodynamic Therapy of Resistant Head and Neck Cancer," J. Am. Chem. Soc., vol. 136, pp. 16712-16715 (Nov. 19, 2014).
Mack et al., "The effects of terbium on the cellular accumulation of cisplatin in MDA-MB-231 human breast tumor cells," Cancer Chemotherapy and Pharmacology. vol. 39, pp. 217-222 (1997).
Maeda et al., "Mechanism of tumor-targeted delivery of macromolecular drugs, including the EPR effect in solid tumor and clinical overview of the prototype polymeric drug SMANCS," J. Controlled Release, vol. 74, pp. 47-61 (2001).
Maggiorella et al., "Nanoscale radiotherapy with hafnium oxide nanoparticles," Future oncology 8, 1167-1181 (2012).
Manna et al., "Metal-Organic Framework Nodes Support Single-Site Magnesium-Alkyl Catalysts for Hydroboration and Hydroamination Reactions," Journal of the American Chemical Society, vol. 138, pp. 7488-7491 (2016).
Matsumura et al., "A New Concept for Macromolecular Therapeutics in Cancer Chemotherapy: Mechanism of Tumoritropic Accumulation of Proteins and the Antitumor Agent Smancs," Cancer Research, vol. 46, pp. 6387-6392 (1986).
Mellman et al., "Cancer immunotherapy comes of age," Nature, vol. 480, pp. 480-489 (2011).
Meng, H.; Liong, M.; Xia, T.; Li, Z.; Ji, Z.; Zink, J. I.; Nel, A. E. ACS nano 4, p. 4539-4550 (2010).

(56) References Cited

OTHER PUBLICATIONS

Merkel et al., "Radiationless decay of singlet molecular oxygen in solution. Experimental and theoretical study of electronic-to-vibrational energy transfer," J. Am. Chem. Soc., vol. 94, No. 21, pp. 7244-7253 (1972).
Min, Y., et al. Antigen-capturing nanoparticles improve the abscopal effect and cancer immunotherapy. Nature nanotechnology 12, 877 (2017).
Moan et al., "The photodegradation of porphyrins in cells can be used to estimate the lifetime of singlet oxygen," Photochem Photobiol., vol. 53, No. 4, pp. 549-553 (1991).
Morris et al., "Nucleic Acid-Metal Organic Framework (MOF) Nanoparticle Conjugates," J. Am. Chem. Soc., vol. 136, No. 20, pp. 7261-7264 (2014).
Mukhopadhyay et al., "Conjugated Platinum (IV)—Peptide Complexes for Targeting Angiogenic Tumor Vasculature," Bioconjugate Chemistry, vol. 19, No. 1, pp. 39-49 (2008).
Notice of allowance and Fee(s) Due, Examiner-Initiated Interview Summary, and Notice of Allowability Corresponding to U.S. Appl. No. 14/131,575 dated Feb. 27, 2017.
Notice of Allowance and Interview Summary corresponding to U.S. Appl. No. 15/034,799 dated Jun. 14, 2019.
Notice of Allowance corresponding to Chinese Patent Application Serial No. 201580068173X dated Aug. 12, 2019.
Notice of Allowance corresponding to U.S. Appl. No. 15/613,847 dated Nov. 6, 2019.
Notice of Allowance corresponding to U.S. Appl. No. 15/518,665 dated Sep. 26, 2018.
Notice of Allowance corresponding to U.S. Appl. No. 15/884,036 dated Apr. 10, 2019.
Notice of Allowance corresponding to U.S. Appl. No. 16/235,752 dated May 6, 2020.
Notice of Allowance and Interview Summary corresponding to U.S. Appl. No. 15/884,036 dated Jun. 24, 2020.
Notification Concerning Transmittal of Copy of International Preliminary Report on Patentability (Chapter I of the Patent CooperationTreaty) corresponding to International Patent Application No. PCT/US2012/045954 dated Jan. 23, 2014.
Notification Concerning Transmittal of Copy of International Preliminary Report on Patentability (Chapter I of the Patent CooperationTreaty) corresponding to International Patent Application No. PCT/US2014/064388 dated May 19, 2016.
Notification Concerning Transmittal of Copy of International Preliminary Report on Patentability and the Written Opinion of the International Searching Authority corresponding to International Application No. PCT/US2015/055574 dated Apr. 27, 2017.
Notification Concerning Transmittal of Copy of International Preliminary Report on Patentability (Chapter I of the Patent CooperationTreaty) corresponding to International Patent Application No. PCT/US2009/034867 dated Sep. 2, 2010.
Notification of Transmittal of the International Search Authority and the Written Opinion of the International Searching Authority, or the Declaration corresponding to PCT/US2015/055574 dated Feb. 18, 2016.
Notification of Transmittal of the International Search Report and the Written Opinion of the International Searching Authority, or the Declaration corresponding to International Application No. PCT/US2012/045954 dated Jan. 28, 2013.
Notification of Transmittal of the International Search Report and the Written Opinion of the International Searching Authority, or the Declaration corresponding to International Application No. PCT/US14/64388 dated Feb. 9, 2015.
Notification of Transmittal of the International Search Report and the Written Opinion of the International Searching Authority, or the Declaration corresponding to International Application No. PCT/US2009/034867 dated Feb. 3, 2010.
Nyman: "Polyoxometalates and Other Metal-Oxo Clusters in Nature," In: Encyclopedia of Geochemistry, Springer International Publishing, pp. 1-5 (2016).
Office Action (Restriction Requirement) corresponding to U.S. Appl. No. 14/131,575 dated Nov. 20, 2015.
Office Action (Restriction Requirement) corresponding to U.S. Appl. No. 15/613,847 dated Jun. 18, 2018.
Office Action (Restriction Requirement) corresponding to U.S. Appl. No. 15/518,665 dated Dec. 12, 2017.
Office Action (Restriction Requirement) corresponding to U.S. Appl. No. 15/884,036 dated Nov. 6, 2018.
Office Action (Restriction Requirement) corresponding to U.S. Appl. No. 16/235,752 dated Jul. 10, 2019.
Office Action corresponding to Chinese Patent Application No. 2014800722580 dated Jun. 27, 2018.
Office Action corresponding to Chinese Patent Application No. 2014800722580 dated Mar. 20, 2019.
Office Action corresponding to Chinese Patent Application No. 2014800722580 dated Nov. 11, 2019.
Office Action corresponding to Chinese Patent Application Serial No. 201580068173X dated Oct. 31, 2018.
Office Action corresponding to Chinese Patent Application Serial No. 201580068173X dated Apr. 10, 2019.
Office Action corresponding to European Application No. 15851357.2 dated Jun. 7, 2019.
Office Action corresponding to European Patent Application Serial No. 12810577.2 dated Jan. 5, 2017.
Office Action corresponding to European Patent Application Serial No. 14860910.0 dated Jan. 29, 2019.
Office Action corresponding to Japanese Application No. 2017-520324 dated Jul. 9, 2019.
Office Action corresponding to Japanese Patent Application No. 2017520324 dated Feb. 12, 2020.
Office Action corresponding to Japanese Patent Application No. 2014-520238 dated Mar. 14, 2016.
Office Action corresponding to Japanese Patent Application No. 2016-528894 dated Jul. 17, 2018.
Office Action corresponding to Japanese Patent Application No. 2016-528894 dated Feb. 4, 2019.
Office Action corresponding to U.S. Appl. No. 14/131,575 dated Aug. 12, 2016.
Office Action corresponding to U.S. Appl. No. 14/131,575 dated Dec. 16, 2016.
Office Action corresponding to U.S. Appl. No. 15/034,799 dated Sep. 21, 2017.
Office Action corresponding to U.S. Appl. No. 15/034,799 dated Mar. 22, 2018.
Office Action corresponding to U.S. Appl. No. 15/034,799 dated Sep. 21, 2018.
Office Action corresponding to U.S. Appl. No. 15/613,847 dated Dec. 10, 2018.
Office Action corresponding to U.S. Appl. No. 15/034,799 dated Mar. 20, 2019.
Office Action corresponding to U.S. Appl. No. 15/613,847 dated Jun. 5, 2019.
Office Action corresponding to U.S. Appl. No. 15/518,665 dated May 16, 2018.
Office Action corresponding to U.S. Appl. No. 15/884,036 dated Jan. 30, 2019.
Office Action corresponding to U.S. Appl. No. 16/235,752 dated Oct. 24, 2019.
Office Action corresponding to U.S. Appl. No. 15/884,036 dated Nov. 21, 2019.
Office Action corresponding to U.S. Appl. No. 16/235,752 dated Feb. 20, 2020.
Official Action (Restriction Requirement) corresponding to U.S. Appl. No. 12/918,748 dated Oct. 18, 2012.
Official Action corresponding to U.S. Appl. No. 12/918,748 dated Mar. 28, 2013.
Notice of Allowance corresponding to Chinese Patent Application No. 201480072258.0 dated Apr. 20, 2020.
Pass, "Photodynamic Therapy in Oncology: Mechanisms and Clinical Use," Journal of the National Cancer Institute, vol. 85, No. 6, pp. 443-456 (1993).

(56) References Cited

OTHER PUBLICATIONS

Pinna et al., "Non-Aqueous Synthesis of High-Purity Metal Oxide Nanopowders Using an Ether Elimination Process," Advanced Materials, vol. 16 (23-24), pp. 2196-2200 (2004).
PubChem Open Chemistry Database, Platinum (2+), date unavailable.
Retif et al. "Nanoparticles for radiation therapy enhancement: the key parameters," Theranostics, vol. 5, pp. 1030-1045 (2015).
Rieter et al., "Nanoscale Coordination Polymers for Platinum-Based Anticancer Drug Delivery," Journal of the American Chemical Society. vol. 130, No. 35, pp. 11584-11585 (2008).
Rieter et al., "Nanoscale Metal-Organic Frameworks as Potential Multimodal Contrast Enhancing Agents," J Am Chem Soc., vol. 128, No. 28, pp. 9024-9025 (2006).
Roberts, et al., "Identification of genes associated with platinum drug sensitivity and resistance in human ovarian cancer cells," Brit J Cancer , vol. 92, pp. 1149-1158 (2005).
Rodgers et al., "Lifetime of 02(IΔ) in Liquid Water As Determined by Time-Resolved Infrared Luminescence Measurements," J. Am. Chem. Soc., vol. 104, pp. 5541-5543 (1982).
Rosi, et al., "Rod Packings and Metal-Organic Frameworks Constructed from Rod-Shaped Sedcondary Building Units," J Am Chem Soc, vol. 127, pp. 1504-1518 (2005).
Salzano et al. "Self-assembly nanoparticles for the delivery of bisphosphonates into tumors," International Journal of Pharmaceutics, vol. 403, No. 1-2, pp. 292-297 (2011).
Samia et al., "Semiconductor Quantum Dots for Photodynamic Therapy," J. Am. Chem. Soc., vol. 125, No. 51, pp. 15736-15737 (2003).
Scandola et al., "Photophysical properties of metal-mediated assemblies of porphyrins," Coord. Chem. Rev., vol. 250, pp. 1471-1496 (2006).
Schaate et al., "Modulated synthesis of Zr-Based metal-organic frameworks: from nano to single crystals," Chem-Eur J, 17, p. 6643-6651 (2011).
Schöder, "Head and Neck Cancer," Nuclear Oncology; Pathophysiology and Clinical Applications, Sprinter Science+Businessd Media New York, pp. 269-295 (2013).
Senge et al., "Temoporfin (Foscan®, 5,10,15,20-Tetra(m-Hydroxyphenyl)chlorin)—A Second-Generation Photosensitizer," Photochem. Photobiol., vol. 87, No. 6, pp. 1240-1296 (Sep. 2011).
Shahzad et al., "Novel strategies for reversing platinum resistance," Drug Resist Updates 12, p. 148-152 (2009).
Sheats, "History of Organometallic Polymers," Journal of Macromolecular Science: Part A—Chemistry, vol. 15, No. 6, pp. 1173-1199 (1981).
Shi et al., "In-vitro osteogenesis of synovium stem cells induced by controlled release of bisphosphate additives from microspherical meso porous silica composite," Biomaterials. vol. 30, No. 23-24, pp. 3996-4005 (2009).
Shmeeda et al. "Delivery of zoledronic acid encapsulated in folate-targeted liposome results in potent in vitro cytotoxic activity on tumor cells," Journal of Controlled Release 146 pp. 76-83 (2010).
Snyder et al., "Subcellular, Time-Resolved Studies of Singlet Oxygen in Single Cells," J. Am. Chem. Soc., vol. 127, pp. 14558-14559 (2005).
Spokoyny et al., "Infinite coordination polymer nano- and microparticle structures," Chem. Soc. Rev., vol. 38, pp. 1218-1227 (2009).
St-Denis et al., "Diffusivity of oxygen in water," Can J Chem Eng., vol. 49, No. 6, pp. 885 (Dec. 1971).
Taylor-Pashow et al., "Post-synthetic modification of iron-carboxylate nanoscale metal-organic frameworks for imaging and drug delivery," Author Manuscript, J Am Chem Soc., pp. 1-10 (2009).
Taylor-Pashow et al., "Postsynthetic Modifications of Iron-Carboxylate Nanoscale Metal-Organic Frameworks for Imaging and Drug Delivery," J Am Chem Soc., vol. 131, No. 40, pp. 14261-14263 (2009).
Tranchemontagne et al., "Secondary building units, nets and bonding in the chemistry of metal-organic frameworks," Chem. Soc. Rev., vol. 38, pp. 1257-1283 (2009).
Uemura et al., "Prussian Blue Nanoparticles Protected by Poly(vinylpyrrolidone)," Journal of the American Chemical Society, vol. 125, No. 26, pp. 7814-7815 (2003).
Vaucher et al., "Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions," Nano Letters. vol. 2, No. 3, pp. 225-229 (2002).
Vaucher et al., "Synthesis of Prussian Blue Nanoparticles and Nanocrystal Superlattices in Reverse Microemulsions," Angew. Chem. Int. Ed. vol. 39, No. 10, pp. 1793-1796 (2000).
Vaughan, et al., "Rethinking ovarian cancer: recommendations for improving outcomes," Nat Rev Cancer , 11, 719-725, pp. 1-19 (2011).
Vesper et al., "Photodynamic therapy (PDT): An evolving therapeutic technique in head and neck cancer treatment," Head & Neck Cancer: Current Perspectives, Advances, and Challenges, Springer Netherlands, vol. 9789400758278, pp. 649-676 (2013).
Wang et al., "Comparison Study of Gold Nanohexapods, Nanorods, and Nanocages for Photothermal Cancer Treatment," ACS Nano, vol. 7, No. 3, pp. 2068-2077 (Feb. 2013).
Wang et al., "Elucidating Molecular Iridium Water Oxidation Catalysts Using Metal-Organic Frameworks: A Comprehensive Structural, Catalytic, Spectroscopic, and Kinetic Study," Journal of the American Chemical Society, vol. 134, pp. 19895-19908 (2012).
Wang et al., "Nanoparticle delivery of cancer drugs," Annual Review of Medicine, vol. 63, pp. 185-198 (2012).
Wang et al., "One-Step Synthesis of β meso-Unsubstituted Dipyrromethane," Synlett, pp. 1267-1268 (1995).
Wang et al., "Postsynthetic modification of metal-organic frameworks," Chem Soc Rev 38, p. 1315-1329 (2009).
Wang et al., "Pt Nanoparticles@Photoactive Metal-Organic Frameworks: Efficient Hydrogen Evolution via Synergistic Photoexcitation and Electron Injection," Journal of the American Chemical Society, vol. 134, pp. 7211-7214 (2012).
Wang et al., "Synergistic Assembly of Heavy Metal Clusters and Luminescent Organic Bridging Ligands in Metal-Organic Frameworks for Highly Efficient X-ray Scintillation," Journal of the American Chemical Society, vol. 136, pp. 6171-6174 (2014).
White et al., "Photooxidation of Diglycine in Confined Media. Application of the Microreactor Model for Spin-Correlated Radical Pairs in Reverse Micelles and Water-in-Oil Microemulsions," Langmuir, vol. 21, No. 7, pp. 2721-2727 (2005).
Wong et al., "Fluorescence Probing of Inverted Micelles. The State of Solublized Water Clusters in Alkane/Diisooctyl Sulfosuccinate (Aerosol OT) Solution," Journal of the American Chemical Society, vol. 98, No. 9, pp. 2391-2397 (1976).
Xiong et al., "Traceable multifunctional micellar nanocarriers for cancer-targeted co-delivery of MDR-1 siRNA and doxorubicin," ACS nano, vol. 5, No. 6, p. 5202-5213 (2011).
Xu et al., "Nanoscale Metal-Organic Frameworks for Ratiometric Oxygen Sensing in Live Cells," Journal of the American Chemical Society, 138, 2158-2161 (2016).
Xu et al., "Reverse micellar synthesis of CdS nanoparticles and self-assembly into a superlattice," Materials Letters, vol. 58, pp. 2623-2626 (2004).
Yamada et al., "Synthesis and Isolation of Cobalt Hexacyanoferrate/ Chromate Metal Coordination Nanopolymers Stabilized by Alkylamino Ligand with Metal Elemental Control," Journal of the American Chemical Society, vol. 126, pp. 9482-9483 (2004).
Yellepeddi et al., "Comparative evaluation of small-molecule chemosensitizers in reversal of cisplatin resistance in ovarian cancer cell," Anticancer Res 32, p. 3651-3658 (2012).
Yu et al., "Immobilization of polymer-stabilized metal colloids by a modified coordination capture: preparation of supported metal colloids with singular catalytic properties," Journal of Molecular Catalysis A: Chemical, vol. 142, pp. 201-211 (1999).
Zhang et al., "Antibody-linked spherical nucleic acids for cellular targeting," Journal of the American Chemical Society, 134, 16488-16491, pp. 1-11 (2012).

(56) References Cited

OTHER PUBLICATIONS

Zhang et al., "Biomimicry in metal-organic material," Coordination Chemistry Reviews, vol. 293-294, pp. 327-356 (2015).
Zhang et al., "Three-Dimensional Lanthanoid-Containing Coordination Frameworks: Structure, Magnetic and Fluorescent Properties," European Journal of Inorganic Chemistry, pp. 766-772 (2005).
Zou, et al., "Enhanced apoptosis of ovarian cancer cells via nanocarrier-mediated codelivery of siRNA and doxorubicin," Int J Nanomed, 7, pp. 3823-3835 (2012).
Duan et al. "Immunostimulatory nanomedicines synergize with checkpoint blockade immunotherapy to eradicate colorectal tumors," nature communications, 10:1899, pp. 1-15 (2019).
He et al. "Self-assembled Nanoscale Coordination Polymers Carrying siRNAs and Cisplatin for Effective Treatment of Resistant Ovarian Cancer," Author Manuscript, available in PMC 2016, pp. 1-25, published in final edited form as Biomaterials, vol. 36, pp. 124-133 (2015).
Office Action corresponding to Chinese Patent Application No. 201780031000X dated Jun. 10, 2020.
Office Action corresponding to Japanese Patent Application No. 2019-167976 dated Jul. 27, 2020.
Wang et al. "Metal-Organic Frameworks as A Tunable Platform for Designing Functional Molecular Materials," Author Manuscript, 32 pages, published in final edited form as: J. Am. Chem. Soc., vol. 135, No. 36, p. 13222-13234 (2013).
Wang et al., "Synergistic Assembly of Heavy Metal Clusters and Luminescent Organic Bridging Ligands in Metal-Organic Frameworks for Highly Efficient X-ray Scintillation," [Supporting information for Journal of the American Chemical Society, vol. 136, pp. 6171-6174 (2014)] 13 pages.
Craig, B. D.; Anderson, D. B., eds. (1995) Handbook of Corrosion Data, Materials Park, Ohio: ASM International, pp. 76 and 77.
Ercole et al. "Cholesterol Modified Self-Assemblies and Their Application to Nanomedicine," Biomacromolecules, vol. 16, pp. 1886-1914 (2015).
Neufeld et al. (2020) High-Z metal-organic frameworks for X-ray radiation-based cancer theranostics, Accepted Manuscript, 11 pages [Published in final edited form as: Chem. Eur. J., vol. 27, Iss. 10, pp. 3229-3237].

Notices of opposition corresponding to European Patent Application No. 15851357.2—1110 dated Apr. 20, 2021.
Office Action corresponding to European Patent Application Serial No. 14860910.0—1109 dated Jan. 27, 2021.
Office Action corresponding to Japanese Patent Application No. 2018-561060 dated Apr. 5, 2021.
Office Action (Restriction Requirement) corresponding to U.S. Appl. No. 16/800,855 dated May 7, 2021.
Office Action corresponding to Chinese Patent Application No. 201780031000X dated Apr. 2, 2021.
Office Action corresponding to U.S. Appl. No. 16/577,818 dated Aug. 5, 2021.
Putaj et al. "Polyoxometalates containing late transition and noble metal atoms," Coordination Chemistry Reviews, vol. 255, Iss. 15-16, pp. 1642-1685 (2011).
Raouane et al. "Lipid Conjugated Oligonucleotides: A Useful Strategy for Delivery," Bioconjugate Chemistry, vol. 23, pp. 1021-1104 (2012).
Wang et al. "Metal-Organic Frameworks as A Tunable Platform for Designing Functional Molecular Materials," Author Manuscript, 32 pages, published in final edited form as: J. Am. Chem. Soc., vol. 135, No. 36, pp. 13222-13234 (2013b).
Wang et al., "Synergistic Assembly of Heavy Metal Clusters and Luminescent Organic Bridging Ligands in Metal-Organic Frameworks for Highly Efficient X-ray Scintillation," [Supporting information for Journal of the American Chemical Society, vol. 136, pp. 6171-6174 (2014c)] 13 pages.
Yoon et al. "Efficient photosensitization by a chlorin-polyoxometalate supramolecular complex," Inorganic Chemistry, vol. 53, No. 1, pp. 3-5 (2014).
Office Action corresponding to European Application No. 17800330.7-1112 dated Sep. 9, 2021.
Interview Summary corresponding to U.S. Appl. No. 16/800,855 dated Oct. 27, 2021.
Office Action corresponding to European Application Serial No. 19151591.5 dated Oct. 27, 2021.
Office Action corresponding to Japanese Patent Application No. 2018-561060 dated Nov. 8, 2021.

* cited by examiner

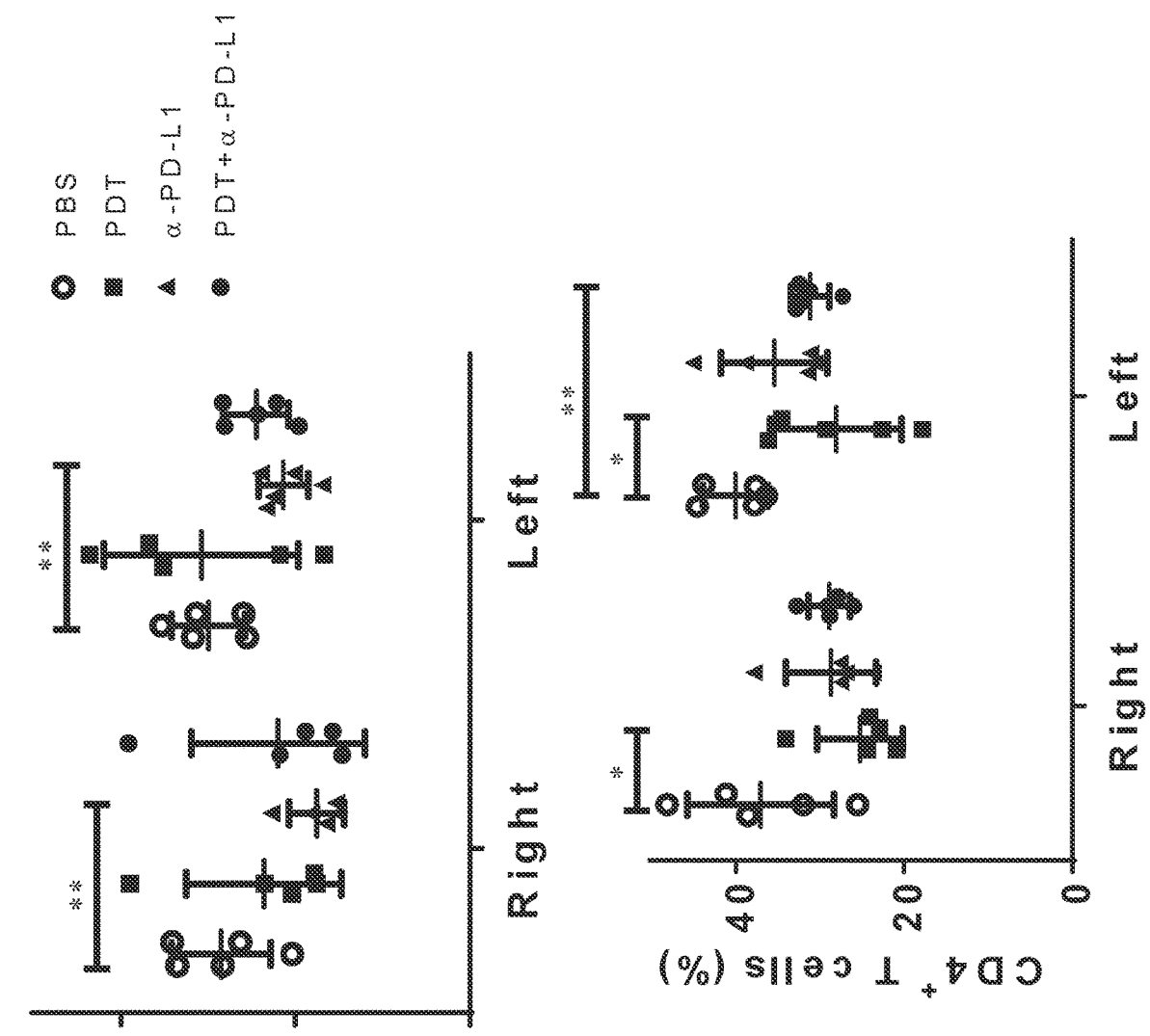

NANOPARTICLES FOR CHEMOTHERAPY, TARGETED THERAPY, PHOTODYNAMIC THERAPY, IMMUNOTHERAPY, AND ANY COMBINATION THEREOF

RELATED APPLICATIONS

The presently disclosed subject matter claims the benefit of U.S. Provisional Patent Application Ser. No. 62/339,594, filed May 20, 2016, the disclosure of which is incorporated herein by reference in its entirety.

GOVERNMENT INTEREST

This invention was made with government support under Grant No. U01 CA198989 awarded by the National Institutes of Health. The government has certain rights in the invention.

TECHNICAL FIELD

The presently disclosed subject matter provides prodrugs (e.g., prodrugs of chemotherapeutic agents) comprising drug moieties bound to lipid moieties via disulfide-containing linkers. The presently disclosed subject matter also provides nanoparticles comprising the prodrugs. The nanoparticles can comprise, for example, a lipid coating layer containing the prodrug and a nanoscale coordination polymer (NCP) nanoparticle core, which can itself optionally comprise a chemotherapeutic agent analogue or prodrug or a combination of two chemotherapeutic agent analogues or prodrugs. The nanoparticles can be further combined with photosensitizers for photodynamic therapy (PDT), targeting agents, and/or immunotherapy agents, such as immunosuppression inhibitors. Thus, the nanoparticle-based compositions of the presently disclosed subject matter can provide synergistic anti-cancer effects by combining multiple treatment modalities in a variety of cancers.

ABBREVIATIONS

° C.=degrees Celsius
%=percentage
μl=microliter
μM=micromolar
Chol=cholesterol
cm=centimeter
CPT=camptothecin
CRT=calriticulin
DCM=dichloromethane
DHA=dihydroartemisinin
DLS=dynamic light scattering
DMF=dimethylformamide
DOPA=dioleoyl-sn-glycero-3-phosphate
DOPC=1,2-dioleoyl-sn-glycero-3-phosphate sodium salt
DSPE-PEG$_{2k}$=1,2-distearoyl-sn-glycero-3-phosphoethanolamine-N-[amino(polyethylene glycol)$_{2000}$]
ET=etoposide
EtOH=ethanol
g=gram
h=hour
IC$_{50}$=fifty percent inhibitory concentration
ICP-MS=inductively coupled plasma-mass spectrometry
kg=kilogram
M=molar
mg=milligram
min=minute
mL=milliliter
mM=millimolar
mmol=millimole
MOF=metal-organic framework
MTX=mitoxantrone
MW=molecular weight
NCP=nanoscale coordination polymer
NIR=near infrared
nm=nanometer
nmol=nanomoles
NMR=nuclear magnetic resonance
OA=oleic acid
OX=oxaliplatin
PBS=phosphate buffered saline
PDI=polydispersity index
PD-L1=programmed death-ligand 1
PDT=photodynamic therapy
PEG=polyethylene glycol
pmol=picomoles
PS=photosensitizer
Pt=platinum
PTX=paclitaxel
PVP=polyvinylpyrrolidone
RES=reticuloendothelial system
rpm=revolutions-per-minute
SBU=secondary building units
sec=seconds
SOSG=singlet oxygen sensor green
TEM=transmission electron microscopy
TFA=trifluoroacetic acid
THF=tetrahydrofuran
Zn=zinc

BACKGROUND

Photodynamic therapy (PDT), where a systemic or locally administrated photosensitizer (PS) is excited by local light irradiation to produce reactive oxygen species (ROS), can selectively kill tumor cells while preserving adjacent normal tissue. PDT does not incur cross resistance with radiotherapy or chemotherapy, and therefore, can be useful in the treatment of cancer patients who have failed radiotherapy and chemotherapy. PDT provokes a strong acute inflammatory reaction observed as localized edema at the targeted site. The inflammation elicited by PDT is a tumor antigen nonspecific process orchestrated by the innate immune system. PDT is particularly effective in rapidly generating an abundance of alarm/danger signals, such as damage-associated molecular patterns (DAMPs), at the treated site that can be detected by the innate immunity alert elements. PDT can enhance anti-tumor immunity via stimulating dendritic cells by dead and dying tumor cells, leading to the recruitment and activation of CD8+ cytotoxic T cells (CTLs) followed by the formation of immune memory cells and resistance to subsequent tumor growth. When combined with other immunotherapeutic agents, not only the effective eradication of a primary tumor, but also suppression/eradication of a distant metastatic tumor or tumors can be accomplished.

Some small molecule chemotherapeutics, including oxaliplatin, paclitaxel, daunorubicin, docetaxel, doxorubicin, cyclophosphamide, dihydroartemisinin, and mitoxantrone, can efficiently cause immunogenic cell death. Some chemotherapeutics are known to be immune-stimulatory. However, many small molecule chemotherapeutics are highly hydrophobic, making delivery of the anticancer agents to tumors difficult.

Accordingly, there is an ongoing need to provide prodrugs and/or other drug delivery platforms for chemotherapeutics to improve their delivery (e.g., their targeted delivery). There is also a need for prodrug and/or other drug delivery platforms that can combine chemotherapeutics, such as those chemotherapeutics with known immunogenic effects, with other treatment modalities, such as PDT modalities and/or immunotherapy agents (e.g., immunosuppression therapeutics), to provide enhanced anticancer therapy.

SUMMARY

In some embodiments, the presently disclosed subject matter provides a prodrug comprising: (a) a monovalent drug moiety; (b) a monovalent lipid moiety; and (c) a bivalent linker moiety comprising a biodegradable bond, wherein the monovalent drug moiety and the monovalent lipid moiety are linked through the linker. Optionally, the monovalent drug moiety is a monovalent derivative of an anticancer drug compound. Further optionally, the monovalent drug moiety is a monovalent derivative of a drug compound selected from the group comprising Etoposide (ET), Paclitaxel (PTX), OTS964, NLG919, OTS167, OTSC41, dihydroartemisin, Camptothecin (CPT), Doxorubicin, Docetaxel, Vincristine, Mitoxantrone, Artesunate, and Capecitabine. Optionally, the biodegradable bond is a disulfide bond.

In some embodiments, the monovalent lipid moiety is a monovalent derivative of cholesterol, oleic acid, lyso-lipid or phosphocholine. In some embodiments, the monovalent lipid moiety is a cholesterol derivative and the monovalent lipid moiety and bivalent linker moiety together have the structure:

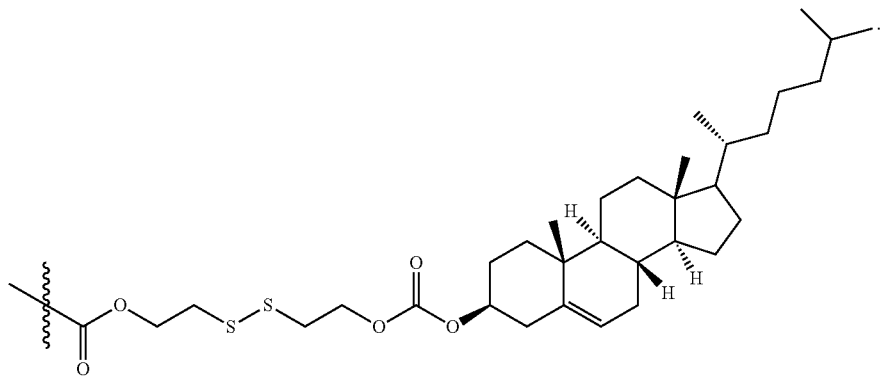 [SMILES: *C(=O)OCCSSCCOC(=O)O[C@H]1CC[C@@]2(C)C(=CC[C@@H]3[C@@H]2CC[C@]2(C)C([C@H](C)CCCC(C)C)CC[C@@H]32)C1]

In some embodiments, the monovalent lipid moiety is an oleic acid derivative and the monovalent lipid moiety and bivalent linker moiety together have the structure:

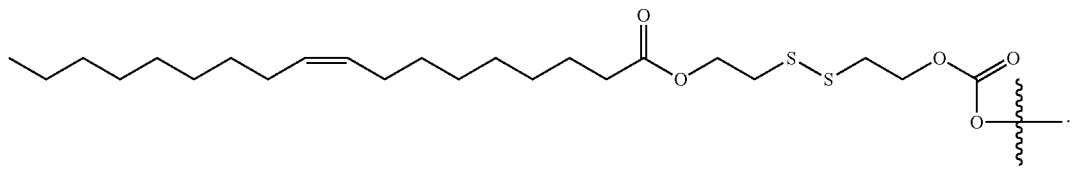 [SMILES: *OC(=O)OCCSSCCOC(=O)CCCCCCC/C=C\CCCCCCCC]

In some embodiments, the monovalent lipid moiety is a lyso-lipid derivative and the monovalent lipid moiety and bivalent linker moiety together have the structure:

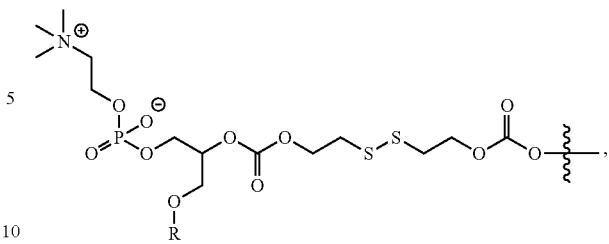

where R is selected from oleyl, stearyl or palmitoleyl. In some embodiments, the monovalent lipid moiety is a phosphocholine derivative and the monovalent lipid moiety and bivalent linker together have the structure:

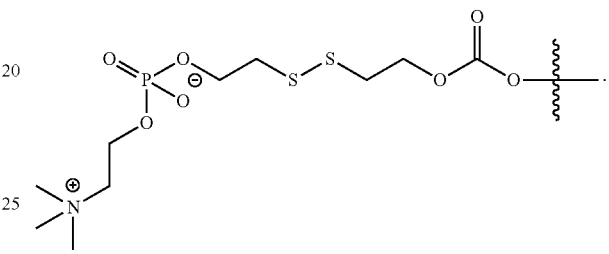

In some embodiments, the presently disclosed subject matter provides a method for treating a disease in a patient in need of treatment wherein the method comprises the steps of: administering to a patient a prodrug comprising a monovalent drug moiety, a monovalent lipid moiety, and a bivalent linker moiety comprising a biodegradable bond, optionally wherein administering the prodrug to the patient comprises administering a nanoparticle comprising the prodrug to the patient; and administering to the patient an immunotherapy agent. In some embodiments, the prodrug is administered by administering a nanoparticle comprising the prodrug and wherein the nanoparticle comprises a nanoscale coordination polymer.

In some embodiments, the method further comprises administering to the patient a photosensitizer and/or a scintillator, and irradiating at least a portion of the patient with light and/or X-rays. In some embodiments, the photosensitizer is a nanoparticle photosensitizer. In some embodiments, the nanoparticle photosensitizer is selected from the group comprising upconversion nanoparticles, optionally wherein the upconversion nanoparticles comprise $NaYF_4$, further optionally wherein the $NaYF_4$ nanoparticles are doped at a ratio of Y:Yb:Er=78%:20%:2% and combined with chlorin e6 or MC540; a photosensitizer embedded in a silica-based nanoparticle, optionally 2-devinyl-2-(1-hexyloxyethyl) pyropheophorbide (HPPH)-loaded silica nanoparticles; polymer micelle-loaded photosensitizers, optionally Zn(II)phthalocyanine-loaded in DSPE-PEG5k polymer micelles; a liposome-based photosensitizer delivery system, optionally a 5,10,15,20-tetrakis(m-hydroxyphenyl)chlorin-encapsulated liposome or a 5-aminolevulinic acid (ALA)-encapsulated liposome; a human serum albumin (HSA)-based photosensitizer delivery system, optionally HSA-pheophorbide a conjugate particles; a dendrimer-based photosensitizer delivery system, optionally a PEG-attached poly(propyleneimine) or poly(amido amine) loaded with rose bengal and PpIX; a porphyrin-, chlorin- or bacteriochlorin-conjugated phospholipid-based bilayer delivery system; a porphyrin-lipid conjugate (pyrolipid) self-assembly nanovesicle (Porphysome); a nanoscale coordination polymer (NCP) particle comprising a lipid coating layer comprising pyrolipid (NCP@Pyrolipid); or a nanoparticle comprising a zinc-pyrophosphate core and a lipid coating layer comprising pyrolipid (Zn@Pyrolipid). In some embodiments, irradiating with light comprises irradiating with infrared light.

In some embodiments, the disease is cancer. In some embodiments, the disease is selected from the group comprising a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, lung cancer, stomach cancer, anogenital cancer, kidney cancer, bladder cancer, colon cancer, prostate cancer, central nervous system cancer, retinal cancer, blood cancer, neuroblastoma, multiple myeloma, lymphoid cancer, and pancreatic cancer.

In some embodiments, the method further comprises administering to the patient an additional treatment. In some embodiments, the additional treatment is a cancer treatment, wherein said cancer treatment is selected from the group comprising surgery, radiotherapy, chemotherapy, toxin therapy, immunotherapy, cryotherapy, and gene therapy. In some embodiments, the chemotherapy comprises administering a drug selected from the group comprising oxaliplatin, doxorubicin, daunorubicin, docetaxel, mitoxanthrone, paclitaxel, digitoxin, digoxin, and septacidin. In some embodiments, the chemotherapy comprises administering a drug formulation selected from the group comprising a polymeric micelle formulation, a liposomal formulation, a dendrimer formulation, a polymer-based nanoparticle formulation, a silica-based nanoparticle formulation, a nanoscale coordination polymer formulation, and an inorganic nanoparticle formulation.

In some embodiments, the immunotherapy agent is selected from the group comprising an anti-CD52 antibody, an anti-CD20 antibody, anti-CD47 antibody, an anti-GD2 antibody, polysaccharide K, and a cytokine. In some embodiments, the immunotherapy agent is selected from the group comprising Alemtuzumab, Ofatumumab, Rituximab, Zevalin, Adcetris, Kadcyla, and Ontak. In some embodiments, the immunotherapy agent is selected from the group comprising a PD-1 inhibitor, a PD-L1 inhibitor, a CTLA-4 inhibitor, an IDO inhibitor, a CCR7 inhibitor, a OX40 inhibitor, a TIM3 inhibitor, and a LAG3 inhibitor.

In some embodiments, the cytokine is selected from the group comprising an interferon and an interleukin. In some embodiments, the cytokine is selected from the group comprising IFN-α, IFN-γ, IL-2, IL-12 and TNF-α.

In some embodiments, the disease is a metastatic cancer.

In some embodiments, the presently disclosed subject matter provides a composition comprising zinc pyrophosphate and a prodrug comprising a monovalent drug moiety, a monovalent lipid moiety, and a bivalent linker moiety comprising a biodegradable bond. In some embodiments, the zinc pyrophosphate is in the form of nanoparticles.

In some embodiments, the presently disclosed subject matter provides a composition comprising a prodrug comprising a monovalent drug moiety, a monovalent lipid moiety, and a bivalent linker moiety comprising a biodegradable bond; and a nanoscale coordination polymer comprising a cisplatin and/or oxaliplatin prodrug. In some embodiment, the composition further comprises siRNA.

In some embodiments, the presently disclosed subject matter provides a nanoscale particle for delivery of therapeutic agents, said nanoscale particle comprising: a core comprising a metal-organic matrix material, optionally wherein the metal-organic matrix material comprises a coordination polymer; and a prodrug, wherein the prodrug comprises a monovalent drug moiety, a monovalent lipid moiety, and a bivalent linker moiety comprising a biodegradable bond.

In some embodiments, the nanoscale particle further comprises at least one nucleic acid chemotherapeutic agent. In some embodiments, the nucleic acid chemotherapeutic agent is a siRNA, a miRNA, or an AS ODN. In some embodiments, the at least one nucleic acid is attached to the metal-organic matrix material core via coordination bonds between phosphate groups on the nucleic acid and metal ions on an outer surface of the core. In some embodiments, the at least one nucleic acid is selected from the group comprising survivin siRNA, ERCC-1 siRNA, P-glycoprotein siRNA (P-gp siRNA), Bcl-2 siRNA, or a mixture thereof.

In some embodiments, the nanoscale particle further comprises at least one photosensitizer.

In some embodiments, the nanoscale particle further comprises at least one non-nucleic acid chemotherapeutic agent incorporated in the metal-organic matrix material core, optionally wherein the at least one non-nucleic acid chemotherapeutic agent is incorporated in the metal-organic matrix material core via a covalent or coordination bond. In some embodiments, the at least one non-nucleic acid chemotherapeutic agent incorporated in the metal-organic matrix material core is selected from the group comprising cisplatin or oxaliplatin prodrugs, gemcitabine, methotrexate, leucovorin, pemetrexed disodium, doxorubicin, vinblastine, vincristine, vindesine, cytarabine, azathioprine, melphalan, imatinib, anastrozole, letrozole, carboplatin, paclitaxel, docetaxel, etoposide, and vinorelbine.

In some embodiments, the nanoscale particle comprises at least two chemotherapeutic agents incorporated in the metal-organic matrix material core. In some embodiments, the non-nucleic acid chemotherapeutic agent is cis, cis, trans-$Pt(NH_3)_2Cl_2(OEt)(O_2CCH_2CH_2COOH)$, optionally wherein the core comprises between about 10 weight % and about 50 weight % of the non-nucleic acid chemotherapeutic agent.

In some embodiments, the nanoscale particle has an average diameter of between about 20 nm and about 140 nm.

In some embodiments, the nanoscale particle further comprises one or more coating agents or layers covering at least a portion of the outer surface of the metal-organic matrix material core, wherein the one or more coating agents or layers are selected from a metal oxide, a polymer, a single lipid layer, a lipid bilayer, and combinations thereof. In some embodiments, the metal-organic matrix material core is coated with a lipid bilayer comprising a cationic lipid and/or a functionalized lipid, wherein said functionalized lipid is a lipid functionalized with a group that can bond to a nucleic acid, and wherein at least one nucleic acid is covalently bonded to the functionalized lipid and/or attached to the cationic lipid via electrostatic interactions. In some embodiments, the lipid bilayer comprises a mixture comprising one or more of a thiol- or dithiol-functionalized 1,2-distearoyl-sn-glycero-3-phosphoethanolamine (DSPE), 1,2-dioleoyl-3-trimethylammonium propane (DOTAP), and 1,2-dioleoyl-sn-glycero-3-phosphocholine (DOPC).

In some embodiments, the one or more coating agents or layers further comprise a passivating agent, optionally a hydrophilic polymer; a targeting agent, optionally a RGD peptide; and/or an imaging agent, optionally a fluorescent moiety. In some embodiments, the lipid bilayer further comprises one or more of 1,2-dioleoyl-sn-glycero-3-phosphate sodium salt (DOPA), cholesterol, and pegylated-DSPE.

In some embodiments, the metal-organic matrix material core comprises a metal bisphosphonate coordination polymer comprising a multivalent metal ion and a bisphosphonate. In some embodiments, the multivalent metal ion is selected from the group comprising $Ca^{2+}$, $Mg^{2+}$, $Mn^{2+}$, $Zn^{2+}$, and combinations thereof.

In some embodiments, the bisphosphonate is a chemotherapeutic prodrug, optionally a cisplatin or oxaliplatin prodrug. In some embodiments, the prodrug comprises a monovalent derivative of DHA. In some embodiments, the bisphosphonate is a bisphosphonate ester of cis, cis-trans-$[Pt(NH_3)_2Cl_2(OH)_2]$ (a cisplatin prodrug) or cis, trans-$[Pt(dach)Cl_2(OH)_2]$. In some embodiments, the multivalent metal ion is $Zn^{2+}$. In some embodiments, the metal-organic matrix material core comprises between about 40 and about 50 weight % of bisphosphonate.

In some embodiments, the nanoscale particle further comprises a lipid single layer or lipid bilayer coating, optionally wherein one or more of survivin siRNA, P-gp siRNA, and Bcl-2 siRNA are attached to the coating. In some embodiments, the nanoscale particle has a diameter between about 20 nm and about 180 nm. In some embodiments, the nanoscale particle has a diameter between about 90 nm and about 180 nm.

In some embodiments, the presently disclosed subject matter provides a method of treating cancer in a subject in need thereof, the method comprising administering to the subject a composition comprising zinc pyrophosphate and a lipid-conjugate prodrug; a nanoscale coordination polymer comprising a cisplatin and/or oxaliplatin prodrug and a lipid-conjugate prodrug, or a composition comprising a nanoscale particle comprising a metal-organic matrix material core and a lipid-conjugate prodrug. In some embodiments, the cancer is selected from lung cancer, pancreatic cancer, ovarian cancer, breast cancer and colon cancer. In some embodiments, the cancer is ovarian cancer, optionally a cisplatin resistant ovarian cancer.

In some embodiments, the method further comprises administering to the subject an immunotherapy agent. In some embodiments, the immunotherapy agent is selected from the group comprising an anti-CD52 antibody, an anti-CD20 antibody, anti-CD47 antibody an anti-GD2 antibody, a cytokine, and polysaccharide K. In some embodiments, the immunotherapy agent is selected from the group comprising Alemtuzumab, Ofatumumab, Rituximab, Zevalin, Adcetris, Kadcyla, and Ontak. In some embodiments, the immunotherapy agent is selected from the group comprising a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor.

In some embodiments, the method further comprises administering to the subject a photosensitizer. In some embodiments, the photosensitizer is a pyrolipid, wherein said pyrolipid is a lipid covalently attached to a porphyrin or a derivative or analog thereof.

In some embodiments, the presently disclosed subject matter provides a pharmaceutical formulation comprising a composition comprising a lipid-conjugate prodrug, optionally wherein the composition comprises a nanoscale particle, and a pharmaceutically acceptable carrier.

In some embodiments, the presently disclosed subject matter provides a method of treating cancer in a subject in need thereof wherein the method comprises administering to the subject a composition comprising a nanoscale particle comprising a lipid-conjugate prodrug and a metal-organic matrix material core and a photosensitizer, and irradiating the subject or a treatment area of the subject with radiation having a wavelength suitable to activate the photosensitizer.

In some embodiments, the cancer is a head and neck cancer, optionally wherein the head and neck cancer is a cisplatin resistant head and neck cancer. In some embodiments, the method further comprises administering to the subject an immunotherapy agent.

In some embodiments, the immunotherapy agent is selected from the group comprising an anti-CD52 antibody, an anti-CD20 antibody, anti-CD47 antibody, an anti-GD2 antibody, polysaccharide K, and a cytokine. In some embodiments, the immunotherapy agent is selected from the group comprising a radiolabeled antibody, an antibody-drug conjugate, and a neoantigen. In some embodiments, the immunotherapy agent is selected from the group comprising Alemtuzumab, Ofatumumab, Rituximab, Zevalin, Adcetris, Kadcyla, and Ontak. In some embodiments, the immunotherapy agent is selected from the group comprising a PD-1 inhibitor, a PD-L1 inhibitor, a CTLA-4 inhibitor, an IDO inhibitor, a CCR7 inhibitor, a OX40 inhibitor, a TIM3 inhibitor, and a LAG3 inhibitor.

Accordingly, it is an object of the presently disclosed subject matter to provide lipid moiety-containing prodrugs, nanoparticles, and nanoparticle formulations comprising the prodrugs, as well as methods of treating disease using the nanoparticles and formulations.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

particle of the presently disclosed subject matter further comprising a lipid coating layer comprising a cholesterol-linked etoposide prodrug and lipid-modified small interfering ribonucleic acids (i.e., NCP-1/ET/siRNAs) in a xenograft tumor model of a cisplatin-resistant ovarian cancer (A2780/CDDP). Tumor volume (in cubic millimeters (mm$^3$)) versus day post treatment is provided for an NCP particle-treated tumor model (circles) and a control (i.e., a phosphate-buffered saline (PBS)-treated model, squares).

Figure 1B:
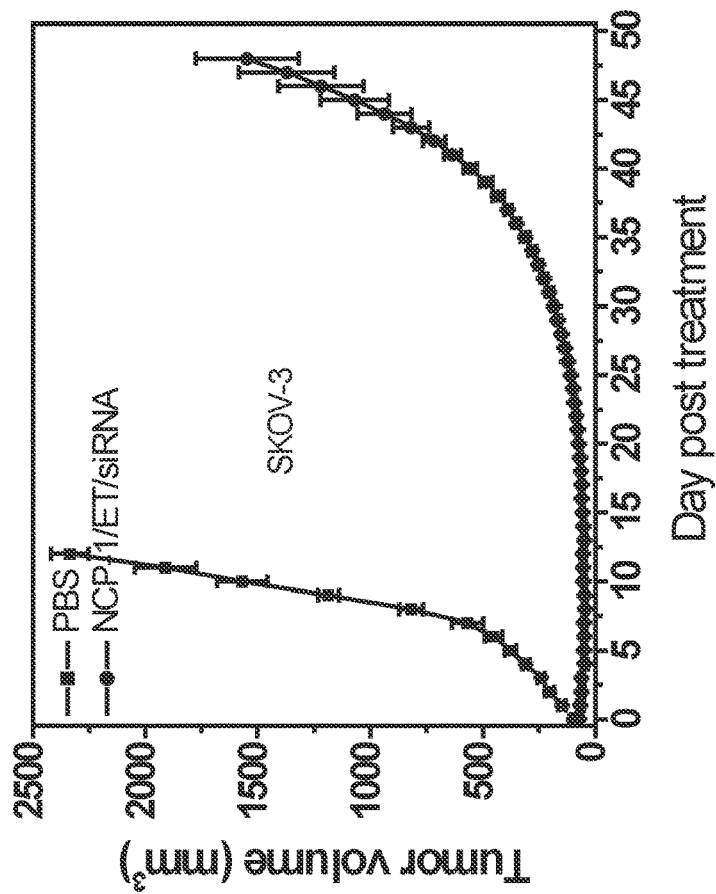
FIG. 1A is a graph showing the antitumor efficacy of a cisplatin-containing nanoscale coordination polymer (NCP)

FIG. 1B is a graph showing the antitumor efficacy of a cisplatin-containing NCP particle of the presently disclosed subject matter further comprising a lipid coating layer comprising a cholesterol-linked etoposide prodrug and lipid-modified small interfering ribonucleic acids (i.e., NCP-1/ET/siRNAs) in a xenograft tumor model of a cisplatin-resistant ovarian cancer (SKOV-3). Tumor volume (in cubic millimeters (mm$^3$)) versus day post treatment is provided for an NCP particle-treated tumor model (circles) and a control (i.e., a phosphate-buffered saline (PBS)-treated model, squares).

Figure 1A:
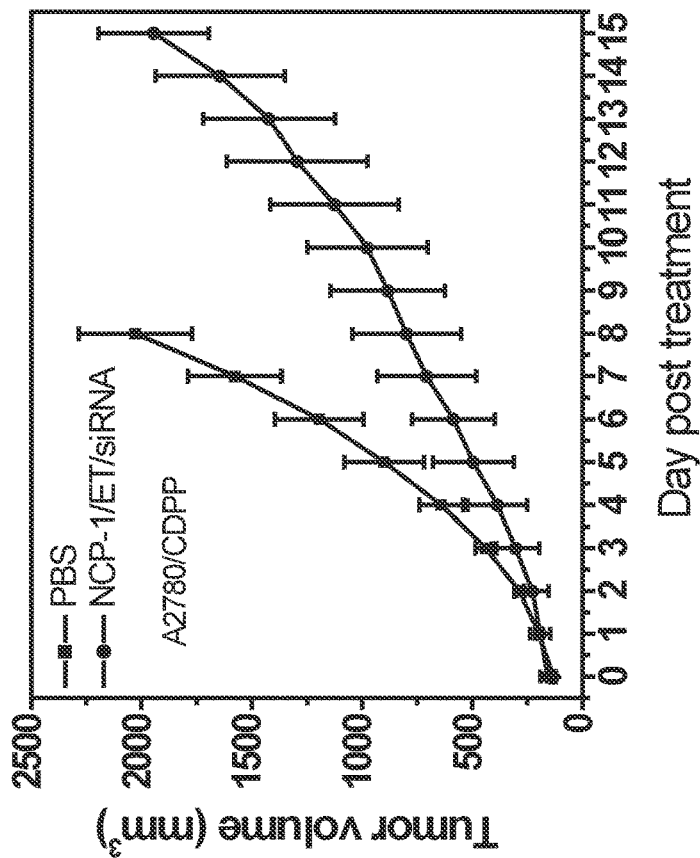
Figure 1C:
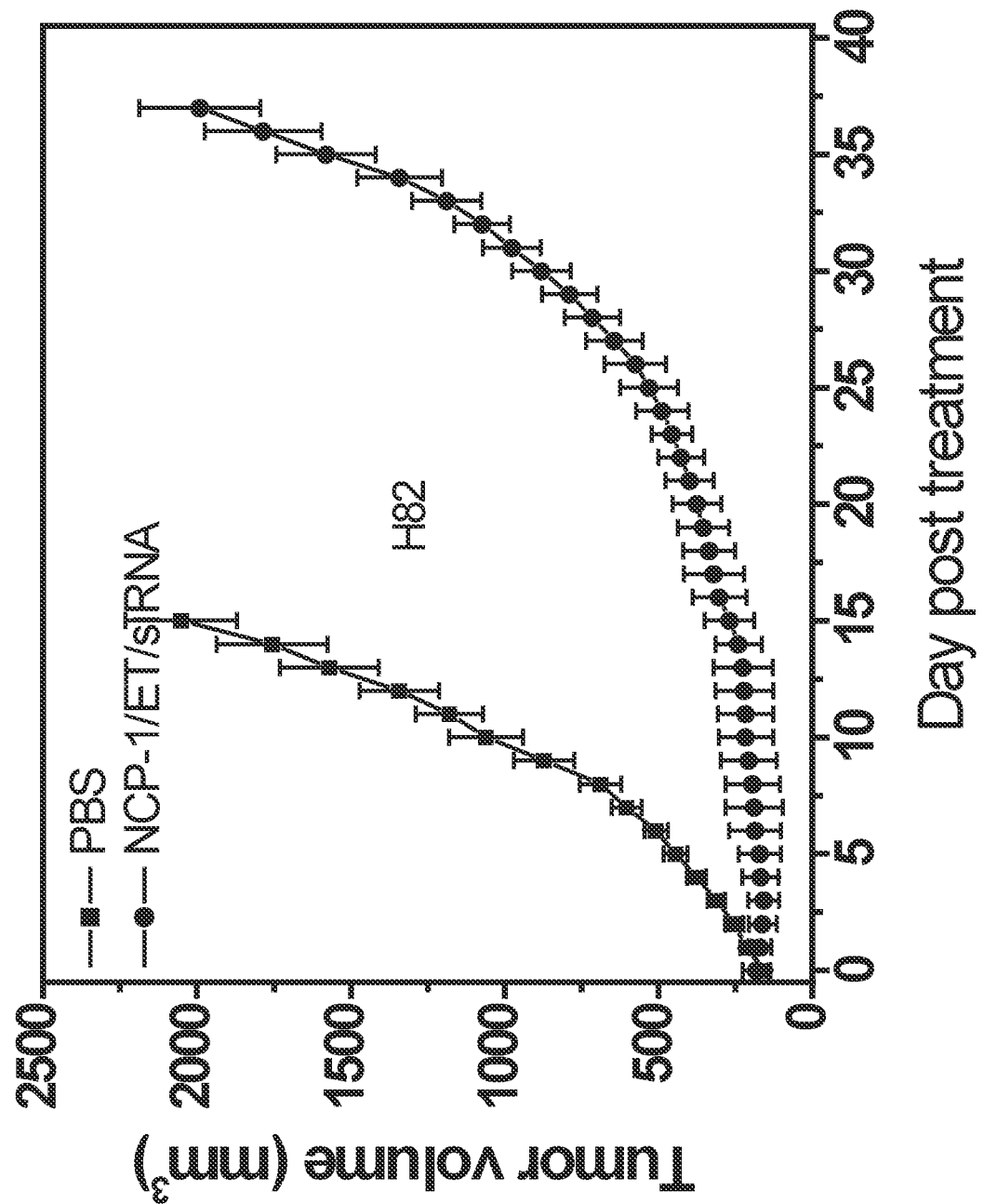

FIG. 1C is a graph showing the antitumor efficacy of a cisplatin-containing NCP particle of the presently disclosed subject matter further comprising a lipid coating layer comprising a cholesterol-linked etoposide prodrug and lipid-modified small interfering ribonucleic acids (i.e., NCP-1/ET/siRNAs) in a xenograft tumor model of a small cell lung cancer (H82). Tumor volume (in cubic millimeters (mm$^3$)) versus day post treatment is provided for an NCP particle-treated tumor model (circles) and a control (i.e., a phosphate-buffered saline (PBS)-treated model, squares).

Figure 2:
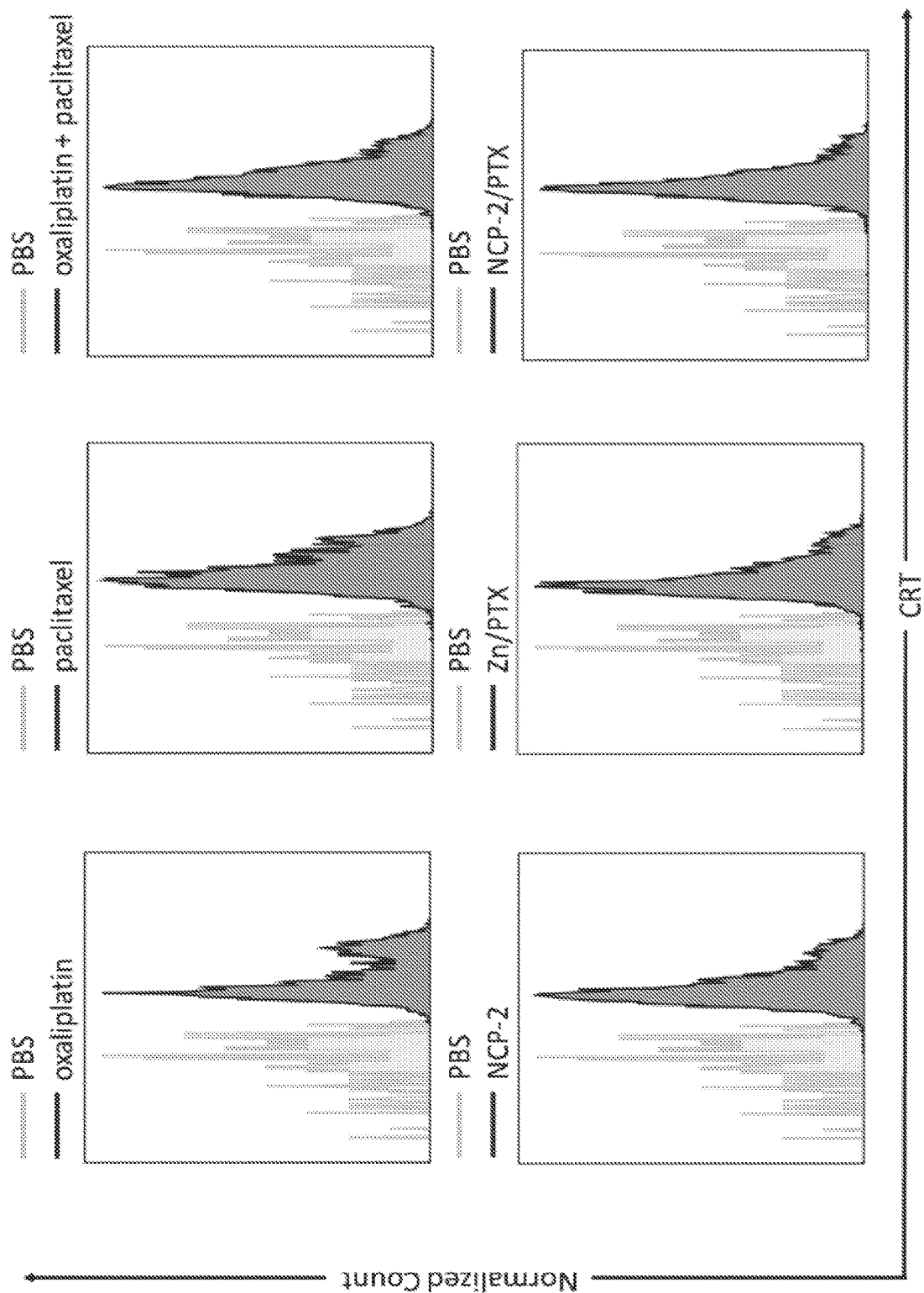

FIG. 2 is a series of graphs showing calriticulin (CRT) exposure on the cell surface of CT26 murine colorectal adenocarcinoma cells induced by platinum (Pt) and/or paclitaxel (PTX) at a concentration of 5 micromolar (μM) as determined by flow cytometry analysis. Cells were treated with oxaliplatin (top left), PTX (top middle), a combination of PTX and oxaliplatin (top right), a NCP comprising zinc (Zn) and an oxaliplatin analogue (NCP-2, bottom left), a combination of Zn and PTX (bottom middle), or NCP-2 coated with a lipid coating comprising a cholesterol-linked PTX (NCP-2/PTX, bottom right). Data in gray from phosphate buffered saline (PBS)-treated cells is shown in each graph as a control.

Figure 3:
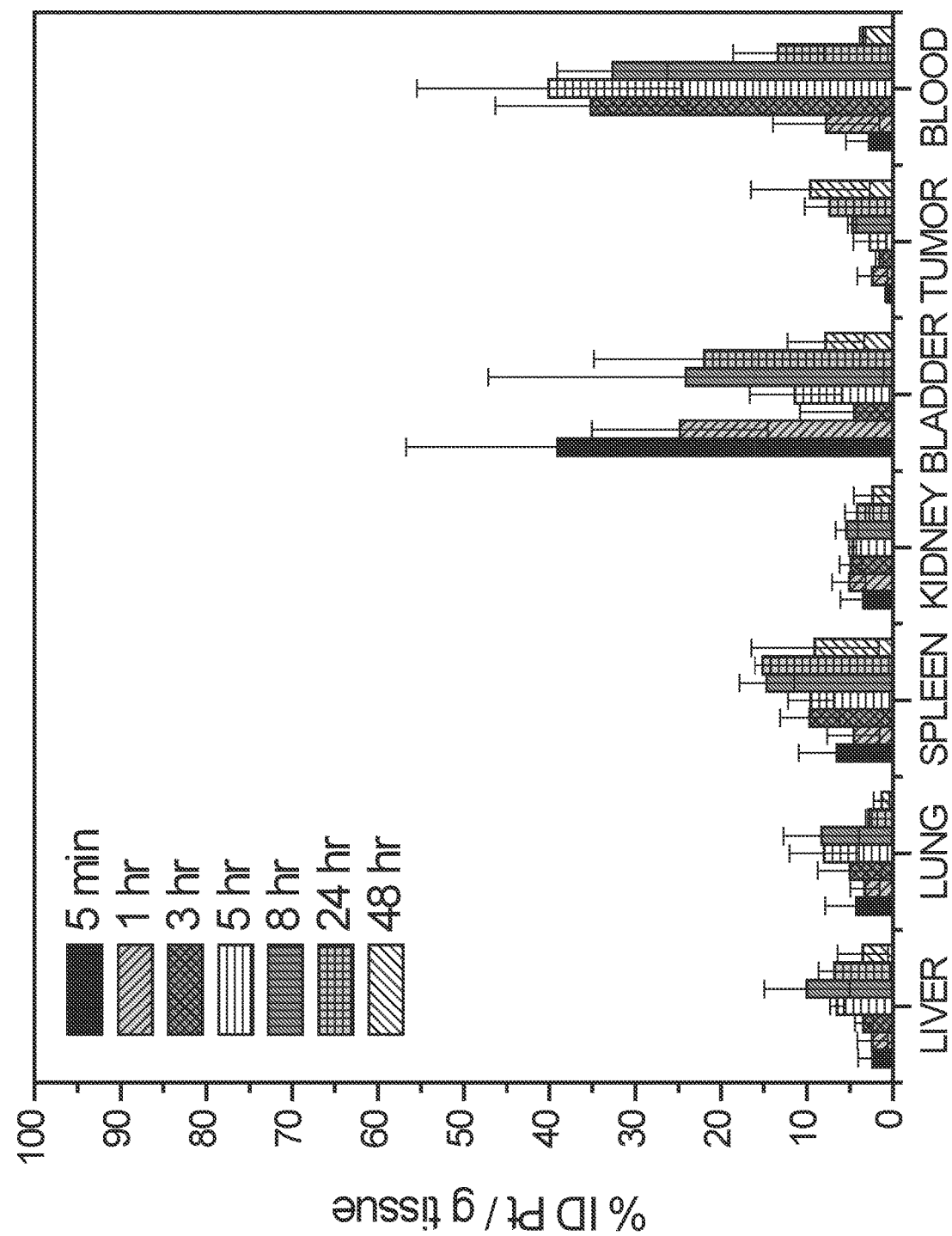

FIG. 3 is a graph showing the platinum (Pt) data from pharmacokinetics and biodistribution of a NCP particle comprising a zinc and oxaliplatin analogue core and a lipid coating layer comprising cholesterol-modified paclitaxel (NCP-2/PTX) after intravenous (i.v.) injection in CT26 murine colorectal adenocarcinoma tumor bearing mice at a dose of 1 milligram per kilogram (mg/kg) expressed as percentage initial dose (% ID) of Pt per gram (g) of tissue. Pt concentration was analyzed via inductively coupled plasma-mass spectrometry (ICP-MS) at 5 minutes, and at 1, 3, 5, 8, 24, and 48 hours, and is expressed in micrograms (μg).

Figure 4:
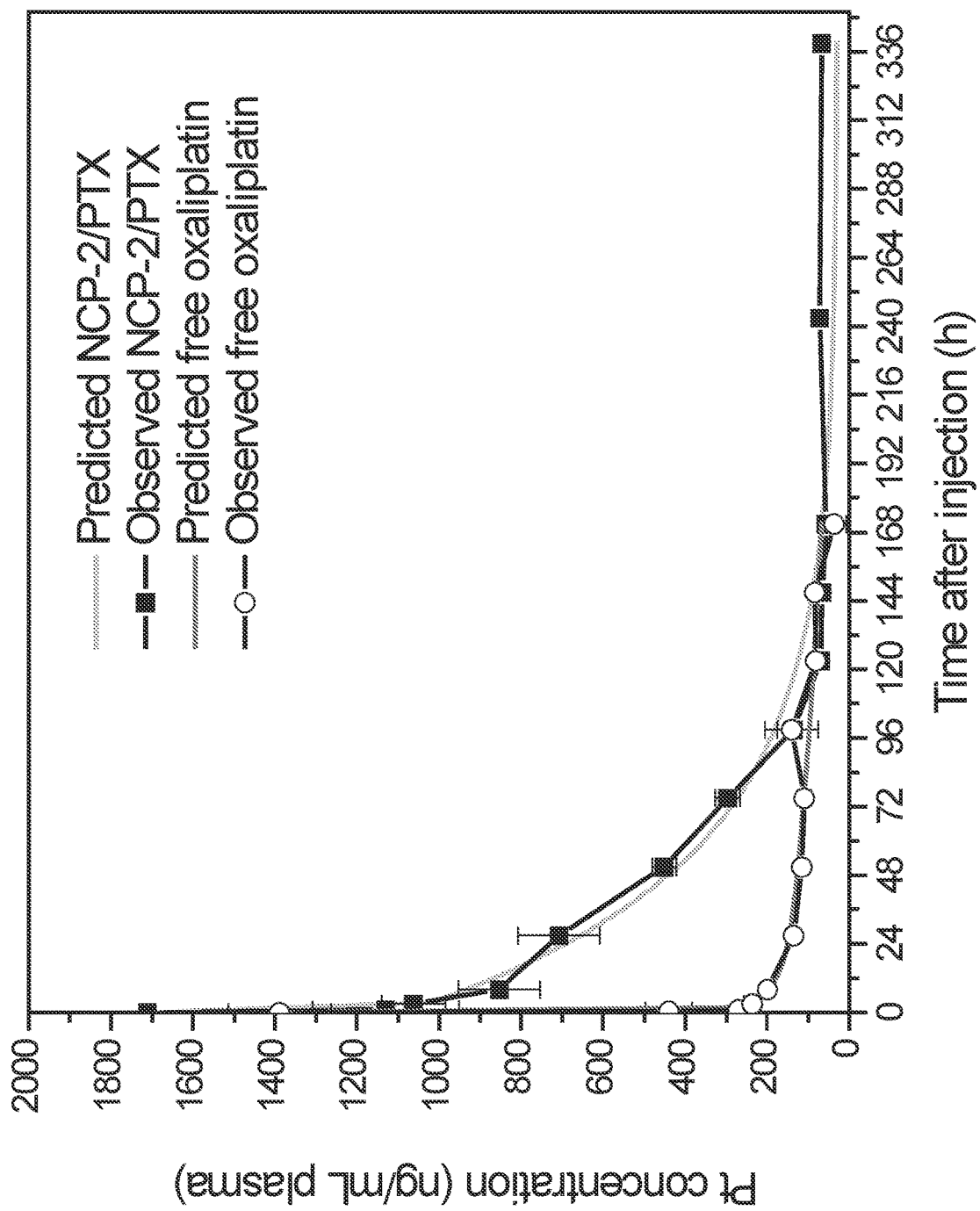

FIG. 4 is a graph showing the pharmacokinetics of free oxaliplatin (observed data, open circles; predicted, dark grey line) and of a NCP particle comprising a zinc and oxaliplatin analogue core and a lipid coating layer comprising cholesterol-modified paclitaxel (NCP-2/PTX) (observed data, black squares; predicted, light grey line) after intravenous (i.v.) injection in Beagle dogs at a dose of 1 milligram per kilogram (mg/kg). The platinum (Pt) concentrations were analyzed via inductively coupled plasma-mass spectrometry (ICP-MS) for up to 336 hours after injection.

Figure 5:
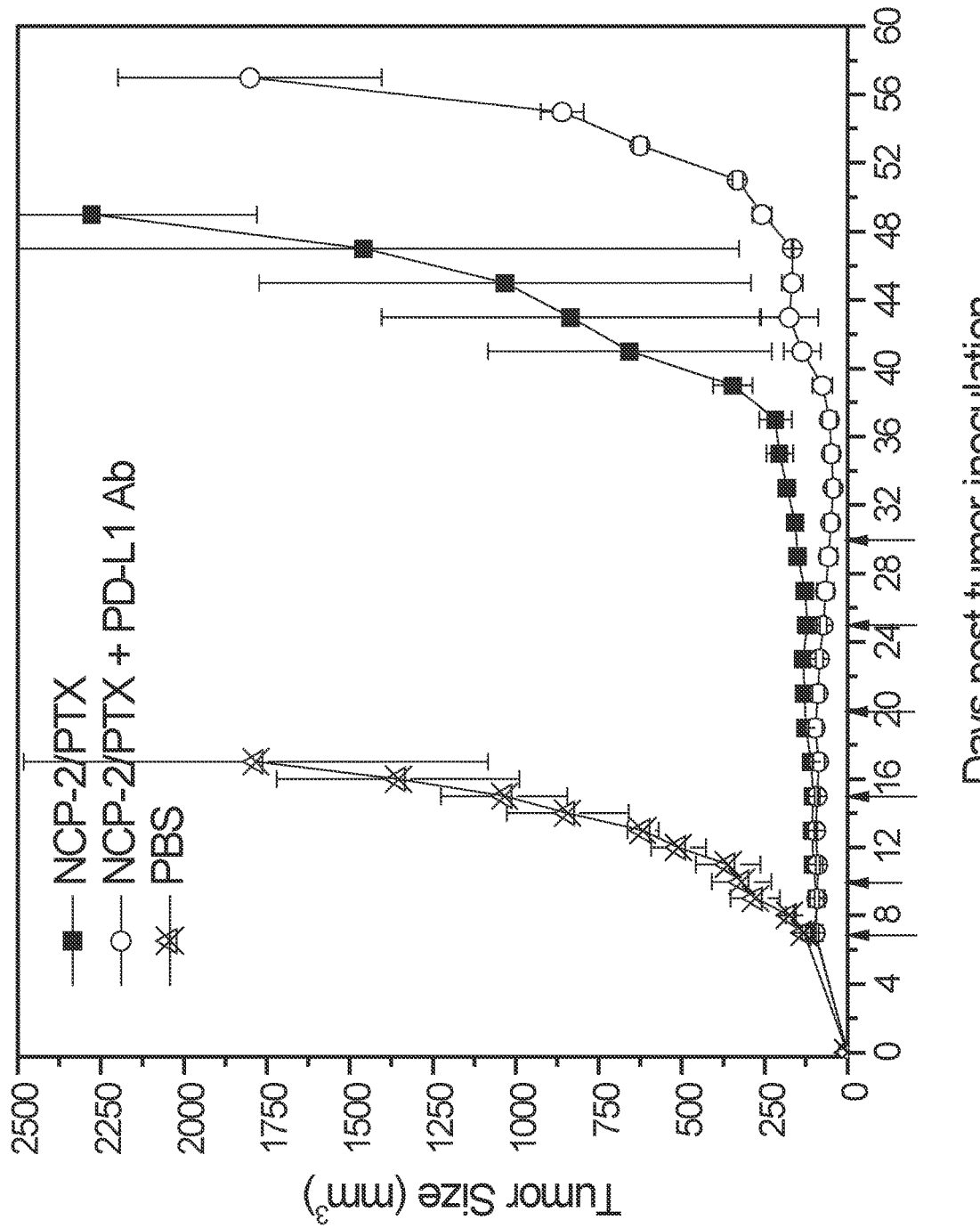

FIG. 5 is a graph showing the in vivo anticancer activity of a NCP particle comprising a zinc and oxaliplatin analogue core and a lipid coating layer comprising cholesterol-modified paclitaxel (NCP-2/PTX) (black squares) and of a combination of NCP-2/PTX and an anti-programmed death-ligand 1 (PD-L1) antibody (Pd-L1 Ab) (open circles) injected intraperitoneally into CT26 murine colorectal adenocarcinoma tumor bearing mice at an oxaliplatin analogue dose of 1 milligram per kilogram (mg/kg) and a paclitaxel dose of 2.24 mg/kg on the days indicated by the arrows (i.e., days 7, 10, 15, 20, 25, and 30). Tumor size (in cubic millimeters (mm$^3$)) at different days following tumor inoculation is shown. For comparison, data from mice injected with phosphate buffered saline (PBS, x-marked triangles) is shown.

Figure 6:
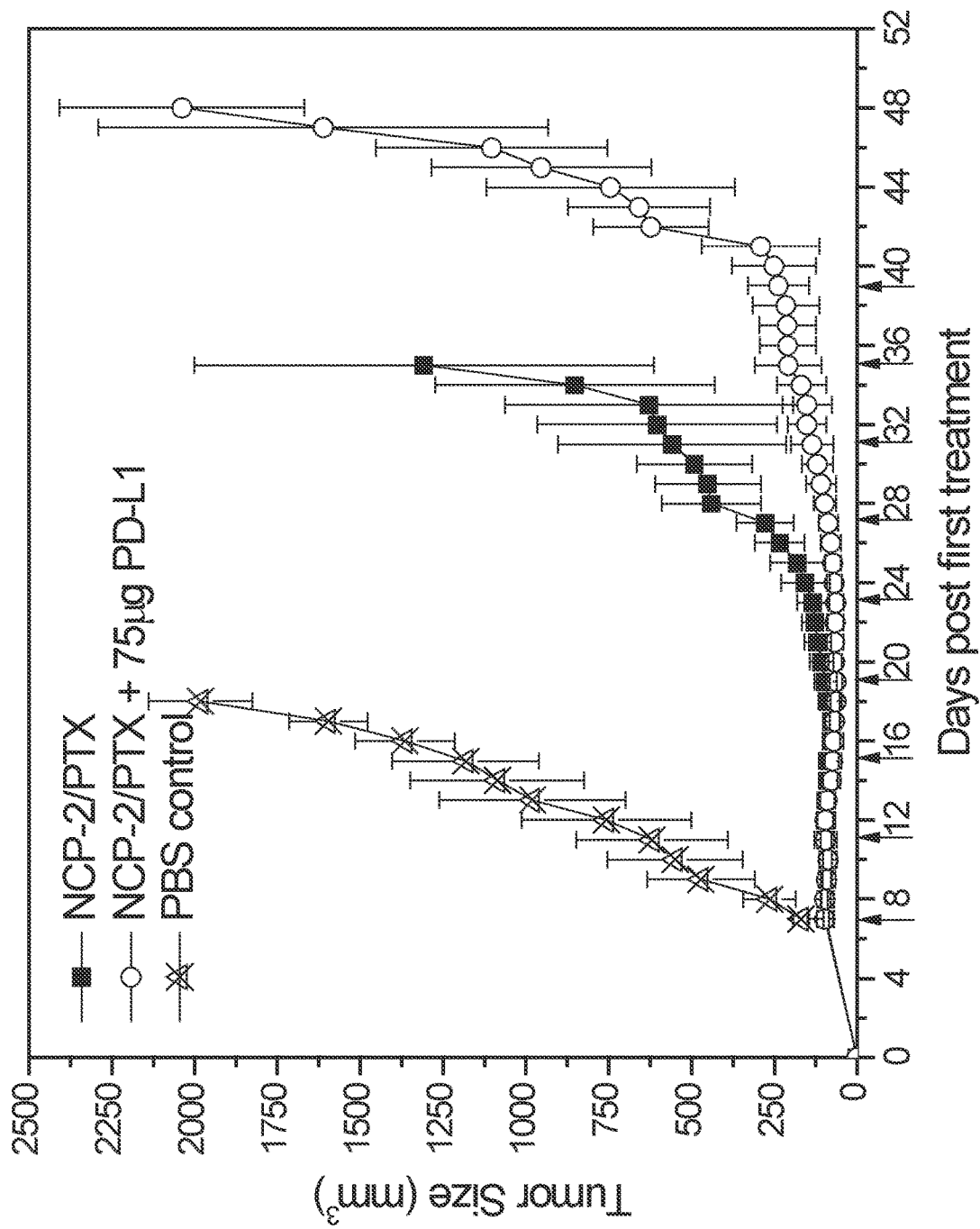

FIG. 6 is a graph showing the in vivo anticancer activity of a NCP particle comprising a zinc and oxaliplatin analogue core and a lipid coating layer comprising cholesterol-modified paclitaxel (NCP-2/PTX) (black squares) and of a combination of NCP-2/PTX and an anti-programmed death-ligand 1 (PD-L1) antibody (Pd-L1 Ab) (open circles) injected intraperitoneally into MC38 murine colorectal carcinoma tumor bearing mice at an oxaliplatin analogue does of 1 milligram per kilogram (mg/kg) and a paclitaxel dose of 2.24 mg/kg on the days indicated by the arrows (i.e., days 7, 11, 15, 19, 23, 31, and 39). Tumor size (in cubic millimeters (mm$^3$)) at different days following first treatment is shown. For comparison, data from mice injected with phosphate buffered saline (PBS, x-marked triangles) is shown.

Figure 7:
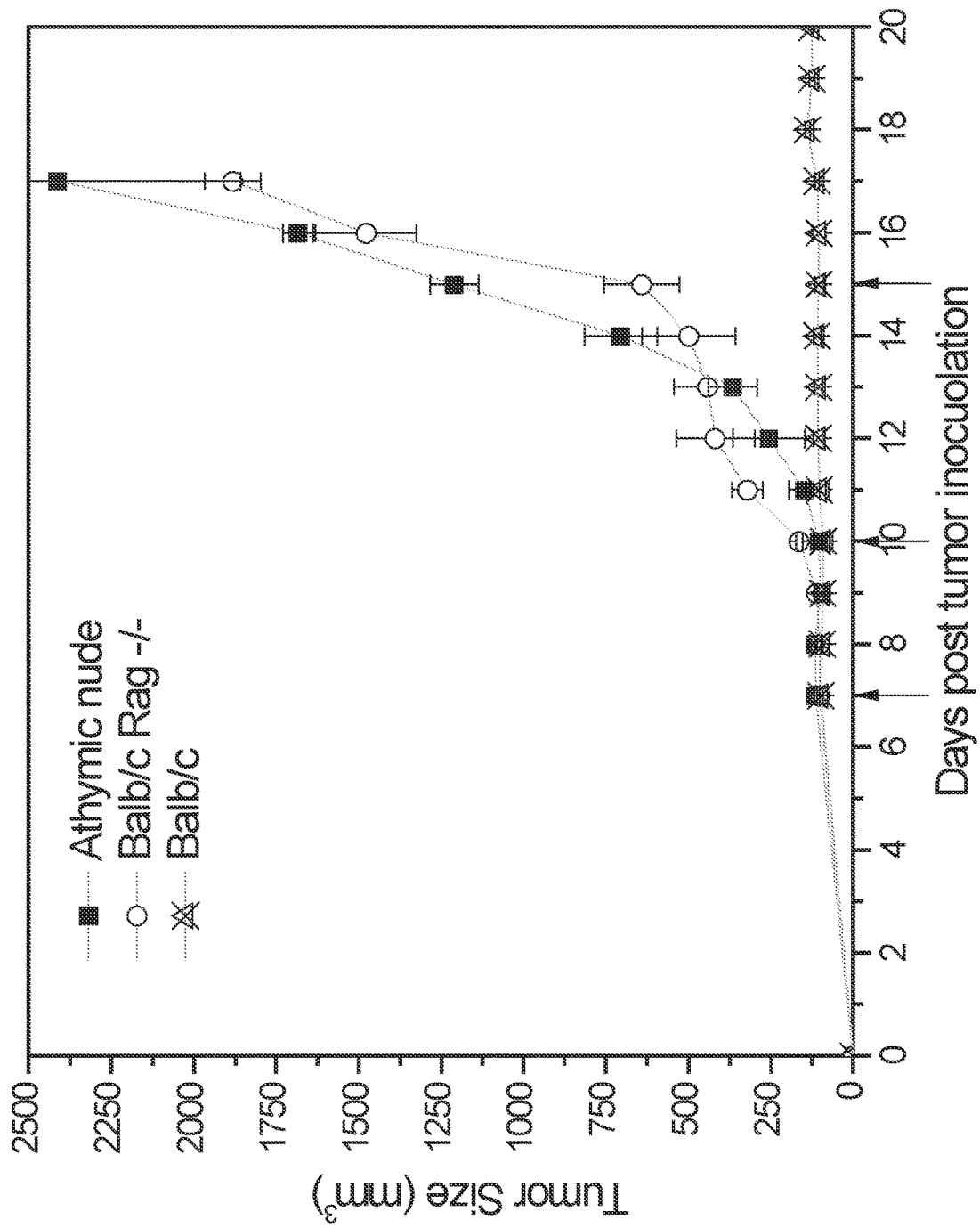

FIG. 7 is a graph showing the in vivo anticancer activity of a NCP particle comprising a zinc and oxaliplatin analogue core and a lipid coating layer comprising cholesterol-modified paclitaxel (NCP-2/PTX) in CT26 murine colorectal adenocarcinoma tumor bearing mice of different immunocompetencies: athymic nude mice (black squares); BALB/c Rag−/− mice (open circles); and BALB/c mice (x-marked triangles). NCP-2/PTX was intraperitoneally injected into the mice at an oxaliplatin analogue does of 1 milligram per kilogram (mg/kg) on the days indicated by the arrows (days 7, 10, and 15).

Figure 8:
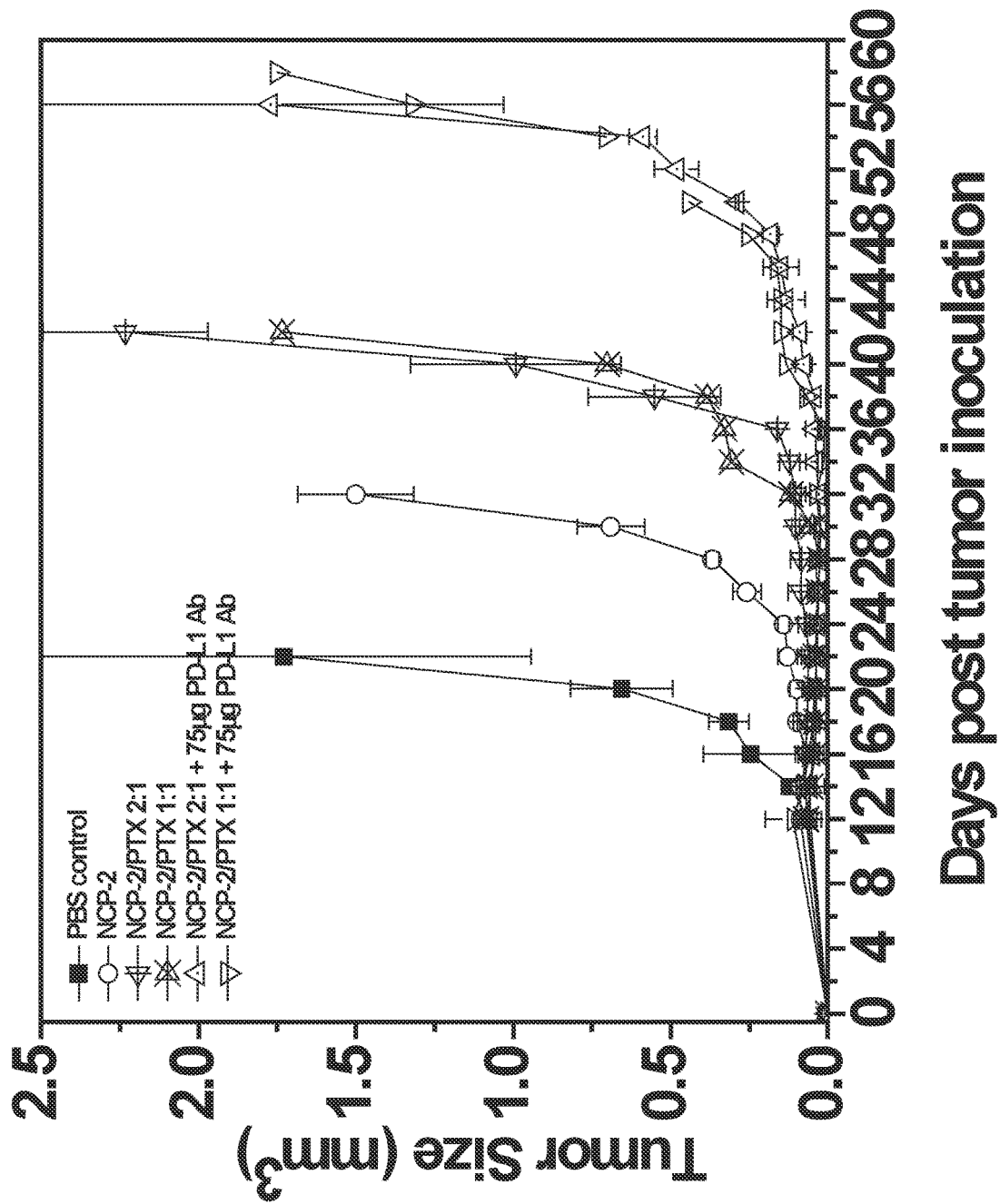

FIG. 8 is a graph showing the in vivo anticancer activity of NCP particles comprising a zinc and oxaliplatin analogue core and a lipid coating layer (NCP-2) in MC38 murine colorectal carcinoma tumor bearing mice. Mice were injected intraperitoneally every four days for a total of five doses at an oxaliplatin analogue dose of 2 milligrams per kilogram (mg/kg). Mice were injected with NCP-2 (open circles), NCP-2 particles that included a cholesterol-modified paclitaxel (PTX) in a lipid coating layer with a molar ratio of oxaliplatin analogue to PTX of 2:1 (NCP-2/PTX 2:1; left-pointing triangles); NCP-2 particles that included a cholesterol-modified paclitaxel (PTX) in the lipid layer with a molar ratio of oxaliplatin analogue to PTX of 1:1 (NCP-2/PTX 1:1; right-pointing triangles); NCP-2/PTX 2:1 and 75 micrograms (μg) of an anti-programmed death-ligand 1 (PD-L1) antibody (NCP-2/PTX 2:1+75 μg PD-L1 Ab; upward-pointing triangles), or NCP-2/PTX 1:1 and 75 μg PD-L1 antibody (NCP-2/PTX1:1+75 μg PD-L1 Ab; downward-pointing triangles). For comparison, data from mice injected with phosphate-buffered saline is shown (black squares).

Figure 9B:
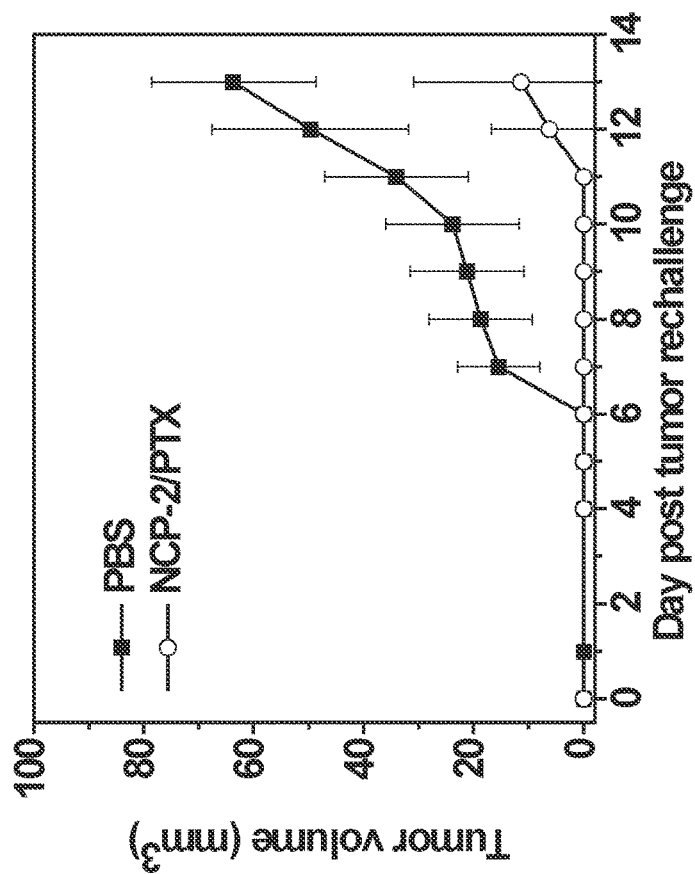
Figure 9A:
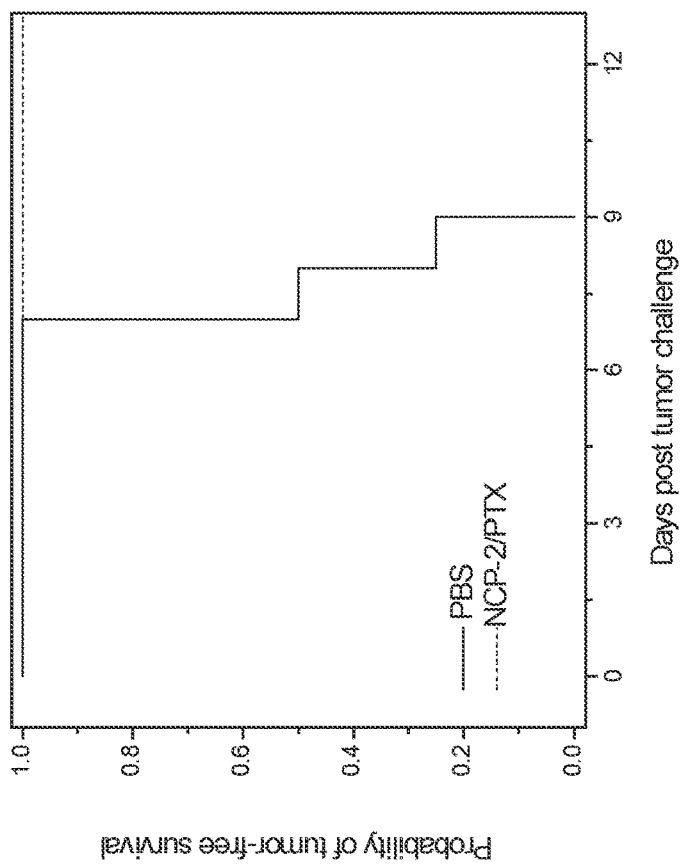

FIG. 9A is a graph showing the probability of tumor-free mice after re-challenge with live tumor cells in mice previously vaccinated with nanoparticle-treated cancer cells. BALB/c mice were inoculated subcutaneously with CT26 murine colorectal adenocarcinoma cells that had been treated with light and a NCP particle comprising a zinc and oxaliplatin analogue core and a lipid coating layer comprising cholesterol-modified paclitaxel (NCP-2/PTX, dotted line). Seven days after inoculation, the mice were re-challenged with live CT26 cells. Probability of tumor-free mice after re-challenge is also shown for mice originally inoculated with phosphate buffered saline (PBS)-treated cancer cells (solid line).

FIG. 9B is a graph showing tumor growth curves of re-challenged tumors in mice inoculated with phosphate buffered saline (PBS, black squares) as a control or inoculated with CT26 murine colorectal adenocarcinoma cells that had been treated with light and a NCP particle comprising a zinc and oxaliplatin analogue core and a lipid coating layer comprising cholesterol-modified paclitaxel (NCP-2/PTX, open circles).

Figure 10:
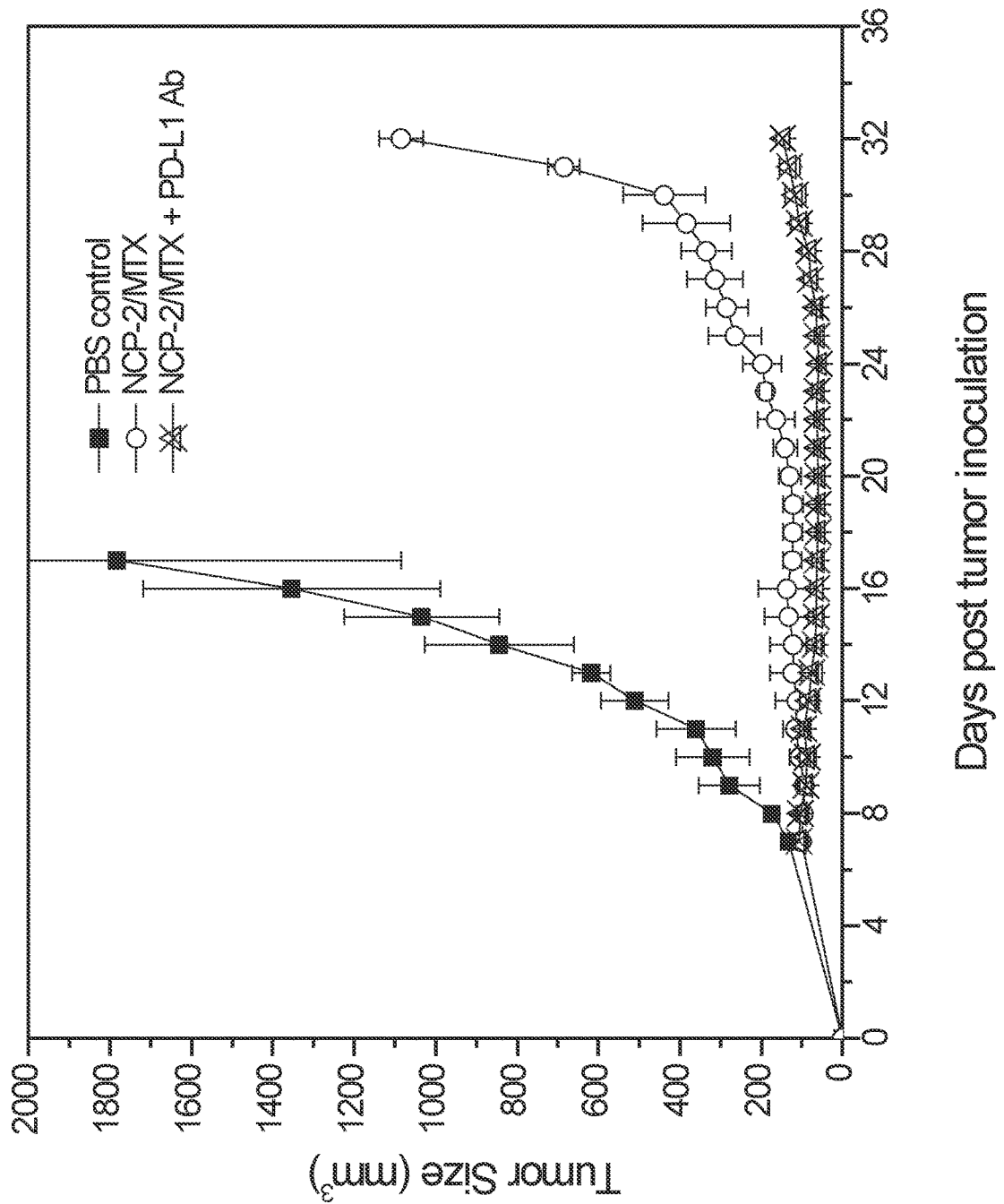

FIG. 10 is a graph of in vivo anticancer activity of a NCP comprising a zinc and oxaliplatin analogue core and a lipid coating layer comprising cholesterol-modified mitoxantrone (NCP-2/MTX) in CT26 murine colorectal adenocarcinoma tumor bearing mice. Tumor size data (in cubic millimeters ($mm^3$)) is provided for mice treated with phosphate buffered saline (PBS, black squares), NCP-2/MTX at an oxaliplatin analogue dose of 1 milligram per kilogram (mg/kg) and a mitoxantrone (MTX) dose of 0.58 mg/kg (open circles) or a combination of MCP-2/MTX and 75 microgram ($\mu$g) of an anti-programmed death-ligand 1 (PD-L1) antibody (MCP-2/MTX+PD-L1 Ab, x-marked triangles). Treatment was performed every four days for a total of six doses beginning on the seventh day after tumor inoculation.

Figure 11:
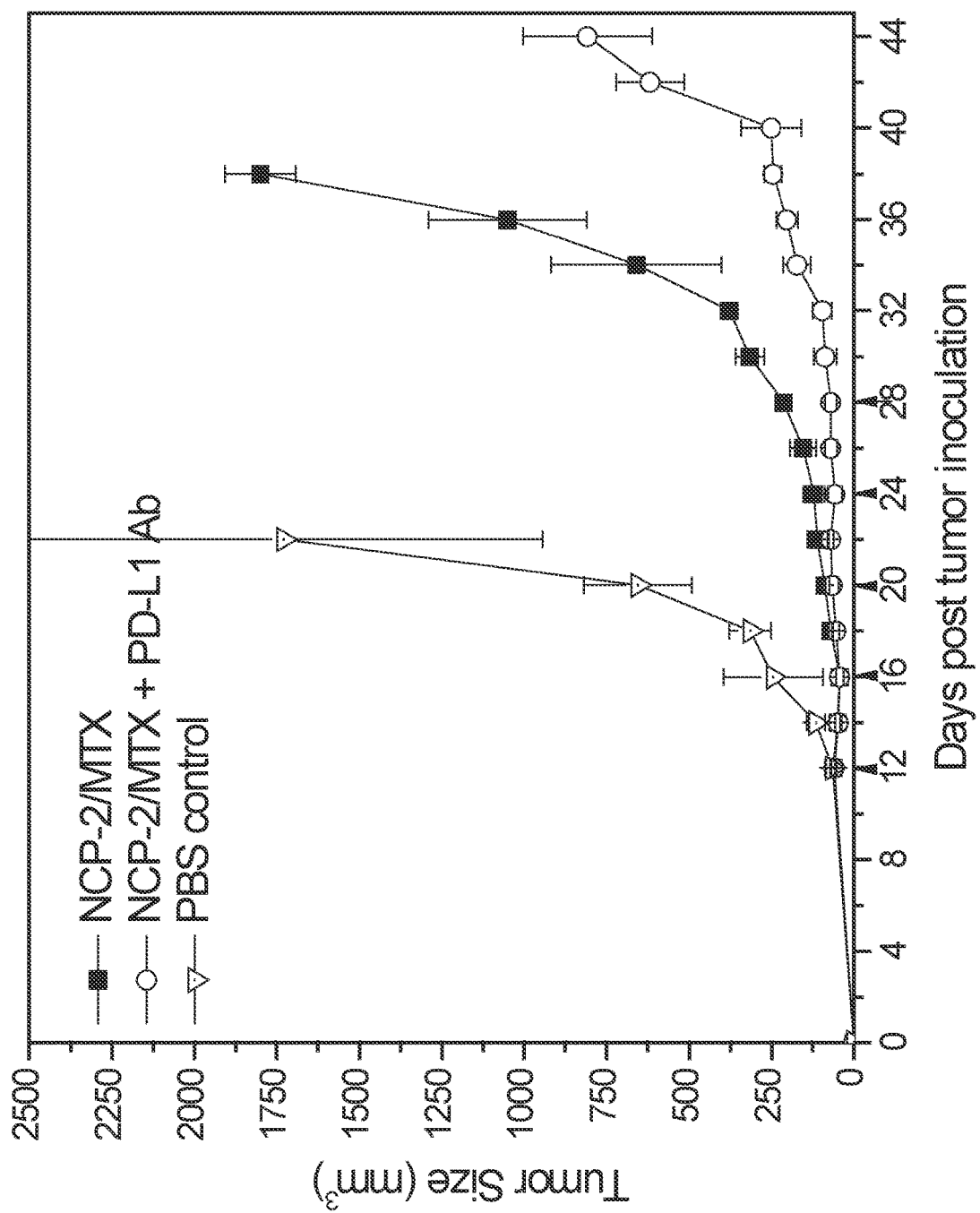

FIG. 11 is a graph of in vivo anticancer activity of a NCP comprising a zinc and oxaliplatin analogue core and a lipid coating layer comprising cholesterol-modified mitoxantrone (NCP-2/MTX) in MC38 murine colorectal carcinoma tumor bearing mice. Tumor size data (in cubic millimeters ($mm^3$)) is provided for mice treated with phosphate buffered saline (PBS, downward-facing triangles), NCP-2/MTX at an oxaliplatin analogue dose of 2 milligram per kilogram (mg/kg) and a mitoxantrone (MTX) dose of 1.16 mg/kg (black squares) or a combination of MCP-2/MTX and 75 microgram ($\mu$g) of an anti-programmed death-ligand 1 (PD-L1) antibody (MCP-2/MTX+PD-L1 Ab, open circles). Treatment was performed every four days starting on the twelfth day after tumor cell inoculation for a total of five doses.

Figure 12A:
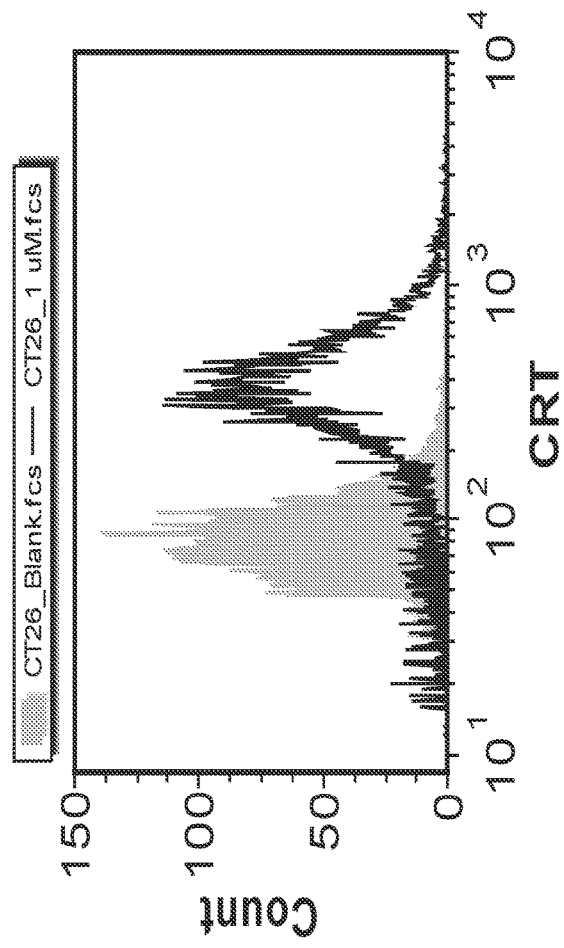

FIG. 12A is a graph showing calriticulin (CRT) exposure on the cell surface of CT26 murine colorectal adenocarcinoma cells induced by dihydroartemisinin (DHA) at a concentration of 1 micromolar ($\mu$M) as determined by flow cytometry analysis. Data in gray from phosphate buffered saline (PBS)-treated cells is shown in each graph as a control.

Figure 12B:
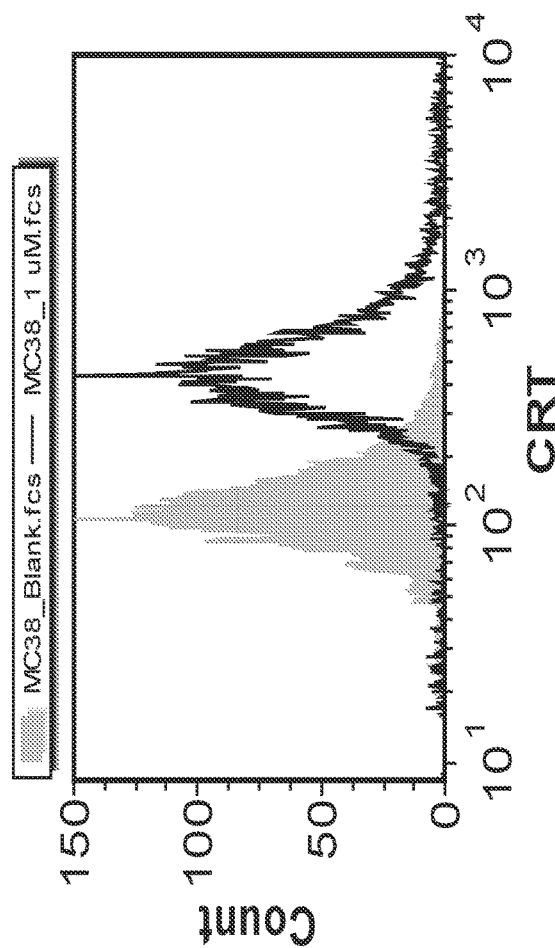

FIG. 12B is a graph showing calriticulin (CRT) exposure on the cell surface of MC38 murine colorectal carcinoma cells induced by dihydroartemisinin (DHA) at a concentration of 1 micromolar ($\mu$M) as determined by flow cytometry analysis. Data in gray from phosphate buffered saline (PBS)-treated cells is shown in each graph as a control.

Figure 13:
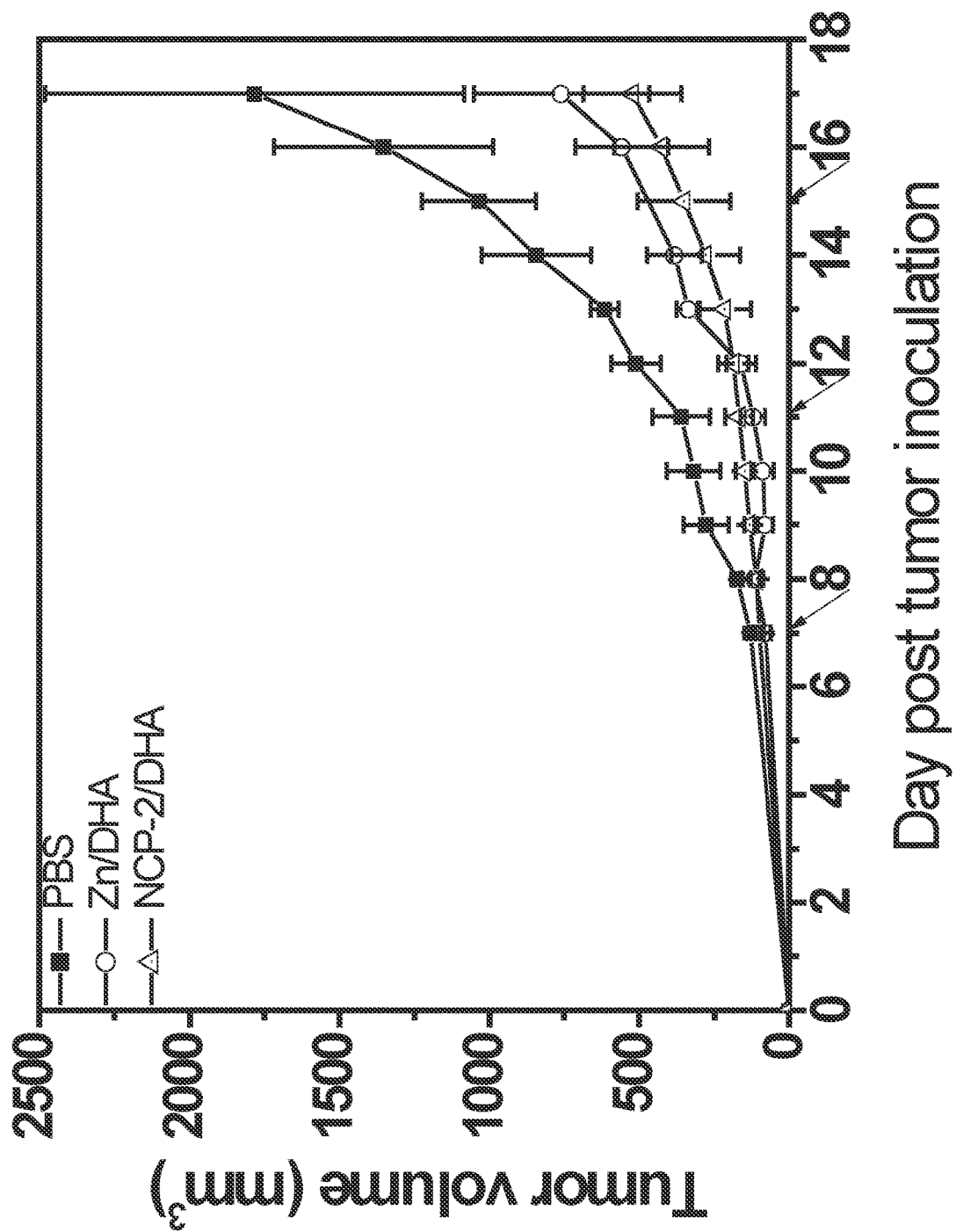

FIG. 13 is a graph showing the in vivo anticancer activity of a NCP particle comprising a zinc and oxaliplatin analogue coordination polymer core and a lipid coating layer comprising cholesterol-modified dihydroartemisinin (NCP-2/DHA, triangles) in CT26 murine colorectal adenocarcinoma tumor bearing mice. For comparison, data is provided for mice treated with phosphate buffered saline (PBS, black squares) and with a combination of zinc and dihydroartemisinin (Zn/DHA, open circles).

Figure 14:
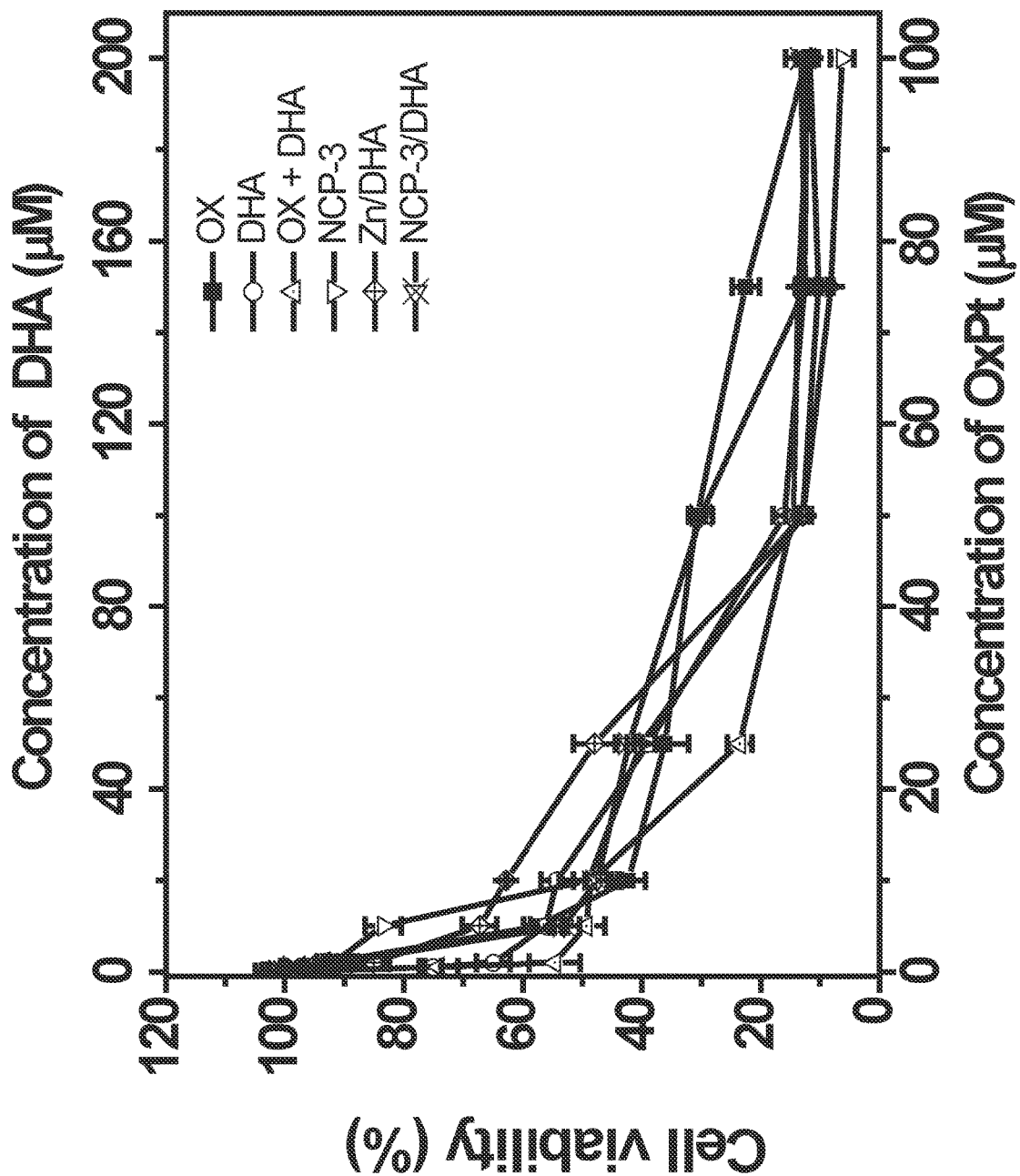

FIG. 14 is a graph showing the percentage (%) cell viability of CT26 murine colorectal adenocarcinoma cells treated with free and nanoparticle drug formulations of oxaliplatin (OX) and dihydroartemisinin (DHA). Cells were treated with one of the following: free OX (black squares); free DHA (open circles); a combination of free OX and free DHA (OX+DHA, upward-pointing triangles); a lipid-coated nanoscale polymer particles comprising a coordination polymer of zinc (Zn) and oxaliplatin prodrug (NCP-3, downward-pointing triangles); a combination of free Zn and free DHA (Zn/DHA, diamonds), or NCP-3 comprising a lipid-modified DHA in its lipid coating layer (NCP-3/DHA, left-pointing, x-marked triangles).

Figure 15:
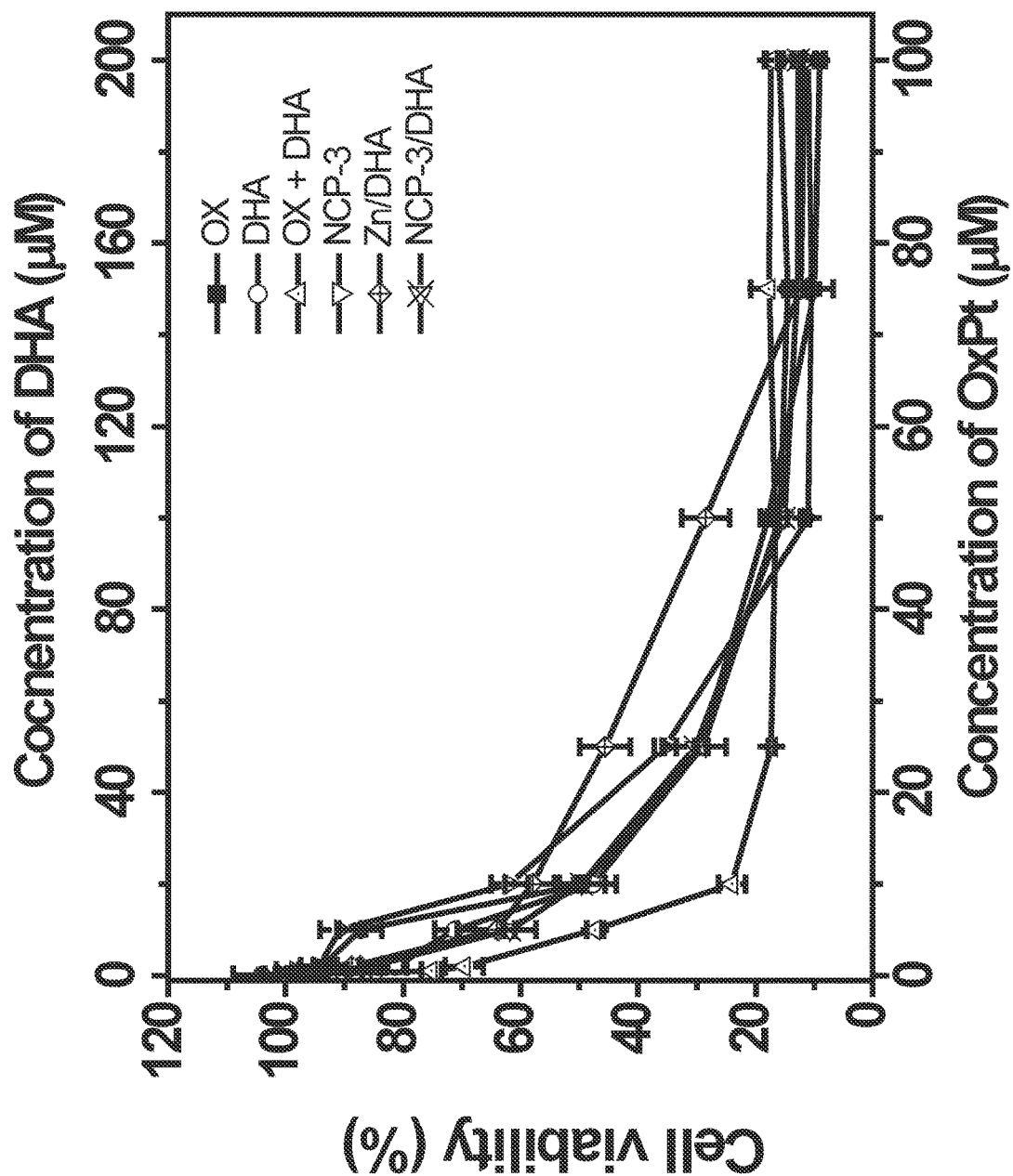

FIG. 15 is a graph showing the percentage (%) cell viability of MC38 murine colorectal carcinoma cells treated with free and nanoparticle drug formulations of oxaliplatin (OX) and dihydroartemisinin (DHA). Cells were treated with one of the following: free OX (black squares); free DHA (open circles); a combination of free OX and free DHA (OX+DHA, upward-pointing triangles); lipid-coated nanoscale polymer particles comprising a coordination polymer of zinc (Zn) and oxaliplatin prodrug (NCP-3, downward-pointing triangles); a combination of free Zn and free DHA (Zn/DHA, diamonds), or NCP-3 comprising a lipid-modified DHA in its lipid coating layer (NCP-3/DHA, left-pointing, x-marked triangles).

Figure 16:
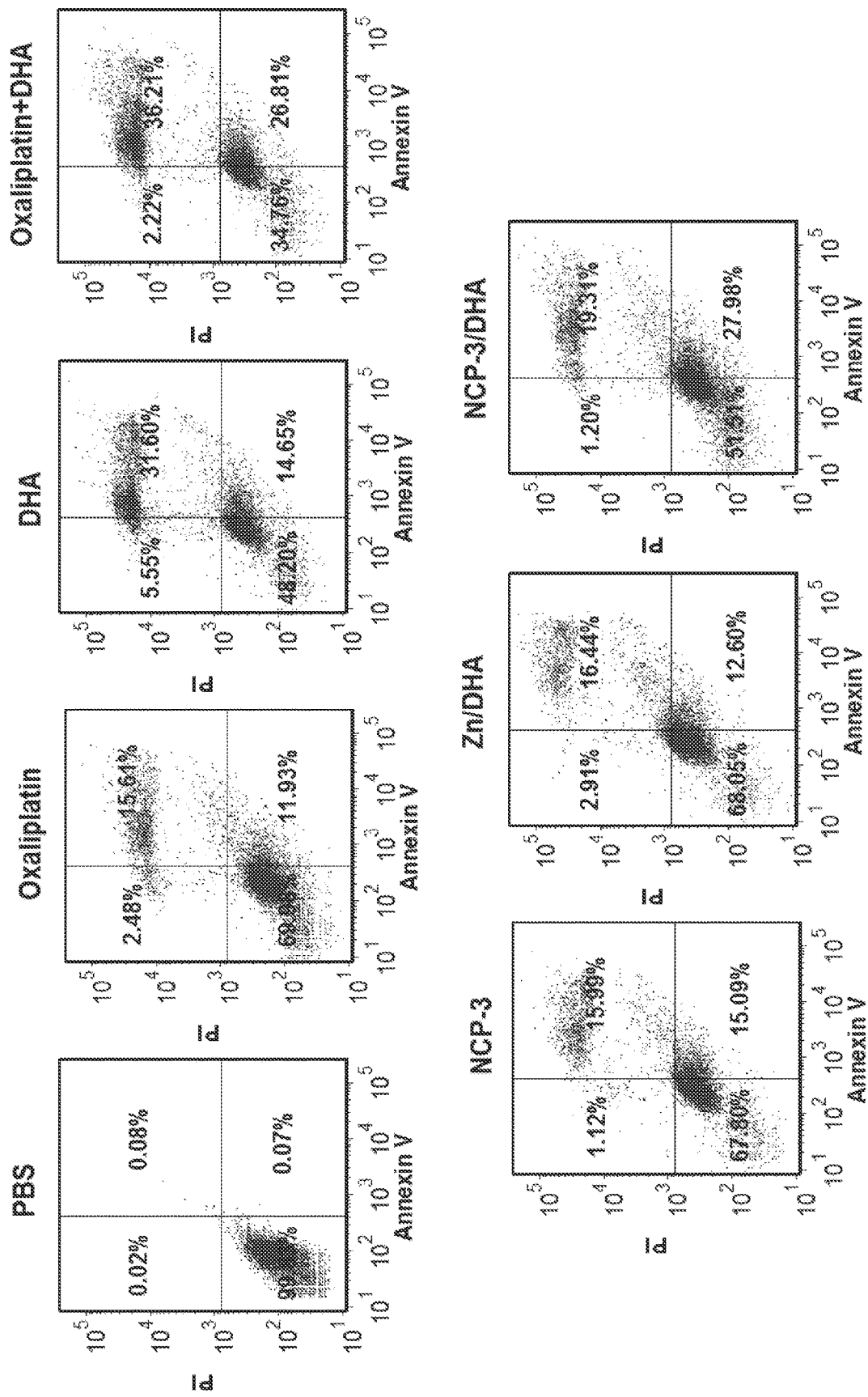

FIG. 16 is a series of plots showing the percentage (%) of apoptotic and necrotic cells after different treatments quantified by cell cytometry. The treatments included: phosphate buffered saline (PBS, top left); free oxaliplatin (top second from left); free dihydroartemisinin (DHA, top second from right); a combination of free oxaliplatin and free DHA (oxaliplatin+DHA, top right); lipid-coated nanoscale polymer particles comprising a coordination polymer of zinc (Zn) and oxaliplatin prodrug (NCP-3, bottom left); a combination of free Zn and free DHA (Zn/DHA, bottom middle); and NCP-3 comprising a lipid-modified DHA in its lipid coating layer (NCP-3/DHA, bottom right).

Figure 17:
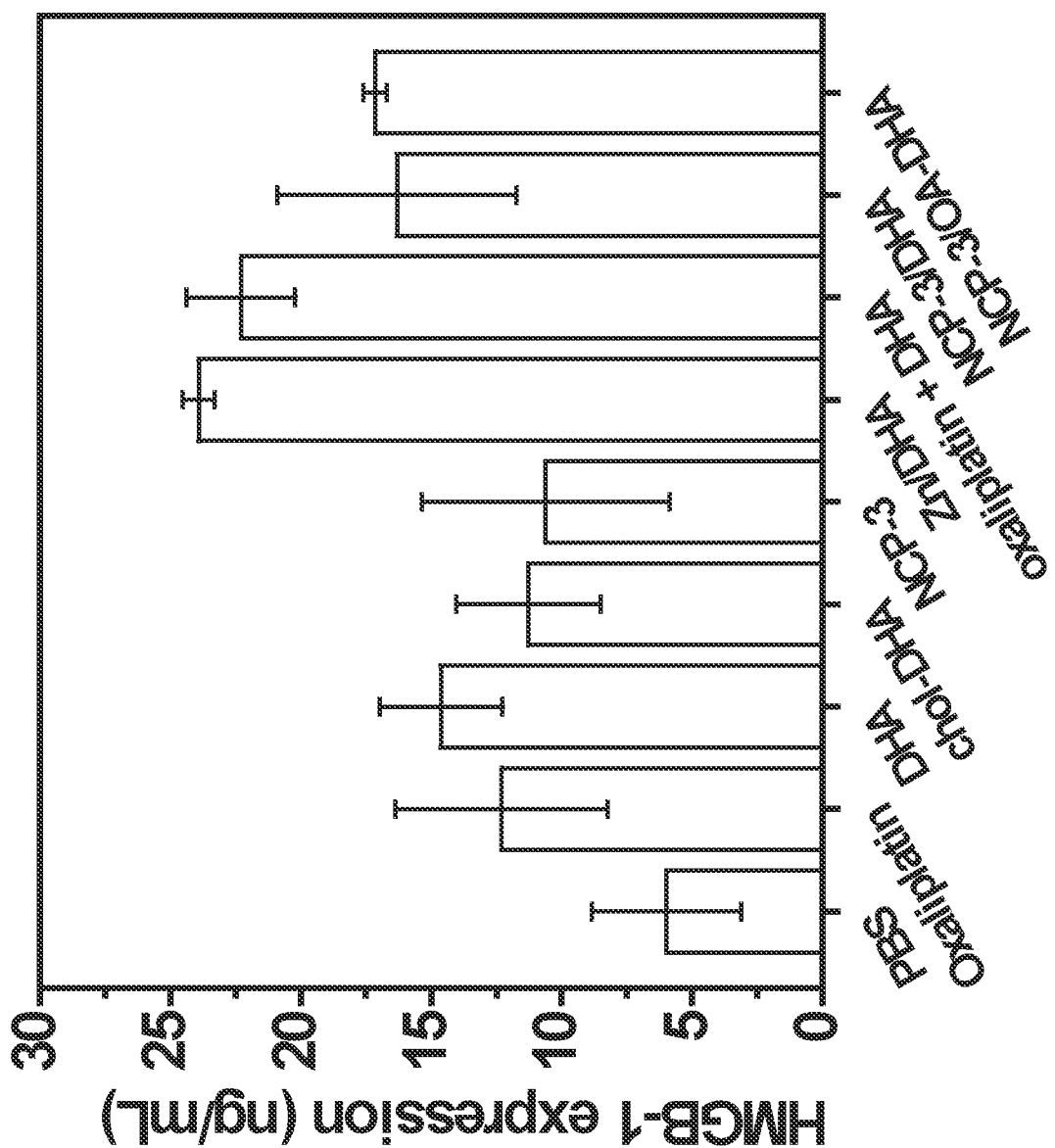

FIG. 17 is a graph of high mobility group box-1 (HMBG-1) protein release/expression (in nanograms per milliliter (ng/mL)) in the medium of CT26 murine colorectal adenocarcinoma cells receiving oxaliplatin and/or dihydroartemisinin (DHA) treatment. Treatments included free oxaliplatin, free DHA, cholesterol-modified DHA (chol-DHA), lipid-coated nanoscale polymer particles comprising a coordination polymer of zinc (Zn) and oxaliplatin prodrug (NCP-3), a combination of free Zn and DHA (Zn/DHA), a combination of free oxaliplatin and free DHA (oxaliplatin+DHA), NCP-3 including cholesterol-modified DHA in its lipid coating layer (NCP-3/DHA), and NCP-3 including oleic acid-modified DHA in its lipid coating layer (NCP-3/OA-DHA). For comparison, release data is provided for cells treated with phosphate buffered saline (PBS) as a control.

Figure 18B:
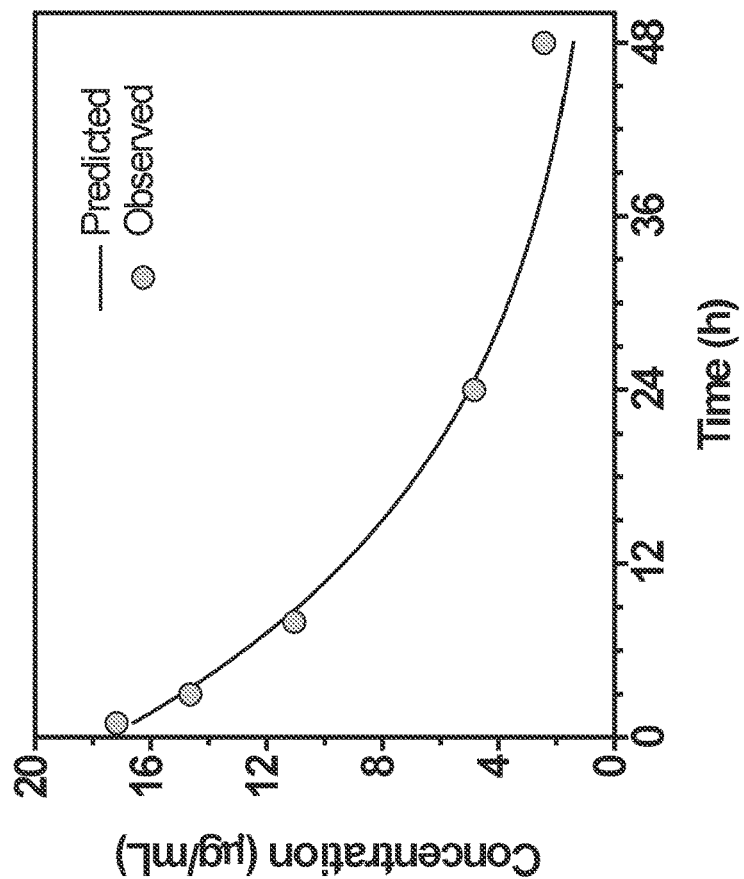
Figure 18A:
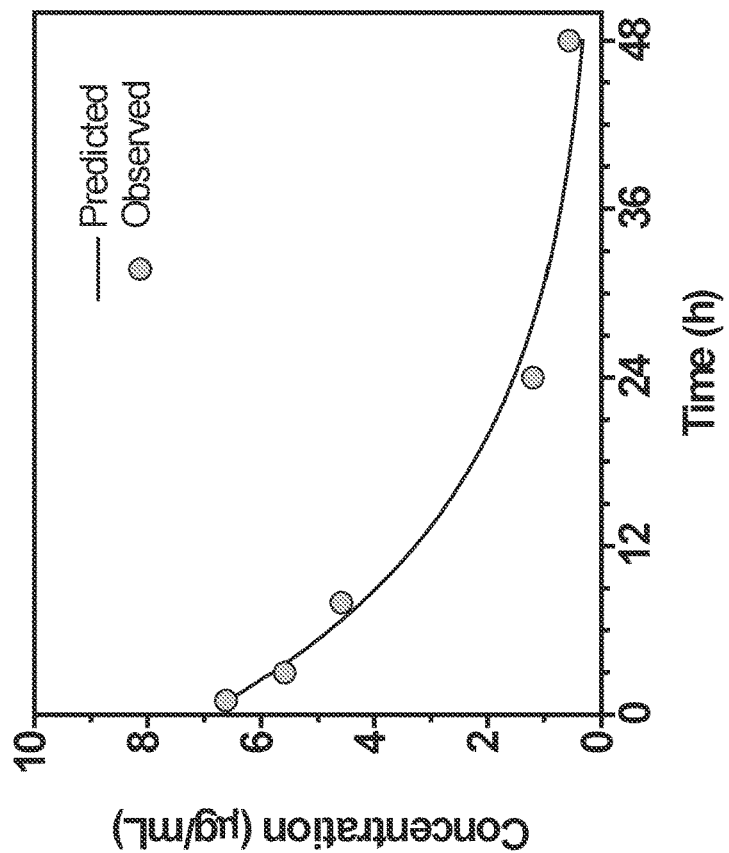

FIG. 18A is a graph showing the pharmacokinetics of platinum measured by inductively coupled plasma-mass spectrometry (ICP-MS) in the plasma of SD/CD rats after intravenous injection of a NCP particle comprising zinc (Zn) and an oxaliplatin prodrug and including dihydroarteminisin incorporated in its lipid coating layer (NCP-3/DHA).

FIG. 18B is a graph showing the pharmacokinetics of cholesterol-modified dihydroarteminisin (Chol-DHA) measured by liquid chromatography mass spectrometry (LC-MS) in the plasma of SD/CD rats after intravenous injection of a NCP particle comprising zinc (Zn) and an oxaliplatin prodrug and including dihydroarteminisin incorporated in its lipid coating layer (NCP-3/DHA).

Figure 19:
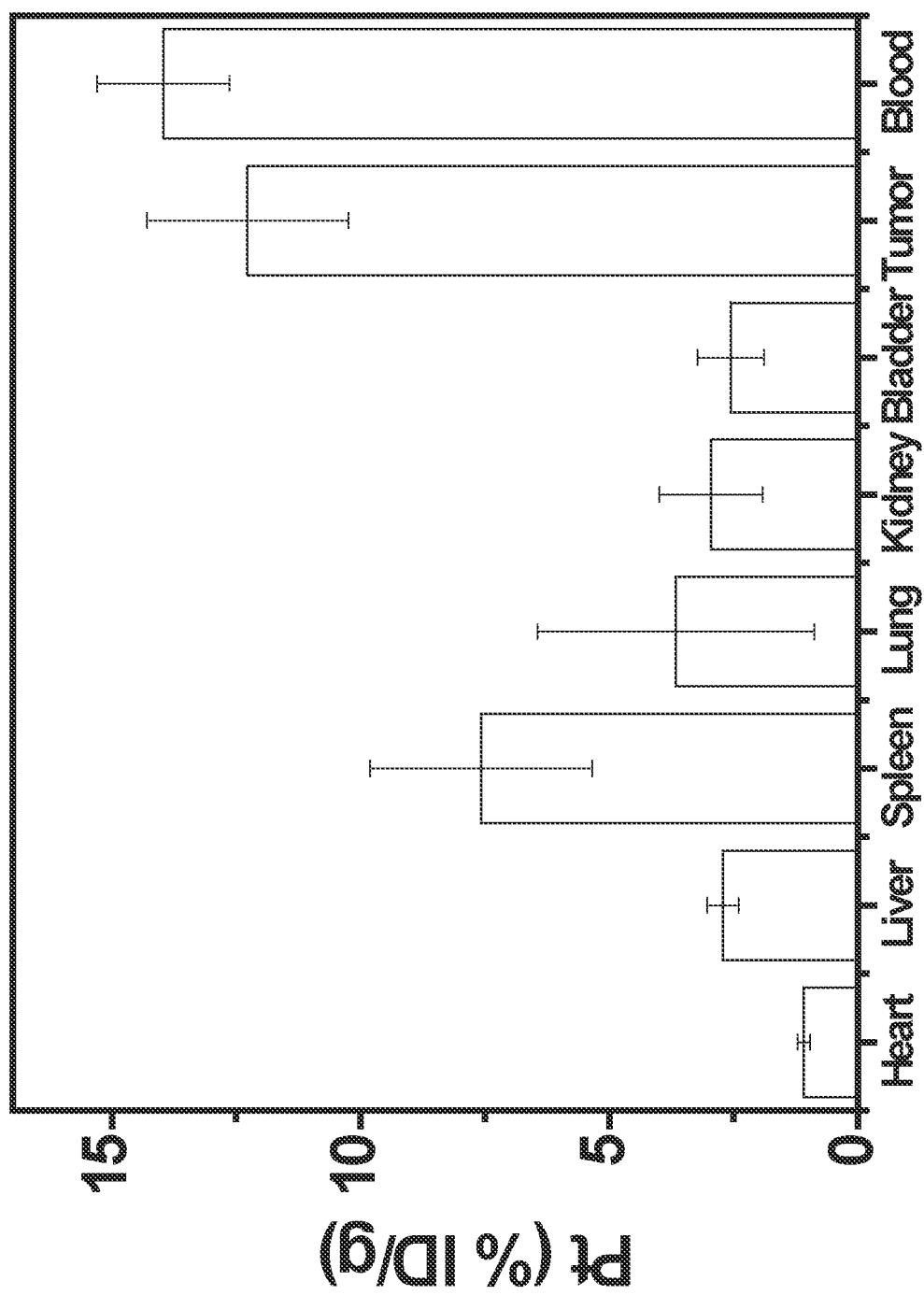

FIG. 19 is a graph of the biodistribution of NCP particles comprising zinc (Zn) and an oxaliplatin prodrug and including dihydroarteminisin incorporated in its lipid coating layer (NCP-3/DHA) after intraperitoneal injection into CT26 murine colorectal adenocarcinoma tumor bearing mice. Platinum (Pt) from the oxaliplatin prodrug was analyzed by inductively coupled plasma-mass spectrometry (ICP-MS).

Figure 20A:
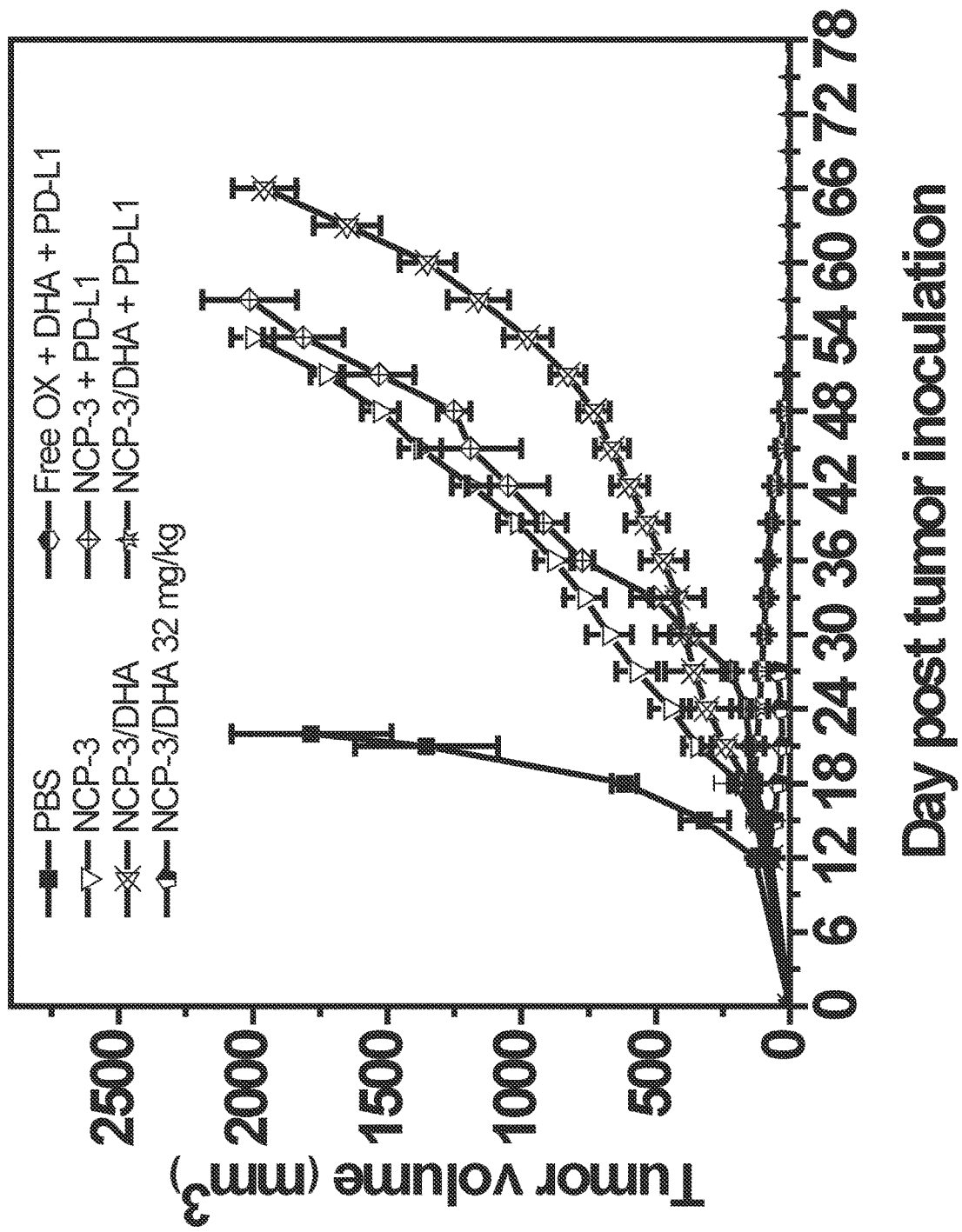

FIG. 20A is a graph showing the in vivo anticancer activity of NCP particles comprising zinc (Zn) and an oxaliplatin (OX) prodrug and including dihydroarteminisin (DHA) incorporated in its lipid coating layer (NCP-3/DHA) with or without checkpoint blockade immunotherapy against CT26 murine colorectal adenocarcinoma tumor bearing mice. Data is provided for mice treated with NCP-3/DHA (left-pointing, x-marked triangles); the same particles without DHA in the lipid coating layer (NCP-3, downward-pointing triangles); a combination of free OX, free DHA, and an anti-programmed death-ligand 1 (PD-L1) antibody (Free OX+DHA+PD-L1, half-filled hexagons); a combination of NCP-3 and PD-L1 antibody (NCP-3+PD-L1, diamonds); a combination of NCP-3/DHA and PD-L1 antibody (NCP-3/DHA+PD-L1, stars), and a higher dosage (32 milligrams per kilogram (mg/kg)) of NCP-3/DHA (half-filled pentagons). As a control, data is shown for mice treated with phosphate buffered saline (PBS, black squares).

Figure 20B:
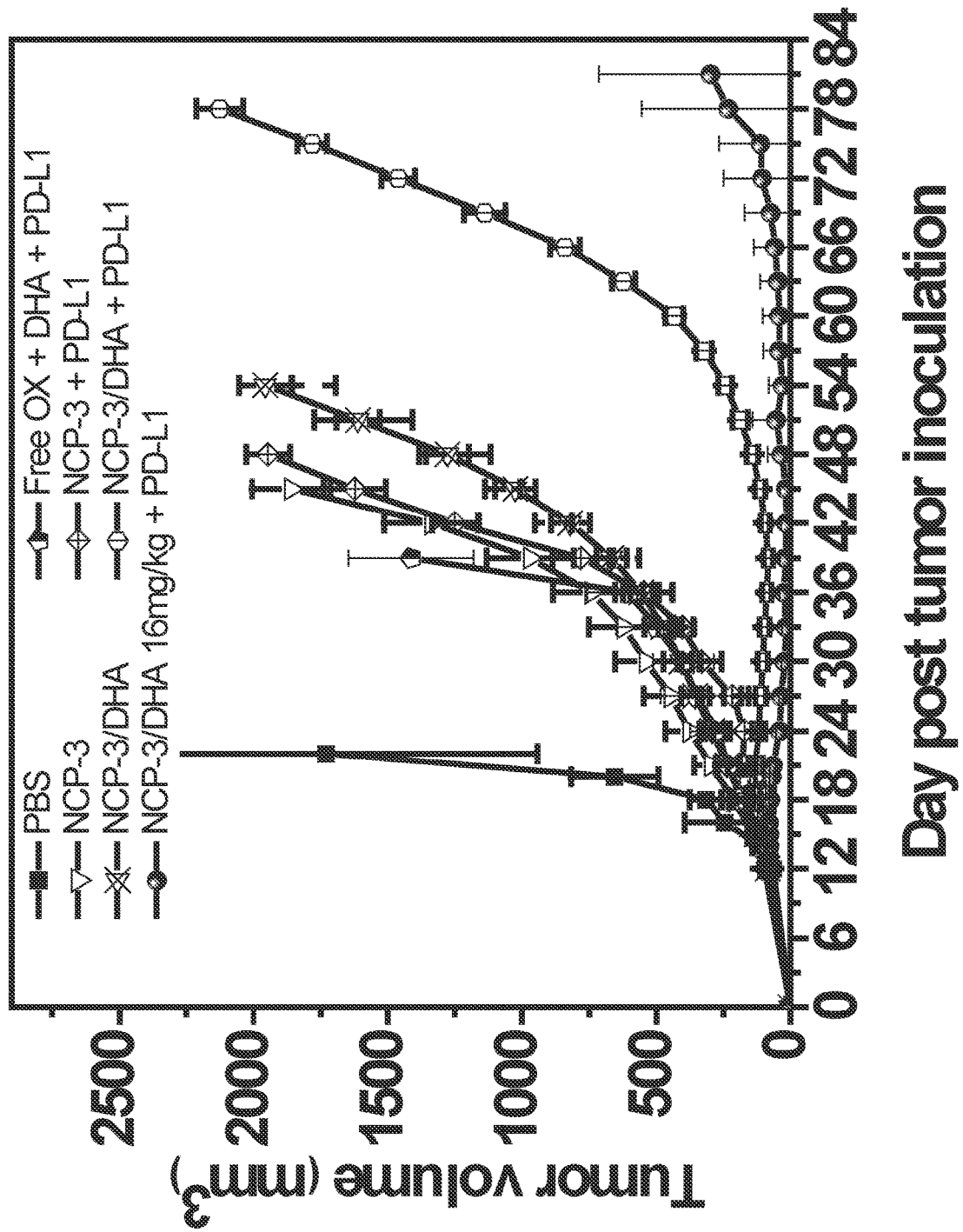

FIG. 20B is a graph showing the in vivo anticancer activity of NCP particles comprising zinc (Zn) and an oxaliplatin (OX) prodrug and including dihydroarteminisin (DHA) incorporated in its lipid coating layer (NCP-3/DHA) with or without checkpoint blockade immunotherapy against MC38 murine colorectal carcinoma tumor bearing mice. Data is provided for mice treated with NCP-3/DHA (left-pointing, x-marked triangles); the same particles without DHA in the lipid coating layer (NCP-3, downward-pointing triangles); a combination of free OX, free DHA, and an anti-programmed death-ligand 1 (PD-L1) antibody (Free OX+DHA+PD-L1, half-filled pentagons); a combination of NCP-3 and PD-L1 antibody (NCP-3+PD-L1, diamonds); a combination of NCP-3/DHA and PD-L1 antibody (NCP-3/DHA+PD-L1, hexagons), and a higher dosage (16 milligrams per kilogram (mg/kg)) of NCP-3/DHA and the PD-L1 antibody (circles). As a control, data is shown for mice treated with phosphate buffered saline (PBS, black squares).

Figure 21:
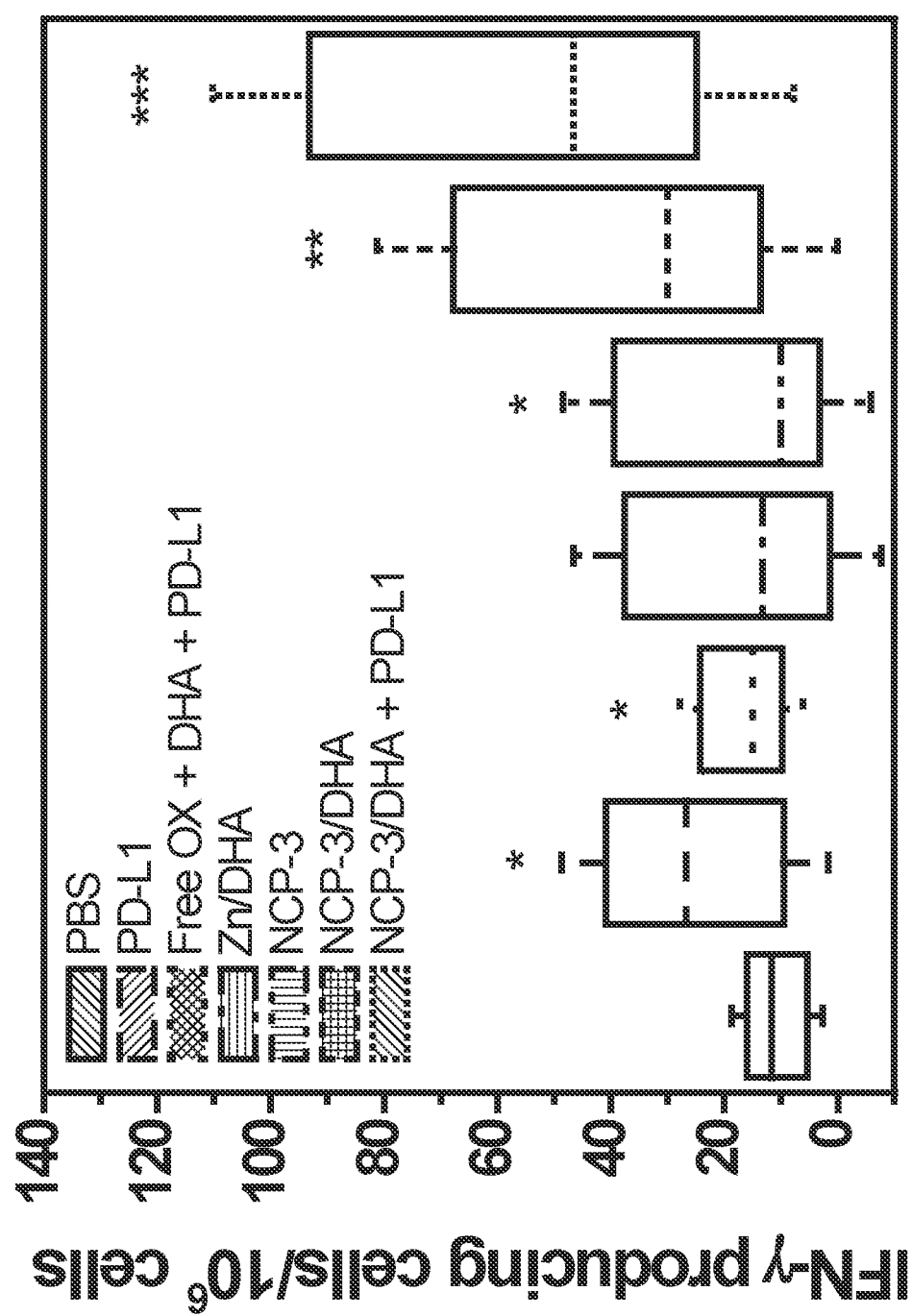

FIG. 21 is a graph of gamma-interferon (IFN-γ) producing T cells detected in spenocytes harvested after treatment with an oxaliplatin (OX) and/or dihydroarteminisin (DHA)-containing or non-containing composition and stimulated with a MC38 tumor-specific lysine-serine-proline repeats (KSP) peptide. Treatments included, from left to right: phosphate buffered saline (PBS), an anti-programmed death-ligand 1 antibody (PD-L1), a combination of free OX, free DHA and PD-L1 antibody (Free OX+DHA+PD-L1), a combination of zinc (Zn) and DHA (Zn/DHA), a lipid-coated NCP particle comprising a core comprising a polymer of Zn and an OX prodrug (NCP-3), the same particle including lipid-modified DHA in the lipid-coating layer (NCP-3/DHA), or a combination of NCP-3/DHA and PD-L1 antibody (NCP-3/DHA+PD-L1).

Figure 22A:
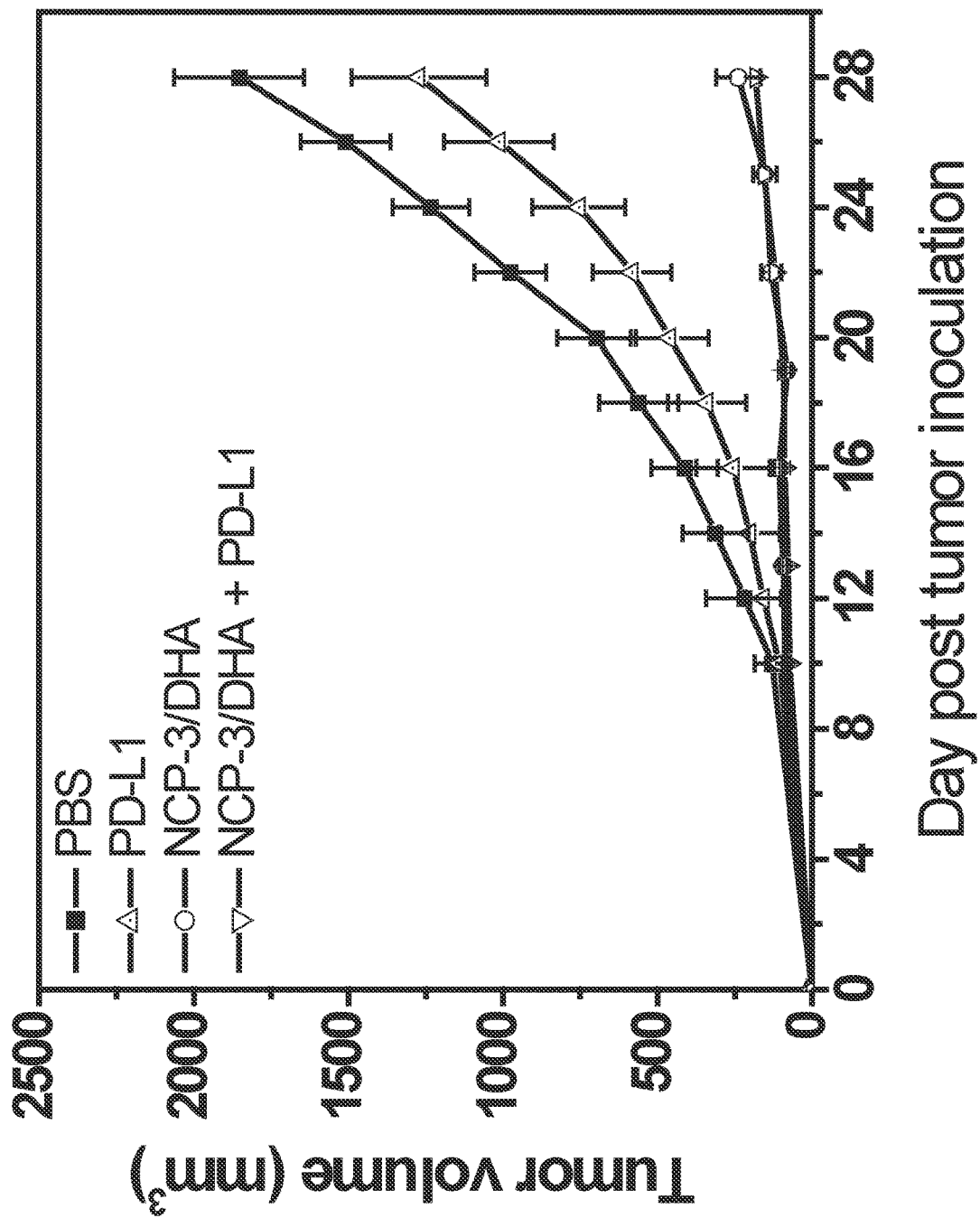

FIG. 22A is a graph showing the in vivo anticancer activity of a lipid-coated NCP particle comprising a core comprising a coordination polymer of zinc and an oxaliplatin prodrug and including a lipid-modified dihydroarteminisin (DHA) in the lipid-coating layer (NCP-3/DHA) against 4T1 triple negative breast cancer tumor bearing mice. Mice were treated with PD-L1 antibody (upward-pointing triangles), NCP-3/DHA (circles), or a combination thereof (downward-pointing triangles). For comparison, data is also provided for mice treated with phosphate buffered saline (PBS, black squares) as a control. Mice were injected intraperitoneally with an oxaliplatin-equivalent dose of 8 milligrams per kilogram once every 3 days starting on day 10.

Figure 22B:
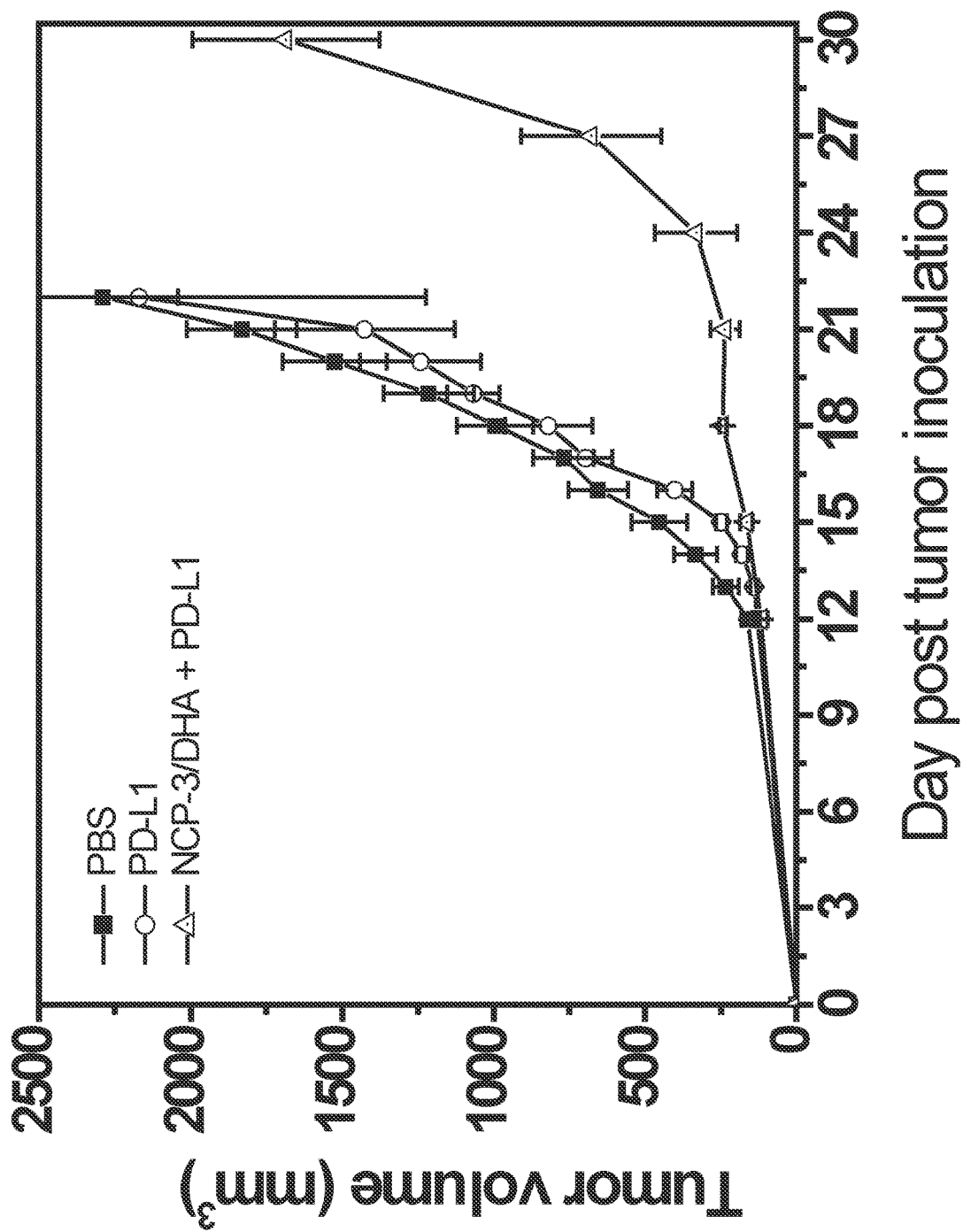

FIG. 22B is a graph showing the in vivo anticancer activity of a lipid-coated NCP particle comprising a core comprising a coordination polymer of zinc and an oxaliplatin prodrug and including a lipid-modified dihydroarteminisin (DHA) in the lipid-coating layer (NCP-3/DHA) against LL/2 non-small cell lung cancer tumor bearing mice. Mice were treated with PD-L1 antibody (circles), or a combination of antibody and NCP-3/DHA (triangles). For comparison, data is also provided for mice treated with phosphate buffered saline (PBS, black squares) as a control. Mice were injected intraperitoneally with an oxaliplatin dose of 8 milligrams per kilogram once every 3 days starting on day 12.

Figure 23A:
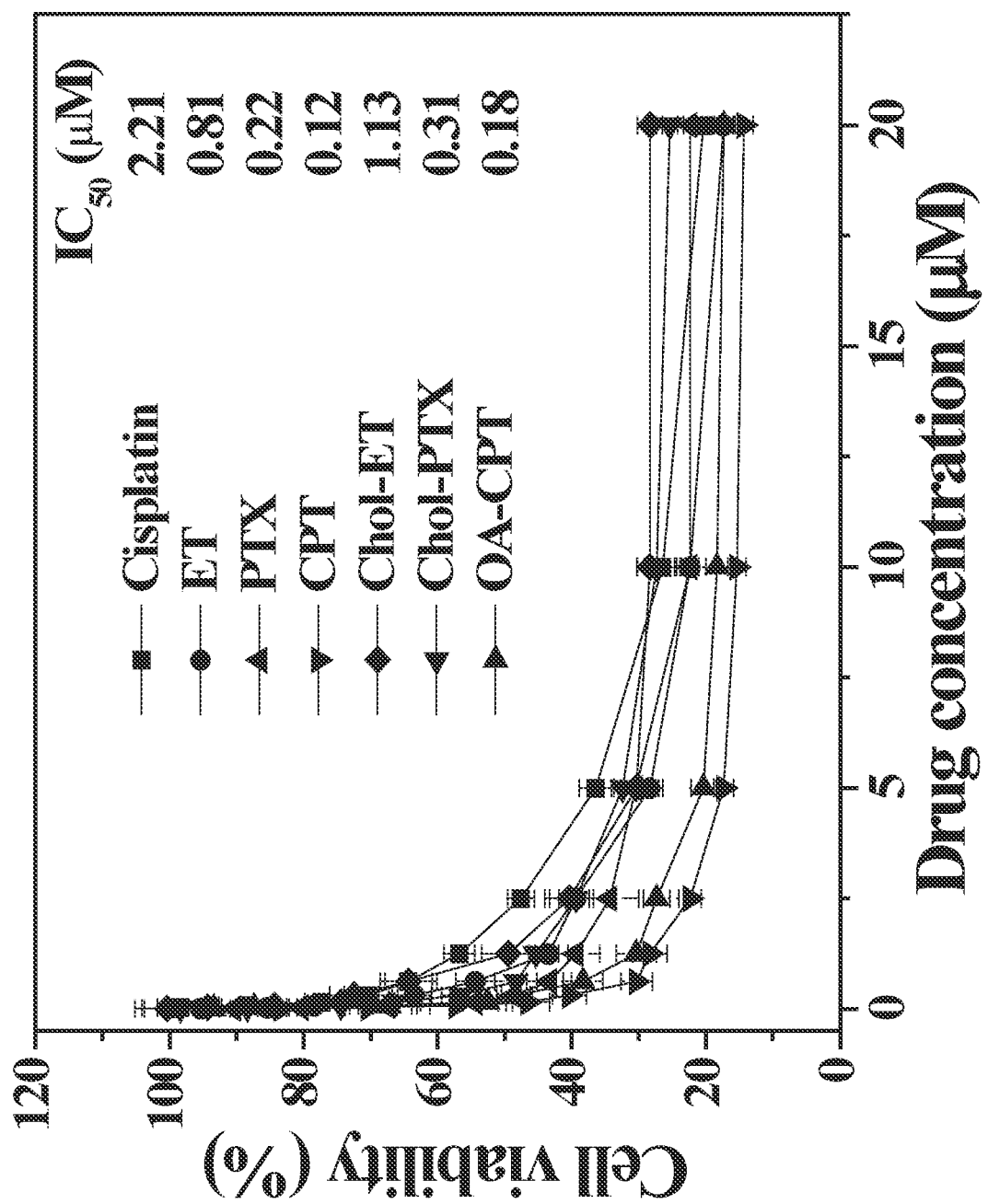

FIG. 23A is a graph showing cytotoxicity in non-small cell lung cancer (NSCLC) A549 cells incubated for 72 hours with compositions including: cisplatin (squares), etoposide (ET, circles), paclitaxel (PTX, upward-pointing triangles), camptothecin (CPT, downward-pointing triangles), cholesterol modified ET (Chol-ET, diamonds), cholesterol-modified PTX (Chol-PTX, leftward-pointing triangles), or oleic acid-modified CPT (OA-CPT, rightward-pointing triangles).

Figure 23B:
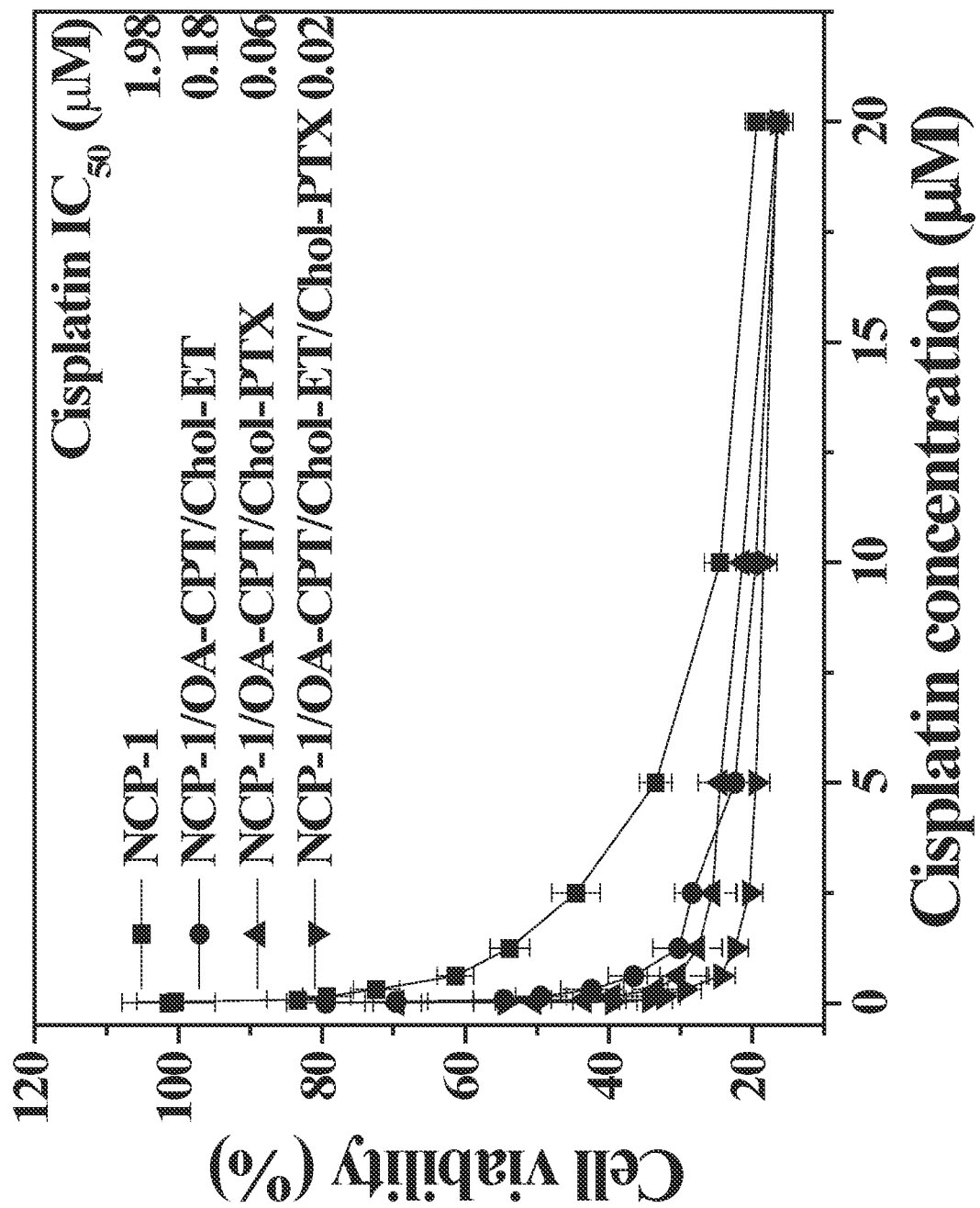

FIG. 23B is a graph showing cytotoxicity in non-small cell lung cancer (NSCLC) A549 cells incubated for 72 hours with compositions including: a NCP particle comprising a cisplatin analogue (NCP-1, squares), NCP-1 with a lipid coating layer comprising oleic acid-modified comptothecin (OA-CPT) and a cholesterol-modified etoposide (Chol-ET) (NCP-1/OA-CPT/Chol-Et, circles), NCP-1 with a lipid coating layer comprising OA-CPT and a cholesterol-modified paclitaxel (Chol-PTX) (NCP-1/OA-CPT/Chol-PTX, upward-pointing triangles), or NCP-1 with a lipid coating layer comprising OA-CPT, Chol-ET and Chol-PTX (NCP-1/OA-CPT/Chol-ET/Chol-PTX, downward-pointing triangles).

Figure 24A:
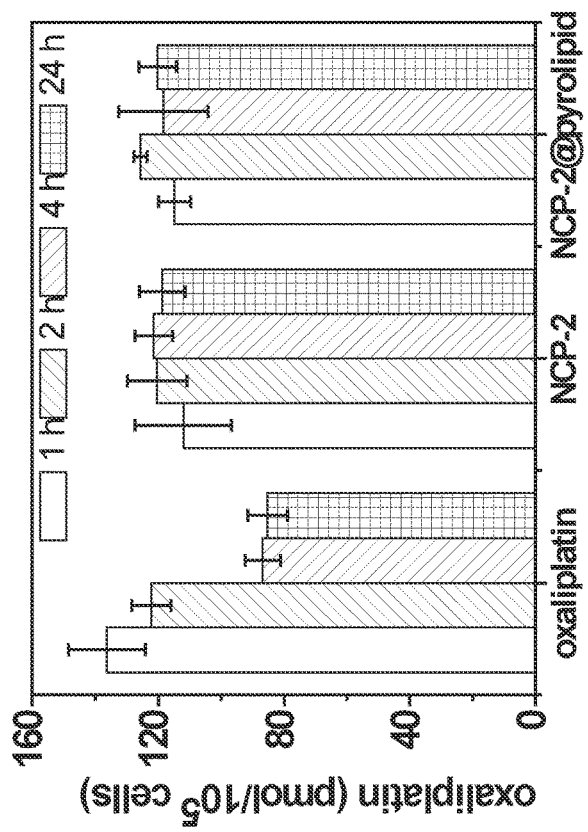

FIG. 24A is a graph showing cellular uptake into CT26 murine colorectal adenocarcinoma cells of, from left to right, oxaliplatin, a NCP particle comprising zinc and an oxaliplatin prodrug (NCP-2), and NCP-2 comprising pyrolipid in a lipid coating layer (NCP-2@pyrolipid). Platinum (Pt) concentration (in picomoles (pmol) per $10^5$ cells) was determined by inductively-coupled plasma-mass spectrometry (ICP-MS) after 1, 2, 4, and 24 hours.

Figure 24B:
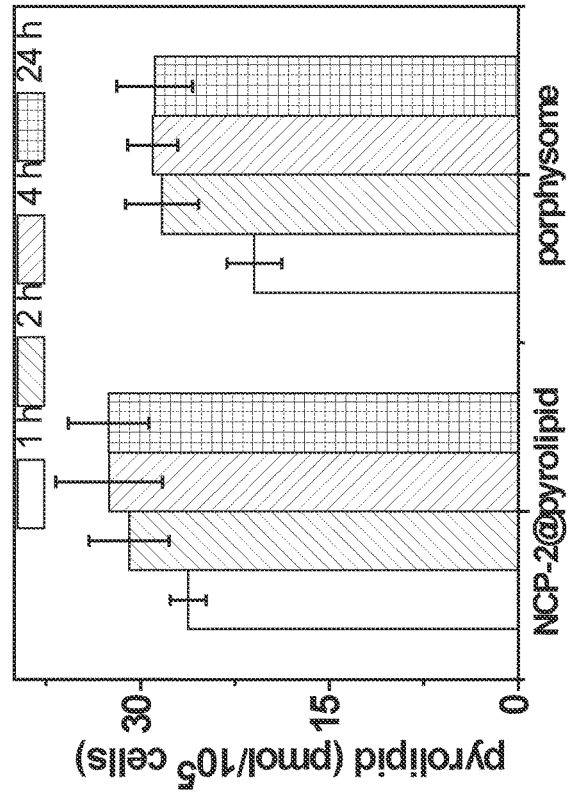

FIG. 24B is a graph showing cellular uptake into CT26 murine colorectal adenocarcinoma cells of, from left to right, a NCP particle comprising a zinc and oxaliplatin prodrug core and pyrolipid in a lipid coating layer (NCP-2@pyrolipid), and of porphysome. Pyrolipid concentration (in picomoles (pmol) per $10^5$ cells) was determined by ultraviolet-visible spectrometry (UV-Vis) after 1, 2, 4, and 24 hours.

Figure 25A:
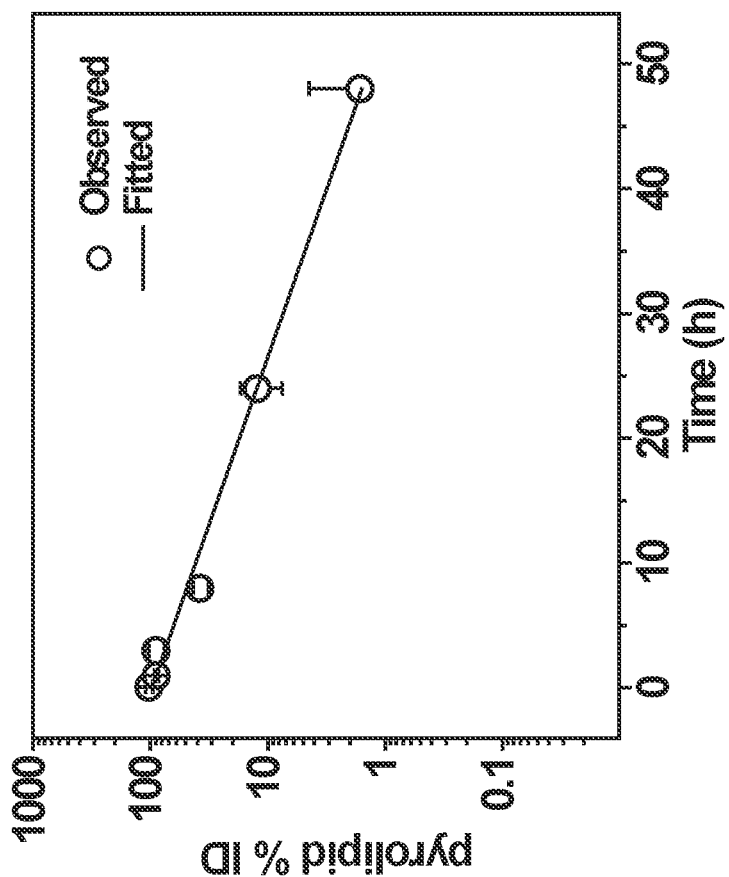

FIG. 25A is a graph showing the percentage (%) of platinum remaining from the initial dose (ID) versus time from the pharmacokinetics and biodistribution of NCP particles comprising a zinc and oxaliplatin prodrug core and pyrolipid in a lipid coating layer (NCP-2@pyrolipid) after intravenous injection into CT26 murine colorectal adenocarcinoma tumor bearing mice. Platinum (Pt) was analyzed by inductively-coupled plasma mass spectrometry (ICP-MS).

Figure 25B:
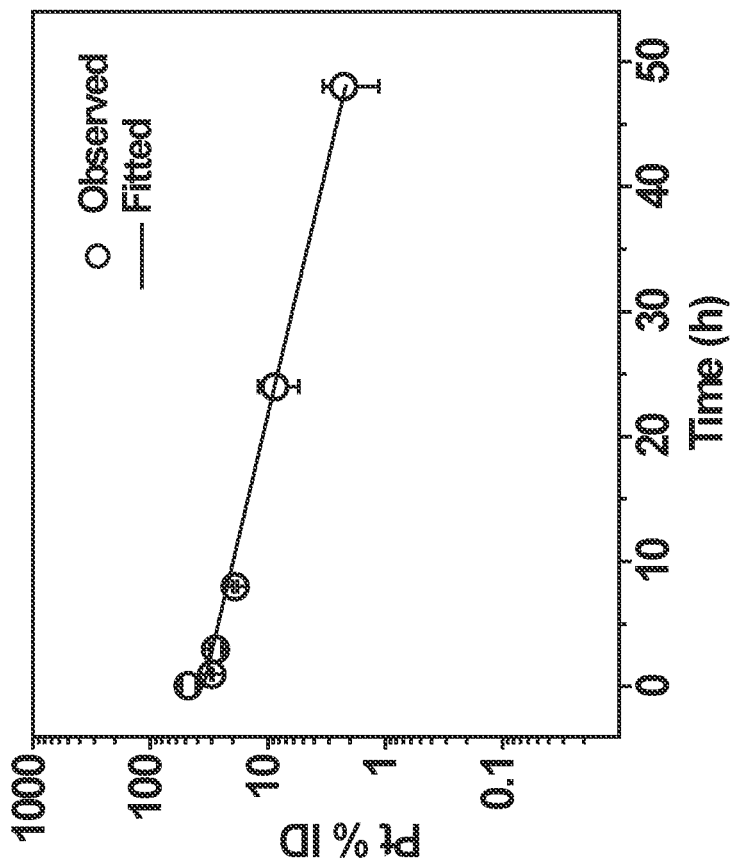

FIG. 25B is a graph showing the percentage (%) of pyrolipid remaining from the initial dose (ID) versus time from the study described for FIG. 25A. Pyrolipid was analyzed via ultraviolet-visible spectrometry (UV-Vis).

Figure 26:
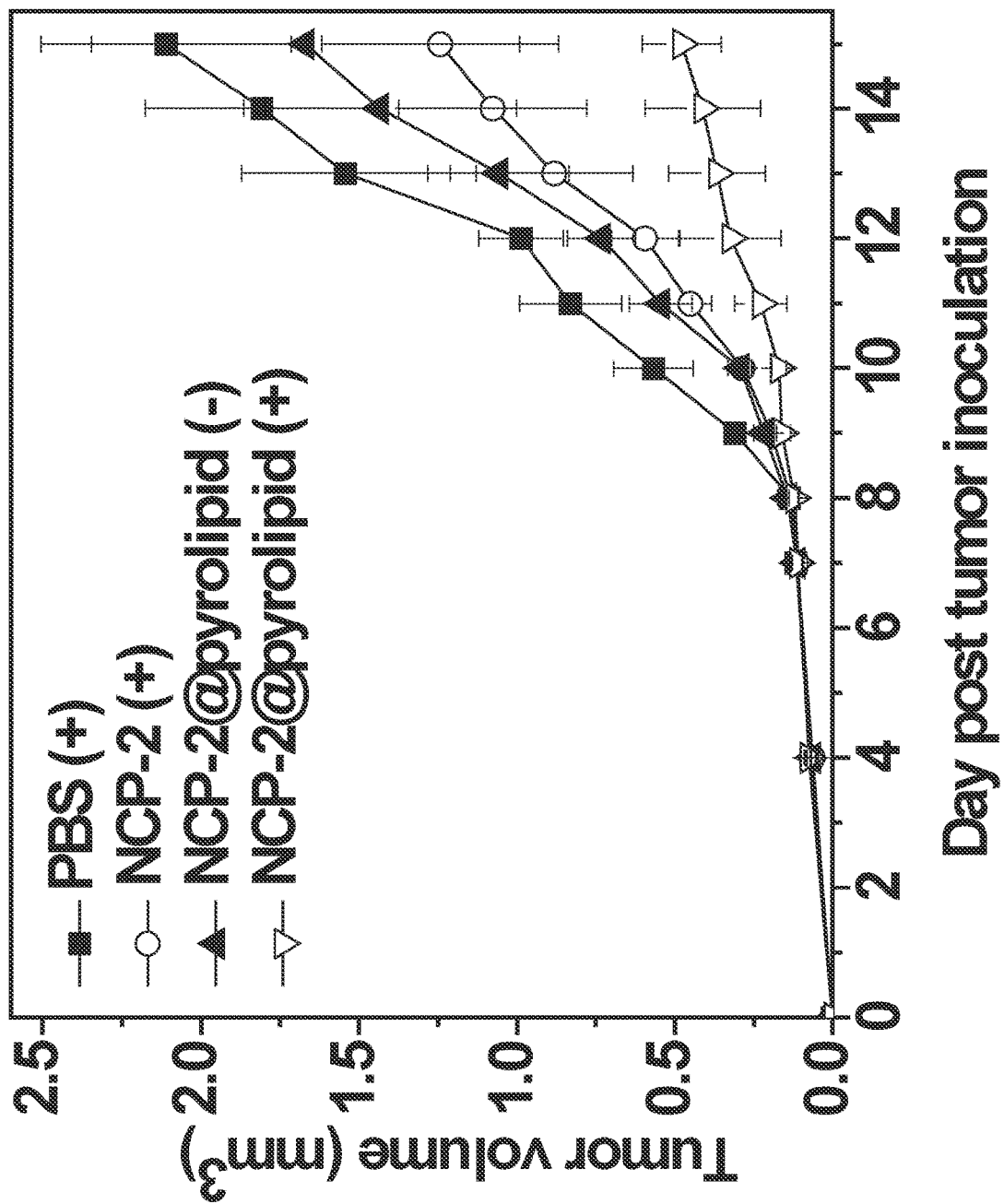

FIG. 26 is a graph showing the in vivo anticancer activity of a lipid-coated NCP particle comprising a core that comprises a polymer of zinc and an oxaliplatin analogue and a lipid-coating layer comprising pyrolipid (NCP-2@pyrolipid) in CT26 murine colorectal adenocarcinoma tumor bearing mice. Mice were intravenously injected with NCP-2@pyrolipid (downward-pointing triangles) or the same NCP particle without pyrolipid (NCP-2, circles) at an oxaliplatin analogue dose of 2 milligrams per kilogram (mg/kg) followed by irradiation (+) at 670 nanometers (nm), 100 milliWatts per square centimeter (mW/cm$^2$) for 30 minutes 24 hours post injection every four days for a total of two treatments. As a control, data is also shown for mice treated with phosphate buffered saline (PBS, squares) or NCP-2@pyrolipid without irradiation (−) (upward-pointing triangles).

Figure 27:
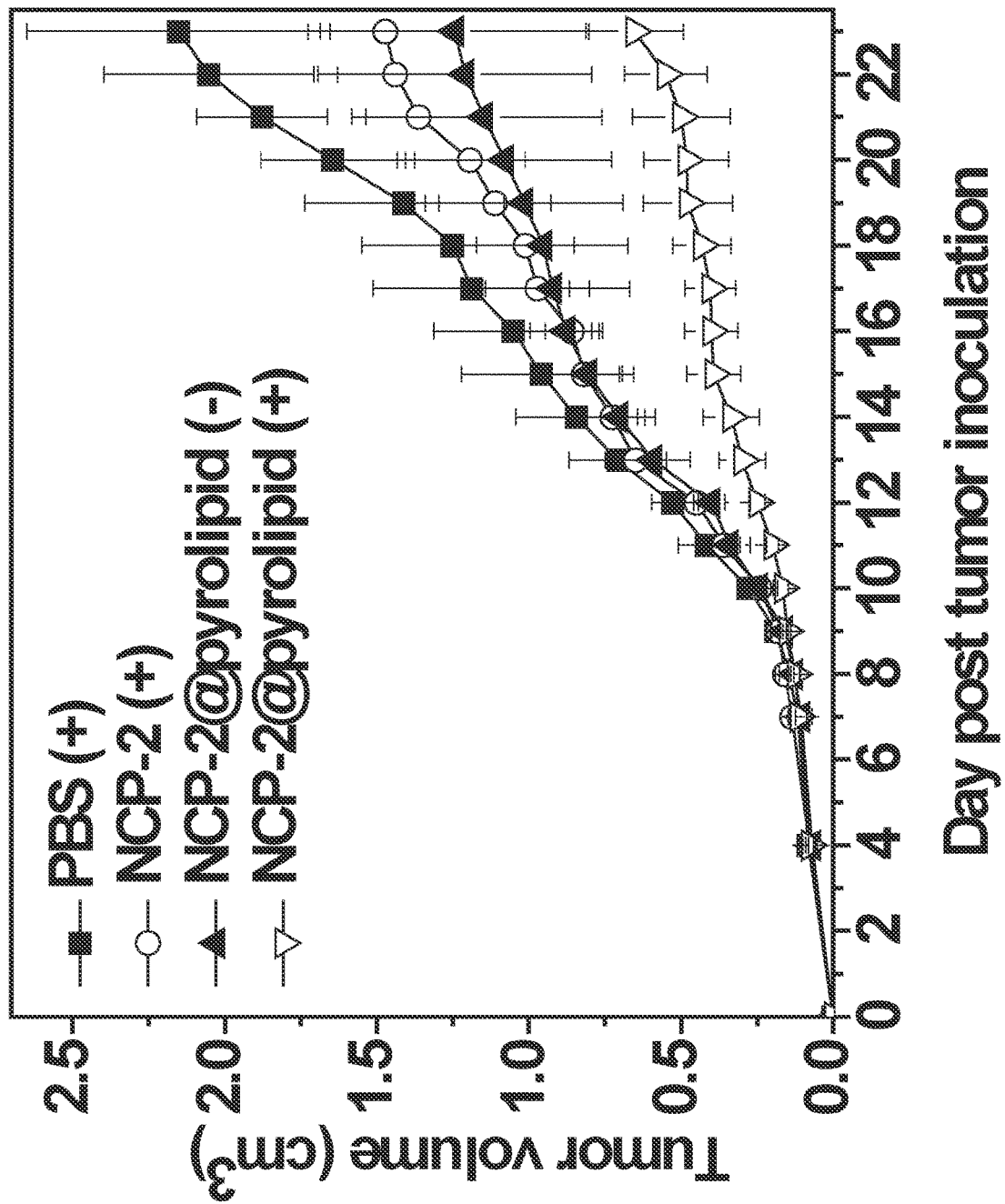

FIG. 27 is a graph showing the in vivo anticancer activity of a lipid-coated NCP particle comprising a core that comprises a polymer of zinc and an oxaliplatin analogue and a lipid-coating layer comprising pyrolipid (NCP-2@pyrolipid) in HT29 human colorectal tumor bearing mice. Mice were intravenously injected with NCP-2@pyrolipid (downward-pointing triangles) or the same NCP particle without pyrolipid (NCP-2) (circles) at an oxaliplatin analogue dose of 2 milligrams per kilogram (mg/kg) followed by irradiation (+) at 670 nanometers (nm), 100 milliWatts per square centimeter (mW/cm$^2$) for 30 minutes 24 hours post injection every four days for a total of four treatments. As a control, data is also shown for mice treated with phosphate buffered saline (PBS, squares) or NCP-2@pyrolipid without irradiation (−) (upward-pointing triangles).

Figure 28A:
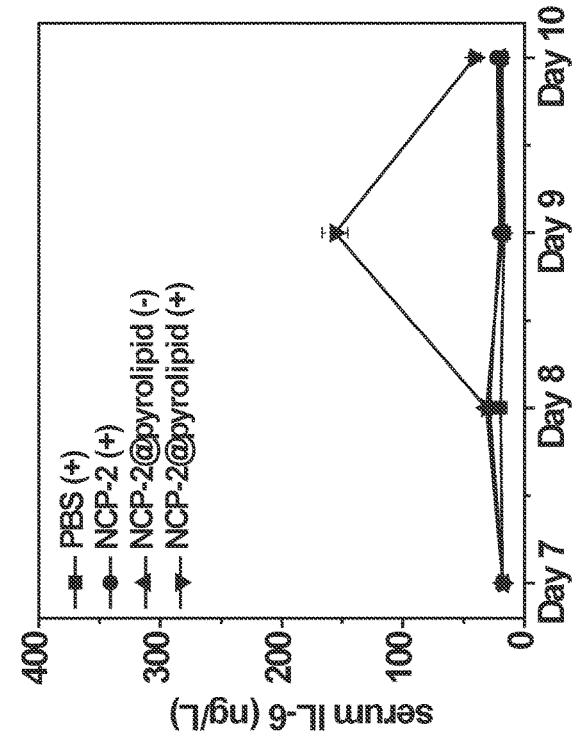

FIG. 28A is a graph of serum gamma interferon (IFN-γ) concentration (in nanograms per liter (ng/L)) in CT26 murine colorectal adenocarcinoma tumor bearing mice on days 7, 8, 9, and 10 post tumor inoculation (days 0, 1, 2, and 3 post first treatment) treated as described in FIG. 26.

Figure 28B:
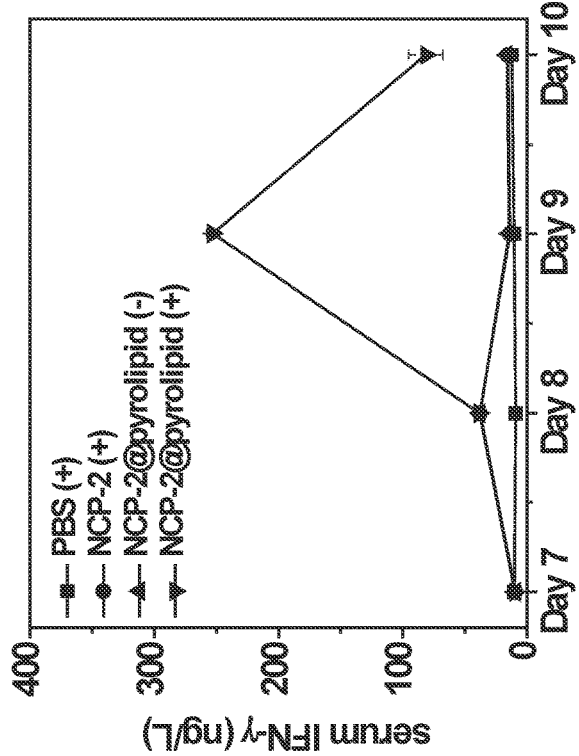

FIG. 28B is a graph of serum interleukin 6 (IL-6) concentration (in nanograms per liter (ng/L)) in CT26 murine colorectal adenocarcinoma tumor bearing mice on days 7, 8, 9, and 10 post tumor inoculation (days 0, 1, 2, and 3 post first treatment) treated as described in FIG. 26.

Figure 28C:
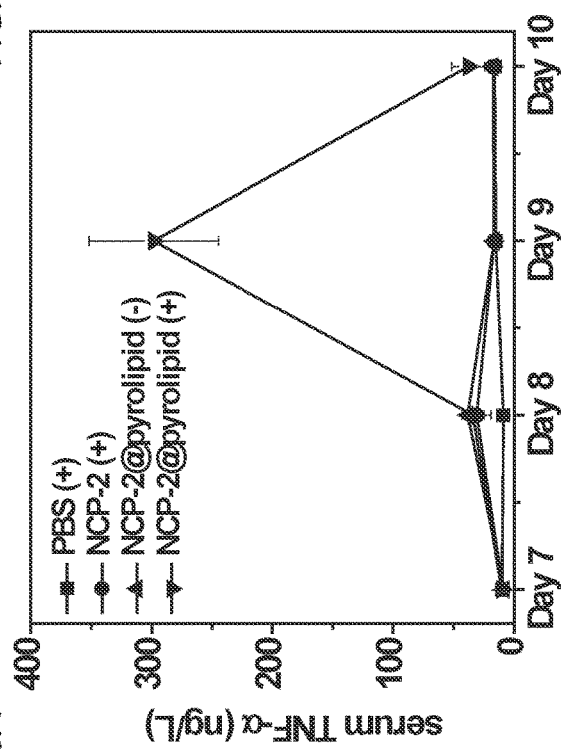

FIG. 28C is a graph of serum tumor necrosis factor alpha (TNF-α) concentration (in nanograms per liter (ng/L)) in CT26 murine colorectal adenocarcinoma tumor bearing mice on days 7, 8, 9, and 10 post tumor inoculation (days 0, 1, 2, and 3 post first treatment) treated as described in FIG. 26.

Figure 29B:
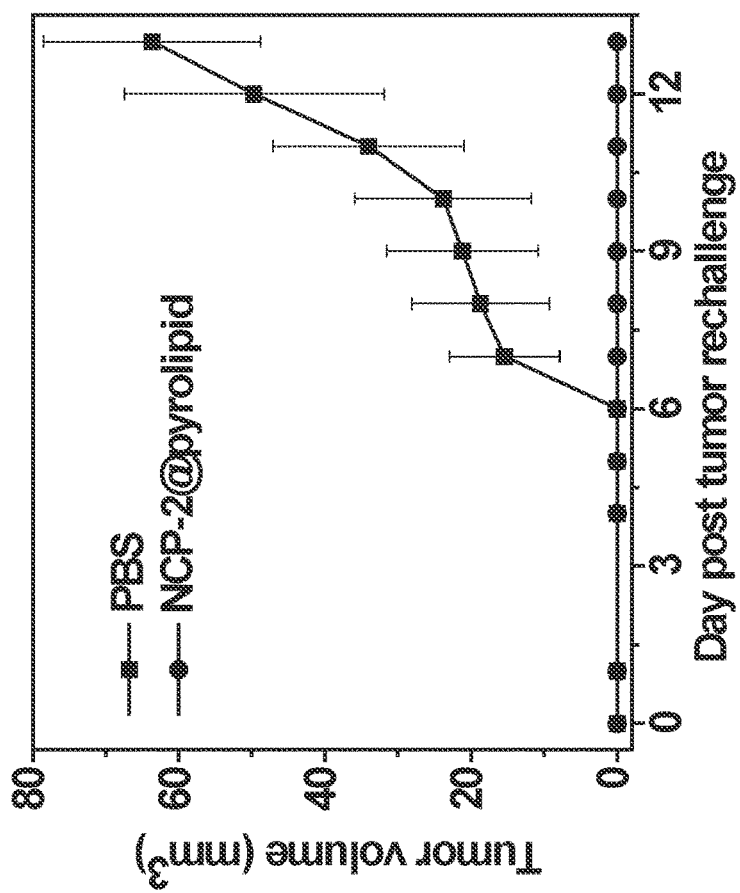
Figure 29A:
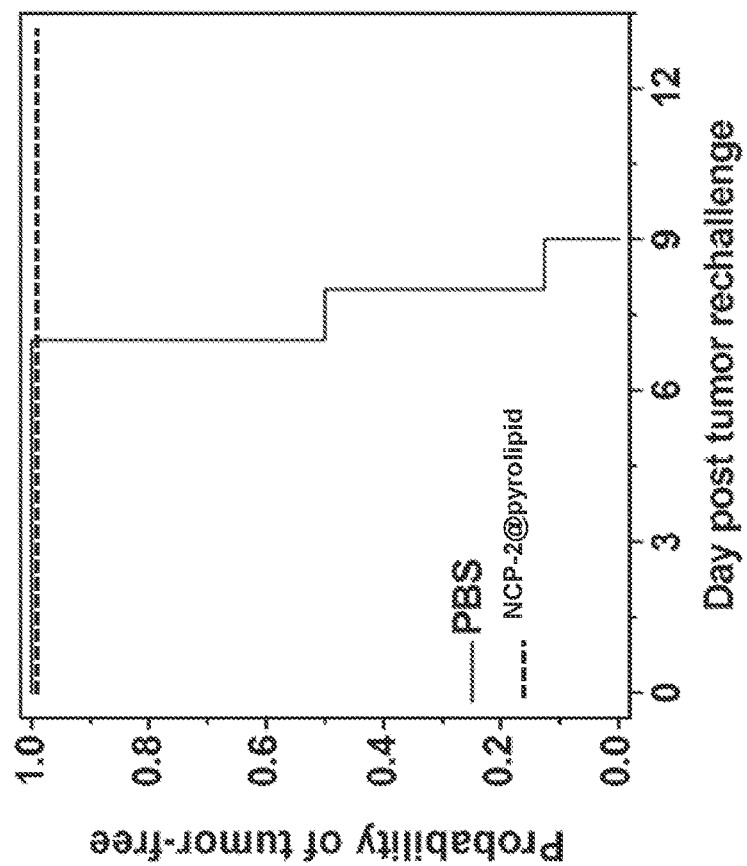

FIG. 29A is a graph showing the probability of tumor-free mice after re-challenge with live tumor cells in mice previously vaccinated with nanoparticle-treated cancer cells. BALB/c mice were inoculated subcutaneously with CT26 murine colorectal adenocarcinoma cells that had been treated with light and a NCP particle comprising a zinc and oxaliplatin analogue core and a lipid coating layer comprising pyrolipid (NCP-2@pyrolipid, dotted line). Seven days after inoculation, the mice were re-challenged with live CT26 cells. For comparison, the probability of tumor-free mice after re-challenge in mice originally vaccinated with phosphate buffered saline (PBS)-treated cancer cells is also shown (solid line).

FIG. 29B is a graph showing tumor growth curves of re-challenged tumors in mice inoculated with phosphate buffered saline (PBS, squares) as a control or inoculated with CT26 murine colorectal adenocarcinoma cells that had been treated with light and a NCP particle comprising a zinc and oxaliplatin analogue core and a lipid coating layer comprising pyrolipid (NCP-2@pyrolipid, circles).

Figure 29C:
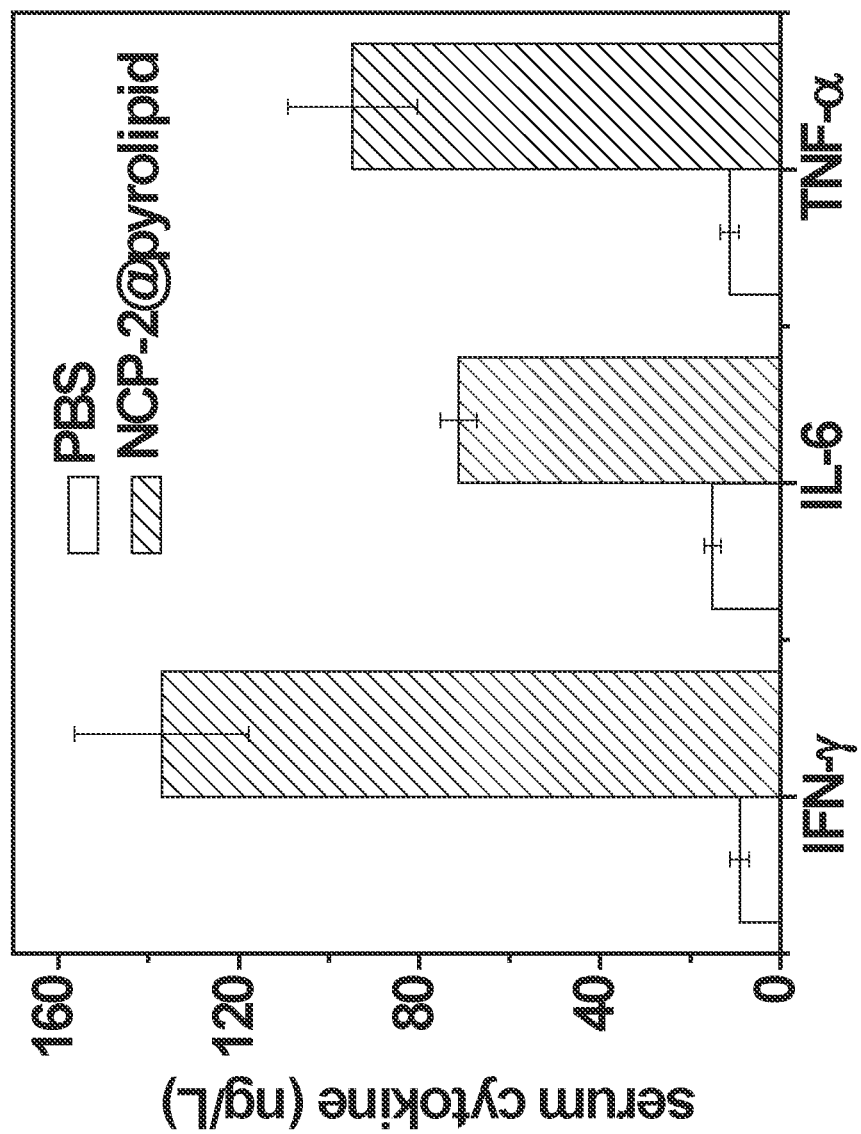
Figure 30B:
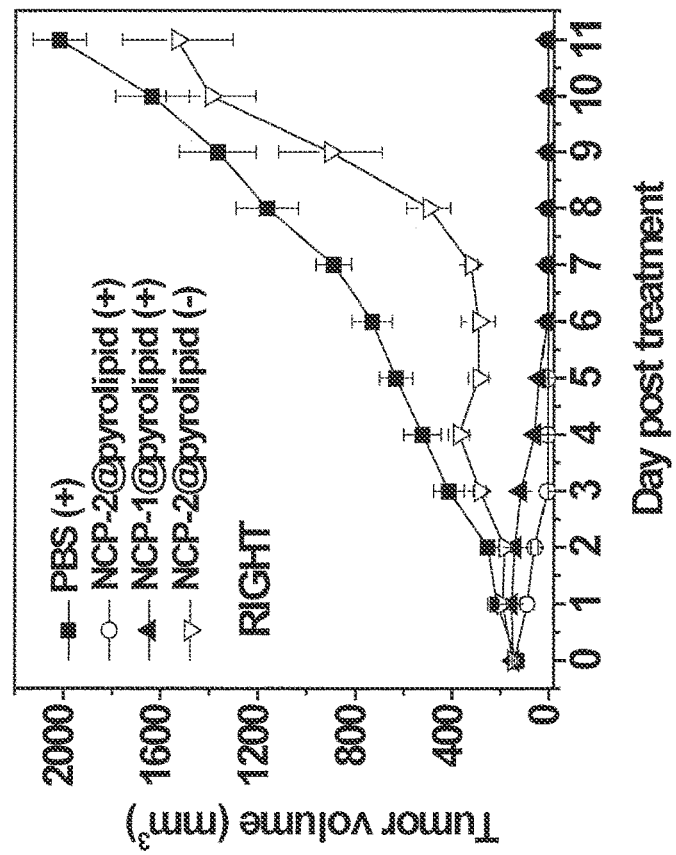
Figure 30A:
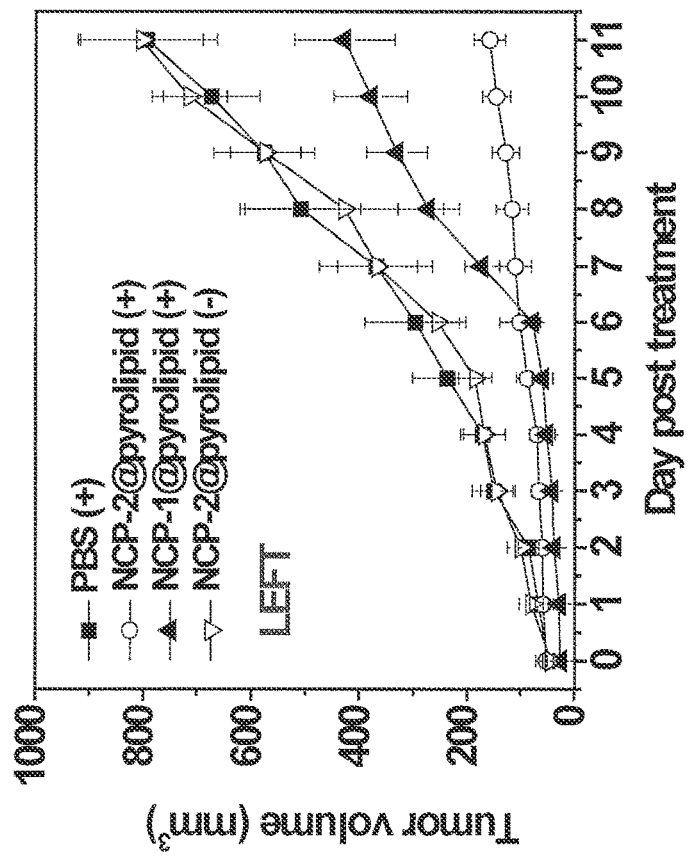

FIG. 29C is a graph showing the serum concentrations (in nanograms per liter (ng/L)) of, from left to right, interferon gamma (IFN-γ), interleukin 6 (IL-6), and tumor necrosis factor alpha (TNF-α) (reported in nanograms per liter (ng/L)) in the mice described for FIG. 30A one day after the first tumor inoculation. Data for mice inoculated with PBS-treated tumor cells is shown in open bars, while data for mice inoculated with nanoparticle/light-treated tumor cells in shown in striped bars.

FIG. 30A is a graph showing the abscopal effect of a NCP particle comprising an oxaliplatin analogue and coated with a lipid coating layer comprising pyrolipid (NCP-2@pyrolipid). The graph shows the tumor growth curves of tumors in the left flank of mice inoculated in both the left and right flanks with CT26 murine colorectal adenocarcinoma cells and then treated in the right flank with NCP-2@pyrolipid and light (NCP-2@pyrolipid (+), circles), NCP-2@pyrolipid without light (NCP-2@pyrolipid (−), downward-pointing triangles), a cisplatin bisphosphonate-containing NCP particle with a pyrolipid-containing lipid coating layer and light (NCP-1@pyrolipid (+), upward-pointing triangles), or phosphate buffered saline and light (PBS (+), squares).

FIG. 30B is a graph showing the antitumor effect of a NCP particle comprising an oxaliplatin analogue and coated with a lipid coating layer comprising pyrolipid (NCP-2@pyrolipid). The graph shows the tumor growth curves of tumors in the right flank of mice inoculated in both the left and right flanks with CT26 murine colorectal adenocarcinoma cells and then treated in the right flank with NCP-2@pyrolipid and light (NCP-2@pyrolipid (+), circles), NCP-2@pyrolipid without light (NCP-2@pyrolipid (−), downward-pointing triangles), a cisplatin bisphosphonate-containing NCP particle with a pyrolipid-containing lipid coating layer and light (NCP-1@pyrolipid (+), upward-pointing triangles), or phosphate buffered saline and light (PBS (+), squares).

Figure 31A:
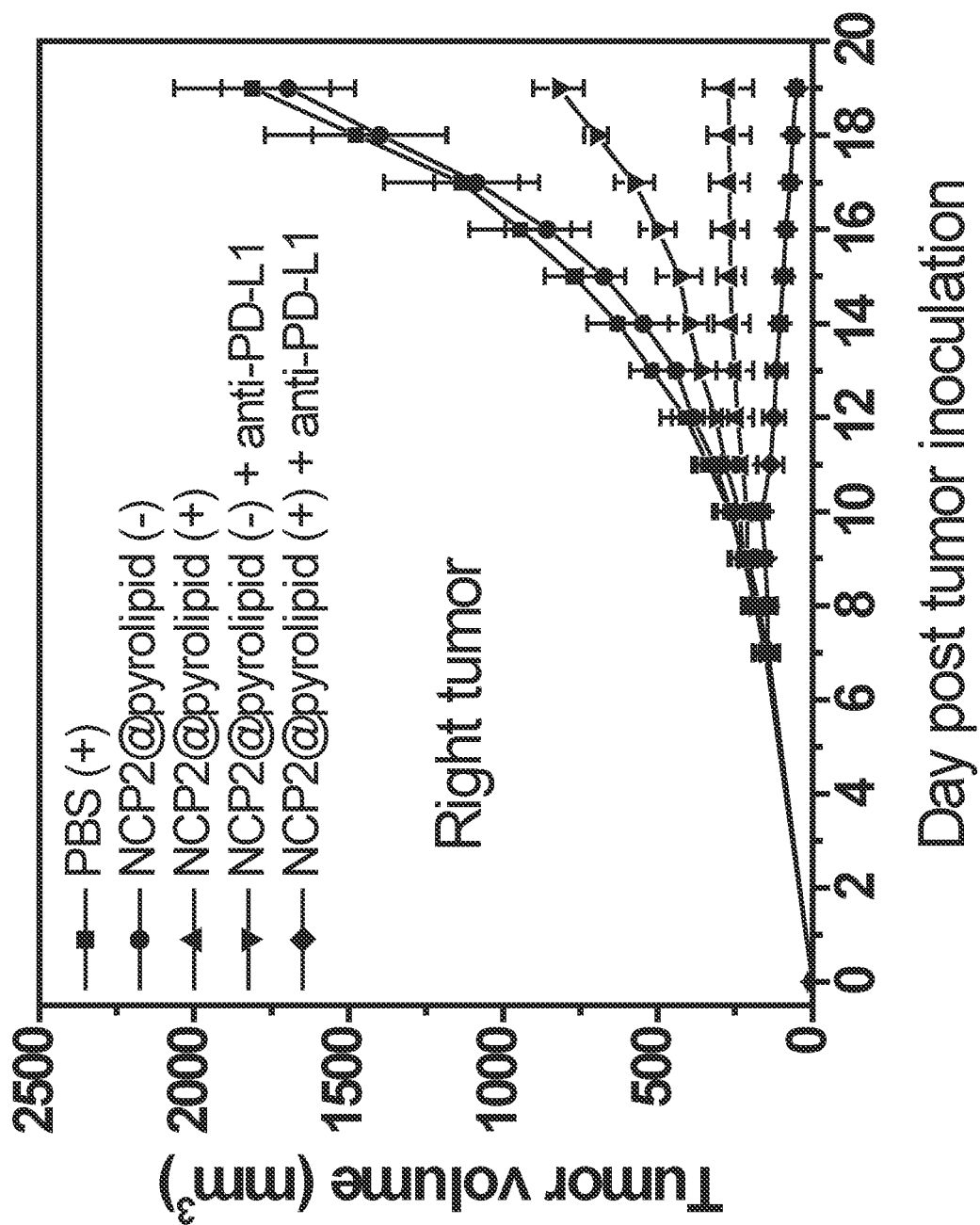

FIG. 31A is a graph of the tumor growth curves of tumors in the right flanks of mice inoculated in both the left and right flanks with MC38 murine colorectal carcinoma cells and then treated in the right flank with a NCP particle comprising an oxaliplatin analogue and coated with a lipid coating layer including pyrolipid (NCP-2@pyrolipid) and light (NCP-2@pyrolipid (+), upward-pointing triangles), NCP-2@pyrolipid without light (NCP-2@pyrolipid (−), circles), NCP-2@pyrolipid, light, and an anti-programmed death-ligand 1 (PD-L1) antibody (NCP-2@pyrolipid (+)+anti-PD-L1, diamonds), NCP-2@pyrolipid and anti-PD-L1 antibody without light (NCP-2@pyrolipid (−)+anti-PD-L1, downward-pointing triangles) or phosphate buffered saline and light (PBS (+), squares).

Figure 31B:
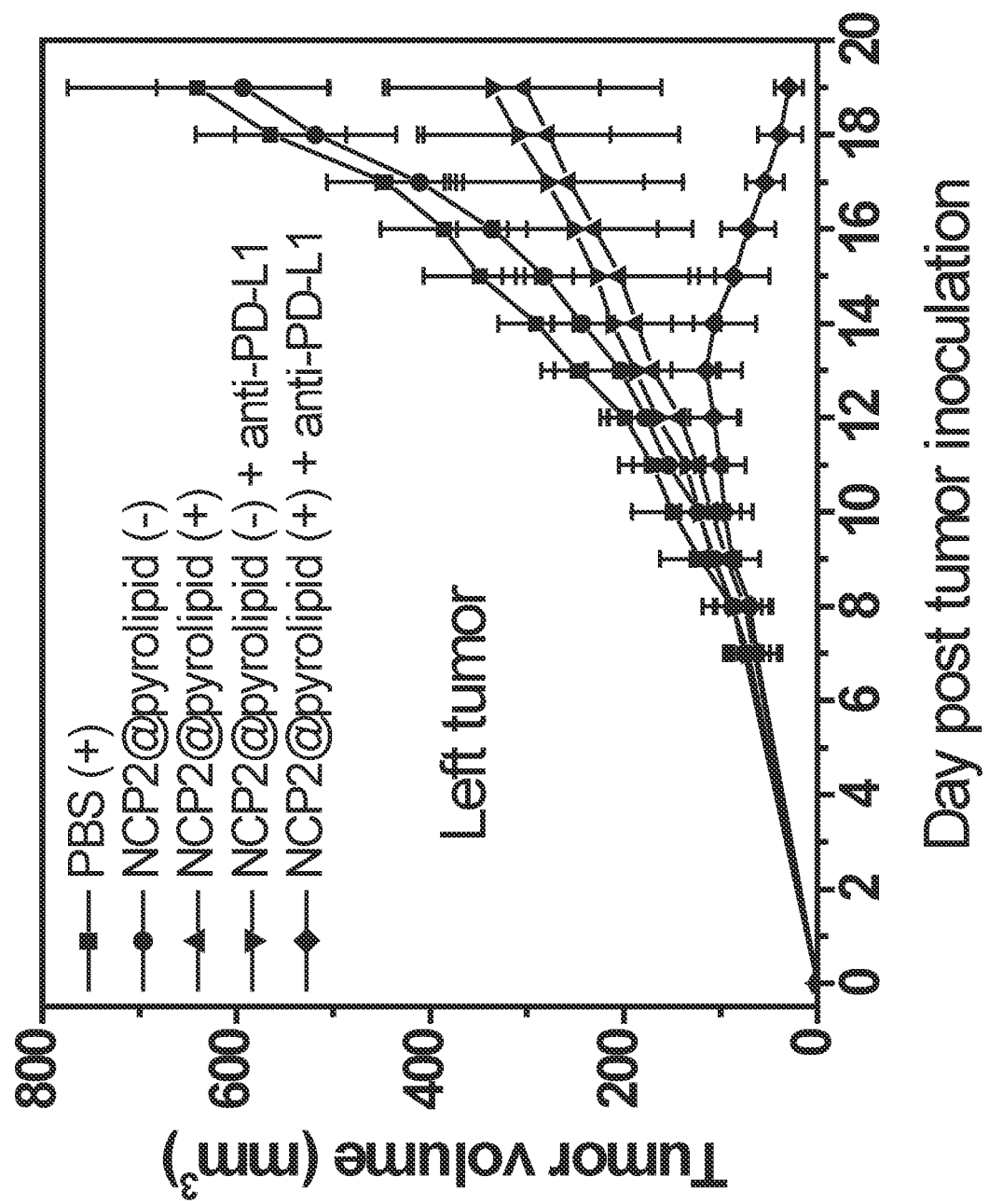

FIG. 31B is a graph of the tumor growth curves of tumors in the left flanks of mice inoculated in both the left and right flanks with MC38 murine colorectal carcinoma cells and then treated in the right flank with a NCP particle comprising an oxaliplatin analogue and coated with a lipid coating layer including pyrolipid (NCP-2@pyrolipid) and light (NCP-2@pyrolipid (+), upward-pointing triangles), NCP-2@pyrolipid without light (NCP-2@pyrolipid (−), circles), NCP-2@pyrolipid, light, and an anti-programmed death-ligand 1 (PD-L1) antibody (NCP-2@pyrolipid (+)+anti-PD-L1, diamonds), NCP-2@pyrolipid and anti-PD-L1 antibody without light (NCP-2@pyrolipid (−)+anti-PD-L1, downward-pointing triangles) or phosphate buffered saline and light (PBS (+), squares).

Figure 32B:
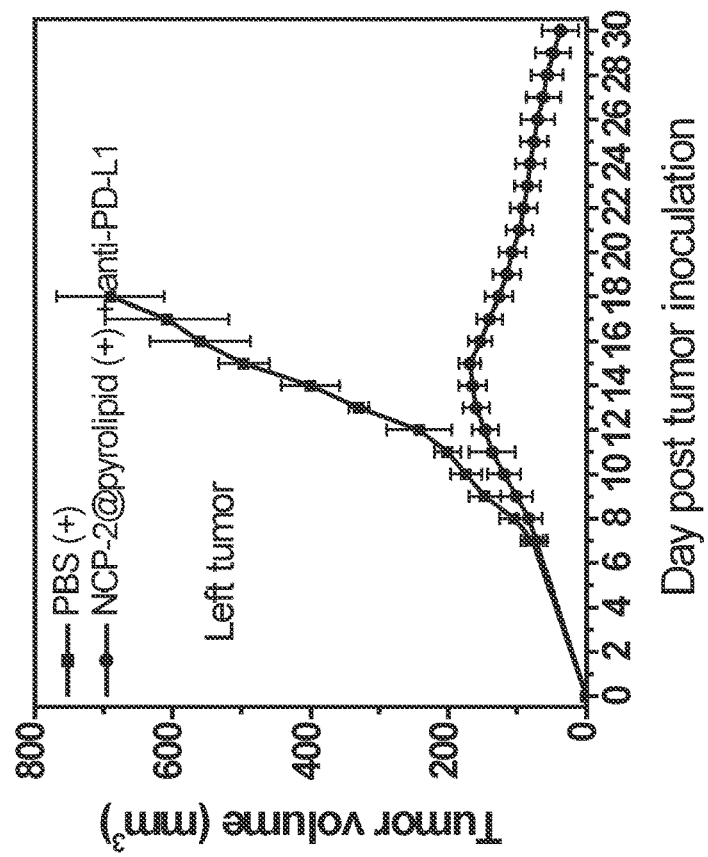
Figure 32A:
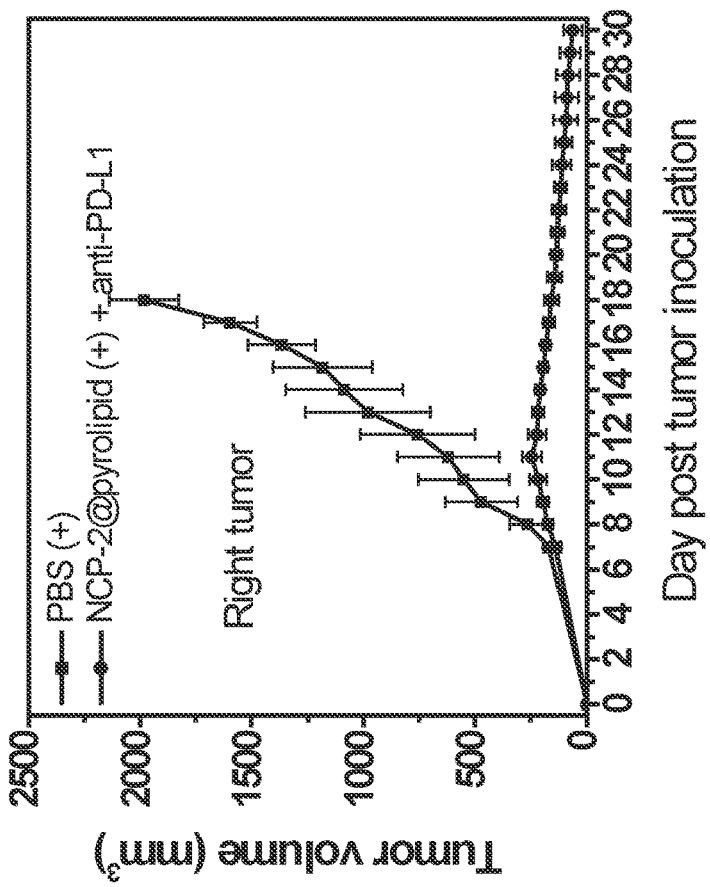

FIG. 32A is a graph of the tumor growth curves of tumors in the right flanks of mice inoculated in both the left and right flanks with CT26 murine colorectal adenocarcinoma cells and then treated in the right flank with a NCP particle comprising an oxaliplatin analogue and coated with a lipid coating layer including pyrolipid (NCP-2@pyrolipid) and light and an anti-programmed death-ligand 1 (PD-L1) antibody (NCP-2@pyrolipid (+)+anti-PD-L1, circles) or phosphate buffered saline and light (PBS (+), squares).

FIG. 32B is a graph of the tumor growth curves of tumors in the left flanks of mice inoculated in both the left and right flanks with CT26 murine colorectal adenocarcinoma cells and then treated in the right flank with a NCP particle comprising an oxaliplatin analogue and coated with a lipid coating layer including pyrolipid (NCP-2@pyrolipid) and light and an anti-programmed death-ligand 1 (PD-L1) antibody (NCP-2@pyrolipid (+)+anti-PD-L1, circles) or phosphate buffered saline and light (PBS (+), squares).

Figure 33A:
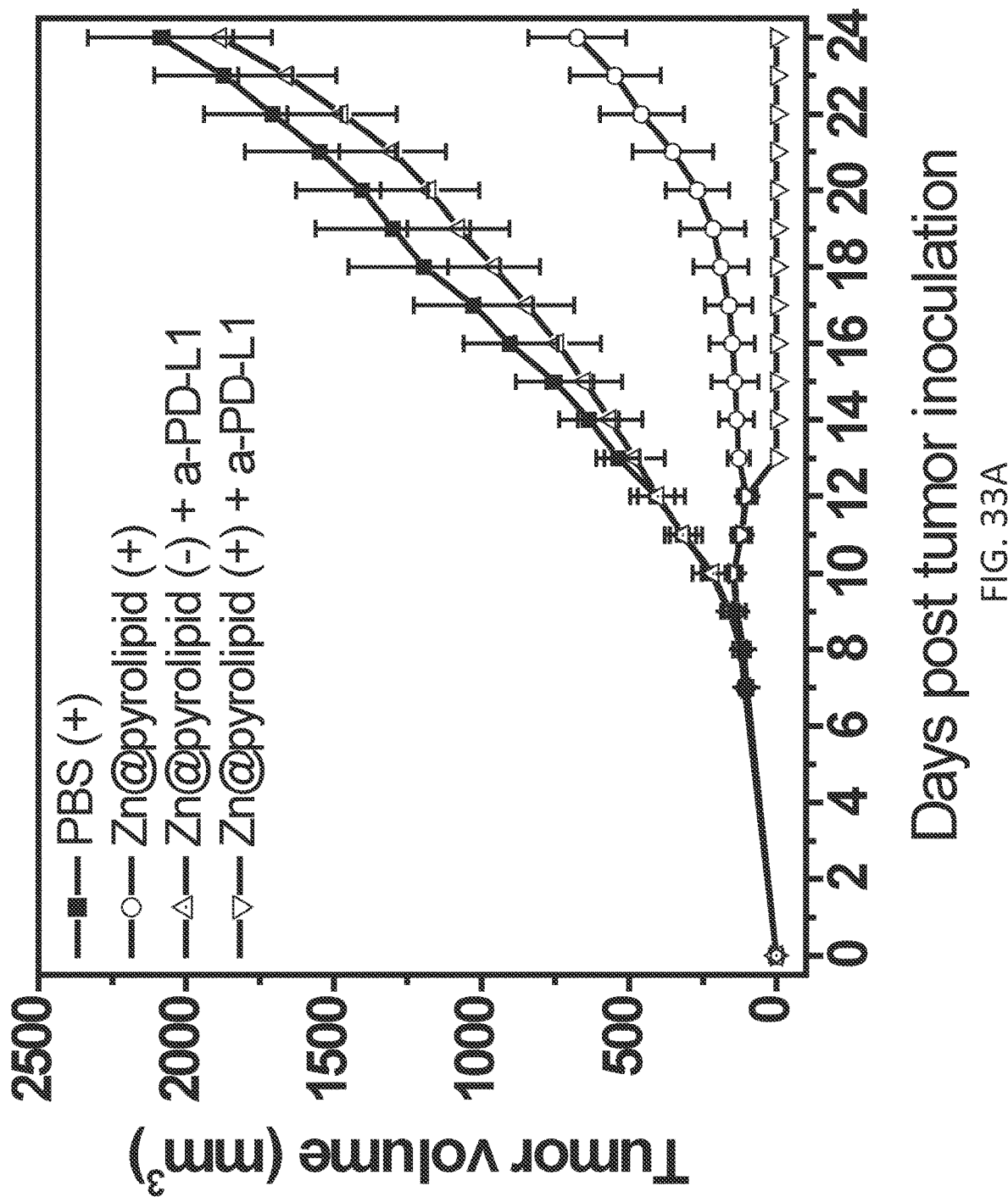

FIG. 33A is a graph of tumor growth curves of 4T1 triple negative breast cancer xenografts treated with a NCP particle comprising a zinc-pyrophosphate core and a lipid coating layer comprising pyrolipid (Zn@pyrolipid) and light (+) (circles), with Zn@pyrolipid, light and an anti-programmed death-ligand 1 (PD-L1) antibody (downward-pointing triangles), Zn@pyrolipid and an anti-PD-L1 antibody (upward-pointing triangles) or phosphate buffered saline (PBS) and light (squares).

Figure 33B:
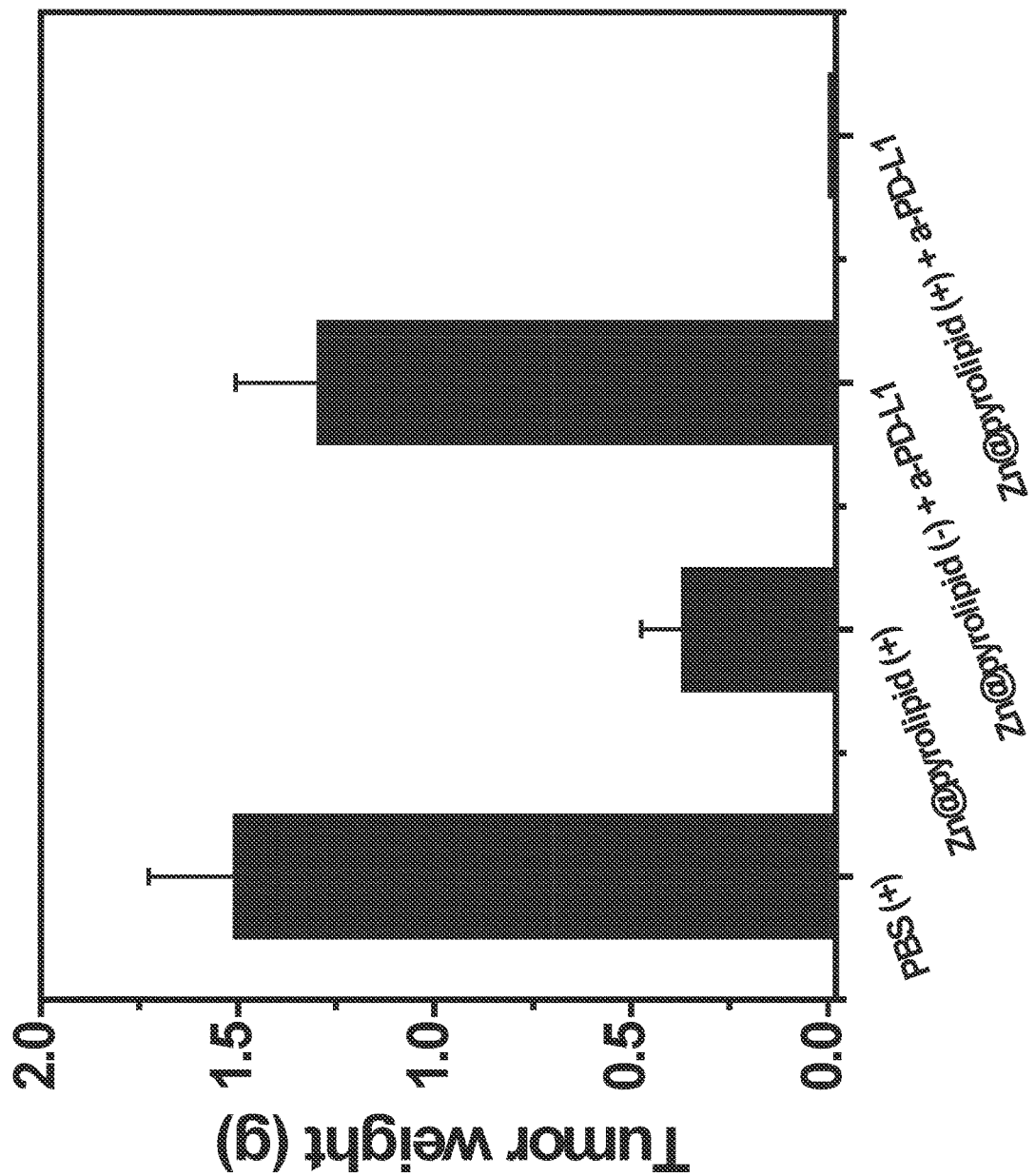

FIG. 33B is a graph of the tumor weights (in grams (g)) at the end of the treatments described in FIG. 33A.

Figure 34A:
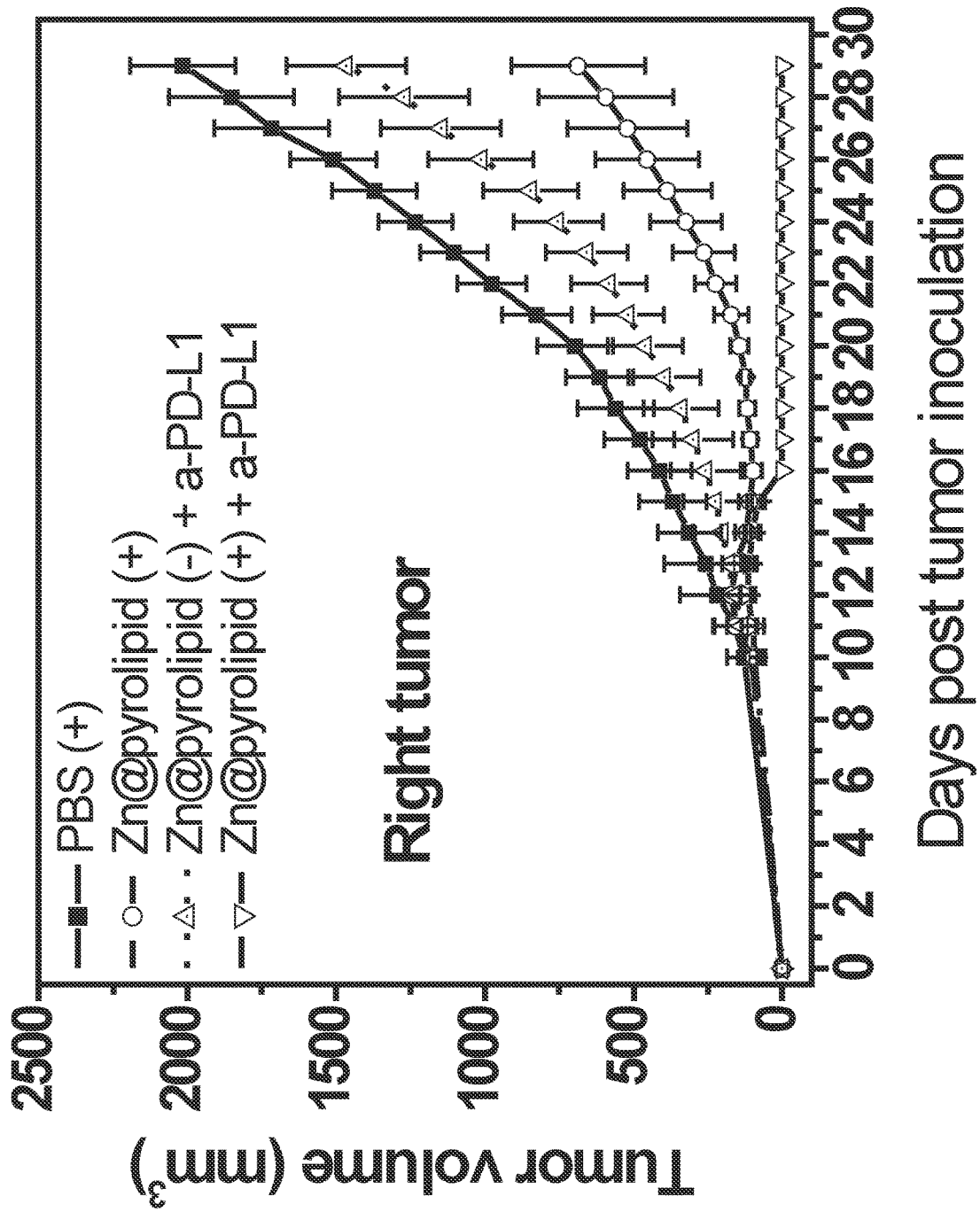

FIG. 34A is a graph of the tumor growth curves of tumors in the right flanks of mice inoculated in both the left and right flanks with 4T1 triple negative breast cancer cells and then treated in the right flank with a NCP particle comprising a zinc-pyrophosphate core and a lipid coating layer comprising pyrolipid (Zn@pyrolipid) and light (+) (circles), with Zn@pyrolipid, light and an anti-programmed death-ligand 1 (PD-L1) antibody (downward-pointing triangles), Zn@pyrolipid and an anti-PD-L1 antibody (upward-pointing triangles), or phosphate buffered saline (PBS) and light (PBS (+), squares).

Figure 34B:
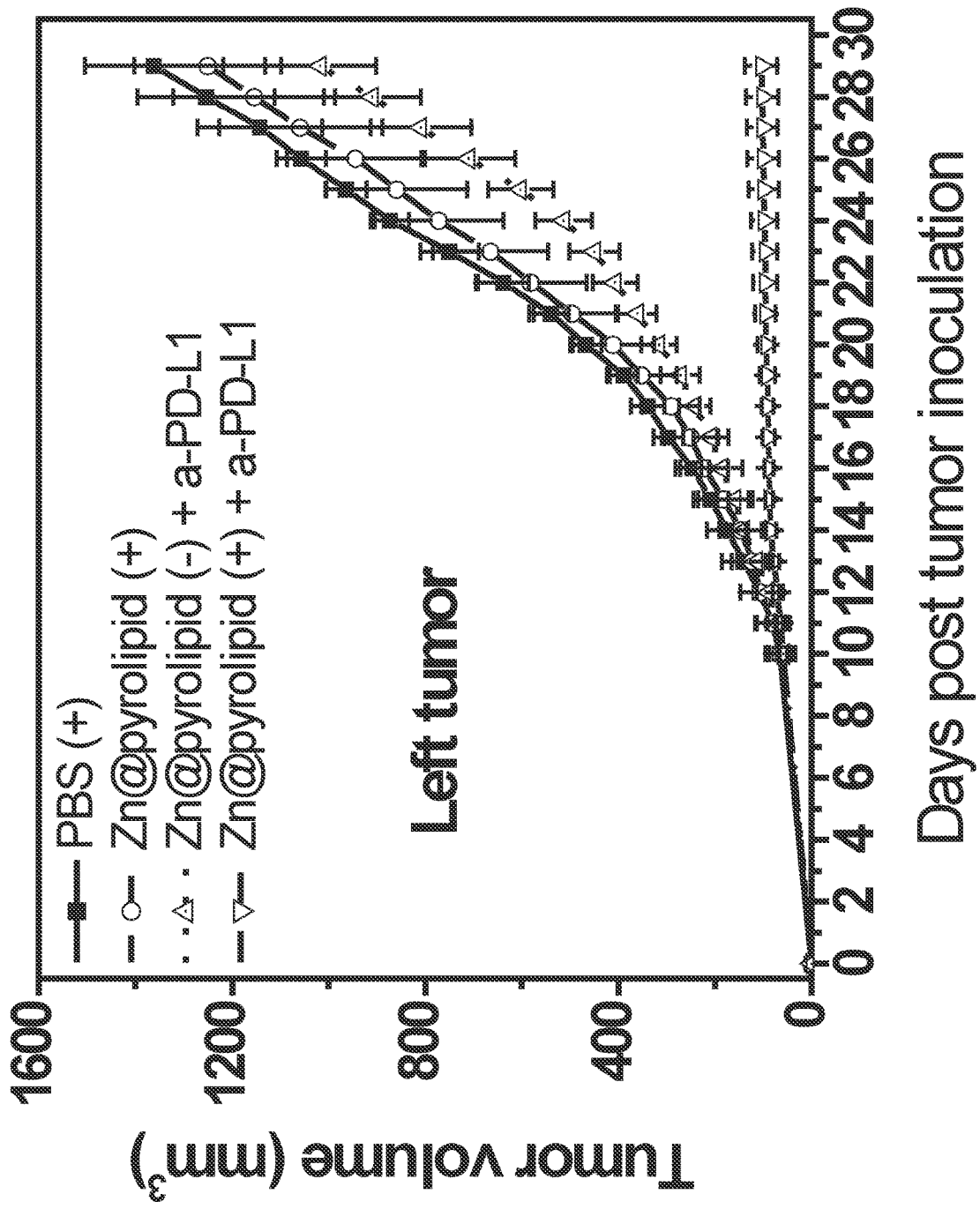

FIG. 34B is a graph of the tumor growth curves of tumors in the left flanks of mice inoculated in both the left and right flanks with 4T1 triple negative breast cancer cells and then treated in the right flank with a NCP particle comprising a zinc-pyrophosphate core and a lipid coating layer comprising pyrolipid (Zn@pyrolipid) and light (+) (circles), with Zn@pyrolipid, light and an anti-programmed death-ligand 1 (PD-L1) antibody (downward-pointing triangles), Zn@pyrolipid and an anti-PD-L1 antibody (upward-pointing triangles), or phosphate buffered saline (PBS) and light (PBS (+), squares).

Figure 34C:
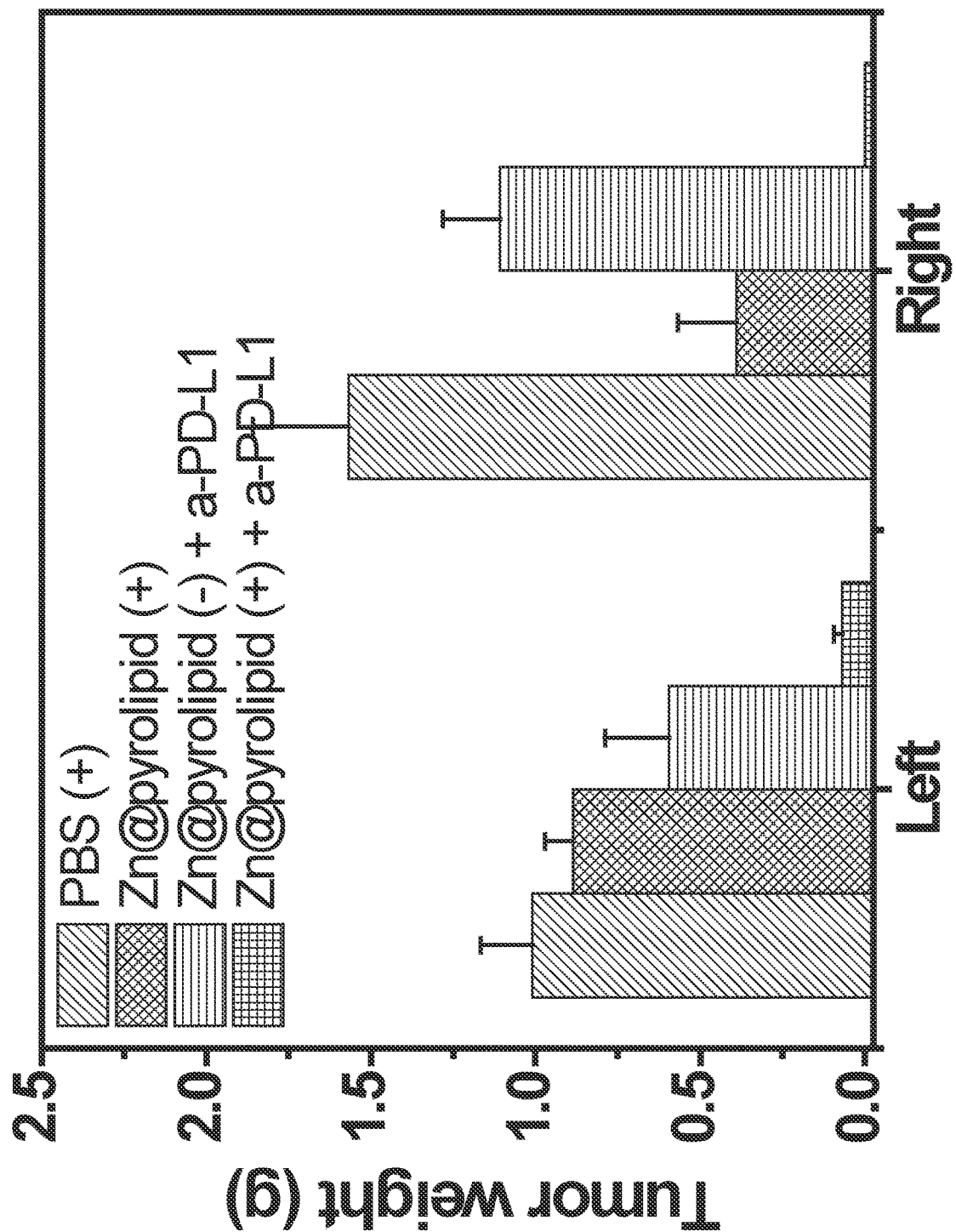

FIG. 34C is a graph showing the tumor weights (in grams (g)) of the tumors in left (left) and right (right) flanks of the mice treated as described for FIGS. 34A and 34B at the end of the treatment period.

Figure 35A:
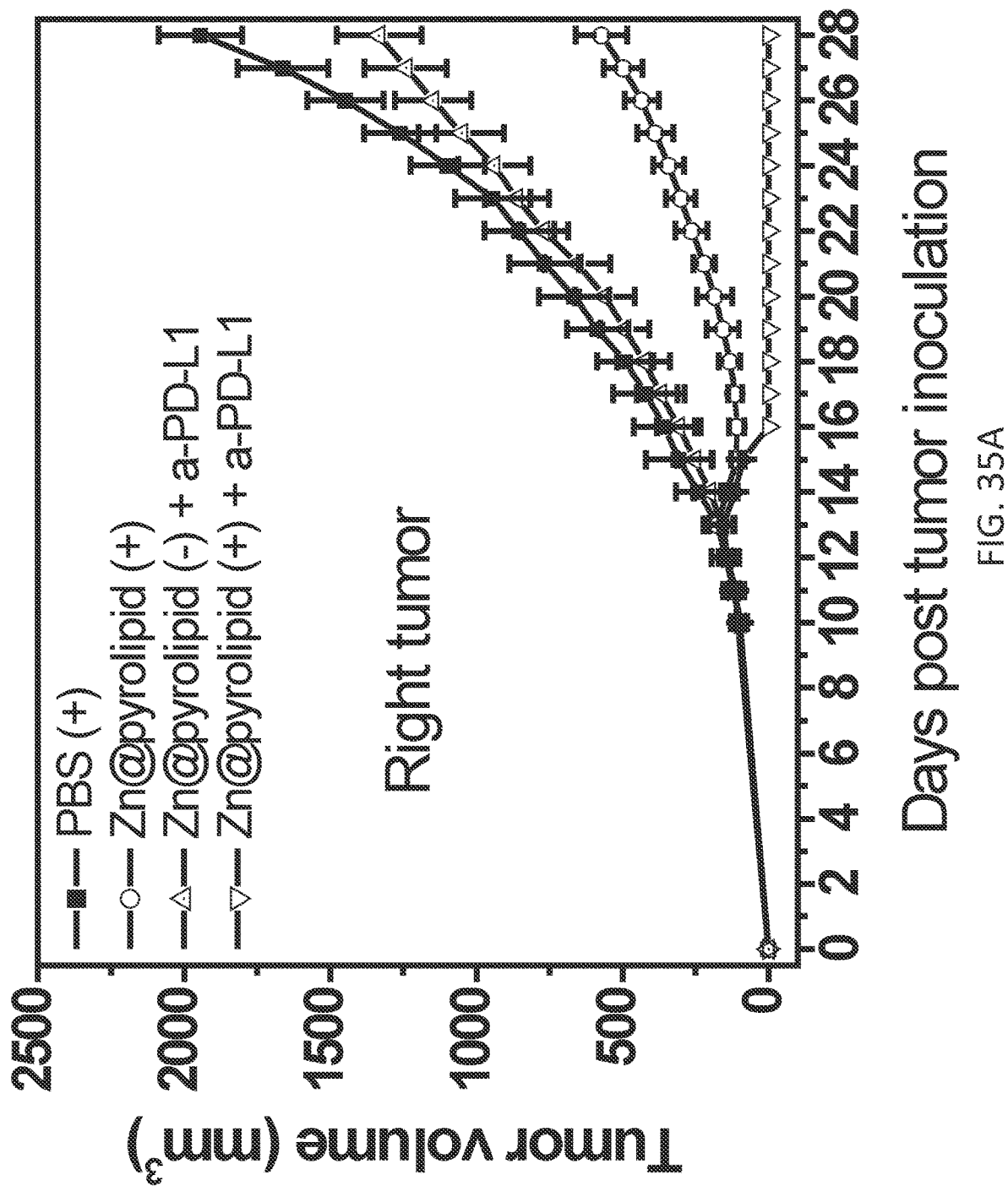

FIG. 35A is a graph of the tumor growth curves of tumors in the right flanks of mice inoculated in both the left and right flanks with TUBO breast cancer cells and then treated in the right flank with a NCP particle comprising a zinc-pyrophosphate core and a lipid coating layer comprising pyrolipid (Zn@pyrolipid) and light (+) (circles), with Zn@pyrolipid, light and an anti-programmed death-ligand 1 (PD-L1) antibody (downward-pointing triangles), Zn@pyrolipid and an anti-PD-L1 antibody (upward-pointing triangles), or phosphate buffered saline (PBS) and light (squares).

Figure 35B:
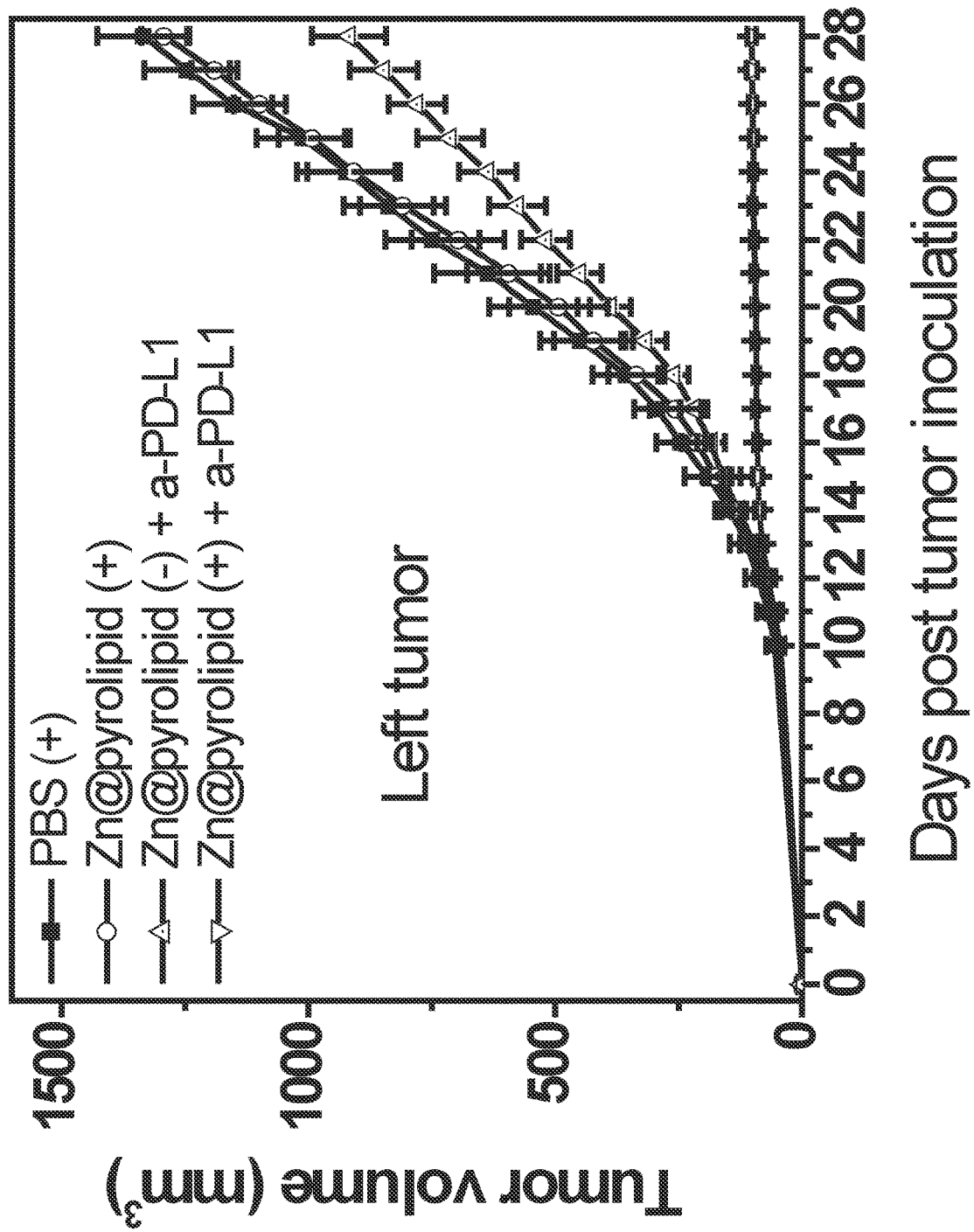

FIG. 35B is a graph of the tumor growth curves of tumors in the left flanks of mice inoculated in both the left and right flanks with TUBO breast cancer cells and then treated in the right flank with a NCP particle comprising a zinc-pyrophosphate core and a lipid coating layer comprising pyrolipid (Zn@pyrolipid) and light (+) (circles), with Zn@pyrolipid, light and an anti-programmed death-ligand 1 (PD-L1) antibody (downward-pointing triangles), Zn@pyrolipid and an anti-PD-L1 antibody (upward-pointing triangles), or phosphate buffered saline (PBS) and light (squares).

Figure 35C:
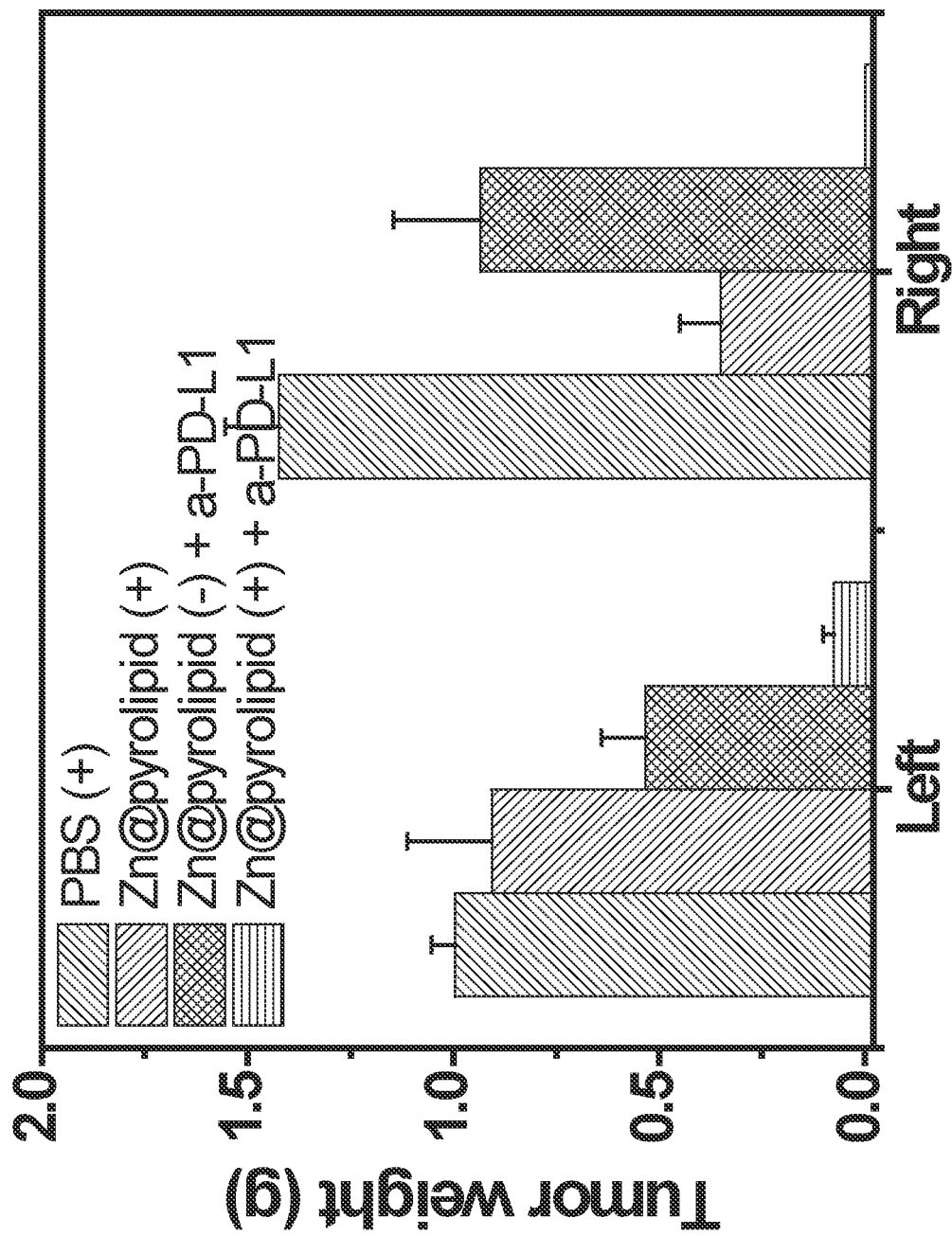

FIG. 35C is a graph showing the tumor weights (in grams (g)) of the tumors in left (left) and right (right) flanks of the mice treated as described for FIGS. 35A and 35B at the end of the treatment period.

Figure 36A:
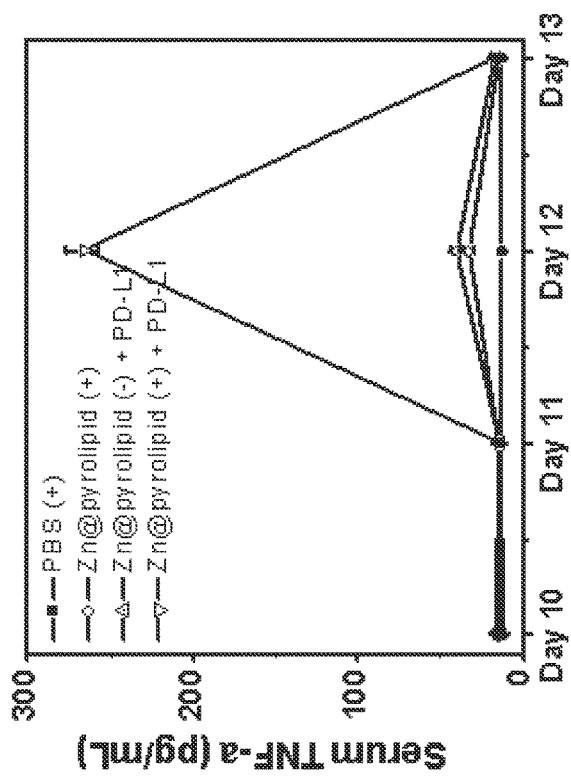

FIG. 36A is a graph of serum tumor necrosis factor alpha (TNF-α) concentration (in picograms per milliliter (pg/mL)) in TUBO breast tumor bearing mice on days 10, 11, 12, and 13 post tumor inoculation (days 0, 1, 2, and 3 post first treatment) treated as described in FIGS. 35A and 35B.

Figure 36B:
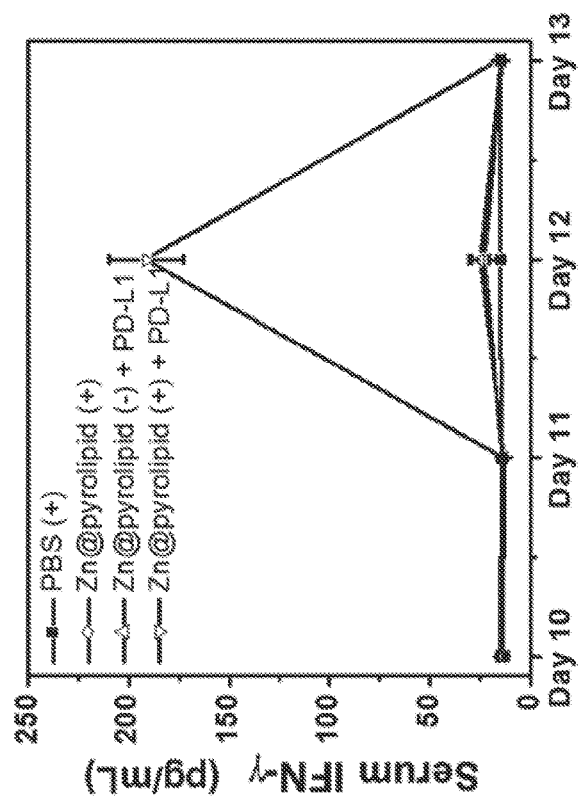

FIG. 36B is a graph of serum interferon gamma (IFN-γ) concentration (in picograms per milliliter (pg/mL)) in TUBO breast tumor bearing mice on days 10, 11, 12, and 13 post tumor inoculation (days 0, 1, 2, and 3 post first treatment) treated as described in FIGS. 35A and 35B.

Figure 36C:
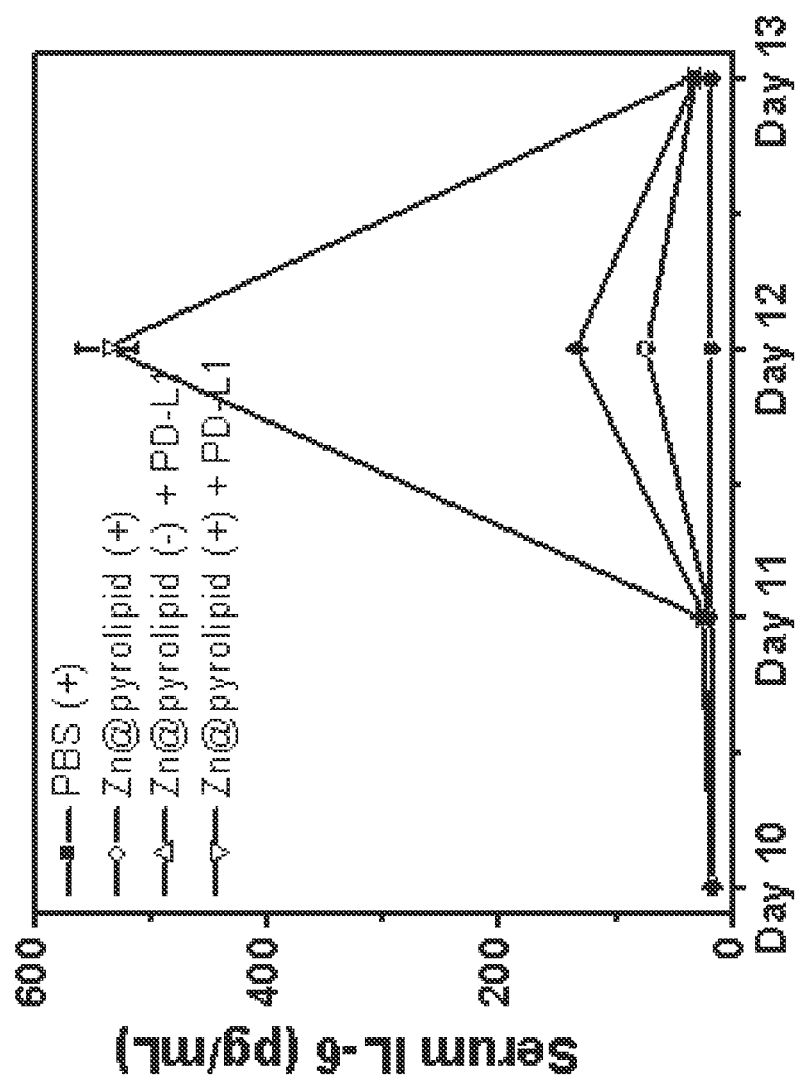

FIG. 36C is a graph of serum interleukin 6 (IL-6) concentration (in picograms per milliliter (pg/mL)) in TUBO breast tumor bearing mice on days 10, 11, 12, and 13 post tumor inoculation (days 0, 1, 2, and 3 post first treatment) treated as described in FIGS. 35A and 35B.

Figure 37A:
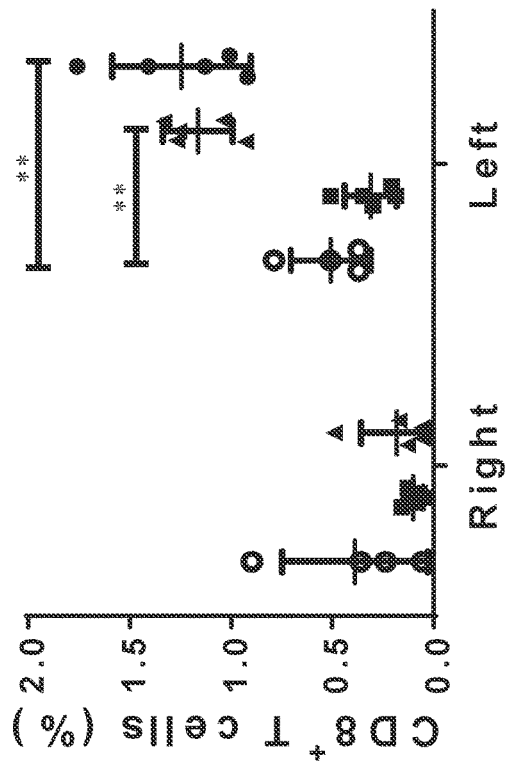

FIG. 37A is a graph showing the proportion of CD45+ lymphocytes in right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

Figure 37C:
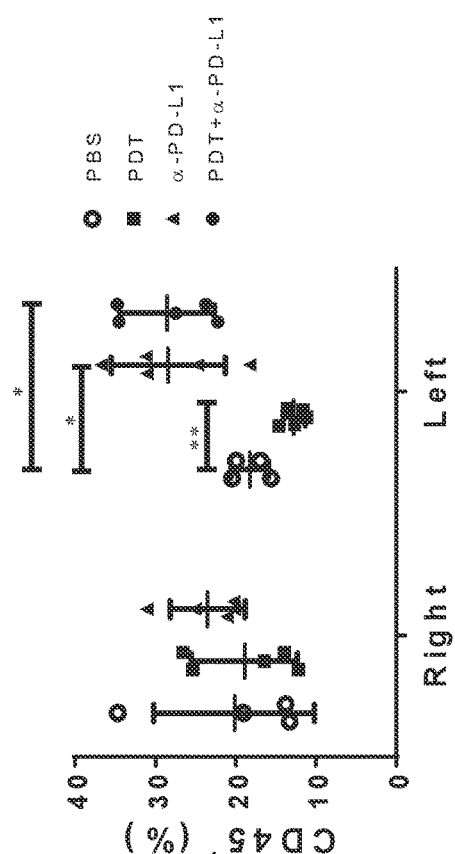
Figure 37B:
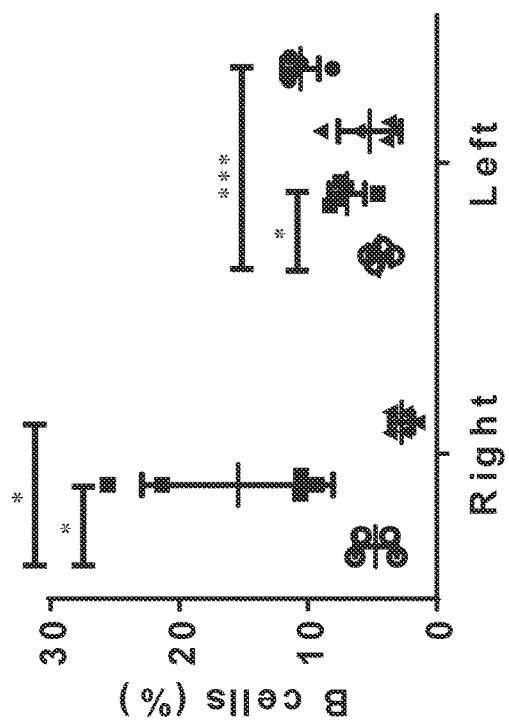

FIG. 37B is a graph showing the proportion of CD8+ T cells in right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

FIG. 37C is a graph showing the proportion of CD4+ T cells in right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

Figure 37D:
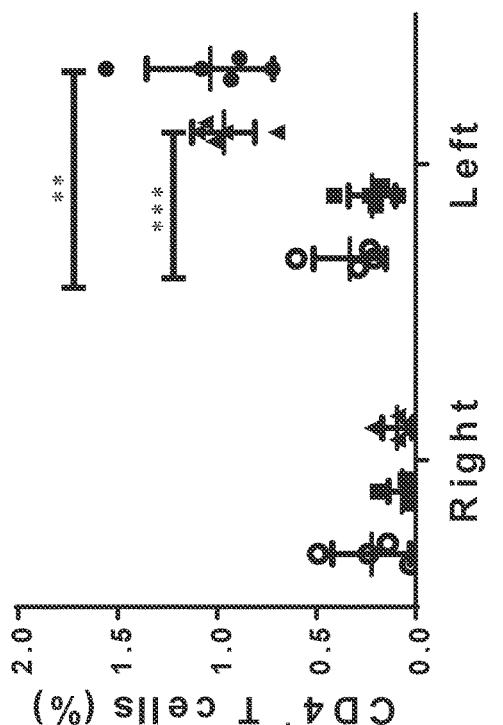

FIG. 37D is a graph showing the proportion of B cells in right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

FIG. 38A is a graph showing the proportion of CD8+ T cells in tumor-draining lymph nodes of right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

FIG. 38B is a graph showing the proportion of CD4+ T cells in tumor-draining lymph nodes of right and left flank TUBO breast tumors models of mice treated in the right flank with phosphate buffered saline (PBS, open circles), photodynamic therapy (PDT, squares) via injection of a zinc-pyrophosphate NCP particle with a pyrolipid-containing lipid coating layer and irradiation, injection of an anti-programmed death-ligand 1 (PD-L1) antibody (α-PD-L1, triangles), or PDT and antibody (black circles). Data is collected on the twelfth day after the first treatment.

DETAILED DESCRIPTION

In some embodiments, the presently disclosed subject matter provides prodrugs comprising drug-lipid conjugates that include biodegradable linkages, such as disulfide bonds. The prodrugs can be prepared from small molecule chemotherapeutics, including, but not limited to, those that are known to have immunological effect, such as the ability to cause immune cell death. The lipid moieties of the prodrugs can enhance incorporation of the prodrugs in lipid coating layers of inorganic and/or metal-organic matrix nanoparticles or other nanoscale drug delivery platforms.

Accordingly, in some embodiments, the presently disclosed subject matter provides nanoparticles that contain chemotherapeutics, such as those that are known to cause immunogenic cell death or to be immune-stimulatory. In some embodiments, the nanoparticle can comprise multiple chemotherapeutics to treat multiple cancer types. The nanoparticles can be combined with PDT modalities or used alone to cause immune-stimulation, leading to effective cancer therapy. These nanoparticles can be further combined with immunotherapy agents, e.g., immunosuppression inhibitors that, for example, target the CTLA-4, PD-1/PD-L1, IDO, LAG-3, CCR-7, or other pathways, or multiple immunosuppression inhibitors targeting a combination of these pathways, to elicit systemic antitumor immunity.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

Numerical ranges recited herein by endpoints include all numbers and fractions subsumed within that range (e.g. 1 to 5 includes, but is not limited to, 1, 1.5, 2, 2.75, 3, 3.90, 4, and 5).

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

The term "disulfide" can refer to the —S—S— group.

The terms "halo", "halide", or "halogen" as used herein refer to fluoro, chloro, bromo, and iodo groups.

The terms "hydroxyl" and "hydroxy" refer to the —OH group.

The terms "mercapto" or "thiol" refer to the —SH group.

The terms "carboxylate" and "carboxylic acid" can refer to the groups —C(=O)O— and —C(=O)OH, respectively. The term "carboxyl" can also refer to the —C(=O)OH group. In some embodiments, "carboxylate" or "carboxyl" can refer to either the —C(=O)O— or —C(=O)OH group.

The term "phosphonate" refers to the —P(=O)$(OR)_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP(=O)(OR')$_2$ group, where R' is H or a negative charge.

Wavy lines, such as in the wavy line shown in the structure:

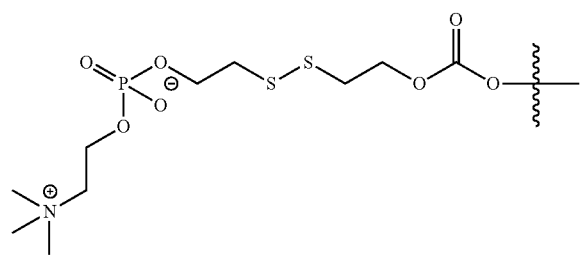 [SMILES: *OC(=O)OCCSSCCOP(=O)([O-])OCC[N+](C)(C)C]

are used in the chemical formulas described herein to indicate the attachment site of the specified structure to another chemical group, for example, to a monovalent derivative of a drug compound.

The term "monovalent" as used herein refers to a chemical moiety that has one site available for chemical bonding to another chemical moiety. Thus, a "monovalent moiety" can be a part of whole molecule that is attached to the remainder of the whole molecule via an attachment at one site on the monovalent moiety.

The term "bivalent" as used herein refers to a chemical moiety that has two sites available for chemical bonding to another chemical moiety or moieties.

The terms "conjugate" and "conjugated" as used herein can refer to the attachment (e.g., the covalent attachment) of two or more components (e.g., chemical compounds, polymers, biomolecule, particles, etc.) to one another. In some embodiments, a conjugate can comprise monovalent moieties derived from two different chemical compounds covalently linked via a bivalent linker moiety (e.g., an optionally substituted alkylene or arylene). In some embodiments, the linker can contain one or more biodegradable bond, such that one or more bonds in the linker can be broken when the prodrug is exposed to a particular physiological environment or enzyme.

The term "prodrug" as used herein, can refer to a compound that, upon administration to a subject or sample, is capable of providing (directly or indirectly) another compound (i.e., a "parent compound") having a desired biological activity (e.g., anticancer activity). In some, but not all, embodiments, the prodrug compound has less of the desired biological activity than the parent compound. In some embodiments, the prodrug compound has no measurable biological activity prior to transformation to the parent compound. In some embodiments, the prodrug itself has the desired activity.

Transformation of the prodrug to the parent compound can take place in the presence of particular enzymes (e.g., esterases) or under certain biological conditions (e.g., at a physiologically relevant pH or in the presence of reducing agents present in a physiological environment). In some embodiments, the prodrug is initially transformed into another prodrug, which is then transformed (sometimes much more slowly) into the parent compound. Prodrugs can provide increased bioavailability and/or enhanced delivery to a biological compartment (e.g., a lysosome, the brain or lymphatic system, etc.) relative to a parent compound. In some embodiments, the prodrug can be more compatible with a particular delivery platform or formulation than the parent compound.

The terms "bonding" or "bonded" and variations thereof can refer to covalent, coordinative, or non-covalent bonding. In some cases, the term "bonding" refers to bonding via a coordinate bond. The term "conjugation" can refer to a bonding process, as well, such as the formation of a covalent linkage or a coordinate bond.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as having more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably. The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —CO$_2$H, —NO$_2$, amino, hydroxyl, thio, thioalkyl, —B(OH)$_2$, —SO$_3$H, PO$_3$H, phosphonate, and heteroatoms (e.g., nitrogen, oxygen, or sulfur) in heterocycles.

The term "coordination site" when used herein with regard to a ligand, e.g., a bridging ligand, refers to a unshared electron pair, a negative charge, or atoms or functional groups cable of forming an unshared electron pair or negative charge (e.g., via deprotonation under at a particular pH).

As used herein, the term "metal-organic matrix material" refers to a solid material comprising both metal and organic components, wherein the organic components include at least one, and typically more than one carbon atom. The material can be crystalline or amorphous. In some embodiments, the matrix material is porous. In some embodiments, the metal-organic matrix material is a coordination polymer, (e.g., a nanoscale coordination polymer (NCP)) which comprises repeating units of coordination complexes comprising metal ions and bridging polydentate (e.g., bidentate) ligands (e.g., organic ligands). In some embodiments, the matrix material contains more than one type of metal ion. In some embodiments, the matrix material can contain metal clusters. In some embodiments, the matrix material is a metal-organic framework (MOF) comprising a coordination complex network that comprises bridging organic ligands.

The term "metal-organic framework" or "MOF" can refer to a solid two- or three-dimensional network comprising both metal and organic components, wherein the organic components include at least one, and typically more than one carbon atom. In some embodiments, the material is crystalline. In some embodiments, the material is amorphous. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate or tridentate) organic ligand. In some embodiments, the material contains more than one type of SBU or metal ion. In some embodiments, the material can contain more than one type of organic bridging ligand. As used herein, an MOF typically refers to a metal-organic matrix material wherein the metal component is a metal cluster or metal oxo cluster, while NCP can refer to a metal-organic matrix material where the metal component is a metal ion. Further, while NCP as used herein typically refers to a metal organic matrix material, in some embodiments an NCP can refer to a coordination polymer that does not include a carbon-containing ligand. For example, the NCP can refer to zinc pyrophosphate.

The terms "nanoscale particle," "nanomaterial," and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

In some embodiments, the nanoparticle is approximately spherical. When the nanoparticle is approximately spherical, the characteristic dimension can correspond to the diameter of the sphere. In addition to spherical shapes, the nanomaterial can be disc-shaped, plate-shaped (e.g., hexagonally plate-like), oblong, polyhedral, rod-shaped, cubic, or irregularly-shaped.

The nanoparticle can comprise a core region (i.e., the space between the outer dimensions of the particle) and an outer surface (i.e., the surface that defines the outer dimensions of the particle). In some embodiments, the nanoparticle can have one or more coating layers surrounding or partially surrounding the nanoparticle core. Thus, for example, a spherical nanoparticle can have one or more concentric coating layers, each successive layer being dispersed over the outer surface of a smaller layer closer to the center of the particle.

"Embedded" can refer to a agent that is bound, for example covalently bound or bound via a coordinative bond, inside or on the surface of the core of the particle (e.g., to a coordination site of a bridging ligand or to a metal ion). Alternatively, agents can be "sequestered", "entrapped", or "trapped" (i.e., non-covalently encapsulated) inside pores, cavities or channels in the metal-organic matrix core of a NCP or MOF particle or interact with a NCP or MOF material via hydrogen bonding, London dispersion forces, or any other non-covalent interaction.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more moieties that can react to form bonds (e.g., covalent or coordination bonds) with moieties on other molecules of polymerizable monomer. In some embodiments, each polymerizable monomer molecule can bond to two or more other molecules/moieties. In some cases, a polymerizable monomer will bond to only one other molecule, forming a terminus of the polymeric material.

Polymers can be organic, or inorganic, or a combination thereof. As used herein, the term "inorganic" refers to a compound or composition that contains at least some atoms other than carbon, hydrogen, nitrogen, oxygen, sulfur, phosphorous, or one of the halides. Thus, for example, an inorganic compound or composition can contain one or more silicon atoms and/or one or more metal atoms.

As used herein "organic polymers" are those that do not include silica or metal atoms in their repeating units. Exemplary organic polymers include polyvinylpyrrolidone (PVO), polyesters, polyamides, polyethers, polydienes, and the like. Some organic polymers contain biodegradable linkages, such as esters or amides, such that they can degrade overtime under biological conditions.

The term "hydrophilic polymer" as used herein generally refers to hydrophilic organic polymers, such as but not limited to, polyvinylpyrrolidone (PVP), polyvinylmethylether, polymethyloxazoline, polyethyloxazoline, polyhydroxy-propyloxazoline, polyhydroxypropylmethacrylamide, polymethy-acrylamide, polydimethylacrylamide, polyhydroxylpropylmethacrylate, polyhydroxyethylacrylate, hydroxymethylcellulose, hydroxyethylcellulose, polyethylene-imine (PEI), polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The term "imaging agent" refers to a chemical moiety that aids in the visualization of a sample. For example, an imaging agent can be a "contrast agent", and can refer to a moiety (a specific part of or an entire molecule, macromolecule, coordination complex, or nanoparticle) that increases the contrast of a biological tissue or structure being examined. The contrast agent can increase the contrast of a structure being examined using, for example, magnetic resonance imaging (MRI), optical imaging, positron emission tomography (PET) imaging, single photon emission computed tomography (SPECT) imaging, or a combination thereof (i.e., the contrast agent can be multimodal).

The term "MRI contrast agent" refers to a moiety that effects a change in induced relaxation rates of water protons in a sample.

The terms "optical imaging agent" or "optical contrast agent" refer to a group that can be detected based upon an ability to absorb, reflect or emit light (e.g., ultraviolet, visible, or infrared light). Optical imaging agents can be detected based on a change in amount of absorbance, reflectance, or fluorescence, or a change in the number of absorbance peaks or their wavelength maxima. Thus, optical imaging agents include those which can be detected based on fluorescence or luminescence, including organic and inorganic dyes.

The terms "fluorophore" and "fluorescent moiety" refer to species that can be excited by visible light or non-visible light (e.g., UV light). Examples of fluorophores include, but are not limited to: quantum dots and doped quantum dots (e.g., a semiconducting CdSe quantum dot or a Mn-doped CdSe quantum dot), fluorescein, fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

The term "photosensitizer" (PS) refers to a chemical compound or moiety that can be excited by light of a particular wavelength, typically visible or near-infrared (NIR) light, and produce a reactive oxygen species (ROS). For example, in its excited state, the photosensitizer can undergo intersystem crossing and transfer energy to oxygen ($O_2$) (e.g., in tissues being treated by PDT) to produce ROSs, such as singlet oxygen ($^1O_2$). Any known type of a photosensitizer can be used in accordance with the presently disclosed subject matter. In some embodiments, the photosensitizer is a porphyrin, a chlorophyll, a dye, or a derivative or analog thereof. In some embodiments, phophyrins, chlorins, bacteriochlorins, or porphycenes can be used. In some embodiments, the photosensitizer can have one or more functional groups, such as carboxylic acid, amine, or isothiocyanate, e.g., for use in attaching the photosensitizer to another molecule or moiety, such as an organic bridging ligand, and/or for providing an additional site or sites to enhance coordination or to coordinate an additional metal or metals. In some embodiments, the photosensitizer is a porphyrin or a derivative or analog thereof. Exemplary porphyrins include, but are not limited to, hematoporphyrin, protoporphyrin and tetraphenylporphyrin (TPP). Exemplary porphyrin derivatives include, but are not limited to, pyropheophorbides, bacteriochlorophylls, chlorophyll a, benzoporphyrin derivatives, tetrahydroxyphenyl chlorins, purpurins, benzochlorins, naphthochlorins, verdins, rhodins, oxochlorins, azachlorins, bacteriochlorins, tolyporphyrins and benzobacteriochlorins. Porphyrin analogs include, but are not limited to, expanded porphyrin family members (such as texaphyrins, sapphyrins and hexaphyrins), porphyrin isomers (such as porphycenes, inverted porphyrins, phthalocyanines, and naphthalocyanines), and TPP substituted with one or more functional groups.

The term "pyrolipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. Pyrolipids and pyrolipid synthesis are described, for example, in U.S. Patent Application Publication No. 2014/0127763, which is incorporated herein by reference in its entirety.

The term "lyso-lipid" refers to a lipid in which one or more acyl group has been removed.

The term "cancer" as used herein refers to diseases caused by uncontrolled cell division and/or the ability of cells to metastasize, or to establish new growth in additional sites. The terms "malignant", "malignancy", "neoplasm", "tumor," "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymphomas).

The term "metastatic cancer" refers to cancer that has spread from its initial site (i.e., the primary site) in a patient's body.

The terms "anticancer drug", "chemotherapeutic", and "anti-cancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. Such more traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

The term "scintillator" refers to a moiety or compound that exhibits luminescence (emits light, e.g., light in the visible or NIR range) when excited by ionizing radiation, such as x-rays.

II. General Considerations

Nanoscale coordination polymers (NCPs) are an emerging class of self-assembled, hybrid nanomaterials whose properties can be tuned by varying the molecular building blocks. NCPs can provide desirable drug delivery platforms for treating disease. See, for example, PCT International Patent Application Publications Nos. WO 2013/009701 and WO 2015/069926, the disclosures of each of which are incorporated herein by reference in their entireties. For instance, NCPs can be used to enhance the delivery of small molecule drugs and biologics to tumor sites via the enhanced permeability and retention (EPR) effect by taking advantage of the leaky blood vasculatures and reduced lymphatic drainage in tumors. NCPs can provide drug delivery by incorporating drug compounds or analogues as part of the particle metal-organic matrix core material, e.g., by covalent linkage or coordination to a matrix component, or, additionally or alternatively, by embedding the drug or drug analogue in pores in the matrix material core. In some embodiments, the particles can comprise coating layers surrounding all or a part of the particle core, wherein therapeutic agents (e.g., therapeutic small molecules or biological agents, e.g., or nucleic acids, proteins or antibodies), photosensitizers, targeting agents, passivating agents, and/or detection/imaging agents can be incorporated into the coating layers.

In one aspect, the presently disclosed subject matter is based on an approach for providing a prodrug suitable for incorporation into NCP particle lipid coating layers, e.g., to provide enhanced delivery of the corresponding parent drugs and for providing NCP combination therapies including the parent drug. The prodrugs can also be useful for incorporation into other nanoparticle drug delivery platforms, such as, but not limited to, polymeric micelles, liposomes, dendrimers, polymer-based nanoparticles, silica-based nanoparticles, nanoscale metal-organic frameworks (MOFs), and inorganic nanoparticles (e.g., gold nanoparticles, iron oxide nanoparticles, etc.).

II.A Prodrugs

For instance, in some embodiments, a suitable prodrug can be provided by conjugating a drug compound to a lipid moiety via a linkage that will degrade in vivo. In some embodiments, the linkage is a disulfide bond. Thus, in some embodiments, the prodrug is a drug-lipid conjugate, wherein the drug-lipid conjugate comprises a linker moiety comprising a disulfide. In some embodiments, the drug compound is a chemotherapeutic agent or a small molecule inhibitor for immunotherapy. In some embodiments, the drug compound comprises a hydroxyl or phenol group and the drug compound can be covalently attached to a linker via a bond involving the oxygen atom of the hydroxyl or phenol. Alternatively, the drug compound can comprise a thiol, primary or secondary amine, or carboxylic acid group that can be used as an attachment site to a linker group as part of forming a prodrug.

In some embodiments, the prodrug comprises a drug compound selected from the group including, but not limited to, Etoposide (ET), Camptothecin (CPT), dihydroartemisinin (DHA), Paclitaxel (PTX), OTSC41, OTS964, OTS167 (see Matsuo et al., Science Translational Medicine, 22 Oct. 2014: 259ra145), Doxorubicin, Docetaxel, Vincristine, Mitoxantrone (MTX), artesunate (ART), Capecitabine, and NLG919 (see U.S. Patent Application Publication No. 2014/0066625, the disclosure of which is incorporated by reference in its entirety) conjugated to a lipid, such as, but not limited to, cholesterol (Chol), oleic acid (OA), a lyso-lipid, or phosphocholine, through a linker, e.g., a disulfide-containing linker. The structure of OTSC41 is shown at the top left of Scheme 1, below, while the structures of OTS964 and NLG919 are shown in the top right and bottom of Scheme 1, respectively. The prodrugs can be readily loaded onto NCP particles during the lipid coating process driven by hydrophobic interactions between the prodrug lipid component (e.g., the Chol or OA) and phospholipids in the lipid coating. The prodrugs retain the antitumor activity of their corresponding parent drugs due to intracellular release of active parent drugs under the reducing environment inside cells.

Scheme 1. Structures of OTSC41, OTS964, and NLG919.

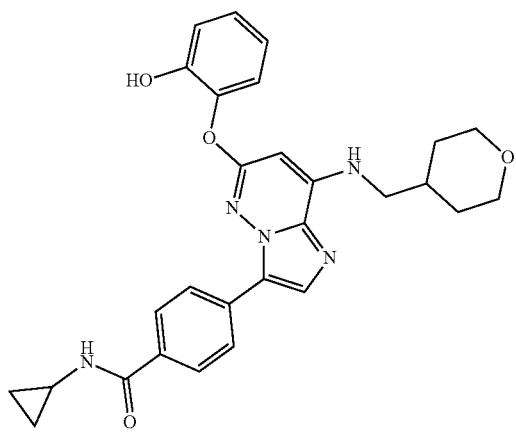

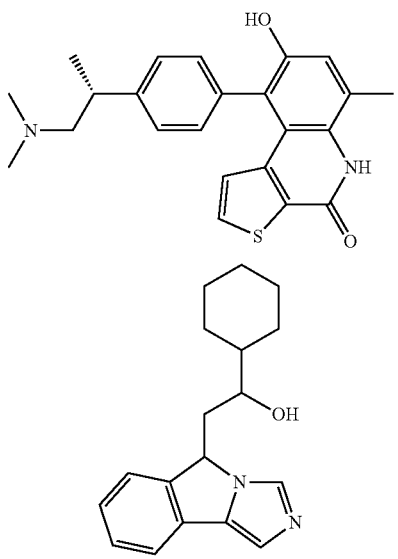

Accordingly, in some embodiments, the presently disclosed subject matter provides a prodrug comprising a lipid-conjugated therapeutic agent parent drug. In some embodiments, the prodrug comprises: (a) a monovalent drug moiety, (b) a monovalent lipid moiety, and (c) a bivalent linker moiety comprising a linkage that will degrade in vivo, such as a disulfide bond, wherein the monovalent drug moiety and the monovalent lipid moiety are linked (e.g., covalently linked) through the linker. The monovalent drug moiety and the monovalent lipid moieties can be monovalent derivatives of a drug compound and a lipid, respectively. For instance, the monovalent derivative can be a deprotonated derivative of a drug compound or lipid that comprises a hydroxyl, thiol, amino, or carboxylic acid group.

In some embodiments, the monovalent drug moiety is a monovalent derivative of a chemotherapeutic agent and/or of a small molecule inhibitor for immunotherapy. In some embodiments, the drug is a chemotherapeutic compound known to cause immunogenic cell death or to be immune-stimulatory. Such compounds include, but are not limited to ET, PTX, OTS964, NLG919, OTS167, OTSC41, DHA, CPT, Doxorubicin, Docetaxel, Vincristine, MTX, ART, and Capecitabine. In some embodiments, the monovalent lipid moiety is a monovalent derivative of cholesterol, oleic acid, a lyso-lipid or phosphocholine. In some embodiments, the bivalent linker moiety can be a derivative of a dihydroxy-substituted disulfide, such as, but not limited to, bis(2-hydroxyethyl) disulfide, dihydroxydiphenyl disulfide, bis(2-hydroxypropyl) disulfide, and the like. Such linkers can be activated for attachment to a drug or lipid by reaction with phosgene or triphosgene, for example, to provide chloroformate groups.

In some embodiments, the monovalent lipid moiety is a cholesterol derivative and the monovalent lipid moiety and bivalent linker moiety together have the structure:

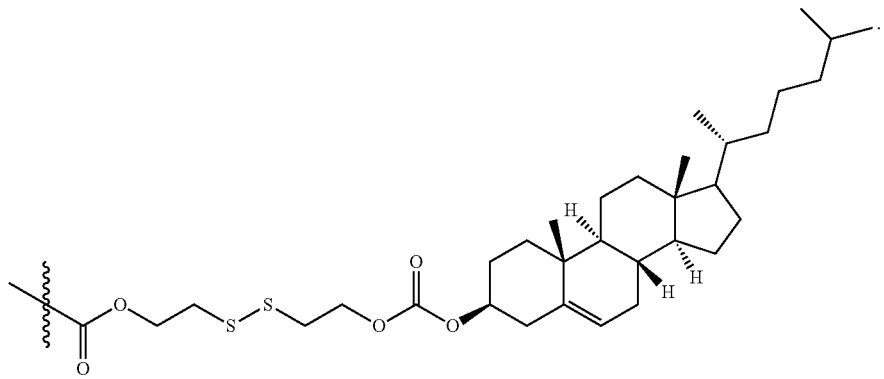 [SMILES: *C(=O)OCCSSCCOC(=O)O[C@H]1CC[C@@]2(C)C(=CC[C@@H]3[C@@H]2CC[C@]2(C)C([C@H](C)CCCC(C)C)CC[C@@H]32)C1]

In some embodiments, monovalent lipid moiety is an oleic acid derivative and the monovalent lipid moiety and bivalent linker moiety together have the structure:

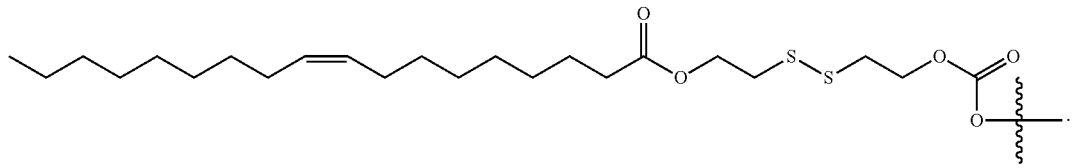 [SMILES: *OC(=O)OCCSSCCOC(=O)CCCCCCC/C=C\CCCCCCCC]

In some embodiments, the monovalent lipid moiety is a lyso-lipid derivative and the monovalent lipid moiety and bivalent linker moiety together have the structure:

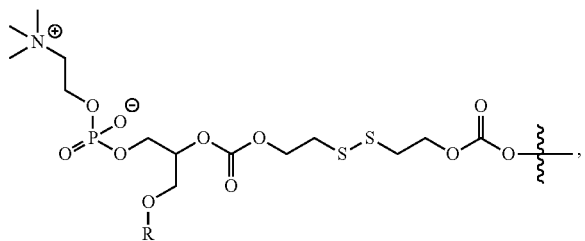

where R is a saturated or unsaturated acyl group. In some embodiments, R is a $C_8$-$C_{26}$ (e.g., a $C_8$, $C_{10}$, $C_{12}$, $C_{14}$, $C_{16}$, $C_{18}$, $C_{20}$, $C_{22}$, $C_{24}$ or $C_{26}$) saturated or unsaturated acyl group. In some embodiments, R is selected from oleyl, stearyl or palmitoleyl.

In some embodiments, the monovalent lipid moiety is a phosphocholine derivative and the monovalent lipid moiety and bivalent linker together have the structure:

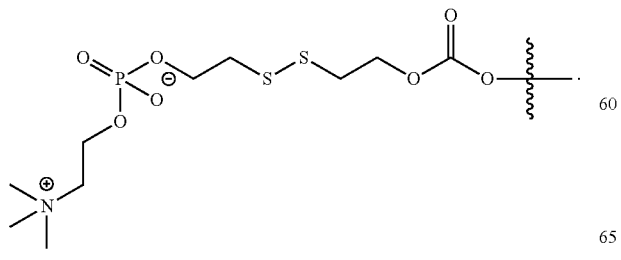

In some embodiments, the monovalent drug moiety and the monovalent lipid moiety are each bonded to a hydroxyl group of bis-(2-hydroxyethyl) disulfide linker (or another linker comprising two hydroxyl groups) via carbonate bonds. Alternatively, one or both of the drug moiety and the lipid moiety can be bonded to the linker via carbamate, thioester, ester, amide, ether, or amine linkages.

Scheme 2. Exemplary Prodrug Linkages

Phenol esters

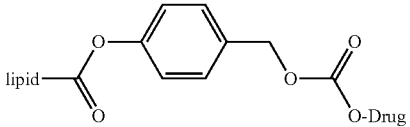

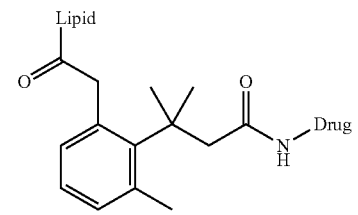

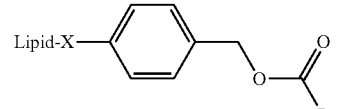

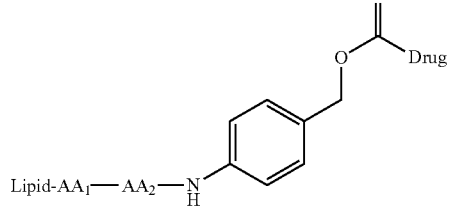

benzyl alcohol-based linkers

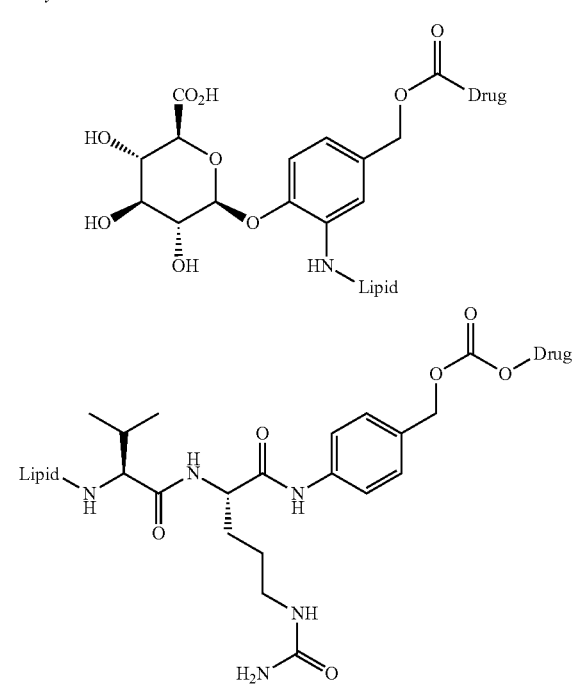

succinimide thioethers hydrazones

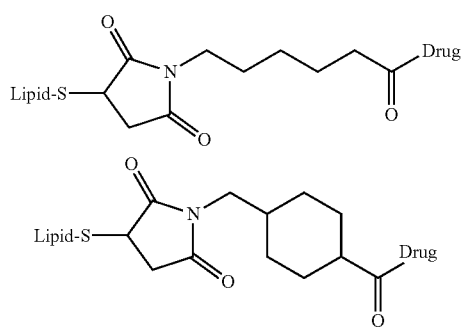

thiazolidine additional disulfides

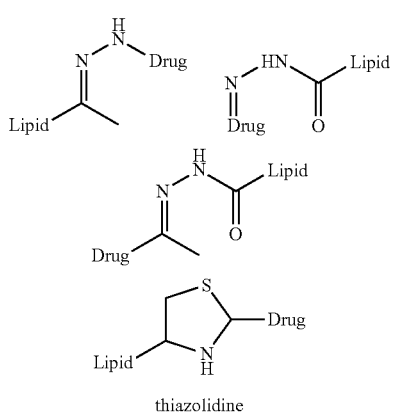

other linkers

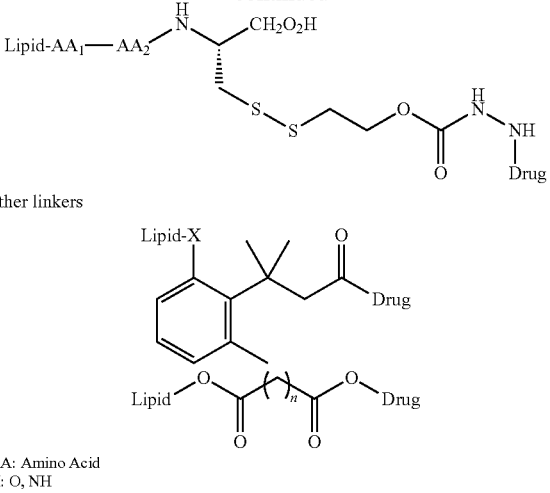

AA: Amino Acid
X: O, NH

In addition to linkers based on dihydroxy-substituted disulfides, any other suitable linker comprising a biodegradable bond can be used in the prodrugs of the presently disclosed subject matter. Scheme 2, above, shows additional exemplary biodegradable linkers suitable for the presently disclosed prodrugs. These linkers can be based on linkers that comprise a phenol group or groups that can form a phenol ester (or carbonate or carbamate) with the lipid and/or drug moiety. Suitable linkers also include linkers that can form a benzyl ester (or carbonate or carbamate) with the lipid or drug moiety. Thus, in some embodiments, suitable linkers can be prepared from phenols or benzyl alcohols. Additional suitable biodegradable linkers include, but are not limited to, linkers based on hydrazones, thiazolidines, thio-substituted succinimides (e.g., prepared from Michael addition of a thiol to a maleimide), other disulfides (i.e., disulfides other than dihydroxy-substituted disulfides), dicarboxylic acids, 3-(hydroxyphenyl)propionic acids, and the like.

In some embodiments, the presently disclosed subject matter provides a composition comprising a lipid conjugate prodrug as described herein for use in treating a disease in a subject in need of treatment thereof. In some embodiments, the composition for use in treating disease comprises a nanoparticle comprising the prodrug (e.g., present as a component of a lipid coating layer present as one or more coating layers coating at least a portion of the surface of the nanoparticle core). In some embodiments, the composition or use in treating a disease further comprises one or more additional therapeutic agents, e.g., one or more chemotherapeutic agents (or analogues or prodrugs thereof), one or more immunotherapy agents, one or more targeting agents, one or more imaging agent, one or more scintillator, one or more photosensitizer, or any mixture thereof.

II.B. Combined Photodynamic Therapy and/or Chemotherapy and/or Immunotherapy

Photodynamic therapy (PDT) is a phototherapy that combines three non-toxic components—a photosensitizer (PS), a light source, and tissue oxygen—to cause toxicity to malignant and other diseased cells. The most widely accepted mechanism of PDT involves energy transfer from the light-excited PS to oxygen molecules in the tissue to generate reactive oxygen species (ROS), particularly singlet oxygen ($^1O_2$), which induces cellular toxicity. PDT can lead to localized destruction of diseased tissues via selective uptake of the PS and/or local exposure to light, providing a minimally invasive cancer therapy.

Selective delivery of chemotherapeutics to tumors is preferred for successful chemotherapy. Similarly, localization of PSs in tumors is preferred for effective PDT. However, many PSs are hydrophobic in nature, which not only leads to insufficient tumor localization, but also causes PS aggregation to diminish the PDT efficacy. Significant synthetic modifications are thus typically employed for rendering these PSs more effective PDT agents in vivo.

An alternative approach is to use nanocarriers to selectively deliver therapeutic or PDT agents to tumors via the enhanced permeation and retention effect (EPR) and sometimes, via active tumor targeting with small molecule or biologic ligands that bind to overexpressed receptors in cancers.

Nanoscale particles, such as those constructed from NCPs and comprising lipid or other coating layers, can be used as a nanocarrier platform for therapeutic and PDT agents. Compared to other nanocarriers, NCPs can combine many beneficial features into a single delivery platform, including tunable chemical compositions and crystalline structures; high porosity; and biodegradability.

PDT can selectively kill tumor cells while preserving adjacent normal tissue. PDT does not incur cross-resistance with radiotherapy or chemotherapy, and therefore, is useful in the treatment of cancer patients who have not responded significantly to traditional radiotherapy and/or chemotherapy. PDT can provoke a strong acute inflammatory reaction observed as localized edema at the targeted site. The inflammation elicited by PDT is a tumor antigen nonspecific process orchestrated by the innate immune system. PDT is particularly effective in rapidly generating an abundance of alarm/danger signals, such as damage-associated molecular patterns (DAMPs), at the treated site that can be detected by the innate immunity alert elements. PDT-mediated enhancement of antitumor immunity is believed due to the stimulation of dendritic cells by dead and dying tumor cells and can be accompanied by the recruitment and activation of CD8+ cytotoxic T cells (CTLs) followed by the formation of immune memory cells and resistance to subsequent tumor growth.

Accordingly, in some embodiments, the presently disclosed subject matter provides a method that combines PDT (or X-ray PDT) with immunotherapy. In some embodiments, the presently disclosed subject matter provides a method of treating a disease in a patient in need of treatment thereof, the method comprising the steps of: administering to a patient a nanoparticle photosensitizer or a scintillator; irradiating at least a portion of the patient with light and/or X-rays; and administering to the patient an immunotherapy agent. In some embodiments, the nanoparticle photosensitizer comprises a NCP. In some embodiments, the nanoparticle comprises a lipid-conjugate prodrug of the presently disclosed subject matter.

A number of inorganic, organic, and hybrid materials are known to strongly absorb near-infrared light to generate single oxygen. The therapeutic use of such PDT materials can be combined with immune checkpoint inhibitor therapy. Exemplary photosensitizers for use in the presently disclosed methods include, but are not limited to: upconversion nanoparticles, such as $NaYF_4$ (for example, doped at a ratio of Y:Yb:Er=78%:20%:2%), combined with chlorin e6 or MC540; photosensitizers embedded in silica-based nanoparticles, such as 2-devinyl-2-(1-hexyloxyethyl) pyropheophorbide (HPPH) loaded silica nanoparticles; polymer micelle loaded photosensitizers, such as Zn(II)phthalocyanine loaded in DSPE-$PEG_{5k}$ polymer micelles; liposome based photosensitizer delivery systems, such as 5,10,15,20-tetrakis (m-hydroxyphenyl)chlorin encapsulated in a liposome and 5-aminolevulinic acid (ALA) encapsulated liposome; human serum albumin (HSA)-based photosensitizer delivery systems, such as HSA-pheophorbide a conjugate particles; dendrimer based photosensitizer delivery systems, such as PEG-attached poly(propyleneimine) or poly(amido amine) loaded with rose bengal and PpIX; porphyrin-, chlorin- or bacteriochlorin-conjugated phospholipid based bilayer delivery systems, such as porphyrin-lipid conjugates (pyrolipid) self-assembly nanovesicles (Porphysome); a NCP particle comprising a lipid coating layer comprising pyrolipid (NCP@Pyrolipid); and a nanoparticle comprising a zinc-pyrophosphate core and a lipid coating layer comprising pyrolipid (Zn@Pyrolipid).

In some embodiments, the disease is cancer. For instance, the cancer can be selected from a cancer such as, but not limited to, a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, lung cancer, stomach cancer, anogenital cancer, kidney cancer, bladder cancer, colon cancer, prostate cancer, central nervous system cancer, retinal cancer, blood cancer, neuroblastoma, multiple myeloma, lymphoid cancer and pancreatic cancer. In some embodiments, the cancer is a metastatic cancer Any suitable immunotherapy agent can be used. For example, the immunotherapy agent can be a known small molecule inhibitor of programmed cell death protein 1 (PD-1), programmed death-ligand 1 (PD-L1, also known as CD274), cytotoxic T lymphocyte associated protein 4 (CTLA-4), indolamine 2,3-deoxygenase (I) (IDO), or C—C chemokine receptor type 7 (CCR7). Small molecule IDO inhibitors include, for instance, INCB24360 and NLG919, among others. In some embodiments, the small molecule inhibitor can be provided as a lipid conjugate prodrug. In some embodiments, the immunotherapy agent can be an antibody or antibody fragment. Immunotherapeutic antibodies for oncology include, but are not limited to, anti-CD51 antibodies (e.g., Alemtuzumab), anti-CD20 antibodies (e.g., Ofatumumab and Rituximab), anti-CD47 antibodies, and anti-GD2 antibodies. Immunotherapy agents can also include conjugated monoclonal antibodies, including, but not limited to, radiolabeled antibodies (e.g., Ibritumomab tiuxetan (Zevalin), etc.) and chemo-labeled antibodies (also known as antibody-drug conjugates (ADCs)), e.g., Brentuximab vedotin (Adcetris), Ado-trastuzumab emtansine (Kadcyla), denileukin diftitox (Ontak), etc. Other immunotherapy agents include cytokines, such as, but not limited to, interferons (i.e., IFN-α, INF-γ), interleukins (i.e. IL-2, IL-12), and tumor necrosis factor alpha (TNF-α) and the like. Further suitable immunotherapeutic agents include, for example, polysaccharide-K, neoantigens, etc.

Accordingly, in some embodiments, the immunotherapy agent is selected from the group comprising an anti-CD52 antibody, an anti-CD20 antibody, anti-CD47 antibody, an anti-GD2 antibody, polysaccharide K and a cytokine. In some embodiments, the immunotherapy agent is selected from the group comprising Alemtuzumab, Ofatumumab, Rituximab, Zevalin, Adcetris, Kadcyla and Ontak. In some embodiments, the immunotherapy agent is selected from the group comprising a PD-1 inhibitor, a PD-L1 inhibitor, a CTLA-4 inhibitor, an IDO inhibitor, a CCR7 inhibitor, a OX40 inhibitor, a TIM3 inhibitor, and a LAG3 inhibitor. In some embodiments, the immunotherapy agent is a prodrug (e.g., a lipid conjugate prodrug) of a small molecule inhibitor immunotherapy agent. In some embodiments, the cytokine is selected from the group comprising an interferon and an interleukin. In some embodiments, the cytokine is selected from the group comprising IFN-α, IFN-γ, IL-2, IL-12 and TNF-α.

In some embodiments, the presently disclosed subject matter proves a combination of PDT based on a nanoparticle PS and immunotherapy for the treatment of multiple cancer types.

In some embodiments, the method comprises administering to the patient an additional treatment (i.e., in addition to the photosensitizer or scintillator and the immunotherapy agent). For example, in some embodiments, the additional treatment is a cancer treatment or a treatment for a side effect of the cancer (e.g., a pain medication). In some embodiments, the additional treatment or additional cancer treatment is selected from the group including, but not limited to surgery, radiotherapy, chemotherapy, toxin therapy, immunotherapy, cryotherapy and gene therapy. The chemotherapy can comprise administering a drug selected from the group comprising oxaliplatin, doxorubicin, daunorubicin, docetaxel, mitoxanthrone, paclitaxel, digitoxin, digoxin, dihydroartemisinin, and septacidin. In some embodiments, the chemotherapy can be administered in a drug formulation such as a polymeric micelle formulation, a liposomal formulation, a dendrimer formulation, a polymer-based nanoparticle formulation, a silica-based nanoparticle formulation, a NCP formulation, and an inorganic nanoparticle formulation. Thus, in some embodiments, the presently disclosed subject matter provides the combination of PDT based on nanoparticle PS, chemotherapy, and immunotherapy for the treatment of multiple cancer types.

In some embodiments, irradiating with light can comprise irradiating with visible or near infrared light. In some embodiments, the light can have a wavelength between about 630 nm and about 1400 nm (e.g., about 670 nm). In some embodiments, the light can have a wavelength of from about 630 nm to about 740 nm (e.g. 630, 640, 650, 660, 670, 680, 690, 700, 710, 720, 730, or about 740 nm).

According to some embodiments of the presently disclosed subject matter, PDT can be combined with inhibitor-based immunotherapy and/or other immunotherapy to cause systemic rejection of established tumors using adaptive immune response, e.g., cytotoxic T cells. When combined with immunotherapeutic agents, not only the effective eradication of a primary tumor, but also suppression/eradication of a distant metastatic tumor or tumors can be accomplished using nanoparticle (e.g., NCP particle)-based PDT effects. In some embodiments, the antitumor efficacy can be enhanced by adding chemotherapeutics that are known to cause immunogenic cell death.

A number of inorganic materials are known to strongly absorb X-rays and convert the absorbed X-ray energy to visible and near-infrared light. The emitted near-infrared light from these X-ray scintillating nanomaterials can then be absorbed by the nearby photosensitizers to enable X-ray induced PDT effects. Other types of materials can also achieve X-ray induced PDT. When this X-ray induced PDT is combined with immune checkpoint inhibitors, excellent radioimmunotherapy can be obtained. Examples of X-ray scintillating nanomaterials include, but are not limited to: $LnO_3$:Ln' nanoparticles, $LnO_2S$ Ln' nanoparticles or $LnX_3$:Ln' nanoparticles, where Ln=Y, La, Ce, Pr, Nd, Sm, Eu, Gd, Tb, Dy, Ho, Er, Tm, Yb, Lu, Ln'=Ce, Pr, Eu, Tb, etc. and X=F, Cl, Br, and I; X-ray scintillator MOFs, such as $M_6(\mu_3-O)_4(\mu_3-OH)_4L_6$, where M=Hf, Zr, or Ce; and L=9,10-anthracenylbisbenzoic acid and other formulations of MOFs containing heavy metal secondary building units; lanthanide based MOFs, in which the SBU can be, but is not limited to, $Ln_4(\mu_4-OH_2)(CO_2)(CO_2)_8(SO_4)_4$, $[Ln(OH_2)(CO_2)_3]n$ (infinite 1-D chain), $[Ln(OH_2)(CO_2)_4]_n$ (infinite 1-D chain), $[Ln(CO_2)_3-Ln(OH_2)_2(CO_2)_3]_n$ (infinite 1-D chain), where Ln=La, Ce, Pr, Nd, Sm, Eu, Gd, Tb, Dy, Ho, Er, Tm, Yb, Lu and/or their mixture combination, and the bridging ligands can include but are not limited to [1,4-benzoic dicarboxylate], [2,5-dimethoxy-1,4-benzenedicarboxylate], [1,3,5-benzoic tricarboxylate], [1,3,5-benzenetrisbenzoate], [5-(pyridin-4-yl)isophthalic acid], [4,4',4"-S-triazine-2,4,6-triyl tribenzoate], [biphenyl-3,4',5-tricarboxylate], [4,4'-[(2,5-Dimethoxy-1,4-phenylene)di-2,1-ethenediyl]bis-benzoic acid], etc.; quantum dots, such as ZnS:M quantum dots (M=Cu, Co, Mn, Eu, etc.) or carbon dots; gold nanoparticles, or platinum or other third-row metal particles; and other X-ray scintillators, such as $SrAl_2O_4$:$Eu^{2+}$, $NaYF_4$:$Tb^{3+}$, and $Er^{3+}$.

When a nanoparticle comprising a scintillator is used, the subject can be irradiated with X-rays in any suitable manner and/or using any suitable equipment, such as that currently being used for delivering X-rays in a medical or veterinary setting. In some embodiments, the X-ray source and/or output can be refined to enhance disease treatment. For instance, the X-rays can be generated using a peak voltage, current and/or, optionally, a filter chosen to minimize DNA damage in the patient due to X-ray irradiation and maximize X-ray absorption by the scintillator.

In some embodiments, the presently disclosed subject matter provides a method that combines treating a subject with one or more immunotherapy agents, one or more chemotherapeutic agents, or with a combination of an one or more immunotherapy agents and one or more chemotherapeutic agents wherein the method comprises administering to a subject at least one of the agents in the form of a lipid-conjugate prodrug. In some embodiments, the method comprises administering a lipid-conjugate prodrug to a subject and administering an immunotherapy agent to the subject. The immunotherapy agent can by any suitable immunotherapy agent, such as one of the immunotherapy agents described above with regard to the combination therapies involving PDT. The lipid-conjugate prodrug can be administered in the form of a nanoparticle, e.g., wherein the lipid-conjugate prodrug is present in a lipid coating layer of a nanoparticle, such as, but not limited to a NCP particle.

In some embodiments the method comprises administering the prodrug (e.g., as part of a nanoparticle), an immunotherapy agent, and at least one additional treatment, such as, but not limited to a cancer treatment (e.g. surgery, radiotherapy, chemotherapy, toxin therapy, immunotherapy, cryotherapy and gene therapy. The chemotherapy can comprise administering a drug selected from the group comprising oxaliplatin, doxorubicin, daunorubicin, docetaxel, mitoxanthrone, paclitaxel, digitoxin, digoxin, dihydroartemisinin, and septacidin. The chemotherapy can comprise administering a drug formulation such as one of the chemotherapy drug formulations described herein above with regard to combination therapies involving PDT, II.C. Particles and Other Compositions Comprising Lipid-Conjugate Prodrugs The lipid-based prodrugs described herein can be combined with any suitable additional drug delivery platform. In some embodiments, the presently disclosed subject matter provides a composition comprising zinc pyrophosphate (i.e., an inorganic compound comprising $Zn^{2+}$ cations and pyrophosphate anions) and a lipid conjugate prodrug (e.g., a prodrug comprising a drug moiety linked to a lipid moiety via a linker comprising a disulfide bond). In some embodiments, the zinc pyrophosphate can be provided in the form of a nanoparticle. In some embodiments, the zinc pyrophosphate nanoparticle can be coated with a lipid coating layer, wherein the lipid coating layer can comprise the lipid conjugate prodrug.

In some embodiments, the presently disclosed subject matter provides a composition comprising a NCP comprising a cisplatin and/or oxaliplatin analogue or prodrug (e.g., as a bridging ligand in the NCP) and a lipid conjugate prodrug. As with the zinc pyrophosphate, the NCP can be provided in the form of a nanoparticle. In some embodiments, the NCP particle can be coated with a lipid coating layer comprising the prodrug. In some embodiments, the composition can further include a nucleic acid therapeutic agent, such as a siRNA, a miRNA or an AS ODN.

In some embodiments, the presently disclosed subject matter provides a nanoscale particle for delivery of therapeutic agents, wherein said nanoscale particle comprises: a core comprising a metal-organic matrix material and a prodrug comprising a drug-lipid conjugate. In some embodiments, the prodrug can be present in a lipid coating layer surrounding all or a portion of the surface of the particle core. In some embodiments, the drug-lipid conjugate comprises a monovalent drug moiety, a monovalent lipid moiety and a bivalent linker moiety comprising a biodegradable bond, e.g., a disulfide bond. The monovalent drug moiety can be, for example, a monovalent derivative of an anticancer drug and/or a small molecule immunotherapy agent. In some embodiments, the monovalent drug moiety can be a monovalent derivative of a drug such as, but not limited to, ET, PTX, OTS964, NLG919, OTS167, OTSC41, DHA, CPT, Doxorubicin, Docetaxel, Vincristine, MTX, ART, and Capecitabine. In some embodiments, the lipid moiety is a monovalent derivative of CHOL, OA, a lyso-lipid, or phosphocholine. In some embodiments, the bivalent linker is a bivalent derivative of bis(2-hydroxyethyl) disulfide or a similar compound. The nanoparticle can comprise any suitable metal-organic matrix. In some embodiments, the metal-organic matrix comprises a coordination polymer (e.g., a NCP).

Neoplastic cells grow within the context of the host environment, and can respond to numerous physical, chemical and cellular challenges. Therefore, those cells develop multiple strategies to control the tumor-host interaction. In order for a neoplasm to grow and spread, it needs to obtain sufficient oxygen and nutrients to break down the extracellular matrix (ECM) in order to invade surrounding tissues and metastasize, and to evade the host immune response. RNA interference (RNAi) technology can be used to target the molecules involved in angiogenesis, invasion/metastasis, and immune evasion for cancer therapy. These target genes include: (1) growth factors (e.g., VEGF, EGF, FGF, PDGF, IL-8, and IGF-1); (2) proteases and protease inhibitors (e.g., Cathepsin, MMP2, Stromelysin, and uPA); (3) oncogenes (e.g., c-myc, ras, c-src, v-raf, c-jun, and VEGFR); (4) signal transduction (e.g., thymidine and phosporylase); (5) enzymes (e.g., RAS-farnesyl, transferase, Geranyl, and Transferase); (6) cytokines (e.g., IL-1, IL-6, and IL-8); and (7) endogenous stimulator (e.g., Ang-1, Angiostatin II, Endothelin, iNOS, PAF, and Cox-2).

The expression of antiapoptotic proteins by cancer cells is one mechanism by which cancer cells develop resistance to chemotherapy or irradiation. Using RNAi to target antiapoptotic proteins represents a promising strategy to be used in conjunction with chemotherapy, PDT, and radiotherapy for cancer treatment. There are also several additional mechanisms that contribute to the chemoresistance or radioresistance, and molecules related to these mechanisms can provide opportunities for RNAi intervention. For example, RNAi targeting multidrug resistance (MDR) genes (e.g., ABCB1, ABCB4, and ABCB5) can be an approach for the treatment of MDR gene-mediated drug resistance. DNA repair mechanisms are important for the maintenance of genomic stability and thus are potential therapeutic targets for cancer. In the stress of chemo- or radiotherapy, cancer cells can overexpress proteins related to DNA repair in order to restore therapy-induced DNA damage. These target genes include excision repair cross-complementing 1 (ERCC1), X-ray repair cross-complementing protein 1 (XRCC1), ribonucleotide reductase, double-strand break signaling/repair proteins ATM, and DNA-dependent protein kinase catalytic subunit.

MicroRNAs (miRNAs) are a class of small, non-coding RNAs that post-transcriptionally control the translation and stability of mRNAs. miRNAs are responsible for maintaining a proper balance of various biological processes, including proliferation, differentiation, and cell death. In cancer, the loss of tumor-suppressive miRNAs enhances the expression of target oncogenes, whereas increased expression of oncogenic miRNAs can repress target tumor suppressor genes. Cancer-related miRNAs have been classified as oncogenic (such as miR-155, miR-21, and miR-17-29), tumor-suppressive (such as miR-15, miR-16, LIN28, DICER), and context-dependent (such as miR-146 and miR-29) genes. Delivering tumor-suppressive miRNAs and silencing oncogenic miRNAs have been successful in various mouse models.

Owing to the ability of miRNAs to target signaling pathways that are often perturbed in cancer, miRNAs also have the potential to sensitize resistant cells. MDR usually involves the increased excretion of a drug through ATP-binding cassette (ABC) transporters. Two of these ABC transporters, ABCC3 and ABCC6, are induced directly by SOX2. miR-9 is identified as a negative regulator of SOX2. Forced expression of miR-9 in a chemotherapy-resistant glioma stem cell lines suppresses SOX2 expression, leading to reduced ABC transporter expression and hence drug retention.

Oligonucleotides are unmodified or chemically modified single-stranded DNA molecules. In general, they are relatively short (13-25 nucleotides) and hybridize to a unique sequence in the total pool of targets present in cells. Antisense oligonucleotides (AS ODNs) are single-stranded DNA fragments found to be able to inhibit mRNA translation. Antitumor AS ODNs are targeted to the genes that are involved in cell division, angiogenesis, metastasis, and cell survival in the presence of apoptotic signals including Bcl-2, Survivin, MDM2, Bcl-XL, RelA, RAS, RAF, BCR-ABL, JNK1,2, TERT, c-myc, and c-myb. Since the majority of cancer cells differ in gene expression profile from normal cells, AS ODNs can be used to specifically suppress the tumor growth with minimal consequences for normal cells. For example, Genta Inc. (Berkeley Heights, N.J., United States of America) has developed an 18-mer phosphothioate AS ODN that is complementary to Bcl-2, known as Genasense™. In addition, AS ODNs targeting MDM2 have been shown to potentiate the effects of growth inhibition, p53 activation and p21 induction by several chemotherapeutic agents.

Accordingly, in some embodiments, the nanoparticle can further comprise at least one nucleic acid therapeutic agent (e.g., a nucleic acid chemotherapeutic agent). The nucleic acid chemotherapeutic agent can be a small interfering ribonucleic acid (siRNA), a miRNA, or an AS ODN. The nucleic acid chemotherapeutic agent can be covalent linked to a lipid molecule and/or attached to a lipid molecule via electrostatic interactions, wherein said lipid molecule can form part of a lipid coating layer surrounding all or a portion of the surface of the nanoparticle core. Additionally or alternatively, at least one nucleic acid can be attached to the metal-organic matrix material core via coordination bonds between phosphate groups on the nucleic acid and metal ions on an outer surface of the core. In some embodiments, nucleic acids such as siRNAs, miRNAs, and AS ODNs, can be directly loaded to the surfaces of NCPs via coordination bonds between metal ions on the NCP outer surface and phosphate groups on nucleic acids.

The nanoparticles can comprise, for example, a single siRNA or pooled siRNAs (including several siRNAs targeting different anti-cancer pathways). These siRNAs can include, but are not limited to, the following: EGFR/ErbB1 siRNA, ErbB2/HER2/Neu siRNA, IGF-1R siRNA, K-ras siRNA, R-ras siRNA, BRAF siRNA, ABL siRNA, c-Src siRNA, Met siRNA, c-Myc siRNA, N-Myc siRNA, Cyclin-D1 siRNA, PI3K siRNA, AKT siRNA, NF-κβ siRNA, EWS/FLI-1 siRNA, HIF siRNA, HPV E7 siRNA, E2F4 siRNA, HPV E6 siRNA, Hdmx siRNA, Notch-1 siRNA, Delta-like-1 siRNA, FLIP siRNA, BCL-2 siRNA, BCL-XL siRNA, Survivin siRNA, XIAP siRNA, Telomerase siRNA, ID1 siRNA, Cks-1 siRNA, Skp-2 siRNA, cathepsin L siRNA, VEGF siRNA, EGF siRNA, FGF siRNA, PDGF siRNA, IL-8 siRNA, IGF-1 siRNA, Cathepsin siRNA, MMP2 siRNA, Stromelysin siRNA, uPA siRNA, c-myc siRNA, ras siRNA, c-src siRNA, v-raf siRNA, c-jun siRNA, VEGFR siRNA, Thymidine siRNA, phosporylase siRNA, RAS-farnesyl siRNA, transferase siRNA, Geranyl siRNA, Transferase siRNA, IL-1 siRNA, IL-6 siRNA, IL-8 siRNA, Ang-1 siRNA, Angiostatin II siRNA, Endothelin siRNA, iNOS siRNA, PAF siRNA, Cox-2 siRNA, ABCB1 siRNA, ABCB4 siRNA, ABCB5 siRNA, P-glycoprotein siRNA, ERCC1 siRNA, and ATM siRNA. The miRNAs can include, but are not limited to, the following: miR-9, miR-15, miR-16, miR-34, miR-181, miR-200, miR 200c, miR-342, miR-630, let-7, LIN28, and DICER. The particles can also include one or more antisense oligonucleotides (AS ODNs). Gene targets of the AS ODNs used can include, but are not limited to, the following: Bcl-2, Survivin, MDM2, Bcl-XL, RelA, RAS, RAF, BCR-ABL, JNK1,2, TERT, c-myc, and c-myb. In some embodiments, the nucleic acid can be used to suppress an immunotherapy target. Thus, in some embodiments, the nucleic acid can be, for example, a siRNA targeting PD-1/PD-L1, a siRNA targeting IDO or a siRNA targeting CCR7. In some embodiments, one nucleic acid is used. In other embodiments, a combination of 2, 3, 4, 5, 6, 7, 8, 9, 10 or more different nucleic acids is used. In some embodiments, the nanoparticle can comprise at least one nucleic acid agent selected from the group comprising, but not limited to, survivin siRNA, ERCC-1 siRNA, P-glycoprotein siRNA (P-gp siRNA), Bcl-2 siRNA, or a mixture thereof.

In some embodiments, the nanoparticle can further comprise at least one photosensitizer (PS). In some embodiments, the PS is embedded or sequestered in the nanoparticle core (e.g., in pores or hollow interior cavities) or covalently attached to an organic moiety within the NCP matrix. In some embodiments, the PS is covalently or non-covalently attached to a lipid coating layer or layers (i.e., a single lipid layer, lipid bilayer, or combination thereof) surrounding a portion of the outer surface of the nanoparticle core. Any suitable PS can be used, such as but not limited to, porphyrins, chlorophylls dyes, or derivatives or analogs thereof. In some embodiments, the coating layer or layers includes a lipid single layer or lipid bilayer comprising a pyrolipid, i.e., a lipid covalently attached to a porphyrin or a derivative or analog thereof.

In some embodiments, the nanoparticle can further comprise at least one non-nucleic acid chemotherapeutic agent incorporated in the metal-organic matrix material core. For example, the at least one non-nucleic acid chemotherapeutic agent can be incorporated in the metal-organic matrix material core via a covalent or a coordination bond. Alternatively, the agent can embedded or sequestered in pores or hollow cavities within the core. Any suitable non-nucleic acid chemotherapeutic agent can be used. In some embodiments, the non-nucleic acid chemotherapeutic agent is selected from the group comprising, but not limited to cisplatin or oxaliplatin prodrugs, gemcitabine, methotrexate, leucovorin, pemetrexed disodium, doxorubicin, vinblastine, vincristine, vindesine, cytarabine, azathioprine, melphalan, imatinib, anastrozole, letrozole, carboplatin, paclitaxel, docetaxel, etoposide, and vinorelbine. The particle can comprise a single non-nucleic acid chemotherapeutic agent incorporated into the metal-organic matrix core or can comprise combinations of 2, 3, 4, 5, 6, or more non-nucleic acid chemotherapeutic agents incorporated in the metal-organic matrix material core. Thus, the presently disclosed subject matter can, in some embodiments, provide a combination of chemotherapies based on a nanoparticle for the treatment of multiple cancer types or a combination of nanoparticle-based chemotherapy and immunotherapy for the treatment of multiple cancer types.

In some embodiments, the non-nucleic acid chemotherapeutic agent is an analogue or prodrug of oxaliplatin or cisplatin. For instance, a suitable cisplatin analogue or prodrug can comprise a platinum coordination complex comprising two $NH_3$ platinum ligands and two chloro ligands (i.e., the four Pt ligands typically present in cisplatin), and at least one or two additional ligand or ligands (e.g., comprising five or six Pt ligands in total), wherein at least one additional Pt ligand or ligands comprises at least two groups that can coordinate to a metal ion. Thus, at least one metal ligand of the platinum coordination complex can coordinate both to the platinum ion of the platinum coordination complex and to a metal ion in a second coordination complex (e.g., another Pt coordination complex). Such a ligand can comprise two or more amino, hydroxyl, and/or carboxylate groups, or a combination of such groups. In some embodiments, the non-nucleic acid chemotherapeutic agent is cis, cis, trans-$Pt(NH_3)_2Cl_2(OEt)(O_2CCH_2CH_2CH_2OOH)$.

In some embodiments, the nanoparticle core can comprise between about 10 weight % and about 50 weight % of the non-nucleic acid chemotherapeutic agent (e.g., about 10, 15, 20, 25, 30, 35, 40, 45, or about 50 weight % of the non-nucleic acid chemotherapeutic agent).

In some embodiments, the nanoscale particle has an average diameter of less than about 500 nm or less than about 250 nm. In some embodiments, the particle has an average diameter of between about 20 nm and about 200 nm. In some embodiments, the nanoscale particle has an average diameter of between about 20 nm and about 140 nm (e.g., about 20, 25, 30, 35, 40, 45, 50, 55, 60, 65, 70, 75, 80, 85, 90, 95, 100, 105, 110, 115, 120, 125, 130, 135, and about 140 nm).

In some embodiments, the nanoscale particle further comprises one or more coating agents or layers covering at least a portion of the outer surface of the metal-organic matrix material core, wherein the one or more coating agents or layers are selected from a metal oxide, a polymer, a single lipid layer, a lipid bilayer, and combinations thereof. Thus, for example, a spherical nanoparticle can have one or more concentric coating layers, each successive layer being dispersed over the outer surface of a smaller layer closer to the center of the particle. In some embodiments, the metal-organic matrix material core is coated with a lipid bilayer comprising a cationic lipid and/or a functionalized lipid, wherein said functionalized lipid is a lipid functionalized with a group that can bond to a nucleic acid, and wherein at least one nucleic acid is covalently bonded to the functionalized lipid and/or attached to the cationic lipid via electrostatic interactions. In some embodiments, the lipid bilayer comprises a mixture comprising one or more of a thiol- or dithiol-functionalized 1,2-distearoyl-sn-glycero-3-phosphoethanolamine (DSPE), 1,2-dioleoyl-3-trimethylammonium propane (DOTAP), and 1,2-dioleoyl-sn-glycero-3-phosphocholine (DOPC). In some embodiments, the lipid bilayer or lipid single layer can comprise or further comprise one or more of the group including but not limited to, cholesterol, 1,2-distearoyl-sn-glycero-3-phosphoethanolamine (DSPE), 1,2-Distearoyl-sn-glycero-3-phosphocholine (DSPC), 1,2-dioleoyl-3-trimethylammonium propane (DOTAP), 1,2-dioleoyl-sn-glycero-3-phosphocholine (DOPC), 1,2-dioleoyl-sn-glycero-3-phosphate sodium salt (DOPA), and pegylated-DSPE. In some embodiments, the lipid bilayer comprises or further comprises one or more of 1,2-dioleoyl-sn-glycero-3-phosphate sodium salt (DOPA), cholesterol, and pegylated-DSPE. In some embodiments, the one or more coating agents or layers further comprise a passivating agent, such as, but not limited to, a hydrophilic polymer (e.g., PEG); a targeting agent, such as, but not limited to a RGD peptide, an aptamer, an oligonucleotide, a polypeptide, an antibody or antibody fragment, or a polysaccharide; and/or an imaging agent, such as an optical imaging agent (e.g., a fluorescent moiety).

In some embodiments, the metal-organic matrix material core comprises a metal bisphosphonate coordination polymer comprising a multivalent metal ion and a bisphosphonate. The multivalent metal ion can be any suitable multivalent metal ion. In some embodiments, the multivalent metal ion is a divalent metal ion, such as, but not limited to, $Ca^{2+}$, $Mg^{2+}$, $Mn^{2+}$, $Zn^{2+}$, and combinations thereof. In some embodiments, the multivalent metal ion is $Zn^{2+}$.

In some embodiments, the bisphosphonate is itself a metal complex wherein two metal ligands are phosphonate-containing groups and wherein the phosphonate groups are available for coordinating to the multivalent metal ion. The bisphosphonate metal complex can comprise other ligands (i.e., those that do not contain a phosphonate group) that can include mono- and bidentate metal ligands, such as, but not limited to, halo (e.g., Cl, Br, F, or I), $NH_3$, alkylamino, hydroxyl, alkoxy, diols and diamines (e.g., diaminocyclohexane). The bisphosphonates can be prepared by providing a suitable metal complex, such as a metal complex with two hydroxyl ligands, and contacting the metal complex with, for example, diethoxyphosphinyl isocyanate, diethoxyphosphinyl isothiocyanate, diethoxyphosphinyl-containing carboxylic anhydride, or diethoxyphosphinyl-containing acyl chloride to form metal ligands that can provide phosphonate groups available for further coordinative bonding. In some embodiments, the bisphosphonate is a platinum metal complex (e.g., cisplatin, oxaliplatin, or a similar complex) wherein two platinum ligands have been replaced by or conjugated to phosphonate-containing groups that are not involved in coordinating to the platinum. In some embodiments, the metal bisphosphonate coordination polymer particle can comprise a lipid coating layer comprising a prodrug of DHA.

Thus, for example, in some embodiments, the bisphosphonate is a chemotherapeutic prodrug, optionally a cisplatin or oxaliplatin prodrug, such as, but not limited to bisphosphonate ester of cis, cis-trans-$[Pt(NH_3)_2Cl_2(OH)_2]$ (a cisplatin prodrug) or cis, trans-$[Pt(dach)Cl_2(OH)_2]$. To provide the bisphosphonate ester, the two hydroxyl ligands can be replaced by a ligand that comprises the formula —O(C=X)—R'—P(=O)(OR)$_2$, wherein each R is independently H, alkyl, substituted alkyl, aralkyl, substituted aralkyl, aryl, substituted aryl, and a negative charge; wherein R' is a bivalent moiety such as —NH— or an alkylene moiety, and X is O or S. In some embodiments, the bisphosphonate can have the formula $PtL_{x-2}[$—O—C(=O)—NH—P(=O)(OR)$_2]_2$, wherein x is an integer that is 3 or greater (e.g., 3, 4, 5, or 6).

In some embodiments, metal-organic matrix material core comprises between about 40 and about 50 weight % of bisphosphonate (e.g., about 40, 41, 42, 43, 44, 45, 46, 47, 48, 49 or 50 weight % of the bisphosphonate). In some embodiments, the particle can further comprise one or more coating layers. In some embodiments, the one or more coating layers comprise a lipid single layer or lipid bilayer coating. In some embodiments, one or more nucleic acid therapeutic agents, such as one or more of survivin siRNA, P-gp siRNA, and Bcl-2 siRNA, are attached to the coating.

In some embodiments, the nanoscale particle has a diameter between about 20 nm and about 180 nm. In some embodiments, the nanoscale particle has a diameter between about 90 nm and about 180 nm (e.g., about 90, 95, 100, 105, 110, 115, 120, 125, 130, 135, 140, 145, 150, 155, 160, 165, 170, 175, or about 180 nm).

In some embodiments, the presently disclosed compositions are provided for use in treating a disease (e.g., cancer) alone or in combination with one or more additional therapeutic agents, e.g., one or more chemotherapeutic agents (or analogues or prodrugs thereof), one or more immunotherapy agents, one or more targeting agents, one or more imaging agent, one or more scintillator, one or more photosensitizer, or any mixture thereof.

II.D. Methods of Treating Cancer with Nanoparticles

In some embodiments, the presently disclosed subject matter provides a method of treating cancer in a subject in need thereof, wherein the method comprises administering to the subject a composition comprising a nanoscale particle as described herein. In some embodiments, the method of treating cancer comprises administering to the subject a composition comprising a nanoscale particle comprising: a core comprising a metal-organic matrix material, and a prodrug comprising a drug-lipid conjugate.

The cancer can be any cancer in need of treatment, such as, but not limited to a skin cancer (e.g., a melanoma), a connective tissue cancer (e.g., a sarcoma), an adipose cancer, a breast cancer, a head and neck cancer, a lung cancer (e.g., mesothelioma), a stomach cancer, a pancreatic cancer, an ovarian cancer, a cervical cancer, an uterine cancer, an anogenital cancer (e.g., testicular cancer), a kidney cancer, a bladder cancer, a colon cancer, a prostate cancer, a central nervous system (CNS) cancer, a retinal cancer, a blood cancer, a neuroblastoma, multiple myeloma, or a lymphoid cancer (e.g., Hodgkin's or non-Hodgkin's lymphomas). In some embodiments, the cancer is lung cancer, pancreatic cancer, ovarian cancer, breast cancer or colon cancer. In some embodiments, the cancer is a metastatic cancer and/or a chemo and/or radio-resistant cancer. In some embodiments, the cancer is ovarian cancer. In some embodiments, the ovarian cancer is a cisplatin resistant cancer.

In some embodiments, the method further comprises administering to the subject an immunotherapy agent. In some embodiments, the immunotherapy agent is selected from an antibody, a small molecule inhibitor, a small molecule inhibitor prodrug, a cytokine, and polysaccharide K. For instance, in some embodiments, the immunotherapy agent is selected from the group including, but not limited to, an anti-CD52 antibody, an anti-CD20 antibody, an anti-CD47 antibody an anti-GD2 antibody, a cytokine, and polysaccharide K. In some embodiments, the immunotherapy agent is selected from the group including, but not limited to, Alemtuzumab, Ofatumumab, Rituximab, Zevalin, Adcetris, Kadcyla and Ontak. In some embodiments, the immunotherapy agent is selected from the group comprising a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor. In some embodiments, more than one (e.g., 2, 3, 4, 5, 6, or more) immunotherapy agent can be administered In some embodiments, the nanoscale particle further comprises a photosensitizer (PS). The nanoscale particle can comprise any suitable PS. In some embodiments, the PS is a pyrolipid, wherein said pyrolipid is a lipid covalently attached to a porphyrin or a derivative or analog thereof.

When the nanoparticle comprises a PS, the method of treating cancer can further comprise irradiating the subject or a treatment area of the subject with radiation (e.g., visible or near infrared light) having a wavelength suitable to activate the photosensitizer. For example, when the nanoparticle comprises a pyrolipid, the method can comprise irradiating the subject with light at a wavelength between about 630 nm and about 740 nm (e.g., 630, 640, 650, 660, 670, 680, 690, 700, 710, 720, 730, or about 740 nm).

The PS-containing nanoparticle can be used to treat any cancer, such as one of the cancers described hereinabove. In some embodiments, the cancer is a head and neck cancer, optionally a cisplatin resistant head and neck cancer.

In some embodiments, the chemotherapy and PDT can be further combined with immunotherapy and an immunotherapy agent can be administered to the subject in addition to or as part of a PS-containing nanoparticle. In some embodiments, the immunotherapy agent is selected from the group including, but not limited to, an anti-CD52 antibody, an anti-CD20 antibody, an anti-CD20 antibody, anti-CD47 antibody, an anti-GD2 antibody, polysaccharide K and a cytokine. In some embodiments, the immunotherapy agent is selected from a radiolabeled antibody, an antibody-drug conjugate, and a neoantigen. In some embodiments, the immunotherapy agent is selected from the group comprising Alemtuzumab, Ofatumumab, Rituximab, Zevalin, Adcetris, Kadcyla and Ontak. In some embodiments, the immunotherapy agent is a small molecule inhibitor, such as, but not limited to, a PD-1 inhibitor, a PD-L1 inhibitor, a CTLA-4 inhibitor, an IDO inhibitor, a CCR7 inhibitor, a OX40 inhibitor, a TIM3 inhibitor, and a LAG3 inhibitor.

In some embodiments, the presently disclosed subject matter provides a pharmaceutical formulation comprising a nanoscale particle as described herein (e.g., a nanoscale particle comprising a core comprising a metal-organic matrix material comprising a coordination polymer and a prodrug comprising a lipid-drug conjugate, optionally further comprising a PS and/or an immunotherapy agent) together with a pharmaceutically acceptable carrier. The pharmaceutically acceptable carrier can be pharmaceutically acceptable in humans.

Thus, the presently disclosed subject matter provides nanoparticles that can comprise multiple chemotherapeutic agents, alone or in combination with one or more immunotherapy agents. The presently disclosed subject matter also provides nanoparticles that contain a PS for use in PDT, alone or in combination with one or more immunotherapy agents and/or one or more chemotherapy agents. These nanoparticle-based therapies can be used to treat multiple cancer types and to treat cancer more efficiently by targeting multiple pathways.

III. Formulations

Thus, the compositions of the presently disclosed subject matter comprise, in some embodiments, a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

IV. Subjects

The methods and compositions disclosed herein can be used on a sample either in vitro (for example, on isolated cells or tissues) or in vivo in a subject (i.e., living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

V. Administration

Suitable methods for administration of a composition of the presently disclosed subject matter include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

In one embodiment, the method of administration encompasses features for regionalized delivery or accumulation at the site to be treated. In some embodiments, a composition is delivered intratumorally. In some embodiments, selective delivery of a composition to a target is accomplished by intravenous injection of the composition followed by photodynamic treatment (light irradiation) of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

VI. Doses

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity (e.g., cytotoxic or PDT activity or chemotherapeutic loading) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Prodrug Synthesis

Several anticancer drugs such as Etoposide (ET), Paclitaxel (PTX), dihydroartemisinin (DHA), and NLG919 were conjugated to cholesterol whereas Camptothecin (CPT) was conjugated to oleic acid (OA) through a disulfide linker. The synthesis of the prodrugs can involve the conversion of the hydroxyl group in either the lipid (Chol) or the anticancer drug (CPT) into an acyl chloride, followed by the direct conjugation with drugs (ET, PTX, NLG919) or lipids (OA) that also have hydroxyl group(s). The disulfide bond can be introduced into the prodrugs either via first functionalizing anti-cancer drugs with bis(2-hydroxyethyl) disulfide (OH—S—S—OH), followed by lipid conjugation (Chol-ET, Chol-PTX, and Chol-NLG919), or modifying the lipid with OH—S—S—OH first, followed by the anticancer drug conjugation (OA-CPT).

Scheme 3. Synthesis of Chol-S—S—OH.

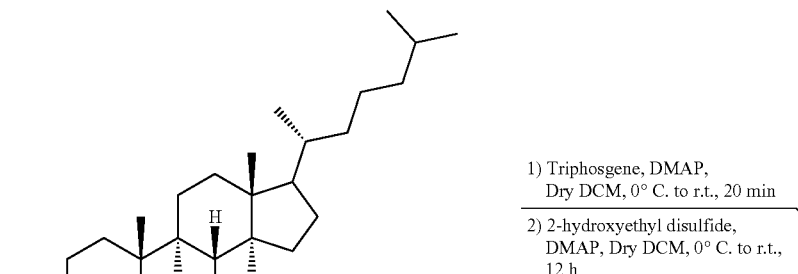

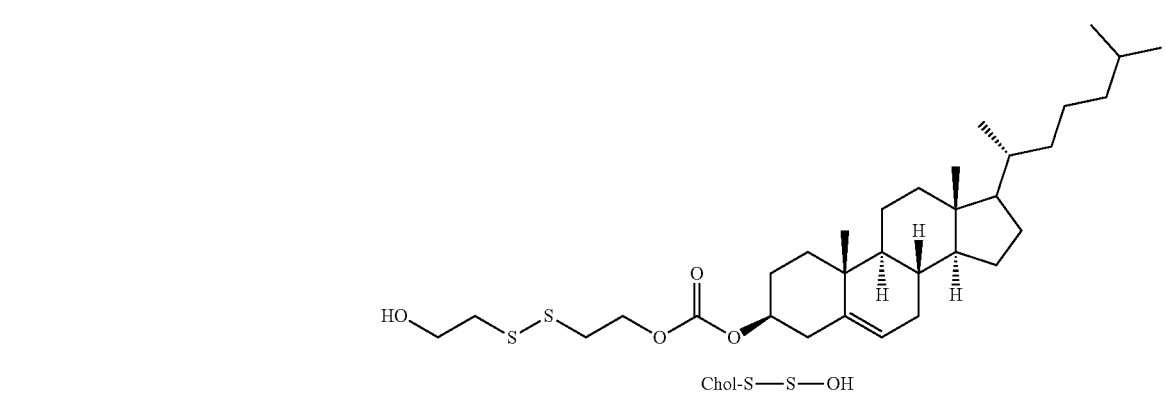

Chol-S—S—OH

As shown in Scheme 3, above, a mixture of Cholesterol (1 eq.) and 4-N,N-dimethylaminopyridine (DMAP, 4 eq.) in anhydrous dichloromethane (DCM), a solution of triphosgene (0.35 eq.) in anhydrous DCM was added dropwise over an ice bath with stirring. The resultant solution was warmed to room temperature and further stirred for 20 minutes and then added dropwise to a solution of bis(2-hydroxyethyl) disulfide (2 eq.) in anhydrous DCM over an ice bath. The reaction mixture was then warmed to room temperature and stirred for 12 hours. After removal of solvent, the residue was purified by column chromatography on silica gel with ethyl acetate/hexane (1:2, v/v). Typical yield: 60%. $^1$H-NMR (500 MHz, CDCl$_3$): 0.65 (s, 3H), 0.83 (d, 3H), 0.84-1.15 (m, 13H), 1.22-1.66 (m, 13H), 1.75-2.02 (m, 5H), 2.37 (m, 2H), 2.85 (m, 3H), 2.92 (t, 2H), 3.83 (t, 2H), 4.34 (t, 2H), 4.44 (m, 1H), 5.37 (d, 1H).

Scheme 4. Synthesis of prodrugs.

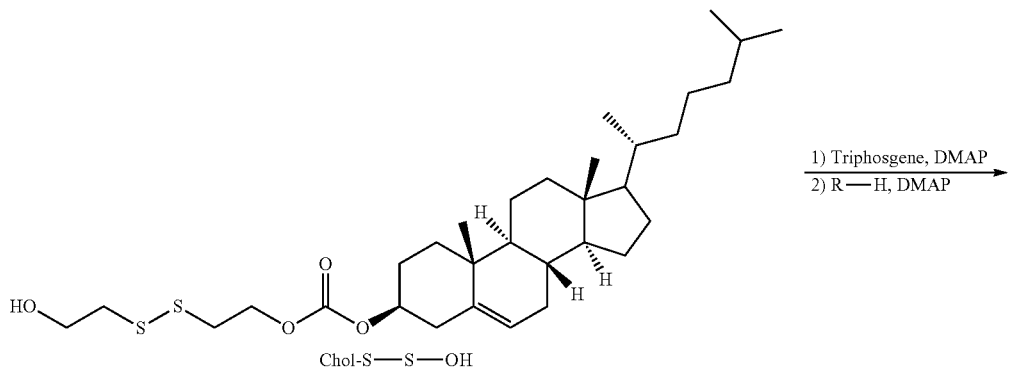

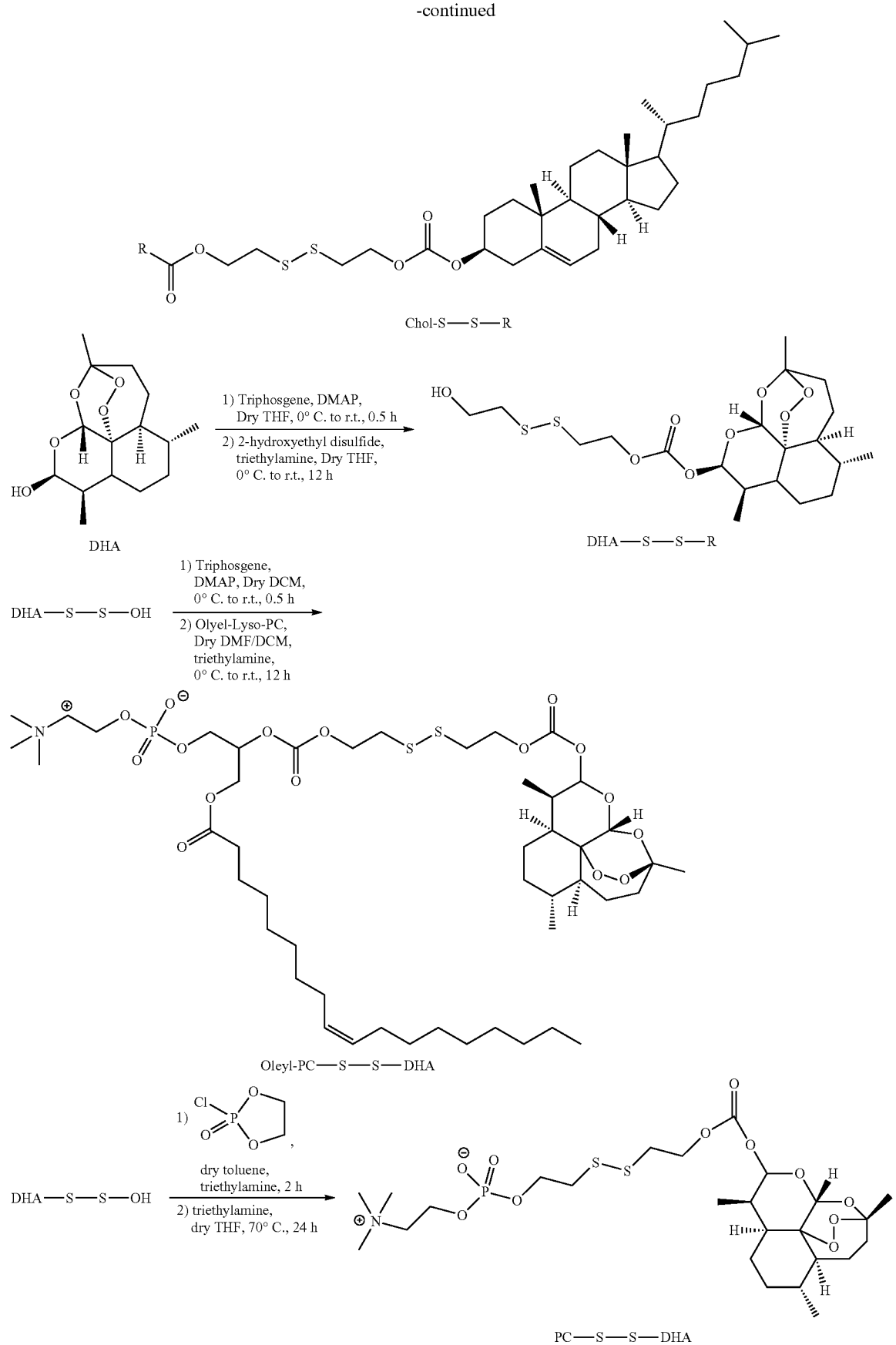

-continued

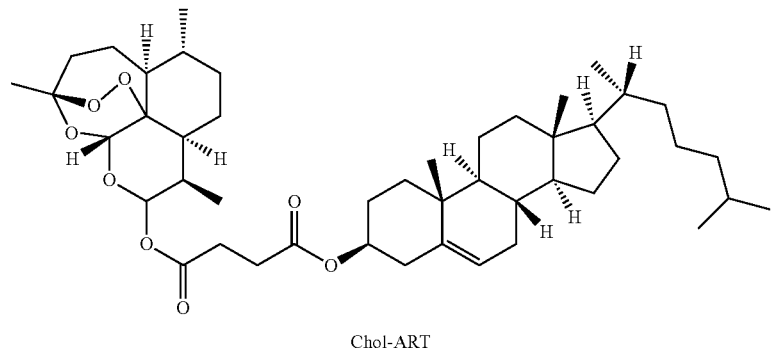

Chol-ART

Chol-ET

As shown in Scheme 4, above, to a mixture of Chol-S—S—OH (1 eq.) and 4-N,N-dimethylaminopyridine (DMAP, 4 eq.) in anhydrous dichloromethane (DCM), a solution of triphosgene (0.35 eq.) in anhydrous DCM was added dropwise over an ice bath with stirring. The resultant solution was warmed to room temperature and further stirred for 1 hour and then added dropwise to a solution of ET (3 eq.) in anhydrous DCM over an ice bath. The reaction mixture was then warmed to room temperature and stirred for 12 hours. After removal of solvent, the residue was purified by column chromatography on silica gel with methanol/DCM (3:97, v/v) to obtain Chol-ET in 65% yield (FIGS. 3 and 4). $^1$H-NMR (500 MHz, CDCl$_3$): 0.66 (s, 3H), 0.84-1.65 (m, 32H), 1.75-2.02 (m, 6H), 2.37 (m, 2H), 2.85 (s, 2H), 2.95 (t, 2H), 2.98 (t, 2H), 3.21 (s, 2H), 3.30 (m, 3H), 3.38 (t, 1H), 3.54 (t, 1H), 3.64 (m, 3H), 3.67 (s, 6H), 4.15 (d, 1H), 4.22 (t, 1H), 4.35 (t, 2H), 4.39 (d, 1H), 4.45 (t, 2H), 4.58 (m, 2H), 4.72 (d, 1H), 4.91 (s, 1H), 5.37 (d, 1H), 5.97 (d, 2H), 6.25 (s, 2H), 6.52 (s, 1H), 6.82 (s, 1H), 7.95 (s, 1H).

Scheme 5. Chemical structures of various prodrugs.

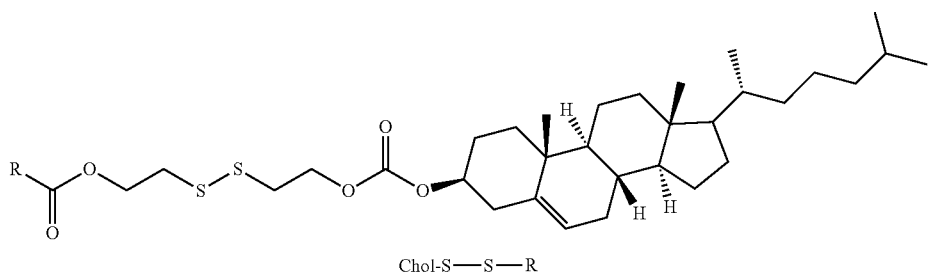

Chol-S—S—R

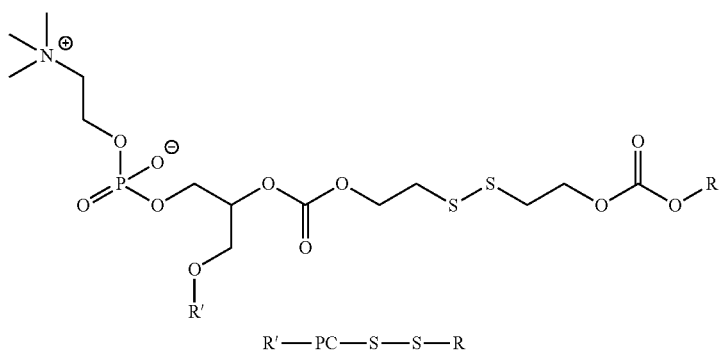

R'—PC—S—S—R

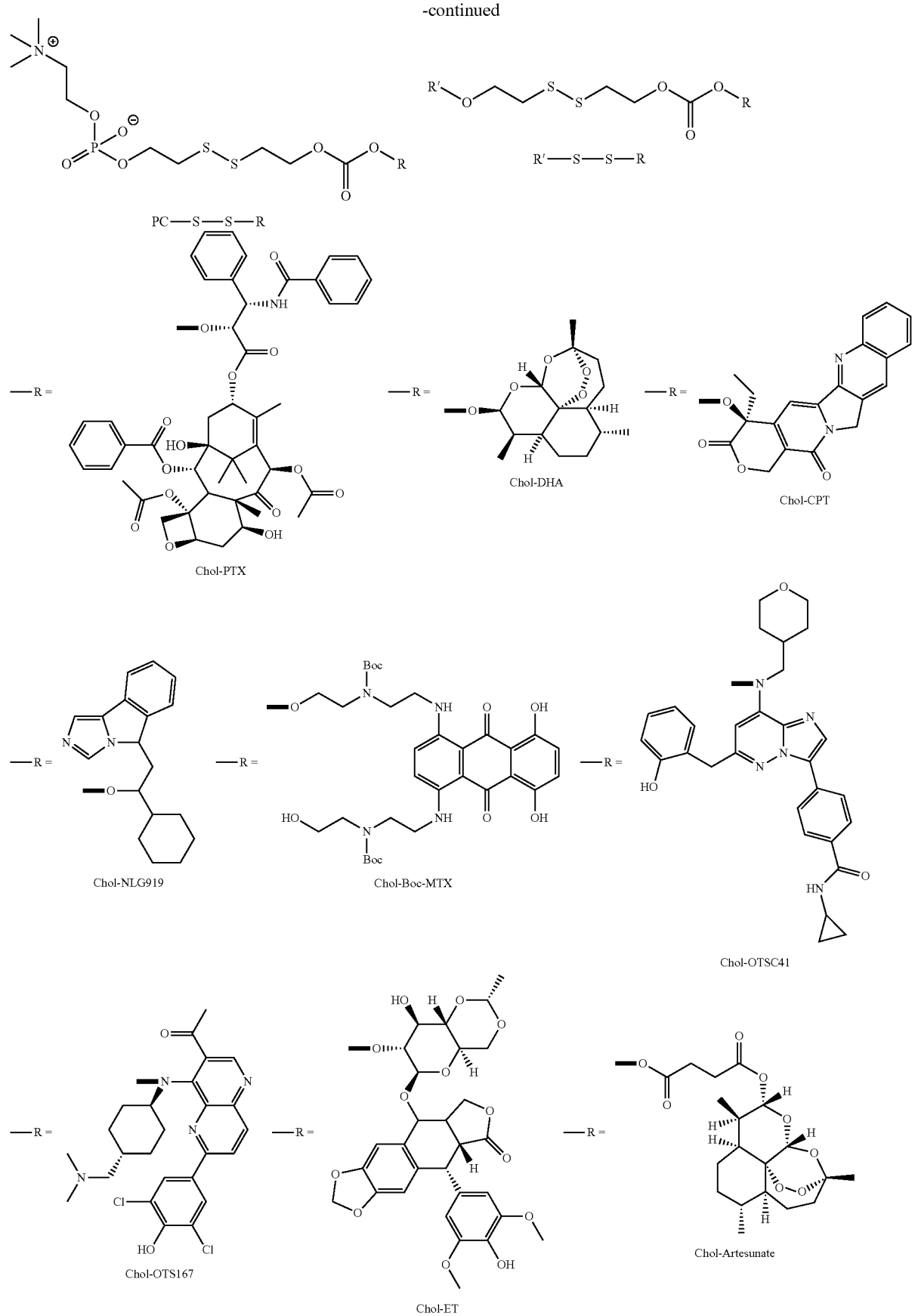

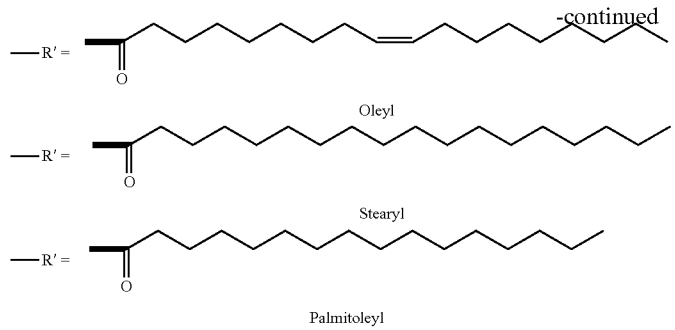

Oleyl

Stearyl

Palmitoleyl

Chol-PTX

To a mixture of Chol-S—S—OH (362 mg, 0.64 mmol, 1 eq.) (see structure in Scheme 5, above) and 4-N,N-dimethylaminopyridine (DMAP, 140 mg, 1.2 mmol 2 eq.) in anhydrous dichloromethane (DCM, 6 mL), a solution of triphosgene (65 mg, 0.21 mmol, 0.33 eq.) in anhydrous DCM (3 mL) was added dropwise over an ice bath with stirring. The resultant solution was warmed to room temperature and further stirred for 1 hour and then added dropwise to a solution of PTX (500 mg, 0.59 mmol, 0.9 eq.) in anhydrous DCM (15 mL) over an ice bath. The reaction mixture was then warmed to room temperature and stirred for 12 hours. After removal of solvent, the residue was purified by column chromatography on silica gel with methanol/DCM (3:97, v/v) to yield 408 mg of Chol-PTX. $^1$H-NMR (500 MHz, CDCl$_3$): 0.65 (s, 3H), 0.87-2.01 (m, 53H), 2.25-2.49 (m, 11H), 2.95 (m, 4H), 3.82 (d, 1H), 4.25 (q, 1H), 4.34 (m, 3H), 4.43 (m, 3H), 4.97 (d, 1H), 5.38 (d, 1H), 5.42 (s, 1H), 5.70 (d, 1H), 6.01 (d, 1H), 6.32 (m, 2H), 7.04 (d, 1H), 7.43 (m, 7H), 7.54 (m, 3H), 7.63 (m, 1H), 7.77 (d, 2H), 8.16 (d, 2H). ESI-MS: m/z=1468.8 ([M+Na]$^+$).

Chol-CPT

To a mixture of Chol-S—S—OH (480 mg, 0.84 mmol, 1 eq.) and 4-N,N-dimethylaminopyridine (DMAP, 140 mg, 1.2 mmol 1.5 eq.) in anhydrous dichloromethane (DCM, 6 mL), a solution of triphosgene (85 mg, 0.28 mmol, 0.33 eq.) in anhydrous DCM (3 mL) was added dropwise over an ice bath with stirring. The resultant solution was warmed to room temperature and further stirred for 1 hour and then added dropwise to a suspension of CPT (200 mg, 0.57 mmol, 0.7 eq.) in anhydrous DCM (50 mL) over an ice bath. The reaction mixture was then warmed to room temperature and stirred for 12 hours. After removal of solvent, the residue was purified by column chromatography on silica gel with hexane/ethyl acetate/triethyl amine (1:2:0.03, v/v) to yield 150 mg of Chol-CPT. $^1$H-NMR (500 MHz, CDCl$_3$): 0.65 (s, 3H), 0.85-1.21 (m, 12H), 1.25-1.65 (m, 13H), 1.85-2.05 (m, 6H), 2.13 (m, 1H), 2.32 (m, 1H), 2.36 (d, 1H), 2.95 (m, 4H), 4.29 (d, 2H), 4.36 (t, 2H), 4.42 (m, 1H), 5.28 (d, 2H), 5.38 (d, 2H), 5.70 (d, 1H), 7.34 (s, 1H), 7.67 (dd, 1H), 7.83 (dd, 1H), 7.93 (d, 1H), 8.22 (d, 1H), 8.40 (s, 1H). ESI-MS: m/z=941.6 ([M+H]$^+$).

Chol-DHA

To a mixture of Chol-S—S—OH (83.5 mg, 0.15 mmol, 1 eq.) and 4-N,N-dimethylaminopyridine (DMAP, 54 mg, 0.44 mmol 3 eq.) in anhydrous dichloromethane (DCM, 2 mL), a solution of triphosgene (15 mg, 0.05 mmol, 0.33 eq.) in anhydrous DCM (1 mL) was added dropwise over an ice bath with stirring. The resultant solution was warmed to room temperature and further stirred for 1 hour and then added dropwise to a solution of DHA (50 mg, 0.17 mmol, 1.1 eq.) in anhydrous DCM (5 mL) over an ice bath. The reaction mixture was then warmed to room temperature and stirred for 12 hours. After removal of solvent, the residue was purified by column chromatography on silica gel with hexane/ethyl acetate (7:1, v/v) to yield 53 mg of Chol-CPT. $^1$H-NMR (500 MHz, CDCl$_3$): 0.65 (s, 3H), 0.88-1.20 (m, 29H), 1.30-1.75 (m, 20H), 1.80-2.08 (m, 8H), 2.37 (m, 3H), 2.61 (m, 1H), 3.00 (m, 4H), 4.41 (m, 4H), 4.52 (m, 1H), 5.42 (d, 1H), 5.47 (s, 1H), 5.60 (d, 1H). ESI-MS: m/z=899.5 ([M+Na]$^+$).

Chol-NLG919

To a mixture of Chol-S—S—OH (109 mg, 0.19 mmol, 1 eq.) and 4-N,N-dimethylaminopyridine (DMAP, 45 mg, 0.38 mmol 2 eq.) in anhydrous dichloromethane (DCM, 2 ml), a solution of triphosgene (20 mg, 0.07 mmol, 0.35 eq.) in anhydrous DCM (1 mL) was added dropwise over an ice bath with stirring. The resultant solution was warmed to room temperature and further stirred for 1 hour and then added dropwise to a solution of NLG919 (100 mg, 0.38 mmol, 2 eq.) in anhydrous DCM (5 mL) over an ice bath. The reaction mixture was then warmed to room temperature and stirred for 12 hours. After removal of solvent, the residue was purified by column chromatography on silica gel with hexane/ethyl acetate (2:1, v/v) to yield 96 mg of Chol-NLG919. $^1$H-NMR (500 MHz, CDCl$_3$): 0.65 (s, 3H), 0.85-1.75 (m, 43H), 1.85-2.05 (m, 6H), 2.20 (m, 1H), 2.42 (m, 3H), 2.96 (m, 4H), 4.28 (m, 2H), 4.38 (t, 2H), 4.81 (m, 1H), 5.23 (m, 1H), 5.41 (d, 2H), 7.28 (t, 2H), 7.40 (t, 1H), 7.55 (dd, 2H), 7.75 (s, 1H). ESI-MS: m/z=875.6 ([M+H]$^+$).

Chol-OTS167

To a mixture of Chol-S—S—OH (35 mg, 0.06 mmol, 1 eq.) and 4-N,N-dimethylaminopyridine (DMAP, 16 mg, 0.12 mmol 2 eq.) in anhydrous N,N-dimethylformamide (DMF, 2 mL), a solution of triphosgene (8 mg, 0.02 mmol, 0.33 eq.) in anhydrous DMF (1 mL) was added dropwise over an ice bath with stirring. The resultant solution was warmed to room temperature and further stirred for 1 hour and then added dropwise to a solution of OTS167 (20 mg, 0.04 mmol, 0.67 eq.) in anhydrous DMF (5 mL) over an ice bath. The reaction mixture was then warmed to room temperature and stirred for 12 hours. The solution was then diluted with 30 ml ethyl acetate, washed by saturated ammonium chloride solution (20 mL×3). After removal of solvent under vacuum, the residue was purified by column chromatography on silica gel with DCM/methanol (10:1, v/v) to yield 20 mg of Chol-OTS167. Confirmed by $^1$H-NMR (500 MHz, CDCl$_3$, a pair of rotamers): 0.65 (s, 3H), 0.86-1.65 (m, 35H), 1.75-2.05 (m, 6H), 2.17-2.40 (m, 8H), 2.70 (d, 3H), 2.95 (m, 9H), 3.02 (d, 2H), 3.10 (d, 2H), 4.40 (m, 2H), 4.45 (m, 1H), 4.61 (m, 2H), 5.38 (m, 1H), 7.96 (m, 2H), 8.07 (m, 2H), 8.23 (d, 1H), 8.98 (s, 1H), 11.22 (s, 1H). ESI-MS: m/z=1079.6 ([M+H]$^+$).

Chol-OTSC41

To a mixture of Chol-S—S—OH (45 mg, 0.08 mmol, 1 eq.) and 4-N,N-dimethylaminopyridine (DMAP, 20 mg, 0.16 mmol 2 eq.) in anhydrous N,N-dimethylformamide (DMF, 2 mL), a solution of triphosgene (6 mg, 0.02 mmol, 0.33 eq.) in anhydrous DMF (1 mL) was added dropwise over an ice bath with stirring. The resultant solution was warmed to room temperature and further stirred for 1 hour and then added dropwise to a solution of OTSC41 (20 mg, 0.04 mmol, 0.5 eq.) in anhydrous DMF (5 mL) over an ice bath. The reaction mixture was then warmed to room temperature and stirred for 12 hours. The solution was then diluted with 30 ml ethyl acetate, washed by saturated ammonium chloride solution (20 mL×3). After removal of solvent under vacuum, the residue was purified by column chromatography on silica gel with DCM/methanol/triethyl amine (200:10:2, v/v) to yield 20 mg of Chol-OTSC41. Confirmed by $^1$H-NMR (500 MHz, CDCl$_3$): 0.65 (s, 3H), 0.88-1.62 (m, 36H), 1.78-2.05 (m, 9H), 2.40 (m, 2H), 2.89 (m, 4H), 3.13 (m, 3H), 3.27 (m, 2H), 3.44 (t, 2H), 3.67 (s, 1H), 4.05 (dd, 2H), 4.33 (t, 1H), 4.40 (t, 2H), 4.49 (m, 1H), 5.40 (d, 2H), 5.95 (s, 1H), 6.02 (s, 1H), 6.25 (s, 1H), 7.35 (t, 3H), 7.62 (d, 2H), 7.78 (s, 1H), 7.89 (d, 2H).

DHA-S—S—OH

To a mixture of DHA (200 mg, 0.7 mmol, 1 eq.) and 4-N,N-dimethylaminopyridine (DMAP, 200 mg, 1.64 mmol, 2.3 eq.) in anhydrous tetrahydrofuran (THF, 4 ml), a solution of triphosgene (70 mg, 0.24 mmol, 0.34 eq.) in anhydrous DCM (1 mL) was added dropwise over an ice bath with stirring. The resulting solution was warmed to room temperature and further stirred for 0.5 hour and then added dropwise to a solution of bis(2-hydroxyethyl) disulfide (215 mg, 1.4 mmol, 2 eq.) in anhydrous DCM (5 mL) over an ice bath. The reaction mixture was then warmed to room temperature and stirred for 12 hours. After removal of solvent, the residue was purified by column chromatography on silica gel with hexane/ethyl acetate (2:1, v/v) to yield 80 mg of DHA-S—S—OH. $^1$H-NMR (500 MHz, CDCl$_3$): 0.93 (d, 3H), 0.98 (d, 3H), 1.25-1.55 (m, 6H), 1.62-1.95 (m, 6H), 2.07 (m, 1H), 2.38 (td, 1H), 2.65 (m, 1H), 2.93 (m, 4H), 3.73 (m, 1H), 3.90 (m, 2H), 4.11 (m, 1H), 4.85 (s, 1H), 5.32 (s, 1H), 5.51 (s, 1H). ESI-MS: m/z=465.2 ([M+H]$^+$).

Oleyl-PC-S—S-DHA

To a mixture of DHA-S—S—OH (500 mg, 1.07 mmol, 1 eq.) and 4-N,N-dimethylaminopyridine (DMAP, 160 mg, 1.2 mmol, 1.1 eq.) in anhydrous dichloromethane (DCM, 4 ml), a solution of triphosgene (110 mg, 0.36 mmol, 0.33 eq.) in anhydrous DCM (1 mL) was added dropwise over an ice bath with stirring. The resulting solution was warmed to room temperature and further stirred for 0.5 hour and then added dropwise to a solution of Oleyl-lyso-PC (500 mg, 0.96 mmol, 0.9 eq.) in a mixture of anhydrous DCM (2 mL), anhydrous DMF (3 mL) and triethylamine (0.2 mL) over an ice bath. The reaction mixture was then warmed to room temperature and stirred for 12 hours. After removal of solvent, the residue was purified by column chromatography on diol silica with DCM/methanol (10:1, v/v) to yield 215 mg of Oleyl-PC-S—S-DHA. $^1$H-NMR (500 MHz, CDCl$_3$): 0.90 (t, 3H), 0.93 (d, 3H), 0.98 (d, 3H), 1.20-1.33 (m, 22H), 1.45-1.70 (m, 9H), 1.75-1.95 (m, 4H), 2.03 (m, 4H), 2.36 (m, 3H), 2.66 (m, 1H), 2.97 (m, 4H), 3.46 (s, 9H), 3.50 (d, 1H), 3.73 (m, 1H), 4.10 (m, 3H), 4.27 (m, 3H), 4.39 (dd, 1H), 4.44 (t, 2H), 4.65 (s, 2H), 4.85 (d, 1H), 5.11 (t, 1H), 5.37 (m, 1H), 5.46 (s, 1H). ESI-MS: m/z=1012.5 ([M+H]$^+$).

PC-S—S-DHA

To a solution of DHA-S—S—OH (200 mg, 0.43 mmol, 1 eq.) in 5 mL anhydrous toluene and 0.2 mL triethylamine, a solution of ethylene glycol chlorophosphate (80 mg, 0.56 mmol, 1.3 eq.) was added dropwise over an ice bath with stirring. The resultant solution was warmed to room temperature and further stirred for 2 hours and then dried under vacuum. The product was transferred to a pressure tube by 2 mL anhydrous THF and cooled over a dry ice-acetone bath. 0.5 mL anhydrous trimethylamine was added to the solution and the pressure tube was sealed and heated at 70° C. for 24 hours. After removal of solvent under vacuum, the product was obtained in 50% yield (137 mg) by purification of column chromatography on diol silica with DCM/methanol (5:1, v/v). $^1$H-NMR (500 MHz, CDCl$_3$): 0.93 (d, 3H), 0.98 (d, 3H), 1.25-1.55 (m, 6H), 1.62-1.95 (m, 6H), 2.07 (m, 1H), 2.38 (td, 1H), 2.65 (m, 1H), 2.93 (m, 4H), 3.45 (s, 9H), 3.73 (m, 1H), 3.95 (m, 2H), 4.15 (m, 1H), 4.20 (m, 2H), 4.45 (m, 2H), 4.85 (s, 1H), 5.32 (s, 1H), 5.44 (s, 1H). ESI-MS: m/z=630.2 ([M+H]$^+$).

Chol-ART

Artesunate (500 mg, 1.3 mmol, 1 eq.), cholesterol (1 g, 2.6 mmol, 2 eq.), 4-N,N-dimethylaminopyridine (DMAP, 16 mg, 0.13 mmol, 0.1 eq.) and 1-Ethyl-3-(3-dimethylaminopropyl)carbodiimide.HCl (EDCl, 350 mg, 1.8 mmol, 1.4 eq.) were dissolved in dry DCM (6 mL) and stirred for 12 hours. Then the mixture was diluted with 50 mL EtOAc and washed by 1M HCl (50 mL, twice) and brine (50 mL). The organic layer was dried over anhydrous sodium sulfide. After removal of solvent under vacuum, the product was further purified by column chromatography on silica gel with EtOAc/hexanes (1:5, v/v). Yield: 832 mg, 83%. $^1$H-NMR (500 MHz, CDCl$_3$): 0.65 (s, 3H), 0.88-1.20 (m, 29H), 1.30-1.75 (m, 20H), 1.80-2.08 (m, 8H), 2.37 (m, 3H), 2.72 (m, 5H), 4.52 (m, 1H), 5.39 (d, 1H), 5.46 (s, 1H), 5.83 (d, 1H). ESI-MS: m/z=753.5 ([M+H]$^+$).

Boc-MTX

As shown in Scheme 6, below, Mitoxantrone (MTX, 300 mg, 0.68 mmol, 1 eq.) was dissolved in 2 mL Na$_2$CO$_3$ solution (2 mg/mL) and mixed with a solution of di-tert-butyl dicarbonate (Boc$_2$O, 500 mg, 2.3 mmol, 3.3 eq.) in 4 mL of 1,4-dioxane. The mixture was stirred at room temperature for 12 h and then extracted by DCM (20 mL×3). The organic phase was combined and concentrated. The residue was purified by column chromatography on silica gel with DCM/methanol (20:1, v/v) to yield 435 mg of Boc-MTX. Confirmed by $^1$H-NMR (500 MHz, CDCl$_3$):

1.51 (s, 18H), 3.45 (d, 4H), 3.56 (s, 8H), 3.79 (s, 4H), 7.05 (s, 3H), 7.12 (s, 2H), 10.32 (s, 1H), 13.36 (s, 2H). ESI-MS: m/z=645.4 ([M+H]$^+$).

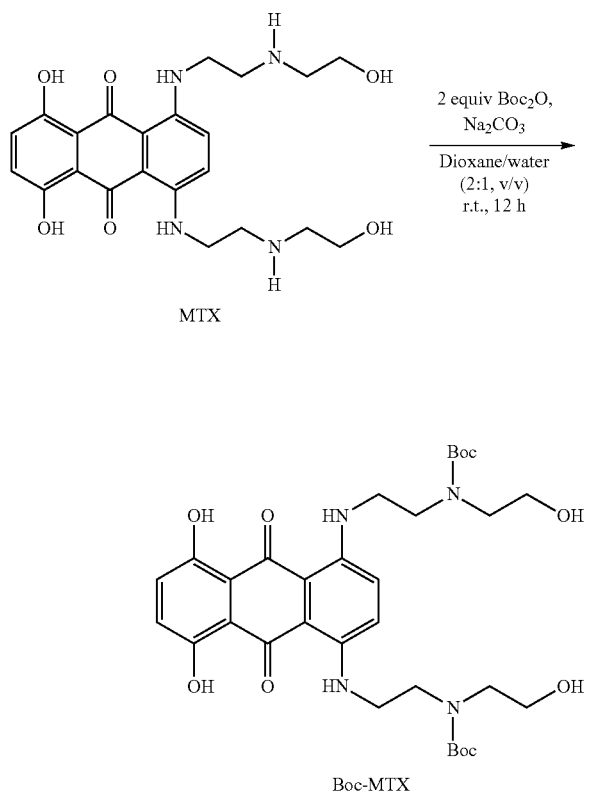

Scheme 6. Synthesis of Boc-MTX.

Chol-Boc-MTX

To a mixture of Chol-S—S—OH (500 mg, 0.88 mmol, 1 eq.) and 4-N,N-dimethylaminopyridine (DMAP, 430 mg, 3.5 mmol, 4 eq.) in anhydrous dichloromethane (DCM, 10 mL), a solution of triphosgene (90 mg, 0.3 mmol, 0.34 eq.) in anhydrous DCM (5 mL) was added dropwise over an ice bath with stirring. The resultant solution was warmed to room temperature and further stirred for 1 hour and then added dropwise to a solution of Boc-MTX (435 mg, 0.68 mmol, 0.77 eq.) in anhydrous DCM (20 mL) over an ice bath. The reaction mixture was then warmed to room temperature and stirred for 12 hours. After removal of solvent under vacuum, the residue was purified by column chromatography on silica gel with DCM/methanol/triethyl amine (200:10:2, v/v) to yield 410 mg of Chol-Boc-MTX. Confirmed by $^1$H-NMR (500 MHz, CDCl$_3$): 0.65 (s, 3H), 0.87-1.65 (m, 53H), 1.75-2.40 (m, 10H), 2.93 (m, 6H), 3.03 (m, 4H), 3.58 (m, 4H), 3.64 (m, 4H), 4.37 (m, 4H), 4.42 (m, 1H), 5.70 (d, 1H) 7.15 (d, 2H), 7.28 (d, 2H), 10.45 (s, 2H), 13.35 (s, 2H). ESI-MS: m/z=1237.8 ([M+H]$^+$).

Chol-MTX

As shown in Scheme 7, below, Chol-Boc-MTX (410 mg, 0.33 mmol) was dissolved in 20 ml trifluoroacetic acid (TFA) and stirred at room temperature for 30 min. The excess TFA was removed by nitrogen gas stream. The residue was recrystallized in tetrahydrofuran/hexane to yield 300 mg Chol-MTX TFA salt. The salt could be further converted to HCl salt by dissolving it in DCM, washing with saturated NaHCO$_3$ solution, 1M HCl and removing solvent. Confirmed by $^1$H-NMR (500 MHz, CDCl$_3$): 0.65 (s, 3H), 0.87-1.65 (m, 35H), 1.75-2.40 (m, 12H), 2.93 (m, 6H), 3.03 (m, 4H), 3.45 (dd, 4H), 3.72 (m, 4H), 4.37 (m, 4H), 4.42 (m, 1H), 5.33 (d, 1H), 6.90 (m, 2H), 7.05 (m, 2H), 10.34 (d, 2H), 13.42 (s, 2H). ESI-MS: m/z=1037.6 ([M+H]$^+$).

Scheme 7. Synthesis of Chol-MTX through deprotection of Chol-Boc-MTX in TFA.

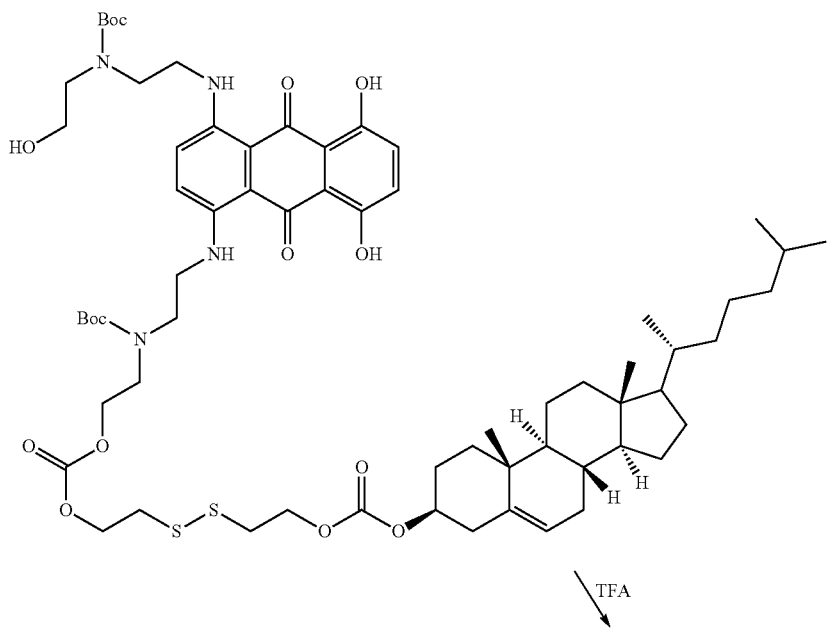

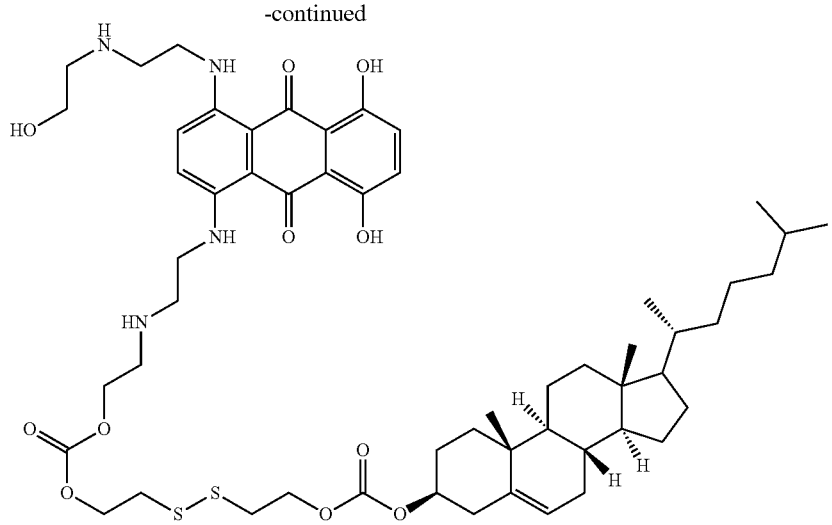

OA-CPT

As shown in Scheme 8, below, Oleic acid (OA, 1 eq.) reacted with OH—S—S—OH (2 eq.), N,N'-Dicyclohexylcarbodiimide (DCC, 1.2 eq.) and 4-Dimethylaminopyridine (DMAP) in DCM N,N'-Dicyclohexylcarbodiimide (DCC, 1.2 eq.) overnight to generate OA-S—S—OH, which was purified by ethyl acetate/hexane (2:3, v/v). $^1$H-NMR (CDCl$_3$, 500 MHz): 0.87 (t, 3H), 1.23-1.30 (m, 20H), 1.60 (t, 2H), 1.98 (q, 4H), 2.30 (t, 2H), 2.35 (t, 1H), 2.86 (t, 2H), 2.91 (t, 2H), 3.87 (t, 2H), 4.33 (t, 2H), 5.33 (m, 2H).

To a mixture of CPT (1 eq.) and 4-N,N-dimethylaminopyridine (DMAP, 4 eq.) in anhydrous dichloromethane (DCM), a solution of triphosgene (0.35 eq.) in anhydrous DCM was added dropwise over an ice bath with stirring. The resultant solution was warmed to room temperature and further stirred for 1 hour and then added dropwise to a solution of OA-S—S—OH (2 eq.) in anhydrous DCM over an ice bath. The reaction mixture was then warmed to room temperature and stirred for 12 hours. After removal of solvent, the residue was purified by column chromatography on silica gel with methanol/DCM (3:97, v/v) to obtain OA-CPT in 65% yield (FIG. 7). $^1$H-NMR (CDCl$_3$, 500 MHz): 0.88 (t, 3H), 1.02 (t, 3H), 1.23-1.31 (m, 20H), 1.59 (t, 2H), 2.00 (q, 4H), 2.17 (m, 1H), 2.27 (m, 3H), 2.88 (t, 2H), 2.95 (t, 2H), 4.27 (t, 2H), 4.38 (m, 2H), 5.32 (m, 2H), 5.34 (m, 2H), 5.40 (d, 1H), 5.61 (d, 1H), 7.35 (s, 1H), 7.69 (t, 1H), 7.85 (t, 1H), 7.96 (d, 1H), 8.24 (d, 1H), 8.42 (s, 1H).

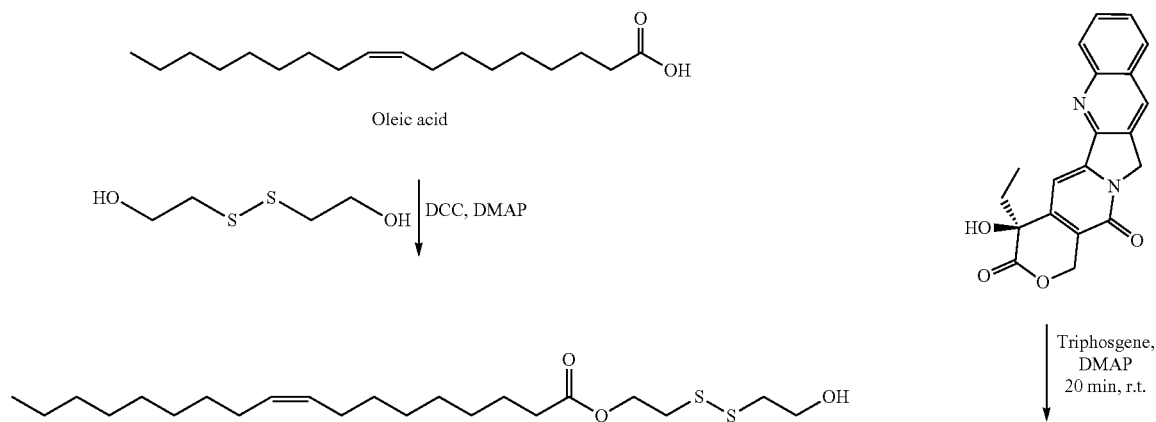

Scheme 8. Synthesis of OA-CPT.

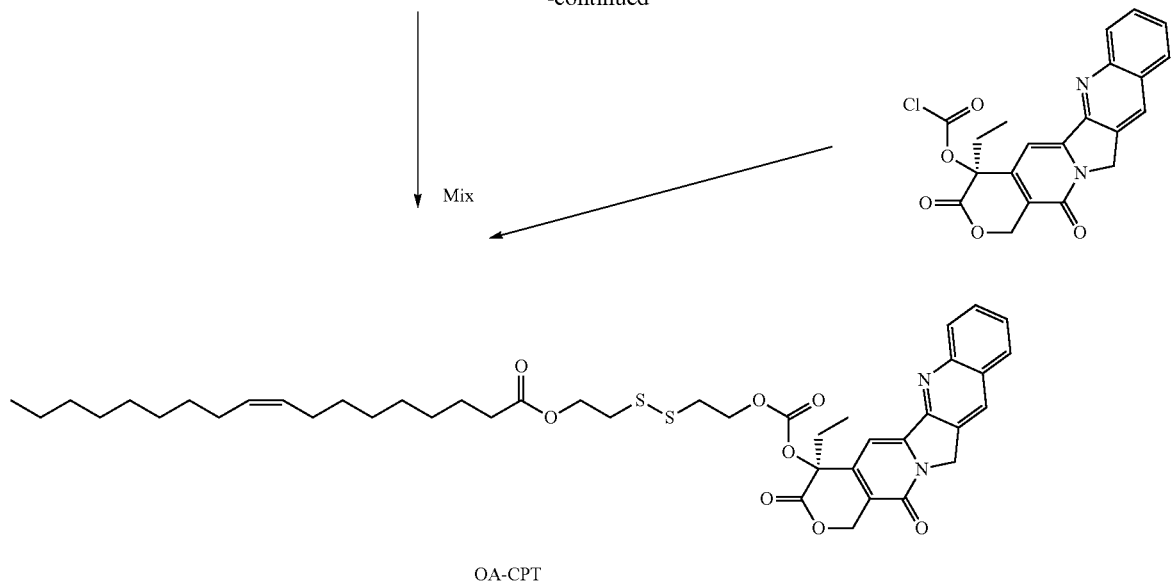

OA-CPT

Example 2

Nanoscale Coordination Polymer Core-Shell Nanoparticles Carrying Etoposide for the Treatment of Small Cell Lung Cancer Synthesis of Zn-Pyrophosphate Particles Microemulsions were first formed by the addition of 4 mL $Na_4P_2O_7 \cdot 10H_2O$ (25 mg/mL in water) and 4 mL Zn $(NO_3)_2 \cdot 6H_2O$ (100 mg/mL in water) to two separate surfactant system mixtures (100 mL, 0.3 M TritonX-100, 1.5 M hexanol in cyclohexane). The separate microemulsions were stirred vigorously for 15 min at room temperate, 400 μL of DOPA solution (200 mg/mL in $CHCl_3$) was added to $Na_4P_2O_7 \cdot 10H_2O$ solution and the stirring was continued for 15 min until a clear solution formed. Then, $Zn(NO_3)_2 \cdot 6H_2O$ solution was added slowly into $Na_4P_2O_7 \cdot 10H_2O$ solution under stirring, the combined solution was allowed to react for 30 min at room temperature. Particles were precipitated after adding 400 mL ethanol and obtained by centrifugation at 12000 rpm for 30 min. The resulting pellet was further washed once with 50% EtOH/cyclohexane and twice with 50% EtOH/THF, and redispersed in THF. Particles were purified by filtration through a 200 nm syringe filter.

Preparation and Characterization of Zn/ET Particles

Zn/ET was obtained by adding a 80 μL THF solution of DSPC, cholesterol, Chol-ET (molar ratio 1:1:0.3, 1:1:0.5 or 1:1:1), DSPE-PEG2k (20 mol %) and Zn-pyrophosphate bare particles to 500 μL 30% (v/v) $EtOH/H_2O$ at 60° C. THF and EtOH were evaporated and the solution was allowed to cool to room temperature before use. The particle size and distribution were determined by DLS. The loading of etoposide was determined by UV-Vis (see Table 1).

TABLE 1

Characterization of Zn/ET particles.

| | Z-Ave (nm) | PDI | Intensity- Ave (nm) | Number- Ave (nm) | Theoretical drug loading | Actual drug loading |
|---|---|---|---|---|---|---|
| Zn-pyrophosphate bare particles[#] | 49.47 ± 0.12 | 0.126 ± 0.01 | 63.04 ± 0.48 | 35.14 ± 0.73 | | |
| Zn particle | 97.35 ± 0.84 | 0.098 ± 0.01 | 108.3 ± 0.62 | 69.02 ± 2.66 | | |
| Zn/ET (1:1:0.3)[$] | 102.6 ± 1.81 | 0.165 ± 0.01 | 122.3 ± 2.67 | 65.56 ± 2.71 | 12.4 wt. % | 9.6 wt. % |
| Zn/ET (1:1:0.5)[$] | 174.2 ± 1.50 | 0.139 ± 0.01 | 203.3 ± 5.48 | 126.0 ± 9.18 | 18.2 wt. % | 15.6 wt. % |
| Zn/ET (1:1:1)[$] | 183.1 ± 2.97 | 0.102 ± 0.01 | 204.2 ± 4.80 | 147.6 ± 6.29 | 34.2 wt. % | 28.8 wt. % |

[#]Measured in THF.
[$]Measured in water.
Data are expressed as mean ± S.D.

In Vitro Cytotoxicity Against Small Cell Lung Cancer Cells

H82 cells seeded on 96-well plates at a density of 2000 cells/well were treated with Zn/ET and free etoposide at various etoposide concentrations for 96 h. The cell viability was then detected by MTS assay (Promega, Madison, Wis., United States of America) and the $IC_{50}$ values were calculated accordingly. Etoposide showed an $IC_{50}$ value of 8.83±0.13 μM against H82 cells after incubation for 96 h, and Zn/ET showed a similar $IC_{50}$ of 9.50±0.63 μM. ET is likely released from Zn/ET via intracellular reduction by endogenous thiol groups as shown below in Scheme 9.

94.15±0.61 nm, number-average diameter of 55.83±6.20 nm, PDI of 0.119±0.01, zeta-potential of −0.67±1.02 mV. The Zn/PTX particle has a drug loading of 7.14%.

In Vitro Cytotoxicity Against Non-Small Cell Lung Cancer Cells

H460 and A549 cells seeded on 96-well plates at a density of 2000 cells/well were treated with Zn/PTX and free PTX at various etoposide concentrations for 72 h. The cell viability was then detected by MTS assay (Promega, USA) and the $IC_{50}$ values were calculated accordingly. PTX showed $IC_{50}$ of 10.79±0.44 μM and 10.09±0.06 μM against H460 and A549 cells after incubation for 72 h, respectively. Zn/PTX showed a similar $IC_{50}$ of 12.03±0.43 μM and 11.07±0.13 μM, respectively, compared to free PTX.

Scheme 9. Release of ET from Chol-Et via intracellular reduction.

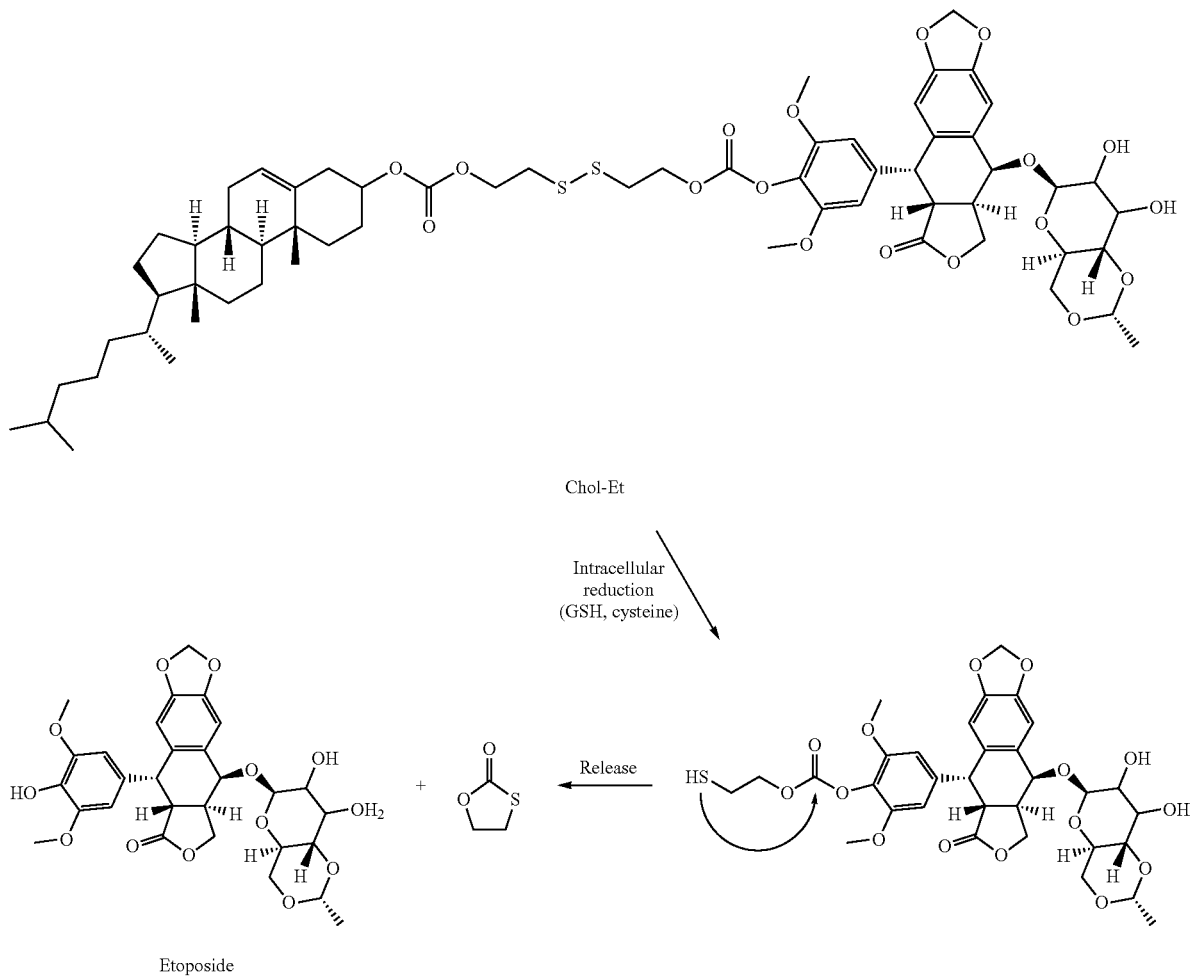

Example 3

Nanoscale Coordination Polymer Core-Shell Nanoparticles Carrying Paclitaxel for the Treatment of Non-Small Cell Lung Cancer Preparation Characterization of Zn/PTX.

Zn/PTX was obtained by adding a 80 μL THF solution of DSPC, cholesterol, Chol-PTX (molar ratio 1:1:0.3), DSPE-PEG2k (20 mol %) and Zn-pyrophosphate bare particles to 500 μL 30% (v/v) EtOH/$H_2O$ at 60° C. THF and EtOH were evaporated and the solution was allowed to cool to room temperature before use. The particle size and distribution were determined by DLS, having a Z-average diameter of

Example 4

Nanoscale Coordination Polymer Core-Shell Nanoparticles Dihydroartemisinin (DHA) for the Treatment of Ovarian Cancer Synthesis and Characterization of Zn/DHA Particles Microemulsions were first formed by the addition of 0.2 mL $Na_4P_2O_7 \cdot 10H_2O$ (25 mg/mL in water) and 0.2 mL $Zn(NO_3)_2 \cdot 6H_2O$ (100 mg/mL in water) to two separate surfactant system mixtures (5 mL, 0.3 M TritonX-100, 1.5 M hexanol in cyclohexane). The separate microemulsions were stirred vigorously for 15 min at room temperate, 20 uL of DOPA solution (200 mg/mL in CHCl$_3$) was added to Na$_4$P$_2$O$_7$.10H$_2$O solution and the stirring was continued for 15 min until a clear solution formed. Then, Zn(NO$_3$)$_2$.6H$_2$O solution was added slowly into Na$_4$P$_2$O$_7$.10H$_2$O solution under stirring, the combined solution was allowed to react for 30 min at room temperature. Particles were precipitated after adding 20 mL ethanol and obtained by centrifugation at 12000 rpm for 30 min. The resulting pellet was further washed once with 50% EtOH/cyclohexane and twice with 50% EtOH/THF, and redispersed in THF. Particles were purified by filtration through 200 nm syringe filter.

Zn/DHA was obtained by adding a 80 μL THF solution of DOPC, cholesterol, Chol-DHA and 20 mol % DSPE-PEG2k and Zn-pyrophosphate bare particles to 500 μL 30% (v/v) EtOH/H$_2$O at 50° C. THF and EtOH were evaporated and the solution was allowed to cool to room temperature before use. The particle size and distribution were determined by DLS. See Table 2.

TABLE 2

Particle size and PDI of Zn/DHA with different drug loading.

| | Z-Ave (nm) | PDI | Intensity-Ave (nm) | Number-Ave (nm) |
|---|---|---|---|---|
| Zn particle | 104.6 ± 2.1 | 0.180 ± 0.01 | 121.9 ± 4.8 | 62.9 ± 3.6 |
| Zn/DHA (5.4%) | 110.2 ± 0.3 | 0.180 ± 0.01 | 135.3 ± 1.3 | 65.3 ± 6.3 |
| Zn/DHA (8.1%) | 130.5 ± 0.4 | 0.179 ± 0.004 | 157.7 ± 2.7 | 78.0 ± 2.1 |
| Zn/DHA (10.8%) | 149.5 ± 2.2 | 0.274 ± 0.01 | 220.6 ± 5.4 | 61.1 ± 1.7 |

In Vitro Cytotoxicity of Zn/DHA in Ovarian Cancer Cells

A2780, A2780/CDDP, and SKOV-3 cells were seeded into 96-well plate at 2000 cells/well for 24 h. Afterwards cells were treated with free DHA or Zn/DHA at various concentrations and incubated for another 72 h. The cell viability was then determined via MTS assay by microplate reader. DHA showed high cytotoxicity, especially on A2780 cells. DHA showed IC$_{50}$ of 0.30±0.11, 2.61±0.18, and 9.90±0.34 μM on A2780, A2780/CDDP and SKOV-3, respectively. Zn/DHA showed IC$_{50}$ values of 0.96±0.15, 3.71±0.55, and 11.88±3.22 for A2780, A2780/CDDP and SKOV-3, respectively.

Example 5

Nanoscale Coordination Polymer Core-Shell Nanoparticles Combine Cisplatin and Etoposide for the Treatment of Small Cell Lung Cancer Preparation and Characterization of NCP-1/ET and NCP-1/ET/siRNAs The solid core of NCP-1 was composed of 1,2-cis,cis,trans-[Pt(NH$_3$)$_2$Cl$_2$(OCONHP(O)(OH)$_2$)$_2$] (PtBp) and Zn$^{2+}$ ions with the dioleoyl-sn-glycero-3-phosphate (DOPA) capping layer in reverse phase microemulsion in a mixture of 0.3 M TritonX-100 and 1.5 M hexanol in cyclohexane. DOPA provides a lipid layer on the bare NCP-1 and facilitates the incorporation of other phospholipids or lipid-containing drugs.

NCP-1/ET was made by coating 84 μL 1,2-dioleoyl-sn-glycero-3-phosphatidylcholine (DOPC) (5 mg/mL), 42 μL Chol (5 mg/mL), 16 μL Chol-ET (15 mg/mL), and 150 μL 1,2-distearoyl-sn-glycero-3-phosphoethanolamine-N-[amino(polyethylene glycol)$_{2000}$] (DSPE-PEG$_{2K}$) (5 mg/mL) onto 0.25 mg bare NCP particles via self-assembly to give a cisplatin to ET molar ratio of 1:1. The Z-average diameter and polydispersity (PDI) of NCP-1/ET were found to be 106.8±1.05 nm and 0.121±0.01, respectively, by dynamic light scattering (DLS) measurements.

In order to effectively load siRNA into NCP-1/ET, thiolated siRNA was conjugated to DSPE-SPDP to generate DSPE-siRNA. The disulfide bond in thiolated siRNA was placed on the 5' end of sense strand of siRNA duplexes in order to circumvent the potential inhibition on the antisense strand. DSPE-siRNA was incorporated into the outer lipid layer via self-assembly along with DOPC, Chol, Chol-ET, and DSPE-PEG$_{2K}$ at a cisplatin to siRNA weight ratio of 4:1 to give NCP-1/ET/siRNAs. Bcl-2, survivin, and ERCC-1 siRNAs were selected as a model for siRNA cocktails targeting multiple drug resistance pathways. Equal amounts of Bcl-2, survivin, and ERCC-1 siRNAs are present in NCP-1/ET/siRNAs. The Z-average diameter and PDI of NCP-1/ET/siRNAs were 100.2±1.10 nm and 0.159±0.01, respectively. See Table 3, below. Owing to the shielding effect of PEG, siRNA could be protected from nuclease degradation in physiological environments. Similar to Chol-ET, siRNA release can be triggered by cleaving the disulfide bond under reducing environment such as in the presence of GSH.

TABLE 3

Particle size and PDI of NCP-1, NCP-1/ET, and NCP-1/ET/siRNAs, as determined by DLS.

| | Z-Ave (nm) | PDI | Intensity-Ave (nm) | Number-Ave (nm) |
|---|---|---|---|---|
| NCP-1 | 102.4 ± 1.09 | 0.132 ± 0.01 | 120.2 ± 2.10 | 69.32 ± 3.87 |
| NCP-1/ET | 106.8 ± 1.05 | 0.121 ± 0.01 | 122.4 ± 0.90 | 71.18 ± 4.17 |
| NCP-1/ET/siRNAs | 100.2 ± 1.10 | 0.159 ± 0.01 | 124.1 ± 4.50 | 67.19 ± 5.43 |

In Vitro Cytotoxicity of NCP-1/ET/siRNA in SCLC

Small cell lung cancer (SCLC) cell lines H82 and H69 cells were seeded into 96-well plate at 2000 cells/well for 24 h. Afterwards, cells were treated by cisplatin, ET, cisplatin+ET, NCP-1, NCP-1/ET, and NCP-1/ET/siRNAs at various concentrations and incubated for another 72 h. The cell viability was then determined via MTS assay by microplate reader. The IC50 of NCP-1/ET/siRNAs on SCLC cells was shown in Table 4, below.

TABLE 4

IC$_{50}$ (μM) of NCP-1/ET/siRNAs on SCLC cells.

| | Cisplatin | Etoposide | Cisplatin + Etoposide | NCP-1 | NCP-1/ET | NCP-1/ET/siRNAs |
|---|---|---|---|---|---|---|
| H82 cells | 7.93 ± 0.70 | 30.9 ± 0.37 | 6.65 ± 0.19 | 22.1 ± 1.28 | 20.2 ± 0.50 | 18.5 ± 0.14 |
| H69 cells | 13.2 ± 0.35 | 42.2 ± 0.61 | 9.79 ± 0.64 | 20.9 ± 0.63 | 18.8 ± 0.39 | 16.3 ± 0.31 |

In Vivo Antitumor Activity of NCP-1/ET/siRNA

The in vivo antitumor activity of NCP-1/ET/siRNA was evaluated on five tumor models, including two cispaltin-resistant ovarian cancers (A2780/CDDP and SKOV-3), two non-small cell lung cancers (H460 and A549) and one small cell lung cancer (H82). NCP-1/ET/siRNAs showed significantly inhibitory effect on all five tumor models, especially on SKOV-3, A549 and H82 tumor models. See FIGS. 1A-1C. The tumors were completely inhibited at the first stage, but began to grow at the last stage after stopping the treatment.

Example 6

Nanoscale Coordination Polymer Core-Shell Nanoparticles Combine Cisplatin and Paclitaxel Characterization of NCP-1-Containing Chol-PTX (NCP-1/Chol-PTX)

The bare NCP-1 comprised by cisplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. The bare NCP-1 particles are then mixed with twice amount of EtOH and centrifuged at 12000 rpm for 30 min to remove the solvent. The particle pellet will be further washed once with 50% EtOH/cyclohexane and twice with 50% EtOH/THF to remove excess amounts of DOPA and re-dispersed in THF. Finally, the bare NCP-1 particles will be further filtered via 200 nm syringe filter prior to any use. NCP-1/Chol-PTX particles were obtained by adding a mixture of DOPC (0.5 mg), Chol (0.25 mg) and Chol-PTX (146 μg), DSPE-PEG$_{2K}$ (20 mol %) (0.9 mg) and bare NCP-1 particles (0.25 mg) to 30% (v/v) EtOH/H$_2$O with vigorous stirring. THF and EtOH were evaporated and the solution was allowed to cool to r.t. prior to use. In this formulation, Cisplatin/PTX=2.1:1 (molar ratio), with drug loading: PTX (4.3%, 853 g/mol, 7.3% for Chol-PTX); Cisplatin:(3.13%, 300 g/mol), respectively. The z-average size for NCP-1/Chol-PTX is 94.1±1.2 nm with PDI at 0.164 and neutral charge (~1.5 mV) in PBS. The NCP-1/Chol-PTX particles have been stable for 10 days in both PBS and PBS-containing 10% FBS solutions. The superior formulation stability could arise from the strong coordination bonding inside the core and the hydrophobic interactions between cholesterol and phospholipids.

Example 7

Nanoscale Coordination Polymer Core-Shell Nanoparticles Combine Cisplatin and OTS167

Preparation and Characterization of NCP-1/OTS167

The bare NCP-1 comprised by cisplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. NCP-1/OTS167 particles were obtained by adding a mixture of DOPC, Chol, Chol-OTS167, DSPE-PEG$_{2K}$ (20 mol %), and bare NCP-1 particles to 30% (v/v) EtOH/H$_2$O with vigorous stirring. THF and EtOH were evaporated and the solution was allowed to cool to r.t. prior to use. Particles with cisplatin to OTS167molar ratio of 1:1, 5:1 and 10:1 were made. The z-average sizes for NCP-1/OTS167 were similar for different formulations with different molar ratios, which is 110-120 nm with PDI ranging from 0.15-0.18. See Table 5.

TABLE 5

Particle size and PDI of NCP-1/OTS167 with different molar ratios.

|  | Z-Ave | PDI | Intensity | Number |
| --- | --- | --- | --- | --- |
| NCP-1 | 101.8 ± 0.90 | 0.161 ± 0.01 | 125.1 ± 3.16 | 60.72 ± 1.05 |
| NCP-1/OTS167 (1:1) | 119.7 ± 2.54 | 0.175 ± 0.02 | 144.4 ± 2.48 | 73.48 ± 7.47 |
| NCP-1/OTS167 (5:1) | 117.7 ± 1.71 | 0.167 ± 0.02 | 151.9 ± 2.24 | 74.83 ± 7.58 |
| NCP-1/OTS167 (10:1) | 109.3 ± 1.04 | 0.153 ± 0.01 | 129.6 ± 1.05 | 66.55 ± 1.23 |

In Vitro Cytotoxicity Against Ovarian Cancer Cell Lines

The synergy between cisplatin and OTS167 was first examined against cisplatin-resistant ovarian cancer cell line A2780/CDDP by comparing free drug cytotoxicities alone or in combination. The IC$_{50}$ of cisplatin was significantly decreased after combination with OTS167 at the molar ratio of 10:1 and 100:1. See Table 6.

TABLE 6

The IC$_{50}$ of cisplatin and OTS167 alone or in combination against A2780/CDDP cells.

|  | OTS167 | Cisplatin | 10:1 | 100:1 | 1000:1 |
| --- | --- | --- | --- | --- | --- |
| OTS167 (nM) | 12.05 ± 0.46 |  | 12.16 ± 0.46 | 12.09 ± 0.40 | 8.77 ± 0.10 |
| Cisplatin (uM) |  | 12.84 ± 0.19 | 0.12 ± 0.005 | 1.21 ± 0.04 | 8.77 ± 0.10 |

The cytotoxicity of NCP-1/OTS167 with different molar ratio was then evaluated. A 100:1 ratio of free cisplatin:OTS167 showed the most promising combination index, and therefore drug ratios of 50:1 and 100:1 were selected for NCP formulation. See Table 7.

TABLE 7

The IC$_{50}$ of NCP-1/OTS167 against A2780/CDDP cells.

|  | OTS167 | Cisplatin | Particle (100:1) | Particle (50:1) |
| --- | --- | --- | --- | --- |
| OTS167 (nM) | 12.05 ± 0.46 |  | 49.05 ± 3.98 | 53.49 ± 5.73 |
| Cisplatin (uM) |  | 12.84 ± 0.19 | 4.91 ± 0.40 | 2.67 ± 0.29 |

Example 8

Nanoscale Coordination Polymer Core-Shell Nanoparticles Combine Cisplatin and OTSC41

Preparation and Characterization of NCP-1/OTSC41

The bare NCP-1 comprised by cisplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. NCP-1/OTSC41 particles were obtained by adding a mixture of DOPC, Chol, Chol-OTSC41, DSPE-$PEG_{2K}$ (20 mol %), and bare NCP-1 particles to 30% (v/v) $EtOH/H_2O$ with vigorous stirring. THF and EtOH were evaporated and the solution was allowed to cool to r.t. prior to use. Particles with cisplatin to OTSC41 molar ratio of 1:1, 5:1 and 10:1 were made. The z-average sizes for NCP-1/OTSC41 were similar for different formulations with different molar ratios, which is around 100 nm with PDI ranging from 0.14-0.16. See Table 8.

TABLE 8

Particle size and PDI of NCP-1/OTSC41 with different molar ratios.

| | Z-Ave (nm) | PDI | Intensity-Ave (nm) | Number-Ave (nm) |
|---|---|---|---|---|
| NCP-1 | 101.8 ± 0.90 | 0.161 ± 0.01 | 125.1 ± 3.16 | 60.72 ± 1.05 |
| NCP-1/ OTSC41 (1:1) | 102.2 ± 0.66 | 0.164 ± 0.01 | 121.4 ± 1.40 | 63.97 ± 4.94 |
| NCp-1/ OTSC41 (5:1) | 106.8 ± 1.35 | 0.157 ± 0.01 | 123.7 ± 3.95 | 58.92 ± 2.54 |
| NCp-1/ OTSC41 (10:1) | 108.1 ± 0.21 | 0.137 ± 0.01 | 126.3 ± 1.15 | 72.93 ± 5.68 |

In Vitro Cytotoxicity Against Ovarian Cancer Cell Lines

The synergy between cisplatin and OTSC41 was first examined against two ovarian cancer lines, including cisplatin-sensitive A2780 cells and cisplatin-resistant A2780/CDDP cells by comparing free drug cytotoxicities alone or in combination. The $IC_{50}$ of cisplatin OTSC41 alone or in combination was shown in Table 9.

TABLE 9

$IC_{50}$ of cisplatin and OTSC41 alone or in combination against A2780 and A2780/CDDP cells.

| | | C41 | Cisplatin | 100:1 | 1000:1 |
|---|---|---|---|---|---|
| A2780 | C41 (nM) | 780.4 ± 32.9 | | 67.9 ± 3.56 | 6.39 ± 0.35 |
| | Cisplatin (uM) | | 3.52 ± 0.41 | 6.79 ± 0.36 | 6.39 ± 0.35 |
| A2780/CDDP | C41 (nM) | 68.8 ± 2.19 | | 473.0 ± 11.4 | 24.5 ± 2.34 |
| | Cisplatin (uM) | | 12.8 ± 1.93 | 47.3 ± 1.14 | 24.5 ± 2.34 |

Example 9

Nanoscale Coordination Polymer Core-Shell Nanoparticles Combine Cisplatin and Dihydroartemisinin for the Treatment of Ovarian Cancer Cumulative research suggests that dihydroartemisinin (DHA) and other artemisinin-based endoperoxide compounds can be cleaved in a Fenton reaction mediated by iron and produces free-radical reactive oxygen species (ROS) to cause damage to tumor cells. DHA has been reported to inhibit the growth of various cancer cells and xenograft tumors, and potentiate the anticancer effect of cisplatin in cisplatin-resistant ovarian cancer. Here, NCP-based core-shell nanoparticles were prepared to co-deliver cisplatin and DHA to treat cisplatin-resistant ovarian cancer.

Preparation and Characterization of NCP-1/DHA Particles

NCP-1 particles carrying cisplatin prodrug were prepared as previously reported. Briefly, a mixture of $Zn(NO_3)_2$ and an cisplatin prodrug, 1,2-cis,cis,trans-$[Pt(NH_3)_2Cl_2(OCONHP(O)(OH)_2)_2]$ (PtBp), with 1,2-dioleoyl-sn-glycero-3-phosphate sodium salt (DOPA) in the Triton X-100/1-hexanol/cyclohexane/water reverse microemulsion was vigorously stirred at room temperature for 30 min to afford spherical DOPA-coated NCP-1 particles. NCP-1 has a cisplatin loading of 25 wt % as determined by inductively coupled plasma-mass spectrometry (ICP-MS).

DOPA-NCP-1 particles were then coated with cholesterol, DOPC, Chol-DHA conjugates, and 20 mol % DSPE-PEG2k to afford a core-shell nanostructure with a solid core carrying cisplatin and a lipid layer containing DHA. Particles with different molar ratios of cisplatin to DHA were formulation by changing the amount of DHA during lipid coating. See Table 10.

TABLE 10

Particle size and PDI of NCP-1/DHA with different molar ratios.

| Molar ratio | Z-Ave (nm) | PDI | Intensity-Ave (nm) | Number-Ave (nm) |
|---|---|---|---|---|
| NCP-1 particle | 94.7 ± 0.92 | 0.165 ± 0.01 | 112.8 ± 1.40 | 59.2 ± 2.35 |
| NCP-1@DHA (4:1) | 100.8 ± 0.78 | 0.170 ± 0.01 | 116.6 ± 1.33 | 60.5 ± 7.26 |
| NCP-1@DHA (2:1) | 110.6 ± 1.79 | 0.169 ± 0.01 | 132.5 ± 3.67 | 68.1 ± 1.39 |
| NCP-1@DHA (1:1) | 123.5 ± 1.48 | 0.187 ± 0.01 | 158.5 ± 5.33 | 71.5 ± 1.72 |

In Vitro Cytotoxicity Against Ovarian Cancer Cell Lines

A2780, A2780/CDDP, and SKOV-3 cells were seeded into 96-well plate at 2000 cells/well for 24 h. Afterwards cells were treated with different formulations at various concentrations and incubated for another 72 h. The cell viability was then determined via MTS assay by microplate reader. After combination with DHA, the cytotoxicity of cisplatin decreased significantly, as shown by significantly decrease in $IC_{50}$. The particles showed similar cytotoxicity, compared to free drugs. See Table 11.

TABLE 11

IC$_{50}$ (µM) of cisplatin and DHA on A2780, A2780/CDDP and SKOV-3 cells treated with various formulations. The numbers in parenthesis refer to DHA concentrations.

| | Cisplatin | DHA | Ciaplatin + DHA 2:1 | Ciaplatin + DHA 1:1 | NCP-1 | Zn/DHA | NCP-1/ DHA 2:1 | NCP-1/ DHA 1:1 |
|---|---|---|---|---|---|---|---|---|
| A2780 | 4.05 ± 0.74 | (0.30 ± 0.11) | 0.46 ± 0.14 (0.24 ± 0.07) | 0.35 ± 0.14 (0.35 ± 0.14) | 8.90 ± 1.36 | (0.96 ± 0.15) | 1.16 ± 0.31 (0.58 ± 0.16) | 0.78 ± 0.14 (0.78 ± 0.14) |
| A2780/CDDP | 19.75 ± 4.01 | (2.61 ± 0.18) | 6.18 ± 1.52 (3.09 ± 0.76) | 3.74 ± 0.15 (3.74 ± 0.15) | 24.56 ± 3.45 | (3.71 ± 0.55) | 8.63 ± 0.84 (4.32 ± 0.42) | 4.75 ± 0.69 (4.75 ± 0.69) |
| SKOV-3 | 34.95 ± 5.43 | (9.90 ± 0.34) | 10.95 ± 1.77 (5.48 ± 0.89) | 9.07 ± 0.15 (9.07 ± 0.15) | 38.04 ± 2.36 | (11.88 ± 3.22) | 14.44 ± 3.59 (7.22 ± 1.80) | 10.58 ± 2.31 (10.58 ± 2.31) |

Example 10

Nanoscale Coordination Polymer Core-Shell Nanoparticles Combine Oxaliplatin Analogue and Paclitaxel for the Treatment of Colorectal Cancer NCP-based core-shell nanoparticles carrying two chemotherapeutic inducers of immunogenic cell death are shown to exhibit substantial anticancer efficacy in the treatment of colorectal cancer. Effective anti-cancer therapy of NCP-2/PTX was demonstrated against two syngeneic murine colorectal cancer models, CT26 and MC38. Efficient anti-tumor immunity was evoked by NCP-2/PTX as demonstrated by early calreticulin (CRT) exposure on the cell surface, antitumor vaccination, and delayed tumor growth.

Preparation and Characterization

NCP-2 particles carrying an oxaliplatin prodrug were prepared as previously reported. Briefly, a mixture of $Zn(NO_3)_2$ and an oxaliplatin analogue prodrug, $Pt(dach)Cl_2(OH)_2$ (dach=R, R-diaminocyclohexane), with 1,2-dioleoyl-sn-glycero-3-phosphate sodium salt (DOPA) in the Triton X-100/1-hexanol/cyclohexane/water reverse microemulsion was vigorously stirred at room temperature for 30 min to afford spherical DOPA-coated NCP-2 particles of 55.33±0.18 nm in Z-average by DLS. NCP-2 has an oxaliplatin loading of 27.6 wt % as determined by ICP-MS.

NCP-2/PTX nanoparticles were prepared by coating NCP-2 core with an asymmetric lipid bilayer containing chol-PTX and PEG. Particles containing either 1:1 or 2:1 molar ratio of $Pt(dach)Cl_2$:paclitaxel were prepared and characterized. A THF solution of 1,2-dioleoyl-sn-glycero-3-phosphocholine (DOPC), cholesterol, 1,2-distearoyl-sn-glycero-3-phosphoethanolamine-N-[methoxy(polyethylene glycol)-2000] (DSPE-PEG2k), and chol-PTX (DOPC:cholesterol:chol-PTX:DSPE-PEG2k=2:2:0.26:1 or 2:2:0.52:1 for 2:1 and 1:1 oxaliplatin:paclitaxel formulations, respectively), and DOPA-capped NCP-2 were added to 500 µL of 30% (v/v) ethanol/water and kept stirring at 1700 rpm at 50° C. for 1 min. The THF and ethanol in the nanoparticle suspension was completely evaporated before subsequent use in in vitro and in vivo experiments.

TEM images of both formulations of NCP-2/PTX demonstrated spherical nanoparticles. NCP-2/PTX possessed Z-average diameter, number-average diameter, and polydispersity index (PDI), of 121.7±0.95 nm, 81.98±4.45 nm, and 0.139±0.01, respectively, for 1:1 molar ratio dispersed in phosphate buffered saline (PBS) by DLS measurement. 2:1 particles showed similar characteristics: 112.0±0.51 nm, 74.26±3.60 nm, and 0.151±0.01 respectively.

In Vitro Cytotoxicity Against Colon Cancer Cell Lines

The cytotoxicity of NCP-2/PTX was evaluated against two colorectal cancer cells including murine colorectal adenocarcinoma CT26 and murine colorectal carcinoma MC38. By combining two chemotherapeutic agents with vastly different solubility requirements, NCP-2/PTX elicited substantial anticancer efficacy owing to synergy between the drugs.

The synergy between oxaliplatin and paclitaxel were first examined by comparing free drug cytotoxicities alone or in combination. The IC$_{50}$ of oxaliplatin was substantially lower than that of paclitaxel by MTS assay, likely due to the hydrophobicity of paclitaxel. Paclitaxel was prepared in a stock solution of 3:1 ethanol:water ratio at 1 mg/ml before subsequent dilution to prepare free drug doses. The combination index (CI$_{50}$) for the two drugs was much more favorable for the 1:1 compared to 2:1 molar ratio, with equal oxaliplatin doses. NCP formulations containing oxaliplatin analogue (NCP-2) or oxaliplatin analogue and paclitaxel at a 1:1 molar ratio showed similar cell killing effects to those of the free drugs. See Table 12.

TABLE 12

Oxaliplatin and paclitaxel IC$_{50}$ values (µM) in CT26 and MC38 cells treated with various formulations. The numbers in parentheses refer to paclitaxel concentrations.

| | Drug ratio | NCP-2/PTX | NCP-2 | oxaliplatin | oxaliplatin + paclitaxel |
|---|---|---|---|---|---|
| CT26 | 2:1 | | | 10.21 ± 0.98 | 9.17 ± 1.84 (4.86 ± 0.92) |
| | 1:1 | 4.66 ± 1.20 (4.66 ± 1.20) | 7.55 ± 0.81 | 7.05 ± 0.95 | 5.74 ± 0.65 (5.74 ± 0.65) |
| MC38 | 1:1 | 2.15 ± 0.28 (2.15 ± 0.28) | 3.72 ± 0.31 | 3.35 ± 0.13 | 2.15 ± 0.28 (2.15 ± 0.18) |

In Vitro Immunogenic Cell Death

The immunogenic cell death induced by NCP-2/PTX was evaluated by immunofluorescence and flow cytometry. For immunofluorescence analysis, CT26 cells were seeded at $5 \times 10^5$ cells per well in 6-well plates and further cultured for 24 h. The culture media were replaced by 2 mL of fresh culture media containing 10% FBS. Oxaliplatin, paclitaxel, chol-PTX, NCP-2, and NCP-2/PTX (1:1) were added to the cells, respectively, at an equivalent oxaliplatin and paclitaxel dose of 5 µM. Cells incubated with PBS served as control. Following incubation of 4 h, the cells were washed with PBS three times, fixed with 4% paraformaldehyde, incubated with AlexaFluor 488-calreticulin (CRT) antibody for 2 h, stained with DAPI, and observed under CLSM using 405 nm and 488 nm lasers for visualizing nuclei and CRT expression on the cell membrane, respectively. For flow cytometry analysis, CT26 cells were seeded at $1 \times 10^6$ cells per well in 6-well plates and further cultured for 24 h. The culture media were replaced by 2 mL of fresh culture media containing 10% FBS. Oxaliplatin, paclitaxel, chol-PTX, NCP-2, and NCP-2/PTX (1:1) were added to the cells, respectively, at an equivalent Pt and/or paclitaxel dose of 5 µM. Cells incubated with PBS served as control. Following incubation of 4 h, the cells were collected, incubated with AlexaFluor 488-CRT antibody for 2 h, and stained with propidium iodide (PI). The samples were analyzed by flow cytometer (LSRII Orange, BD, Franklin Lakes, N.J., United States of America) to identify cell surface CRT. The fluorescence intensity of stained cells was gated on PI-negative cells. See FIG. 2.

Pharmacokinetics and Biodistribution

A pharmacokinetic (pK) and biodistribution study of NCP-2/PTX was carried out on CT26 tumor bearing BALB/c mice after intraperitoneal injection. The oxaliplatin distribution was quantified by ICP-MS. Additionally, the pharmacokinetics and biodistribution of a NCP particle comprising a zinc and oxaliplatin analogue core and a lipid coating layer comprising cholesterol-modified paclitaxel (NCP-2/PTX) after intravenous (i.v.) injection in CT26 murine colorectal adenocarcinoma tumor bearing mice at a dose of 1 milligram per kilogram (mg/kg) showed greater presence in the blood compared to liver, lung, spleen, kidney, bladder, and tumor. Platinum (Pt) concentration was analyzed via inductively coupled plasma-mass spectrometry (ICP-MS) at 5 minutes, and at 1, 3, 5, 8, 24, and 48 hours, and is expressed in micrograms (µg). Results of the pharmacokinetics and biodistribution were expressed as percentage of the initial dose (% ID). See FIG. 3.

To better understand the relationship between nanoparticle dose and animal size, a pharmacokinetic study of NCP-2/PTX by intravenous injection was carried out on Beagle dogs. The oxaliplatin distribution was quantified by ICP-MS. See FIG. 4.

In Vivo Efficacy

Two colorectal mouse models including BALB/c mice bearing murine colorectal adenocarcinoma CT26 and C57Bl/6 mice bearing colorectal carcinoma MC38 were employed to assess the in vivo anticancer activity of NCP-2/PTX. See FIGS. 5 and 6. $5 \times 10^6$ cells were injected into the right flank and treatment began on day 7, after all tumors had reached 100-150 mm$^3$ in size. CT26 or MC38 tumor bearing mice were treated by intraperitoneal injection at equivalent oxaliplatin doses of 1 mg/kg and paclitaxel doses of 2.24 mg/kg (1) PBS, (2) NCP-2/PTX, or (3) NCP-2/PTX+PD-L1 antibody on the indicated days for a total of 6-10 doses. Consistent, low oxaliplatin analogue doses of NCP-2/PTX significantly delayed tumor growth in both CT26 and MC38 murine mouse models.

To investigate the role of different immune cells in the anti-cancer efficacy of NCP-2/PTX, $5 \times 10^6$ CT26 cells were implanted into the right flank regions of immunocompromised athymic nude mice deficient in mature T cells, or Rag−/− BALB/c mice deficient in both T and B cells. See FIG. 7. NCP-2/PTX at a dose of 1 mg oxaliplatin analogue/kg and 2.24 mg paclitaxel/kg was ineffective at treating CT26 on either of these immunocompromised models, compared to the significantly enhanced anticancer effect on immunocompotent BALB/c mice.

To establish more representative mouse models of colorectal cancer, fewer cells ($1 \times 10^6$ MC38 cells) were injected into the right flank region of C57BL/6 mice and allowed to grow for longer periods of time to establish an immunosuppressive tumor environment before beginning treatment. MC38 tumor bearing mice were treated by intraperitoneal injection at equivalent oxaliplatin analogue doses of 2 mg/kg and antibody doses of 75 g for (1) PBS, (2) NCP-2, (3) NCP-2/PTX (1:1), (4) NCP-2/PTX (2:1), (5) NCP-2/PTX (1:1)+PD-L1 antibody, or (6) NCP-2/PTX (2:1)+PD-L1 antibody every four days for a total of 5 doses. See FIG. 8.

Antitumor Vaccination

Inspired by the robust immunogenic response evoked by NCP-2/PTX, the antitumor vaccination capability of NCP-2/PTX was further evaluated. A total of $5 \times 10^5$ CT26 cells, treated with PBS or NCP-2/PTX, were inoculated subcutaneously to the right flank region of BALB/c mice. One week after, these mice were re-challenged by injecting $1 \times 10^5$ CT26 cells on the contralateral flank. The animals were checked daily for tumor development using calipers and body weight evolution. See FIGS. 9A and 9B. All mice were sacrificed when the right tumor size of PBS group exceeded 2 cm$^3$.

Example 11

Nanoscale Coordination Polymer Core-Shell Nanoparticles Combine Oxaliplatin Analogue and Mitoxantrone for the Treatment of Colorectal Cancer NCP-based core-shell nanoparticles carrying two chemotherapeutic inducers of immunogenic cell death are shown to exhibit substantial anticancer efficacy in the treatment of colorectal cancer.

Preparation and Characterization

NCP-2 particles carrying an oxaliplatin prodrug were prepared as previously reported. NCP-2/MTX nanoparticles were prepared by coating NCP-2 core with an asymmetric lipid bilayer containing chol-MTX and PEG. Particles containing a 2:1 or 1:1 molar ratio of oxaliplatin:mitoxantrone were prepared and characterized. A THF solution of 1,2-dioleoyl-sn-glycero-3-phosphocholine (DOPC), cholesterol, 1,2-distearoyl-sn-glycero-3-phosphoethanolamine-N-[methoxy(polyethylene glycol)-2000] (DSPE-PEG2k), and chol-MTX (DOPC:cholesterol:chol-MTX:DSPE-PEG2k=2: 2:0.30:1 or 2:2:0.60:1 for 2:1 and 1:1 oxaliplatin analogue: mitoxantrone molar ratios, respectively), and DOPA-capped NCP-2 were added to 500 µL of 30% (v/v) ethanol/water and kept stirring at 1700 rpm at 50° C. for 1 min. The THF and ethanol in the nanoparticle suspension was completely evaporated before subsequent use in in vitro and in vivo experiments. The particle size and distribution were determined by DLS. See Table 13.

TABLE 13

| Characterization data for NCP-2/MTX nanoparticles. | | | |
|---|---|---|---|
| Drug ratio (oxaliplatin analogue:mitoxantrone) | Z-ave | PDI | Number ave |
| 1:0 | 97.2 | 0.164 | 62.6 |
| 1:1 | 90.1 | 0.213 | 41.0 |
| 2:1 | 100.0 | 0.195 | 57.5 |

In Vitro Cytotoxicity Against Cell Lines

The cytotoxicity of NCP-2/MTX was evaluated against two syngeneic cancer cell lines: colorectal adenocarcinoma CT26 and colorectal carcinoma MC38. By combining two chemotherapeutic agents with vastly different solubility requirements, NCP-2/MTX elicited substantial anticancer efficacy owing to synergy between the drugs. The synergy between oxaliplatin and mitoxantrone were first examined by comparing free drug cytotoxicities alone or in combination. The combination index ($CI_{50}$) for the two drugs was much more favorable for the 2:1 compared to 1:1 molar ratio, with equal Pt doses. NCP formulations containing oxaliplatin analogue (NCP-2) or oxaliplatin analogue and mitoxantrone at a 1:1 molar ratio (NCP-2/MTX) showed similar cell killing effects to those of the free drugs. See Table 14.

TABLE 14

Oxaliplatin and paclitaxel $IC_{50}$ values (μM) in CT26 and MC38 cells treated with various formulations. The numbers in parentheses refer to paclitaxel concentrations.

|  | Drug ratio | NCP-2/MTX | NCP-2 | oxaliplatin | oxaliplatin + mitoxantrone |
|---|---|---|---|---|---|
| CT26 | 2:1 | 1.49 ± 0.32 (0.74 ± 0.16) | 7.55 ± 0.81 | 7.05 ± 0.59 | 1.91 ± 0.12 (0.95 ± 0.06) |
|  | 1:1 | — | — | — | 0.76 ± 0.03 (0.76 ± 0.03) |
| MC38 | 1:1 | 0.59 ± 0.069 (0.59 ± 0.069) | 3.72 ± 0.31 | 3.35 ± 0.13 | 0.21 ± 0.036 (0.21 ± 0.036) |

In Vivo Efficacy

A colorectal mouse model of murine colorectal adenocarcinoma CT26 was employed to assess the in vivo anticancer activity of NCP-2/MTX. 5×10⁶ CT26 cells were injected into the right flank and treatment began on day 7, after all tumors had reached 100-150 mm³ in size. CT26 tumor bearing mice were treated by intraperitoneal injection at equivalent oxaliplatin analogue doses of 1 mg/kg and paclitaxel doses of 0.58 mg/kg (1) PBS, (2) NCP-2/MTX (2:1), or (3) NCP-2/MTX (2:1)+75 μg PD-L1 antibody every four days for a total of 6 doses. Consistent, low doses of chemotherapeutics in NCP-2/MTX significantly delayed tumor growth in CT26 murine mouse models and synergized with checkpoint blockade immunotherapy to sustain tumor growth inhibition. See FIG. 10.

A colorectal mouse model of murine colorectal carcinoma MC38 was employed to assess the in vivo anticancer activity of NCP-2/MTX. 1×10⁶ MC38 cells were injected into the right flank and treatment began on day 12, after all tumors had reached 50-70 mm³ in size. MC38 tumor bearing mice were treated by intraperitoneal injection at equivalent oxaliplatin doses of 2 mg/kg and mitoxantrone doses of 1.16 mg/kg (1) PBS, (2) NCP-2/MTX (2:1), or (3) NCP-2/MTX (2:1)+75 μg PD-L1 antibody every four days for a total of 5 doses. See FIG. 11.

Example 12

Nanoscale Coordination Polymer Core-Shell Nanoparticles Combine Oxaliplatin Analogue and DHA Preparation and Characterization of NCP-2/DHA The bare NCP-2 comprised by oxaliplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. The bare NCP-2 particles are then mixed with twice amount of EtOH and centrifuged at 12000 rpm for 30 min to remove the solvent. The particle pellet was further washed once with 50% EtOH/cyclohexane and twice with 50% EtOH/THF to remove excess amounts of DOPA and re-dispersed in THF. Finally, the bare NCP-2 particles were filtered via 200 nm syringe filter prior to any use. The NCP-2 particle has a Z-average diameter and PDI of 78.56±1.03 nm and 0.147±0.01, respectively. NCP-2/DHA was formulated by adding a mixture of DOPC, Chol, Chol-DHA, DSPE-PEG$_{2K}$ and bare NCP-2 particles to 30% (v/v) EtOH/H$_2$O with vigorous stirring. THF and EtOH were evaporated and the solution was allowed to cool to r.t. prior to use. In this formulation with Oxaliplatin/DHA=1:2 (molar ratio), the NCP-2/DHA particle has a number-averaged diameter, Z-averaged diameter, and PDI of 51.90±1.06 nm, 80.74 nm±0.79 nm, and 0.152, respectively.

In Vitro Cytotoxicity Against Colon Cancer Cell Lines

The cytotoxicity of NCP-2/DHA was evaluated against two colon cancer cell lines CT26 and MC38. The synergy between oxaliplatin and DHA was first examined by comparing free drug cytotoxicities alone or in combination. The combination index ($CI_{50}$) for the two drugs was lower than 1 in some drug effect levels, indicating the syngestic effect between two drugs. NCP formulations containing oxaliplatin analogue (NCP-2), DHA or oxaliplatin and DHA at a 1:1 molar ratio showed similar cell killing effects to those of the free drugs. See Table 15.

TABLE 15

Oxaliplatin and DHA $IC_{50}$ values (μM) in CT26 and MC38 cells treated with various formulations. The numbers in parentheses refer to DHA concentrations.

|  | Oxaliplatin | DHA | Oxaliplatin + DHA | NCP-2 | Zn/DHA | NCP-2/DHA |
|---|---|---|---|---|---|---|
| CT26 | 5.77 ± 1.06 | 7.77 ± 2.68 | 8.11 ± 1.17 (8.11 ± 1.17) | 11.03 ± 2.58 | 8.51 ± 1.37 | 6.74 ± 1.24 (6.74 ± 1.24) |

TABLE 15-continued

Oxaliplatin and DHA IC$_{50}$ values (µM) in CT26 and MC38 cells treated with
various formulations. The numbers in parentheses refer to DHA concentrations.

| | Oxaliplatin | DHA | Oxaliplatin + DHA | NCP-2 | Zn/DHA | NCP-2/DHA |
|---|---|---|---|---|---|---|
| MC38 | 7.87 ± 1.32 | 4.83 ± 1.12 | 4.28 ± 1.20 (4.28 ± 1.20) | 11.70 ± 2.10 | 8.31 ± 1.47 | 9.18 ± 1.48 (9.18 ± 1.48) |

In Vitro Immunogenic Cell Death

The immunogenic cell death induced by DHA was evaluated by immunofluorescence and flow cytometry. For immunofluorescence analysis, CT26 and MC38 cells were seeded at 5×10$^5$ cells per well in 6-well plates and further cultured for 24 h. The culture media were replaced by 2 mL of fresh culture media containing 10% FBS. DHA was added to the cells at a dose of 1 µM. Cells incubated with PBS served as control. Following incubation of 24 h, the cells were washed with PBS three times, fixed with 4% paraformaldehyde, incubated with AlexaFluor 488-calreticulin (CRT) antibody for 2 h, stained with DAPI, and observed under CLSM using 405 nm and 488 nm lasers for visualizing nuclei and CRT expression on the cell membrane, respectively. For flow cytometry analysis, CT26 and MC38 cells were seeded at 1×10$^6$ cells per well in 6-well plates and further cultured for 24 h. The culture media were replaced by 2 mL of fresh culture media containing 10% FBS. DHA was added to the cells at a dose of 1 µM. Cells incubated with PBS served as control. Following incubation of 24 h, the cells were collected, incubated with AlexaFluor 488-CRT antibody for 2 h, and stained with propidium iodide (PI). The samples were analyzed by flow cytometer (LSRII Orange, BD, USA) to identify cell surface CRT. The fluorescence intensity of stained cells was gated on PI-negative cells. Both flow cytometry and confocal imaging indicated that DHA caused significant immunogenic cell death. See FIGS. 12A and 12B.

In Vivo Efficacy

A colorectal mouse model of murine colorectal adenocarcinoma CT26 was employed to assess the in vivo anticancer activity of NCP-2/DHA. 5×10$^6$ CT26 cells were injected into the right flank and treatment began on day 7, after all tumors had reached 100-150 mm$^3$ in size. CT26 tumor bearing mice were treated by intraperitoneal injection of NCP-2/DHA at an oxaliplatin analogue dose of 2 mg/kg. NCP-2/DHA particles inhibited the growth of CT26 tumor models. See FIG. 13.

Example 13

Nanoscale Coordination Polymer Core-Shell Nanoparticles Combine Oxaliplatin and DHA Synthesis of Phosphocoline-Conjugated DHA (PC-DHA)

To a solution of DHA-S—S—OH (200 mg, 0.43 mmol, 1 eq.) in 5 mL anhydrous toluene and 0.2 mL triethylamine, a solution of ethylene glycol chlorophosphate (80 mg, 0.56 mmol, 1.3 eq.) was added dropwise over an ice bath with stirring. The resultant solution was warmed to room temperature and further stirred for 2 hours and then dried under vacuum. The product was transferred to a pressure tube by 2 mL anhydrous THF and cooled over a dry ice-acetone bath. 0.5 mL anhydrous trimethylamine was added to the solution and the pressure tube was sealed and heated at 70° C. for 24 hours. After removal of solvent under vacuum, the product was obtained in 50% yield (137 mg) by purification of column chromatography on diol silica with DCM/methanol (5:1, v/v). $^1$H-NMR (500 MHz, CDCl$_3$): 0.93 (d, 3H), 0.98 (d, 3H), 1.25-1.55 (m, 6H), 1.62-1.95 (m, 6H), 2.07 (m, 1H), 2.38 (td, 1H), 2.65 (m, 1H), 2.93 (m, 4H), 3.45 (s, 9H), 3.73 (m, 1H), 3.95 (m, 2H), 4.15 (m, 1H), 4.20 (m, 2H), 4.45 (m, 2H), 4.85 (s, 1H), 5.32 (s, 1H), 5.44 (s, 1H). ESI-MS: m/z=630.2 ([M+H]$^+$).

Synthesis of Oleic Acid-Conjugated DHA (OA-DHA)

To a mixture of DHA-S—S—OH (500 mg, 1.07 mmol, 1 eq.) and 4-N,N-dimethylaminopyridine (DMAP, 160 mg, 1.2 mmol, 1.1 eq.) in anhydrous dichloromethane (DCM, 4 ml), a solution of triphosgene (110 mg, 0.36 mmol, 0.33 eq.) in anhydrous DCM (1 mL) was added dropwise over an ice bath with stirring. The resulting solution was warmed to room temperature and further stirred for 0.5 hour and then added dropwise to a solution of Oleyl-lyso-PC (500 mg, 0.96 mmol, 0.9 eq.) in a mixture of anhydrous DCM (2 mL), anhydrous DMF (3 mL) and triethylamine (0.2 mL) over an ice bath. The reaction mixture was then warmed to room temperature and stirred for 12 hours. After removal of solvent, the residue was purified by column chromatography on diol silica with DCM/methanol (10:1, v/v) to yield 215 mg of Oleyl-PC-S—S-DHA. $^1$H-NMR (500 MHz, CDCl$_3$): 0.90 (t, 3H), 0.93 (d, 3H), 0.98 (d, 3H), 1.20-1.33 (m, 22H), 1.45-1.70 (m, 9H), 1.75-1.95 (m, 4H), 2.03 (m, 4H), 2.36 (m, 3H), 2.66 (m, 1H), 2.97 (m, 4H), 3.46 (s, 9H), 3.50 (d, 1H), 3.73 (m, 1H), 4.10 (m, 3H), 4.27 (m, 3H), 4.39 (dd, 1H), 4.44 (t, 2H), 4.65 (s, 2H), 4.85 (d, 1H), 5.11 (t, 1H), 5.37 (m, 1H), 5.46 (s, 1H). ESI-MS: m/z=1012.5 ([M+H]$^+$).

Preparation and Characterization

NCP-3 particles carrying an oxaliplatin prodrug. Briefly, a mixture of Zn(NO$_3$)$_2$ and an oxaliplatin prodrug, Pt(dach)(oxalate)(OH)$_2$ (dach=R, R-diaminocyclohexane), with 1,2-dioleoyl-sn-glycero-3-phosphate sodium salt (DOPA) in the Triton X-100/1-hexanol/cyclohexane/water reverse microemulsion was vigorously stirred at room temperature for 30 min to afford spherical DOPA-coated NCP-3 particles of 60.53±0.69 nm in Z-average by dynamic light scattering (DLS). NCP-3 has an oxaliplatin loading of 28.2 wt % as determined by inductively coupled plasma-mass spectrometry (ICP-MS).

The bare NCP-3 particles will be further filtered via 200 nm syringe filter prior to any use. NCP-3/DHA was formulated by adding a mixture of DSPC, Chol, DHA conjugate, DSPE-PEG$_{2K}$ and bare NCP-3 particles to 30% (v/v) EtOH/H$_2$O with vigorous stirring. THF and EtOH were evaporated and the solution was allowed to cool to r.t prior to use. In all formulations, Oxaliplatin/DHA=1:2 (molar ratio). Small sized particles (92.94 nm±0.30) with PDI of 0.156 were observed. All future instances of NCP-3/DHA refer to NCP-3/chol-S—S-DHA. NCP-3/DHA-OA-DHA refers to a 1:1 mixture of chol-S—S-DHA and OA-DHA conjugates. Characterization of the particles is described in Table 16.

TABLE 16

Particle size and PDI of NCP-2/DHA.

|  | Z-Ave | PDI | Intensity | Number |
|---|---|---|---|---|
| NCP-3 bare | 60.53 ± 0.69 | 0.081 ± 0.007 | 61.17 ± 0.82 | 43.42 ± 0.55 |
| NCP-3 | 89.21 ± 1.17 | 0.136 ± 0.014 | 102.20 ± 0.60 | 55.37 ± 2.28 |
| NCP-3/DHA | 80.74 ± 0.79 | 0.152 ± 0.01 | 92.94 ± 1.35 | 51.90 ± 1.06 |
| NCP-3/PC-DHA | 78.20 ± 0.74 | 0.204 ± 0.009 | 120.88 ± 0.89 | 41.96 ± 2.62 |
| NCP-3/OA-DHA | 89.46 ± 0.77 | 0.119 ± 0.014 | 102.43 ± 2.31 | 56.16 ± 2.38 |
| NCP-3/DHA-OA-DHA | 91.57 ± 0.74 | 0.164 ± 0.007 | 110.33 ± 1.86 | 51.81 ± 2.59 |

In Vitro Cytotoxicity Against Colon Cancer Cell Lines

The cytotoxicity of NCP-3/DHA was evaluated against two colon cancer cell lines CT26 and MC38. DHA, chol-S—S-DHA, OA-DHA, and PC-DHA showed fairly similar $IC_{50}$ values. The synergy between oxaliplatin and DHA were first examined by comparing free drug cytotoxicities alone or in combination. NCP formulations containing oxaliplatin (NCP-3), DHA or oxaliplatin and DHA at a 1:1 molar ratio showed similar cell killing effects to those of the free drugs. See Table 17 and FIGS. 14 and 15.

TABLE 17

Oxaliplatin and DHA $IC_{50}$ values (μM) in CT26 and MC38 cells treated with various formulations. The numbers in parentheses refer to DHA concentrations.

|  | Oxaliplatin | DHA | Oxaliplatin + DHA | NCP-3 | Zn/DHA | NCP-3/DHA |
|---|---|---|---|---|---|---|
| CT26 | 10.3 ± 1.62 | 6.25 ± 1.53 | 3.62 ± 0.87 (6.72 ± 1.74) | 12.98 ± 1.54 | 13.57 ± 2.15 | 10.44 ± 1.85 (20.88 ± 3.70) |
| MC38 | 12.8 ± 1.32 | 9.68 ± 1.12 | 3.44 ± 0.65 (6.88 ± 1.30) | 15.77 ± 1.12 | 13.47 ± 1.58 | 8.99 ± 0.42 (17.98 ± 0.84) |

Apoptosis

CT26 cells seeded in 24-well plates at $1\times10^5$ cells/well were first incubated with NCP-3/DHA or appropriate controls for 24 h at an oxaliplatin concentration of 10 μM. The floating and adherent cells were collected and stained with Alexa Fluor 488 AnnexinV/dead cell apoptosis kit (Invitrogen, USA) according to manufacturer's instructions. The apoptosis and necrosis were examined by a flow cytometry (LSRII Blue, BD, Franklin Lakes, N.J., United States of America). Both oxaliplatin and DHA individually caused necrosis, but the combination therapy evoked a high level of apoptosis. See FIG. 16.

In Vitro Immunogenic Cell Death The immunogenic cell death induced by NCP-3/DHA was evaluated by flow cytometry and ELISA. For flow cytometry analysis, CT26 cells were seeded at $1\times10^6$ cells per well in 6-well plates and further cultured for 24 h. The culture media were replaced by 2 mL of fresh culture media containing 10% FBS. Oxaliplatin, DHA, chol-DHA, oxaliplatin+DHA, NCP-3, Zn/DHA and NCP-3/DHA were added to the cells, respectively, at equivalent oxaliplatin and/or DHA dose of 10 μM and 20 μM, respectively. Cells incubated with PBS served as control. Following incubation of 24 h, the cells were collected, incubated with AlexaFluor 488-CRT antibody for 2 h, and stained with PI. The samples were analyzed by flow cytometer (LSRII Orange, BD, Franklin Lakes, N.J., United States of America) to identify cell surface CRT. The fluorescence intensity of stained cells was gated on PI-negative cells. Both oxaliplatin and DHA individually caused cell surface CRT expression with slightly increased CRT exposure in cells treated with NCP-3/DHA compared to Zn/DHA.

The release of high mobility group box-1 (HMGB-1) protein after ICD was evaluated by ELISA. CT26 cells were seeded at $1\times10^6$ cells per well in 6-well plates and further cultured for 24 h. The culture media were replaced by 2 mL of fresh culture media containing 10% FBS. Oxaliplatin, DHA, chol-DHA, oxaliplatin+DHA, NCP-3, Zn/DHA, NCP-3/DHA, and NCP-3/OA-DHA were added to the cells, respectively, at equivalent oxaliplatin and/or DHA dose of 10 μM and 20 μM, respectively. Cells incubated with PBS served as control. Following incubation of 48 h, the supernatant was collected and analyzed by an ELISA kit (Chondrex, Inc., Redmond, Wash., United States of America) by microplate reader. Both oxaliplatin and DHA individually caused ICD leading to HMGB-1 release, with significantly release by cells treated with Zn/DHA. See FIG. 17.

Pharmacokinetics

A pK study of NCP-3/DHA was carried out on SD/CD rats. The oxaliplatin distribution was quantified by ICP-MS and the chol-DHA concentration in the blood was quantified by LC-MS after extraction by THF. Both oxaliplatin and chol-DHA concentrations in blood versus time were fitted by a one-compartment model. Blood circulation half-lives of oxaliplatin and chol-DHA were determined to be (11.8±0.6) and (13.3±1.2) h, respectively, and did not exhibit statistically significant difference. See FIGS. 18A and 18B. One-compartment model fit of NCP-3/OA-DHA exhibited a blood circulation half-life of 18.1±3.1 h for oxaliplatin.

Biodistribution

A preliminary biodistribution study of NCP-3/DHA was carried out on CT26 tumor bearing BALB/c mice. See FIG. 19. The oxaliplatin distribution was quantified by ICP-MS. NCP-3/DHA exhibited low uptake by the mononuclear phagocyte system (MPS) as evidenced by the low % ID/g (percent injected dose per gram tissue) in liver (<2.7±0.3%), spleen (<7.6±2.2%), and kidney (<3.0±1.0%).

Toxicity

Toxicity studies of NCP-3/DHA by i.p. injection were performed on BALB/c and C57BL/6 mice. Single dose injections of NCP-3/DHA at 50 and 60 mg oxaliplatin/kg showed minimal weight loss in BALB/c and C57BL/6 mice, respectively. A once-weekly repeated dose of NCP-3/DHA at 60 mg oxaliplatin/kg on C57BL/6 showed mice could tolerate at least 4 repeated doses without significant toxicity. NCP-3/OA-DHA intraperitoneally injected into C57BL/6 mice at an oxaliplatin dose of 24 mg/kg once every 3 days for a total of 8 doses also showed minimal body weight loss and toxicity.

In Vivo Efficacy

Two colorectal mouse model of murine colorectal adenocarcinoma CT26 and MC38 were employed to assess the in vivo anticancer activity of NCP-3/DHA. $1\times10^6$ CT26 or MC38 cells were injected into the right flank and treatment began on day 12, after all tumors had reached 80-100 mm$^3$ in size. CT26 or MC38 tumor bearing mice were treated by intraperitoneal injection of NCP-3/DHA and appropriate controls. NCP-3/DHA particles inhibited the growth of both CT26 and MC38 tumor models. See FIGS. 20A and 20B. In combination with checkpoint blockade immunotherapy, NCP-3/DHA could effectively eradicate all mice with CT26 tumor models at an oxaliplatin dose of 8 mg/kg. Up to 60% of MC38 tumor-bearing mice treated with NCP-3/DHA at an oxaliplatin dose of 16 mg/kg exhibited tumor eradication. NCP-3/DHA at an equivalent oxaliplatin dose of 8 mg/kg was also able to cause tumor growth inhibition on mice bearing LL/2 tumors.

Immune Assay by ELISPOT

At day 12 post first treatment, the spleens were harvested and ground into single-cell suspensions. The splenocytes were treated with ACK lysis buffer and then analyzed by Enzyme-Linked ImmunoSpot (ELISPOT, eBioscience, San Diego, Calif., United States of America). Chemotherapy and immunotherapy alone increased tumor-specific T cells, but NCP-3/DHA and NCP-3/DHA+PD-L1 showed the greatest increase in tumor-specific immune response. See FIG. 21.

Anticancer Activity Against Other Cancers

A triple negative breast cancer 4T1 and a non-small cell lung cancer LL/2 tumor model were also used to evaluate the in vivo efficacy of NCP-3/DHA in combination with immunotherapy. See FIGS. 22A and 22B. $2\times10^6$ 4T1 cells or $1.5\times10^6$ LL/2 cells were injected into the right flank and treatment began on day 10 or day 12, respectively, after all tumors had reached 80-100 mm$^3$ in size. Mice were treated by intraperitoneal injection at equivalent oxaliplatin doses of 8 mg/kg. Repeated doses of NCP-3/DHA significantly inhibited tumor growth in both the 4T1 and LL/2 tumor models. NCP-3/OA-DHA at equivalent oxaliplatin and DHA doses was also able to cause tumor growth inhibition on mice bearing LL/2 tumors.

Example 14

Nanoscale Coordination Polymer Core-Shell Nanoparticles Combine Oxaliplatin Analogue and IDO Inhibitor NLG919

Chemical Synthesis of Cholesterol-Linked NLG919 (Chol-NLG919)

First, the hydroxyl group in cholesterol was converted to acyl chloride by mixing cholesterol (1 eq.), triphosgene (0.35 eq.), and DMAP (4 eq.) in DCM for 20 min with stirring at r.t. The resultant Chol-COCl (1 eq.) was then added dropwise into OH—S—S—OH (2 eq.) in DCM and the reaction mixture was stirred overnight to produce Chol-S—S—OH, which was purified by column chromatography with ethyl acetate/hexane (1:2, v/v). Then, the hydroxyl moiety in Chol-S—S—OH (1 eq.) was further converted to acyl chloride by reacting with triphosgene (0.35 eq.) and DMAP (4 eq.) in DCM for 20 min to yield Chol-S—S—COCl. The mixture was then added dropwise into NLG919 (1.7 eq.) in DCM to generate Chol-NLG919, which was subsequently subject to column chromatography with methanol/DCM (3:97, v/v) with yield of 62.2%. The identity of Chol-NLG919 was confirmed by $^1$H-NMR, $^{13}$C-NMR, and ESI-MS. The active NLG919 will be readily released following the cleavage of the disulfide bond inside cells by GSH and/or cysteine.

Characterization of NCP-2/Chol-NLG919

The bare NCP-2 comprised by oxaliplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. The bare NCP-2 particles are then mixed with twice amount of EtOH and centrifuged at 12000 rpm for 30 min to remove the solvent. The particle pellet will be further washed once with 50% EtOH/cyclohexane and twice with 50% EtOH/THF to remove excess amounts of DOPA and re-dispersed in THF. Finally, the bare NCP-2 particles will be further filtered via 200 nm syringe filter prior to any use. NCP-2/Chol-NLG919 was formulated by adding a mixture of DOPC (0.5 mg), Chol (0.25 mg) and Chol-NLG919 (62 μg), DSPE-PEG$_{2K}$ (20 mol %) (0.9 mg) and bare NCP-2 particles (0.25 mg) to 30% (v/v) EtOH/H$_2$O with vigorous stirring. THF and EtOH were evaporated and the solution was allowed to cool to r.t prior to use. In this formulation, Oxaliplatin/NLG919=2.18:1 (molar ratio); Drug loading: NLG919 (1.02%, 282.17 g/mol, 3.16% for Chol-NLG919); Oxaliplatin:(3.13%, 397.3 g/mol). Small sized particle (85.2 nm±0.8) with PDI of 0.152 and near neutral charge (~2.1 mV) were observed. Besides, the NCP-2/Chol-NLG919 particles have been stable for 14 days in both PBS and PBS-containing 10% FBS solutions with no noticeable size, PDI, and zeta potential changes. The enhanced formulation stability is likely to stem from the strong coordination bonding inside the core and the hydrophobic interactions between cholesterol and phospholipids.

Example 15

Nanoscale Coordination Polymer Core-Shell Nanoparticles Combine Cisplatin, Camptothecin, Etoposide, and Paclitaxel Synthesis of Oleic Acid-Conjugated Camptothecin (OA-CPT)

OA-CPT was synthesized as follows. First, oleic acid (OA, 1 eq.) reacted with OH—S—S—OH (2 eq.) in DCM for overnight to generate OA-S—S—OH, which was purified by ethyl acetate/hexane (2:3, v/v). In parallel, hydroxyl group in CPT was converted to acyl chloride by mixing CPT (1 eq.), triphosgene (0.35 eq.), and DMAP (4 eq.) in DCM for 20 min with stirring at r.t. The resultant CPT-COCl (1 eq.) was then added dropwise into OA-S—S—OH (2 eq.) in DCM and the reaction mixture was stirred overnight to form OA-CPT. The structure of OA-CPT is shown below in Scheme 10. OA-CPT was purified via column chromatography with methanol/DCM (3:97, v/v) with yield of 65%. The identity of OA-CPT was confirmed by $^1$H-NMR, $^{13}$C-NMR, and ESI-MS. The active CPT will be readily released following the cleavage of the disulfide bond inside cells by GSH and/or cysteine.

Scheme 10. Structure of OA-CPT.

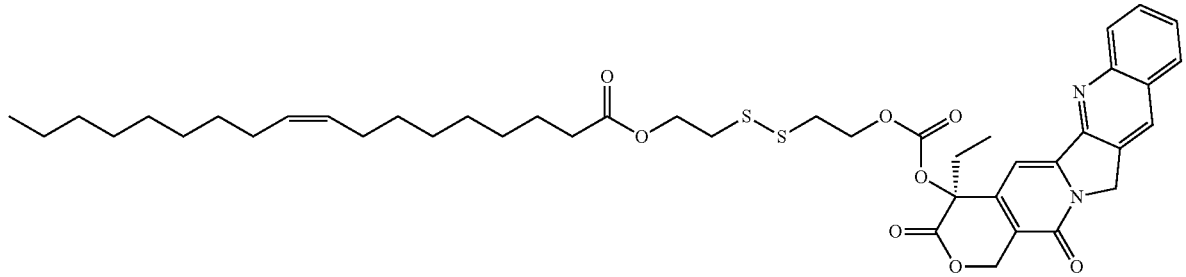

Characterization of NCP-1/OA-CPT/Chol-PTX, NCP-1/OA-CPT/Chol-ET, and NCP-1/OA-CPT/Chol-ET/Chol-PTX The bare NCP-2 comprised by oxaliplatin-bisphosphonates, $Zn^{2+}$ ions, and dioleoyl-sn-glycero-3-phosphate (DOPA), was prepared in a mixture of 0.3 M TritonX-100 and 1.5 M hexanol in cyclohexane with DOPA sticking out in the medium, which provides a lipid layer on the bare NCP and facilitates the incorporation of other phospholipids or lipid-containing drugs. The bare NCP-2 particles are then mixed with twice amount of EtOH and centrifuged at 12000 rpm for 30 min to remove the solvent. The particle pellet will be further washed once with 50% EtOH/cyclohexane and twice with 50% EtOH/THF to remove excess amounts of DOPA and re-dispersed in THF. Finally, the bare NCP-2 particles will be further filtered via 200 nm syringe filter prior to any use. NCP-1/OA-CPT/Chol-PTX was formulated by adding a mixture of DOPC (0.5 mg), Chol (0.25 mg), OA-CPT (57.2 μg), and Chol-PTX (106.2 μg), DSPE-PEG$_{2K}$ (20 mol %) (0.9 mg) and bare NCP-1 particles (0.25 mg) to 30% (v/v) EtOH/H$_2$O with vigorous stirring. THF and EtOH were evaporated and the solution was allowed to cool to r.t. prior to use. The particle was found to be 71.2±0.6 nm in size with PDI at 0.113 and zeta potential at 0.15 mV in PBS. In this formulation, Cisplatin loading is at 3.38%; CPT loading is at 1.25%, and 2.86% for OA-CPT; ET loading is at 2.14% and 5.49% for Chol-ET; PTX loading is at 3.13%, and 5.31% for Chol-PTX; Spherical and non-dispersed nanoparticles were confirmed in TEM. The NCP-1/OA-CPT/Chol-PTX has been stable for 10 days in both PBS and PBS-containing 10% FBS solutions with no significant size, PDI, and zeta potential changes.

NCP-1/OA-CPT/Chol-ET was prepared by adding a mixture of DOPC (0.5 mg), Chol (0.25 mg), OA-CPT (57.2 μg), and Chol-ET (109.8 μg), DSPE-PEG$_{2K}$ (20 mol %) (0.9 mg) and bare NCP-1 particles (0.25 mg) to 30% (v/v) EtOH/H$_2$O with vigorous stirring. THF and EtOH were evaporated and the solution was allowed to cool to r.t prior to use. In this formulation, Cisplatin loading is at 3.38%; CPT loading is at 1.25%, and 2.86% for OA-CPT; ET loading is at 2.14% and 5.49% for Chol-ET. The particle was found to be 56.4±0.7 nm in size with PDI at 0.152 and zeta potential at 0.12 mV in PBS. Spherical and non-dispersed nanoparticles were confirmed in TEM. The NCP-1/OA-CPT/Chol-ET has been stable for 10 days in both PBS and PBS-containing 10% FBS solutions with no significant size, PDI, and zeta potential changes.

NCP-1/OA-CPT/Chol-ET/Chol-PTX was formulated by adding a mixture of DOPC (0.5 mg), Chol (0.25 mg), OA-CPT (57.2 μg), Chol-ET (109.8 μg), and Chol-PTX (106.2 μg), DSPE-PEG$_{2K}$ (20 mol %) (0.9 mg) and bare NCP-1 particles (0.25 mg) to 30% (v/v) EtOH/H$_2$O with vigorous stirring. THF and EtOH were evaporated and the solution was allowed to cool to r.t prior to use. In this formulation, Cisplatin loading is at 3.38%; CPT loading is at 1.25%, and 2.86% for OA-CPT; ET loading is at 2.14% and 5.49% for Chol-ET; PTX loading is at 3.13%, and 5.31% for Chol-PTX. The particle was found to be 64.2±0.9 nm in size with PDI at 0.183 and zeta potential at 1.02 mV in PBS. Spherical and non-dispersed nanoparticles were confirmed in TEM. The NCP-1/OA-CPT/Chol-ET/Chol-PTX particles are stable for 7 days in both PBS and PBS-containing 10% FBS solutions with no significant size, PDI, and zeta potential changes. The strong coordination bonding inside the NCP core and the interactions between Chol and/or OA and phospholipids led to the formulations stability.

Cytotoxicity of NCP-1/OA-CPT/Chol-ET/Chol-PTX in A549 NSCLC Cells

A549 cells were seeded into 96-well plate at 2000 cells/well for 24 h. Afterwards, cells were treated by cisplatin, ET and Chol-ET, PTX and Chol-PTX, CPT and OA-CPT, NCP-1, NCP-1/OA-CPT/Chol-PTX, NCP-1/OA-CPT/Chol-ET, and NCP-1/OA-CPT/Chol-ET/Chol-PTX at various concentrations and incubated for another 72 h. The cell viability was then determined via MTS assay by microplate reader. As shown in FIGS. 23A and 23B, Chol-ET, Chol-PTX, and OA-CPT exhibited similar cytotoxicity in A549 cells as free ET, PTX and CPT, respectively, which suggested that active ET, PTX, and CPT can be readily liberated from lipid-linked prodrugs. Combination of cisplatin, OA-CPT, and Chol-ET led to a significant synergistic effect as evidenced by CI$_{50}$=0.73. Likewise, potent synergy was obtained in NCP-1/OA-CPT/Chol-ET/Chol-PTX with CI50=0.41. However, highest synergistic effect was realized by combing cisplatin, OA-CPT, Chol-ET, and Chol-PTX into single nanoparticle formulation, in which CI50=0.28 was achieved. These data clearly imply that a prodrug strategy involving conjugating anticancer drugs with a lipid (Chol or OA) using a linker including a disulfide bond results in a prodrug that remains as active as parent drug.

Example 16

Nanoscale Coordination Polymer Core-Shell Nanoparticles Combine Chemotherapy and Photodynamic Therapy to Elicit Potent Anti-Tumor Immunity Approximately 150,000 patients are diagnosed with colorectal cancer in the United States every year, with one third dying from metastatic disease. The five year survival rate for localized colorectal cancer is ~89% while this number drops to only ~12% for cancers that have metastasized to the liver, lungs, or peritoneum. Effective therapy for advanced colorectal cancer requires treatment of both primary tumors and metastatic tumors that can go undetected in the early stage. Numerous studies have shown that the stimulation of the host immune system can lead to the generation of anti-tumor immune response, which is capable of controlling metastatic tumor growth. Considering the highly metastatic characteristics of colorectal cancer and poor 5-year survival rate of patients with advanced colorectal cancer, there is a clear clinical interest in the development of an effective therapeutic modality for colorectal cancer that both control primary tumor growth and stimulate anti-tumor immunity for controlling the metastatic disease and subsequent tumor growth.

Nanoscale coordination polymers (NCPs) can comprise hybrid nanomaterials constructed from metal-connecting points and organic bridging ligands via self-assembly. NCPs possess several advantages over existing nanocarriers in biomedical applications such as the high tunability of composition and structure, versatility of combining multiple therapeutic agents or modalities in one nanoplatform, and intrinsic biodegradability due to the labile metal-organic ligand bonds. Recently, NCP-based core-shell nanoparticles carrying high payloads of cisplatin and the photosensitizer pyrolipid, NCP@pyrolipid were described for combined chemotherapy and photodynamic therapy (PDT). NCP@pyrolipid showed superior potency and efficacy in tumor regression in the cisplatin-resistant human head and neck cancer SQ20B xenograft mouse model. Photodynamic therapy (PDT) is an FDA-approved anticancer modality that has been shown to enhance anti-tumor immunity. Kroemer and coworkers have demonstrated the immunogenic cell death induced by oxaliplatin in murine colorectal cancer models. Recent studies also suggested that immune response elicited against the residual cancer cells can contribute to the complete eradication of micrometastases and cancer stem cells. Thus, along with the effective apoptosis/necrosis caused by both PDT and oxaliplatin, the combination therapy of oxaliplatin and PDT could be particularly efficient by simultaneously killing the tumor cells and stimulating an immune response against tumor cells. This can cause tumor inhibition/regression not only in the primary tumor site but also in the distant metastatic tumors.

NCP-based core-shell nanoparticles carrying oxaliplatin and photosensitizer pyrolipid (NCP-2@pyrolipid) are shown herein to provide enhanced anti-tumor immunity for achieving superior anticancer efficacy in colorectal cancers and can be used in the treatment of metastatic colorectal cancer. Inheriting all the merits of NCP-based nanoparticles including high drug loading, prolonged systemic circulation via intravenous injection, and ideal biocompatibility, NCP-2@pyrolipid combines two therapeutic modalities, oxaliplatin and PDT, which not only kill the cancer cells but also elicit strong immunogenic response for the control and eradication of metastatic tumor nodules. Effective anticancer therapy with NCP-2@pyrolipid is demonstrated against two colorectal cancer models including syngeneic CT26 murine colorectal cancer model and HT29 human colorectal cancer xenografts. Efficient anti-tumor immunity evoked by NCP-2@pyrolipid such as early calreticulin (CRT) exposure on the cell surface, successful antitumor vaccination, and abscopal effect, is also demonstrated.

Preparation and Characterization

NCP-2 particles carrying an oxaliplatin analogue prodrug were prepared as previously reported. Briefly, a mixture of $Zn(NO_3)_2$ and an oxaliplatin prodrug, $Pt(dach)Cl_2(OH)_2$ (dach=R, R-diaminocyclohexane), with DOPA in the Triton X-100/1-hexanol/cyclohexane/water reverse microemulsion was vigorously stirred at room temperature for 30 min to afford spherical DOPA-coated NCP-2 particles of 55.33±0.18 nm in Z-average by DLS.

NCP-2 has an oxaliplatin analogue loading of 27.6 wt % as determined by ICP-MS. NCP-2@pyrolipid nanoparticles were prepared by coating NCP-2 core with an asymmetric lipid bilayer containing pyrolipid and PEG. A tetrahydrofuran (THF) solution (80 µL) of pyrolipid, cholesterol, 1,2-distearoyl-sn-glycero-3-phosphocholine (DSPC), 1,2-distearoyl-sn-glycero-3-phosphoethanolamine-N-[methoxy (polyethylene glycol)-2000] (DSPE-PEG2k) (DSPC/cholesterol/pyrolipid/DSPE-PEG2k=2:1:0.8:1 in molar ratios), and DOPA-capped NCP-2 were added to 500 µL of 30% (v/v) ethanol/water and kept stirring at 1700 rpm at 60° C. for 1 min. The THF and ethanol in the nanoparticle suspension was completely evaporated before subsequent use in in vitro and in vivo experiments. NCP-2@pyrolipid is a core-shell nanostructure with DOPA-capped coordination polymer NCP-2 carrying an oxaliplatin analogue as a solid core and a self-assembled and asymmetric lipid bilayer as a shell. The NCP-2 cores were constructed from the coordination between $Zn^{2+}$ and phosphate groups of the oxaliplatin analogue prodrug, which were further capped with a monolayer of DOPA via Zn-phosphate interactions between NCPs and DOPA molecules and hydrophobic-hydrophobic interactions among DOPA molecules. The lipid shell contains pyrolipid as photosensitizer for PDT and 20 mol % of PEG-coating to minimize mononuclear phagocyte system (MPS) uptake and prolong blood circulation after systemic injection. This core-shell structured NCP-2@pyrolipid can take advantages of efficient cancer cell killing induced by chemotherapy and PDT as well as the anti-tumor immunity evoked by oxaliplatin analogue and PDT to enable the effective treatment of both primary and metastatic colorectal cancers.

TEM images of NCP-2@pyrolipid demonstrated the formation of uniform and spherical nanoparticles. DLS measurements gave a Z-average diameter, number-average diameter, PDI, and zeta potential of 83.00±0.98 nm, 51.19±0.11 nm, 0.143±0.011, and −3.67±0.85 mV, respectively, of NCP-2@pyrolipid dispersed in PBS. The small sizes and near neutral surface charge of NCP-2@pyrolipid suggests their potential in in vivo applications.

When dispersed in THF, the lipid bilayer of NCP-2@pyrolipid dissolved and pyrolipid shows a broad Soret band around 400 nm and a distinct Q-band at 669 nm.

Porphysome was prepared by following the procedure reported by Zheng and coworkers. As reported previously, pyrolipid can incorporate into the highly oriented and asymmetric lipid bilayer with a high loading. When the lipid bilayer is intact, the pyrolipid excited states are highly quenched, and therefore no energy transfer to triplet oxygen was observed as evidenced by the low amount of $^1O_2$ generated determined by the singlet oxygen sensor green (SOSG) reagent. After addition of Triton X-100 to NCP-2@pyrolipid and porphysome to disrupt the lipid bilayer, pyrolipid regained its fluorescence and efficiently generated similar amount of $^1O_2$ by SOSG.

Cellular Uptake

The time-dependent cellular uptake of NCP-2@pyrolipid was evaluated in CT26 cells with an incubation time ranging from 1 h to 24 h. Free oxaliplatin, porphysome, and the original NCP-2 carrying a cisplatin prodrug and coated with 1,2-dioleoyl-sn-glycero-3-phosphocholine (DOPC), cholesterol, and DSPE-PEG2k served as comparisons. The Pt and pyrolipid concentrations in the cells after incubating with NCP particles, oxaliplatin, or porphysome were determined by ICP-MS and fluorimetry, respectively. As depicted in FIGS. 24A and 24B, the cellular uptake of NCP-2@pyrolipid in terms of both oxaliplatin analogue and pyrolipid was rapid and mostly completed within 1 h, as evidenced by the stable uptake amounts of both oxaliplatin analogue and pyrolipid over time up to 24 h. Except for free oxaliplatin of which the cellular uptake amount dropped significantly with time, cellular uptake of oxaliplatin analogue and pyrolipid remain stable throughout the 24-h experiment, suggesting, without wishing to be bound by any one theory, that the internalization of NCP-2@pyrolipid can lead to the reduced efflux of oxaliplatin analogue by changing the dynamics, porosity, and permeability of the cell membrane.

In Vitro PDT Cytotoxicity

The cytotoxicity of NCP-2@pyrolipid was evaluated against two colorectal cancer cells including murine colorectal adenocarcinoma CT26 and human colorectal adenocarcinoma HT29 cells. By combining chemotherapy of oxaliplatin and PDT modalities into one single nanoparticle, NCP-2@pyrolipid induces apoptosis/necrosis as well as elicit immunogenic cell death upon LED light irradiation. As shown in Table 18, oxaliplatin $IC_{50}$ of free oxaliplatin, NCP-2, and NCP-2@pyrolipid in dark showed no significant difference in both cell lines, suggesting, without wishing to be bound by theory, pyrolipid does not cause cytotoxicity without light activation. However, upon irradiation at 54 J/cm$^2$ light irradiation (670 nm), the oxaliplatin $IC_{50}$ of NCP-2@pyrolipid was decreased by ~4-fold and ~5-fold in CT26 and HT29 cells, respectively. The pyrolipid $IC_{50}$ values also significantly dropped for NCP-2@pyrolipid with irradiation accordingly. No toxicity was observed for porphysome under light and dark in both cell lines within the tested pyrolipid concentration range.

In Vitro PDT Evoked Immunogenic Cell Death

Calreticulin (CRT) is a distinct biomarker exposed on the surface of cells undergoing immunogenic cell death (ICD). The immunogenic cell death induced by NCP-2@pyrolipid was evaluated by immunofluorescence and flow cytometry. For immunofluorescence analysis, CT26 cells were seeded at 5×10$^5$ cells per well in 6-well plates and further cultured for 24 h. The culture media were replaced by 2 mL of fresh culture media containing 10% FBS. Oxaliplatin, NCP-2, NCP-2@pyrolipid, and porphysome were added to the cells, respectively, at an equivalent Pt dose of 5 μM and pyrolipid dose of 1.6 μM. Cells incubated with PBS served as control. After 24-h incubation, the cells were irradiated with LED light (670 nm) at 100 mW/cm$^2$ for 15 min (equal to 90 J/cm$^2$). Following further incubation of 4 h, the cells were washed with PBS three times, fixed with 4% paraformaldehyde, incubated with AlexaFluor 488-CRT antibody for 2 h, stained with DAPI, and observed under CLSM using 405 nm and 488 nm lasers for visualizing nuclei and CRT expression on the cell membrane, respectively. For flow cytometry analysis, CT26 cells were seeded at 1×10$^6$ cells per well in 6-well plates and further cultured for 24 h. The culture media were replaced by 2 mL of fresh culture media containing 10% FBS. Oxaliplatin, NCP-2, NCP-2@pyrolipid, and porphysome were added to the cells, respectively, at an equivalent oxaliplatin dose of 5 μM and pyrolipid dose of 1.6 μM. Cells incubated with PBS served as control. After 24-h incubation, the cells were irradiated with LED light (650 nm) at 100 mW/cm$^2$ for 15 min (equal to 90 J/cm$^2$). Following further incubation of 4 h, the cells were collected, incubated with AlexaFluor 488-CRT antibody for 2 h, and stained with PI. The samples were analyzed by flow cytometer (LSRII Orange, BD, Franklin Lakes, N.J., United States of America) to identify cell surface CRT. The fluorescence intensity of stained cells was gated on PI-negative cells. CT26 murine colorectal adenocarcinoma cells were treated with phosphate buffered saline (PBS, free oxaliplatin, a NCP comprising zinc (Zn) and an oxaliplatin analogue (NCP-2, porphysome, or NCP-2 comprising pyrolipid in a lipid coating layer (NCP-2@pyrolipid with or without light irradiation. Calriticulin (CRT) exposure on the cell surface was determined by flow cytometry analysis. Cells treated with PBS and porphysome without irradiation show no surface CRT expression while significant amounts of CRT were detected on the surface of cells treated with oxaliplatin, NCP-2, and NCP-2@pyrolipid with or without irradiation and porphysome with irradiation. This result suggests that both oxaliplatin and PDT can effectively evoke ICD.

TABLE 18

Oxaliplatin and pyrolipid $IC_{50}$ values (μM) in CT26 and HT29 cells treated with various formulations. The numbers in parenthesis refer to pyrolipid concentrations.

|  | irradiation[a] | NCP-2@pyrolipid | NCP-2 | oxaliplatin | Porphysome[b] |
|---|---|---|---|---|---|
| CT26 | Yes | 1.00 ± 0.30 (0.22 ± 0.09) | 5.07 ± 1.02 | 4.97 ± 0.49 | >2.21 |
|  | No | 3.97 ± 0.60 (0.88 ± 0.21)[c] | 4.74 ± 0.67 | 5.05 ± 0.95 | N/A |
| HT29 | Yes | 0.32 ± 0.15 (0.09 ± 0.04) | 1.96 ± 0.47 | 1.87 ± 0.31 | >2.83 |
|  | No | 1.27 ± 0.44 (0.36 ± 0.12)[c] | 1.42 ± 0.49 | 1.44 ± 0.32 | N/A |

[a]Cells were irradiated with LED light (670 nm) at 60 mW/cm$^2$ for 15 min (equals to 54 J/cm$^2$).
[b]Porphysome containing no cisplatin served as controls. The amount of pyrolipid in the porphysome was the same as NCP-2@pyrolipid under the studied concentrations.
[c]The dark cytotoxicity comes entirely from the action of oxaliplatin in these formulations.

Pharmacokinetics and Biodistribution

A pharmacokinetic (pK) and biodistribution study of NCP-2@pyrolipid was carried out on CT26 tumor bearing BALB/c mice. The Pt distribution was quantified by ICP-MS and the pyrolipid concentration in the blood was quantified by UV-vis spectroscopy after extraction by methanol as we previously reported. See FIGS. 25A and 25B. Both Pt and pyrolipid concentrations in blood versus time were fitted by a one-compartment model. Blood circulation half-lives of Pt and pyrolipid were determined to be (11.8±1.9) and (8.4±2.6) h, respectively, and did not exhibit statistically significant difference. Besides the prolonged blood circulation, NCP-2@pyrolipid exhibited low uptake by the MPS as evidenced by the low % ID/g (percent injected dose per gram tissue) in liver (<7.1±2.5%), spleen (<10.4±4.3%), and kidney (<9.1±2.5%).

In Vivo PDT Efficacy and Immunogenic Response

Two colorectal adenocarcinoma mouse models including BALB/c mice bearing murine colorectal cancer CT26 and nude mice with subcutaneous xenografts of human colorectal cancer HT29 were employed to assess the in vivo anticancer activity of NCP-2@pyrolipid. All doses were based on free oxaliplatin or pyrolipid equivalents. CT26 or HT29 tumor bearing mice were treated by intravenous injection of (1) PBS, (2) NCP-2 at an oxaliplatin analogue dose of 2 mg/kg, (3) and (4) NCP-2@pyrolipid at an oxaliplatin dose of 2 mg/kg every four days for a total of two treatments for CT26 model and four treatments for HT29 model. Twenty four hours post injection, mice in group (1)-(3) were anesthetized with 2% (v/v) isoflurane and tumors were irradiated with a 670 nm LED at an irradiance of 100 mW/cm$^2$ for 30 min. As shown in FIGS. 26 and 27, NCP-2@pyrolipid combined with light irradiation led to efficient tumor inhibition on both CT26 and HT29 subcutaneous tumor mouse models.

For evaluating the immunogenic response in mice bearing CT26 tumors receiving NCP-2@pyrolipid and PDT treatment, blood was collected on Day 7, 8, 9, and 10, and the serum TNF-α, IFN-γ, and IL-6 production was determined by ELISA (R&D Systems, Minneapolis, Minn., United States of America) to evaluate the immunogenic response evoked by the treatment. The significantly elevated TNF-α, IFN-γ, and IL-6 levels in the serum of mice treated with NCP-2@pyrolipid and PDT confirmed the robust immunogenic response evoked by the treatment. See FIGS. 28A-28C. Without wishing to be bound by any one theory, the slightly increased pro-inflammatory cytokine production levels in mice treated with NCP-2 (+) and NCP-2@pyrolipid (−) could be due to the immunogenic response induced by oxaliplatin analogue.

Antitumor Vaccination

Inspired by the robust immunogenic response evoked by NCP-2@pyrolipid and PDT in vivo, the antitumor vaccination capability of NCP-2@pyrolipid was further evaluated. A total of 5×10$^5$ CT26 cells, treated with PBS or NCP-2@pyrolipid and light irradiation, were inoculated subcutaneously to the right flank region of 6-week-old male BALB/c mice. One week after, these mice were re-challenged by injecting 1×10$^5$ CT26 cells on the contralateral flank. The animals were checked daily for tumor development using calipers and body weight evolution. The blood was collected one day after the first tumor injection, and the serum TNF-α, IFN-γ, and IL-6 production was determined by ELISA (R&D Systems, Minneapolis, Minn., United States of America) to evaluate the immunogenic response. All mice were sacrificed when the right tumor size of PBS group exceeded 2 cm$^3$. As shown in FIGS. 29A-29C, NCP-2@pyrolipid and PDT achieved 100% success in antitumor vaccination against the re-challenge of healthy tumor cells.

Abscopal Effect of NCP-2@Pyrolipid

The abscopal effect of NCP-2@pyrolipid upon light irradiation was evaluated against subcutaneous CT26 tumor bearing BALB/c mice. Tumor bearing mice were established by subcutaneous inoculation of CT26 cell suspension (2×10$^6$ cells per mouse) into the right flank region and CT26 cell suspension (4×10$^5$ cells per mouse) into the left flank region of the same mouse. Four groups were included for comparison: (1) PBS+irradiation (2) NCP-2@pyrolipid+irradiation (3) NCP-1@pyrolipid (NCP carrying cisplatin and pyrolipid)+irradiation (4) NCP-2@pyrolipid dark control. When the right tumors reached ~100 mm$^3$, NCPs were intratumorally injected at an oxaliplatin analogue dose of 2 mg/kg. Twelve hour post-injection, mice were anesthetized with 2% (v/v) isoflurane and tumors were irradiated with LED light at 100 mW/cm$^2$ for 30 min (180 J/cm$^2$). The NCPs were injected every three day for a total two injections. LED light irradiation was performed daily on six consecutive days. To evaluate the therapeutic efficacy, tumor growth was monitored. The tumor size was measured with a digital caliper every day. Tumor volumes were calculated as follows: (width$^2$×length)/2.

Local injection of NCP-2@pyrolipid plus LED light irradiation not only led to tumor regression/eradication of the treated right tumors, but also inhibited the growth of the distant left tumors, suggesting, without wishing to be bound by any one theory, that the combination therapy successfully evokes immunoresponse in immunocompetent mouse models of colorectal cancer. The treatment of NCP-1@pyrolipid successfully suppressed/eradicated the right tumors, however showed limited inhibition on the growth of the left tumors. See FIGS. 30A and 30B. This result indicates that the combined immunogenic response evoked by oxaliplatin analogue and PDT elicits an abscopal effect.

Example 17

Nanoscale Coordination Polymer Core-Shell Nanoparticles Combine Chemotherapy, Photodynamic Therapy, and PD-L1 Antibody for Anti-Tumor Immunity In order to further enhance the immunotherapeutic effects of NCP-2/pyrolipid in the presence of light activation, we add an immune checkpoint inhibitor in the treatment regimen. The abscopal effect of NCP-2@pyrolipid plus light irradiation in combination with checkpoint blockade PD-L1 antibody was evaluated against subcutaneous MC38 tumor bearing mice. C57BL/6 mice were injected s.c. with 5×10$^5$ MC38 cells into the right flank (primary tumor) and 1×10$^5$ MC38 cells into the left flank (secondary tumor). When the primary tumors reached ~100 mm$^3$, mice were randomly divided into five groups (n=6): PBS with irradiation as control; NCP@pyrolipid without irradiation; NCP@pyrolipid with irradiation; NCP@pyrolipid without irradiation plus anti-PD-L1; and NCP@pyrolipid with irradiation plus anti-PD-L1. NCP@pyrolipid was i.p. injected into animals at an oxaliplatin analogue dose of 2 mg/kg every three days for a total of three injections. Twenty-four hours after injection, mice were anesthetized with 2% (v/v) isoflurane, and primary tumors were irradiated with a 670 nm LED at a light dose of 180 J/cm$^2$ given at 100 mW/cm$^2$. After irradiation, mice were immediately i.p. injected with PD-L1 antibody at a dose of 50 µg/mouse. Primary and secondary tumor sizes were measured with a digital caliper and calculated as follows: (width$^2$×length)/2.

Systemically injected NCP-2@pyrolipid plus LED light irradiation in combination with PD-L1 antibody not only led to tumor regression/eradication of the treated right tumors but also suppressed/eradicated the growth of the distant left tumors (see FIGS. 31A and 31B), suggesting, without wishing to be bound by any one theory, the combination therapy evoked robust immunoresponse for the effective treatment of both primary and distant/metastatic colorectal cancers. The incorporation of checkpoint blockade PD-L1 antibody into the treatment significantly enhanced the abscopal effect and anticancer efficacy of NCP-2@pyrolipid PDT.

The abscopal effect provided by the combination of NCP@pyrolipid with PDT and anti-PD-L1 on another bilateral syngeneic mouse model of colorectal cancer CT26 was also studied. When the primary tumors reached ~100 mm³, mice received i.p. injections of NCP@pyrolipid at an oxaliplatin dose of 2 mg/kg every other day for a total of two injections. Twenty-four hours after injection, the primary tumors were irradiated at a light dose of 180 J/cm2 (670 nm, 100 mW/cm²). After irradiation, mice were immediately i.p. injected with anti-PD-L1 at a dose of 75 μg/mouse. The combination therapy again led to the effective tumor regression of not only the primary tumors but also the distant tumors after two treatments. See FIGS. 32A and 32B.

Example 18

Zn-Pyrophosphate Core-Shell Nanoparticles Combine Photodynamic Therapy and PD-L1 Antibody for Anti-Tumor Immunity Preparation of Pyrolipid-Loaded Zn-Pyrophosphate Particles (Zn@Pyrolipid)

Zn@pyrolipid was obtained by adding a 80 μL THF solution of DSPC, cholesterol, pyrolipid (molar ratio 1:1:0.5), DSPE-PEG2k (20 mol %) and Zn-pyrophosphate bare particles to 500 μL 30% (v/v) EtOH/H₂O at 60° C. THF and EtOH were evaporated and the solution was allowed to cool to room temperature before use. The particle size and distribution were determined by DLS. See Table 19.

TABLE 19

Characterization of Zn@pyrolipid particles.

|  | Z-Ave | PDI | Intensity | Volume | Number |
|---|---|---|---|---|---|
| Zn-pyrophosphate bare particles[#] | 49.47 ± 0.12 | 0.126 ± 0.01 | 63.04 ± 0.48 | 44.98 ± 0.36 | 35.14 ± 0.73 |
| Zn@pyrolipid[$] | 98.67 ± 0.42 | 0.125 ± 0.01 | 115.3 ± 1.23 | 89.36 ± 1.28 | 67.36 ± 2.78 |

[#]Measured in THF.
[$]Measured in water. Data are expressed as mean ± S.D.

Pyrolipid Loading Amount

The pyrolipid loading amount was quantified with a UV-Vis spectrophotomer (UV-2401PC, Shimadzu, Japan). After lipid coating, Zn@pyrolipid was centrifuged at 13000 rpm for 30 min. The precipitate of Zn@pyrolipid was redispersed in tetrahydrofuran (THF), and the pyrolipid amount in the nanoparticle suspension was determined by UV-Vis absorption at 669 nm. The pyrolipid loading was determined to be 10.6±0.8 wt. %.

Fluorescence Quenching of Zn@Pyrolipid

The fluorescence of Zn@pyrolipid with intact or disrupted lipid layer was measured to calculate the fluorescence quenching efficiency. Zn@pyrolipid was diluted in PBS as intact samples or PBS containing 0.5% Triton X-100 to disrupt the lipid layer. The samples were subjected to spectrofluorophotometer (RF-5301 PC, Shimadzu, Kyoto, Japan) for fluorescence measurement (excitation: 427 nm, emission: 600-750 nm). The fluorescence intensity at 675 nm for Zn@pyrolipid with intact lipid layer was normalized to Zn@pyrolipid with disrupted lipid layer to calculate the quenching efficiency. The fluorescence intensity of intact Zn@pyrolipid was 2.7% of that of Zn@pyrolipid with disrupted lipid layer.

Singlet Oxygen Generation

The singlet oxygen sensor green (SOSG) reagent (Life Technologies, USA) was employed for the detection of singlet oxygen generated by Zn@pyrolipid. After lipid coating, Zn@pyrolipid was centrifuged at 13000 rpm for 30 min. The supernatant was discarded and the pellet was re-suspended with PBS. Five microliter of freshly prepared SOSG solution in methanol (5 mM) was mixed with 2 mL of Zn@pyrolipid intact in PBS or disrupted with 0.5% Triton X-100. Free pyrolipid at the same pyrolipid concentration as Zn@pyrolipid served as a control. Samples were treated with LED with a wavelength of 660 nm and energy irradiance of 60 mW/cm² for 10 s, 20 s, 30 s, 40 s, 50 s, 75 s, 100 s, and 250 s, and SOSG fluorescence was measured by exciting at 504 nm and emission at 525 nm. There was no pyrolipid fluorescence contribution within this emission window. When the lipid bilayer is intact, Zn@pyrolipid generated very little singlet oxygen, possibly due to the pyrolipid excited states being highly quenched, and not transferring energy to triplet oxygen. After addition of Triton X-100 to disrupt the lipid bilayer, the $^1O_2$ generation efficiency of Zn@pyrolipid was similar to that of free pyrolipid at the same concentration.

Cellular Uptake and Efflux of Zn@Pyrolipid

4T1 triple negative breast cancer cells and B16F10 murine melanoma cells were seeded on 24-well plates at a density of 1×10⁵ cells/well and incubated for 24 h. Zn@pyrolipid and free pyrolipid were added to the cells at a pyrolipid dose of 2 μM, respectively. After incubating for 1, 2, 4, and 24 h, cells were collected, washed with PBS three times, and counted with a hemocytometer. The cells were centrifuged at 3,000 rpm for 5 min and the cell pellet was lysed with 0.5% (w/v) SDS (pH 8.0). The fluorescence intensity of pyrolipid was determined by fluorimetry ($\lambda_{ex}$=427 nm, $\lambda_{em}$=675 nm). Results were expressed as the amount of pyrolipid (pmol) per 10⁵ cells. The cellular uptake of Zn@pyrolipid in both cell lines was rapid and mostly completed within 1 h, as indicated by the stable uptake amounts of pyrolipid over time up to 24 h.

The efflux of pyrolipid was quantified as follows. After incubation with Zn@pyrolipid and free pyrolipid for 4 h, the culture medium was discarded and the cells were washed with PBS three times. Five microliters of fresh culture medium were added to each well and the cells were further incubated for 1, 2, 4, and 24 h. The pyrolipid amount in the culture medium was quantified by fluorimetry after adding 0.5% Triton X-100 ($\lambda_{ex}$=427 nm, $\lambda_{em}$=675 nm). Results were expressed as the percent of the amount of pyrolipid being effluxed compared to the 4 h cellular uptake amount. Zn@pyrolipid showed negligible efflux (<2%) during 24 h incubation in both cell lines. Efflux of free pyrolipid increased a little bit over time, but was still lower than 3%.

Cytotoxicity

4T1 and B16F10 cells seeded on 96-well plates at a density of 2500 cells/well were treated with Zn@pyrolipid and free pyrolipid at various pyrolipid concentrations. After 24 h incubation, the cells were irradiated with LED light (660 nm) at 60 mW/cm² for 15 min (equal to 54 J/cm²). The cells without irradiation treatment served as controls. After incubation for additional 48 h, the cell viability was detected by (3-(4,5-dimethylthiazol-2-yl)-5-(3-carboxymethoxyphenyl)-2-(4-sulfophenyl)-2H-tetrazolium) (MTS) assay (Promega, Madison, Wis., United States of America) and the $IC_{50}$ values were calculated accordingly. Zn particles with or without irradiation did not present any toxicity on both cell lines, suggesting that Zn particles can serve as a safe and reliable nanocarrier for drug delivery. Zn@pyrolipid and free pyrolipid without irradiation also induced no cytotoxicity on both cells, indicating that Zn@pyrolipid is safe, and the particle can be injected without worries regarding toxicity. After irradiation, Zn@pyrolipid and free pyrolipid exhibited very high cytotoxicity, as shown by significantly decrease in the $IC_{50}$ values. See Table 20.

TABLE 20

$IC_{50}$ values of Zn@pyrolipid and free pyrolipid under light and dark in 4T1 and B16F10 cells after 72 h incubation.

|  | 4T1 cells | | B16F10 cells | |
| --- | --- | --- | --- | --- |
|  | 60 mW/cm² 15 min | Dark | 60 mW/cm² 15 min | Dark |
| Pyrolipid | 0.22 ± 0.01 | >5 | 0.32 ± 0.01 | >5 |
| Zn@pyrolipid | 0.42 ± 0.02 | >5 | 0.41 ± 0.01 | >5 |

Apoptosis

4T1 and B16F10 cells seeded in 24-well plates at $1\times10^5$ cells/well were first incubated with Zn@pyrolipid and free pyrolipid for 24 h at a pyrolipid concentration of 0.2 µM, and cells were then irradiated with LED light (660 nm) at 60 mW/cm² for 15 min (equal to 54 J/cm²). Following further incubation of 48 h, the floating and adherent cells were collected and stained with Alexa Fluor 488 AnnexinV/dead cell apoptosis kit (Invitrogen, Carlsbad, Calif., United States of America) according to manufacturer's instructions. The apoptosis and necrosis were examined by flow cytometry (LSRII Blue, BD, Franklin Lakes, N.J., United States of America). Zn@pyrolipid and free pyrolipid did not induce any apoptosis without irradiation, compared to blank control, but evoked high level of apoptosis under irradiation. Zn@pyrolipid and free pyrolipid after irradiation induced 71.61% and 90.18% apoptosis on 4T1 cells, and 63.72% and 85.79% apoptosis on B16F10 cells, respectively.

Pharmacokinetics and Biodistribution

The 4T1 tumor model was generated by an orthotopic injection of $5\times10^4$ cells into the mammary fat pad of the Balb/c female mice and tumors were allowed to grow until 100 mm³ before they received intravenous administration of Zn@pyrolipid at a pyrolipid dose of 6 mg/kg. Mice were sacrificed (n=3) at 5 min, 3, and 24 h after administration, and the blood, heart, liver, spleen, lung, kidney, bladder and tumor were harvested. The blood was immediately centrifuged at 5000 rpm for 10 min to harvest plasma samples. Pyrolipid were extracted from plasma by deproteinization using methanol, followed by centrifugation at 13 000 rpm for 10 min. Organs and tumor were homogenized in 1 mL methanol, followed by centrifugation at 13 000 rpm for 10 min. The content of pyrolipid in supernatants was then measured by fluorescence microplate reader ($\lambda_{ex}$=427 nm, $\lambda_{em}$=675 nm). To verify the viability of this method, the blood, organs and tumor excised from blank mice were processed using the same extraction method as described above. The emission spectra (600-750 nm) of blank blood, organs and tumor at the same excitation wavelength were recorded on spectrofluorophotometer (RF-5301 PC, Shimadzu, Kyoto, Japan).

Pyrolipid concentrations in blood versus time were fitted best by a one-compartment model with nonlinear elimination. Blood circulation half-life of pyrolipid was determined to be 14.8±1.9 h. In addition to the prolonged blood circulation time, Zn@pyrolipid showed low distribution in liver, spleen, and kidney, suggesting Zn@pyrolipid can avoid MPS uptake. The slow blood clearance and low MPS uptake led to the high tumor accumulation, with a highest tumor uptake of 15.6%±2.5 ID/g at 24 h post i.v. administration.

In Vivo Efficacy on 4T1 Orthotopic Model

Mice bearing 4T1 tumor were randomly divided into four groups (n=6): PBS with irradiation as control; Zn@pyrolipid without irradiation plus anti-PD-L1; Zn@pyrolipid with irradiation; Zn@pyrolipid with irradiation plus anti-PD-L1. Zn@pyrolipid was intravenously (i.v.) injected to animals at a pyrolipid dose of 6 mg/kg every two days for a total three injections. Twenty four hours after injection, mice were anesthetized with 2% (v/v) isoflurane and tumors were irradiated with a 670 nm LED at a light dose of 180 J/cm² given at 100 mW/cm². After irradiation, mice were intraperitoneally (i.p.) injected immediately with PD-L1 antibody at a dose of 50 µg/mouse. The tumor size was measured every day with a digital caliper and calculated as follows: (width²×length)/2. At the end of the experiment, mice were sacrificed, and tumors were excised, weighed (see FIG. 33B) and photographed. Lungs were also harvested, sectioned at 10 µm thickness and stained with (H&E), and observed for histological examination of metastases with light microscopy. As shown in FIG. 33A, the primary tumor disappeared at day 13 after treatment by Zn@pyrolipid (+)+PD-L1 antibody, and did not recur. The growth of tumor treated with Zn@pyrolipid plus irradiation was inhibited at the first several days, but tumors began to grow fast at the last several days. The tumor volume treated with PD-L1 antibody showed a little bit of decrease, but did not have significant difference compared to PBS control group.

The metastasis to the lungs was examined by the gross appearance of tumor nodules. Many tumor nodules in lungs treated with PBS, Zn@pyrolipid with irradiation, and Zn@pyrolipid without irradiation but plus PD-L1 antibody were observed. For Zn@pyrolipid with irradiation plus PD-L1 antibody treated group, only 1 or 2 tumor nodules were observed, indicating that the combination of PDT with PD-L1 antibody can significantly prevent the lung metastasis of breast cancer. The lungs were further sectioned and stained with H&E, and the percentage of metastasis area in total lung area was calculated. About 36.8%, 30.7% and 26.4% of lung were occupied by tumor nodules in PBS, Zn@pyrolipid with irradiation, and Zn@pyrolipid without irradiation but plus PD-L1 antibody treated group, respectively. For Zn@pyrolipid with irradiation plus PD-L1 antibody treated group, only 0.4% of the lung was occupied by tumor nodules.

Abscopal Effect on 4T1 and TUBO Models

Balb/c mice were injected s.c. with $5\times10^4$ 4T1 cells or $1\times10^6$ TUBO cells in the right flank (primary tumor) and $1\times10^4$ 4T1 cells or $2\times10^5$ TUBO cells in the left flank (secondary tumor). When the primary tumors reached ~100 mm$^3$, mice were randomly divided into four groups (n=6): PBS with irradiation as control; Zn@pyrolipid without irradiation plus anti-PD-L1; Zn@pyrolipid with irradiation; Zn@pyrolipid with irradiation plus anti-PD-L1. Zn@pyrolipid was i.v. injected to animals at a pyrolipid dose of 6 mg/kg every two days for a total three injections. Twenty four hours after injection, mice were anesthetized with 2% (v/v) isoflurane and primary tumors were irradiated with a 670 nm LED at a light dose of 180 J/cm$^2$ given at 100 mW/cm$^2$. After irradiation, mice were i.p. injected immediately with PD-L1 antibody at a dose of 50 µg/mouse. The primary and secondary tumor sizes were measured every day with a digital caliper and calculated as follows: (width$^2$× length)/2. All mice were sacrificed when the primary tumor size of control group exceeded 2 cm$^3$, and the excised tumors were photographed and weighed.

After treatment, the growth curves of right tumors were similar to that of the 4T1 orthotopic model. The left tumors treated with Zn@pyrolipid with irradiation plus PD-L1 were significantly inhibited, and did not show obvious growth. Zn@pyrolipid with irradiation inhibited right tumor growth at the first several days, but tumors began to grow fast at the last several days, and Zn@pyrolipid with irradiation didn't show any inhibitory effect on the left tumors. PD-L1 antibody itself had some effect on tumor growth—both right and left tumors grew a little bit slower compared to PBS group. See FIGS. 34A-34C. The abscopal effect of Zn@pyrolipid with irradiation plus PD-L1 antibody on TUBO model was similar to that of the 4T1 model (see FIGS. 35A-35C), confirming that the PD-L1 blockade improves the abscopal tumor-specific immune response caused by PDT of Zn@pyrolipid.

Serum Cytokines Concentration

Blood was collected daily from TUBO tumor-bearing mice from Day 10 after tumor inoculation, when the mice received the first Zn@pyrolipid injections, to Day 13. The serum was separated and analyzed by ELISA to determine cytokine production of IL-6, TNF-α, and IFN-γ.

Release of such cytokines indicates acute inflammation, an important mechanism in inducing antitumor immunity. Significantly high IL-6, TNF-α, and IFN-γ levels were noted in mice treated by Zn@pyrolipid with irradiation plus PD-L1 antibody on Day 12, suggesting the successful activation of the innate immune response and acute inflammation. Zn@pyrolipid with irradiation, and Zn@pyrolipid without irradiation plus PD-L1 also increased the cytokine levels, compared to PBS group, but the increased degree was significantly lower than that of Zn@pyrolipid with irradiation plus PD-L1 antibody. See FIGS. 36A-36C.

Immune Assay by Flow Cytometry

At day 12 post first treatment, tumor-draining lymph nodes were harvested and ground using the rubber end of a syringe. Tumors were harvested, treated with 1 mg/mL collagenase I (GIBCO™, Thermo Fisher Scientific, Waltham, Mass., United States of America) for 1 h, and ground using the rubber end of a syringe. Cells were filtered through nylon mesh filters and washed with PBS. The single-cell suspension was incubated with anti-CD16/32 (clone 93; eBiosciences, San Diego, Calif., United States of America) to reduce nonspecific binding to FcRs. Cells were further stained with the following fluorochrome-conjugated antibodies: CD45 (30-F11), CD3e (145-2C11), CD4 (GK1.5), CD8 (53-6.7), Foxp3 (FJK-16s), CD11b (M1/70), Ly6C (HK1.4), Ly6G (RB6-8C5), F4/80 (BM8), B220 (RA3-6B2) and PI staining solution (all from eBiosciences, San Diego, Calif., United States of America). LSR FORTESSA (BD Biosciences, Franklin Lakes, N.J., United States of America) was used for cell acquisition, and data analysis was carried out using FlowJo software (TreeStar, Ashland, Oreg., United States of America).

Zn@pyrolipid with irradiation in combination with anti-PD-L1 significantly increased the proportion of infiltrating CD8$^+$ T cells in the left tumor, an essential step to induce the abscopal effect. In the left tumors, the percentage of infiltrating CD45 leukocytes, CD4$^+$ T cells, and B cells were also significantly increased. See FIGS. 37A-37D. Interestingly, CD8$^+$ and CD4$^+$ T cells in lymph nodes decreased at day 12 after first treatment (see FIGS. 38A and 38B), possibly because the CD8$^+$ and CD4$^+$ T cells migrated from lymph nodes to the tumor site to kill the tumor cells. All these results indicated that the immune system was activated by the combination treatment of PDT with PD-L1 blockade.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A nanoscale particle for delivery of therapeutic agents, said nanoscale particle comprising:
   a core comprising a metal bisphosphonate coordination polymer comprising a multivalent metal ion and a bisphosphonate, wherein said bisphosphonate comprises a cisplatin and/or oxaliplatin prodrug; and
   a coating layer covering at least a portion of an outer surface of the core, wherein said coating layer comprises an asymmetric lipid bilayer wherein said asymmetric lipid bilayer comprises a prodrug comprising: (a) a monovalent drug moiety, wherein said monovalent drug moiety is a monovalent derivative of an anticancer drug compound selected from the group consisting of Etoposide (ET), Paclitaxel (PTX), NLG919, OTS167, OTSC41, dihydroartemisin, Camptothecin (CPT), Docetaxel, Mitoxantrone, and Artesunate, (b) a monovalent lipid moiety, and (c) a bivalent linker comprising a disulfide bond, wherein said monovalent drug moiety and said monovalent lipid moiety are linked through the bivalent linker.

2. The nanoscale particle of claim 1, wherein the monovalent lipid moiety is a monovalent derivative of cholesterol, oleic acid, a lyso-lipid, or phosphocholine.

3. The nanoscale particle of claim 2, wherein the monovalent lipid moiety is a cholesterol derivative and the monovalent lipid moiety and the bivalent linker moiety together have the structure:

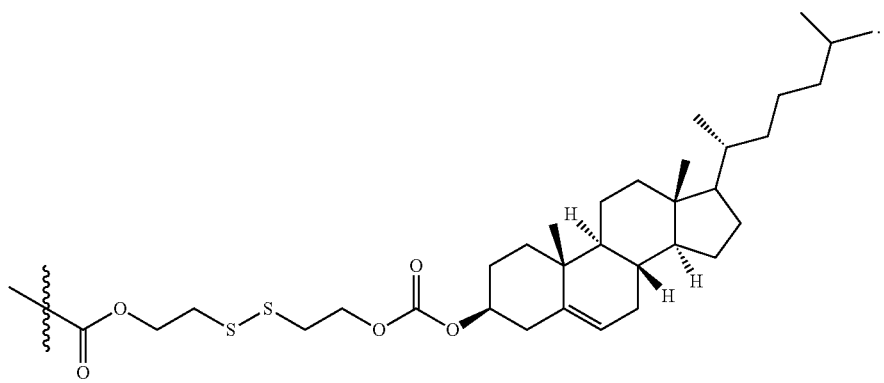 [SMILES: *C(=O)OCCSSCCOC(=O)O[C@H]1CC[C@@]2(C)C(=CC[C@@H]3[C@@H]2CC[C@]2(C)C([C@H](C)CCCC(C)C)CC[C@@H]32)C1]

4. The nanoscale particle of claim 2, wherein the monovalent lipid moiety is an oleic acid derivative and the monovalent lipid moiety and the bivalent linker moiety together have the structure:

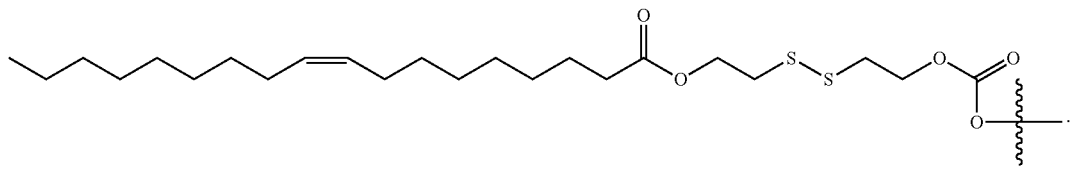 [SMILES: *OC(=O)OCCSSCCOC(=O)CCCCCCC/C=C\CCCCCCCC]

5. The nanoscale particle of claim 2, wherein the monovalent lipid moiety is a lyso-lipid derivative and the monovalent lipid moiety and the bivalent linker moiety together have the structure:

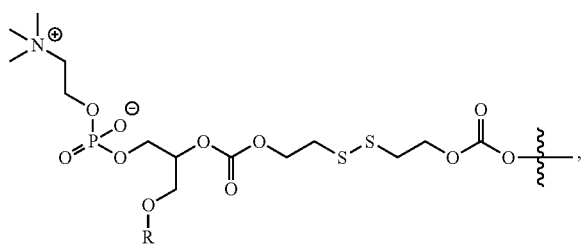

where R is selected from oleyl, stearyl, or palmitoleyl.

6. The nanoscale particle of claim 1, further comprising at least one nucleic acid chemotherapeutic agent.

7. The nanoscale particle of claim 6, wherein the nucleic acid chemotherapeutic agent is a siRNA, a miRNA, or an AS ODN.

8. The nanoscale particle of claim 6, wherein the at least one nucleic acid is selected from the group consisting of survivin siRNA, ERCC-1 siRNA, P-glycoprotein siRNA (P-gp siRNA), Bcl-2 siRNA, and a mixture thereof.

9. The nanoscale particle of claim 1, further comprising at least one additional non-nucleic add chemotherapeutic agent incorporated in the core, wherein said additional non-nucleic acid chemotherapeutic agent is selected from the group consisting of gemcitabine, methotrexate, leucovorin, pemetrexed disodium, doxorubicin, vinblastine, vincristine, vindesine, cytarabine, azathioprine, melphalan, imatinib, anastrozole, letrozole, carboplatin, paclitaxel, docetaxel, etoposide, and vinorelbine.

10. The nanoscale particle of claim 1, wherein the cisplatin and/or oxaliplatin prodrug is cis, cis, trans-$Pt(NH_3)_2Cl_2(OEt)(O_2CCH_2CH_2COOH)$, optionally wherein the core comprises between about 10 weight % and about 50 weight % of the cisplatin and/or oxaliplatin prodrug.

11. The nanoscale particle of claim 1, wherein the nanoscale particle has an average diameter of between about 20 nm and about 140 nm.

12. The nanoscale particle of claim 1, wherein the asymmetric lipid bilayer comprises a cationic lipid and/or a functionalized lipid, wherein said functionalized lipid is a lipid functionalized with a group that can bond to a nucleic acid, and wherein at least one nucleic acid is covalently bonded to the functionalized lipid and/or attached to the cationic lipid via electrostatic interactions.

13. The nanoscale particle of claim 1, wherein the asymmetric lipid bilayer comprises a mixture comprising one or more of a thiol- or dithiol- functionalized 1,2-distearoyl-sn-glycero-3-phosphoethanolamine (SSPE), 1,2-dioleoyl-3-trimethylammonium propane (DOTAP), and 1,2-dioleoyl-sn- glycero-3-phosphocholine (DOPC).

14. The nanoscale particle of claim 1, wherein the coating layer further comprises at least one of a passivating agent, wherein said passivating agent is optionally a hydrophilic polymer; a targeting agent, wherein said targeting agent is optionally a RGD peptide; and an imaging agent, wherein said imaging agent is optionally a fluorescent moiety.

15. The nanoscale particle of claim 1, wherein the asymmetric lipid bilayer further comprises one or more of 1,2-dioleoyl-sn-glycero-3- phosphate sodium salt (DOPA), cholesterol, and pegylated-DSPE.

16. The nanoscale particle of claim 1, wherein the multivalent metal ion is selected from the group consisting of $Ca^{2+}$, $Mg^{2+}$, $Mn^{2+}$, $Zn^{2+}$, and combinations thereof.

17. The nanoscale particle of claim 1, wherein the monovalent drug moiety of the prodrug is a monovalent derivative of dihydroartemisin (DHA).

18. The nanoscale particle of claim 17, wherein the bisphosphonate is a bisphosphonate ester of cis, cis-trans-[Pt(NH$_3$)$_2$Cl$_2$(OH)$_2$] (a cisplatin prodrug) or cis, trans-[Pt(dach)Cl$_2$(OH)$_2$].

19. The nanoscale particle of claim 1, wherein the multivalent metal ion is $Zn^{2+}$.

20. The nanoscale particle of claim 1, wherein the core comprises between about 40 and about 50 weight % of bisphosphonate.

21. The nanoscale particle of claim 1, wherein one or more of survivin siRNA, P-gp siRNA, and Bcl-2 siRNA are attached to the coating layer.

22. The nanoscale particle of claim 1, wherein the nanoscale particle has a diameter between about 20 nm and about 180 nm.

23. The nanoscale particle of claim 1, wherein the nanoscale particle has a diameter between about 90 nm and about 180 nm.

24. The nanoscale particle of claim 1, wherein the monovalent drug moiety is a monovalent derivative of a drug compound selected from the group consisting of Etoposide (ET), Paclitaxel (PTX), NLG919, OTS167, OTSC41, dihydroartemisin, Camptothecin (CPT), Mitoxantrone, and Artesunate.

25. The nanoscale particle of claim 1, wherein the monovalent lipid moiety is a monovalent derivative of cholesterol.

26. A pharmaceutical formulation comprising a composition comprising a nanoscale particle of claim 1 and a pharmaceutically acceptable carrier.

27. A method of treating cancer in a subject in need thereof, the method comprising administering to the subject a composition comprising a nanoscale particle of claim 1.

28. The method of claim 27, wherein the cancer is selected from lung cancer, pancreatic cancer, ovarian cancer, breast cancer, and colon cancer.

29. The method of claim 27, wherein the cancer is ovarian cancer, optionally a cisplatin resistant ovarian cancer.

30. The method of claim 27, further comprising administering to the subject an immunotherapy agent.

31. The method of claim 30, wherein the immunotherapy agent is selected from the group consisting of an anti-CD52 antibody, an anti-CD2O antibody, anti-CD47 antibody, an anti-GD2 antibody, a cytokine, and polysaccharide K.

32. The method of claim 30, wherein the immunotherapy agent is selected from the group consisting of Alemtuzumab, Ofatumumab, Rituximab, Zevalin, Adcetris, Kadcyla, and Ontak.

33. The method of claim 30, wherein the immunotherapy agent is selected from the group consisting of a PD-1 inhibitor, a PD-L1 inhibitor, a CTLA-4 inhibitor, an IDC inhibitor, a CCR7 inhibitor, a OX40 inhibitor, a TIM3 inhibitor, and a LAGS inhibitor.

34. The method of claim 27, wherein the cancer is a head and neck cancer, optionally wherein the head and neck cancer is a cisplatin resistant head and neck cancer.

\* \* \* \* \*